United States Patent
Mecozzi et al.

(10) Patent No.: US 11,464,738 B2
(45) Date of Patent: Oct. 11, 2022

(54) IONIC LIQUID-BASED NANOEMULSION FORMULATION FOR THE EFFICIENT DELIVERY OF HYDROPHILIC AND HYDROPHOBIC THERAPEUTIC AGENTS

(71) Applicant: Wisconsin Alumni Research Foundation, Madison, WI (US)

(72) Inventors: Sandro Mecozzi, Madison, WI (US); Moira Esson, Medina, OH (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 17/040,916

(22) PCT Filed: May 10, 2019

(86) PCT No.: PCT/US2019/031773
§ 371 (c)(1),
(2) Date: Sep. 23, 2020

(87) PCT Pub. No.: WO2019/217854
PCT Pub. Date: Nov. 14, 2019

(65) Prior Publication Data
US 2021/0361573 A1 Nov. 25, 2021

Related U.S. Application Data

(60) Provisional application No. 62/736,201, filed on Sep. 25, 2018, provisional application No. 62/670,637, filed on May 11, 2018.

(51) Int. Cl.
| | |
|---|---|
| A61K 9/107 | (2006.01) |
| A61K 45/06 | (2006.01) |
| A61K 47/10 | (2017.01) |
| A61K 47/14 | (2017.01) |
| A61K 47/18 | (2017.01) |
| A61K 47/20 | (2006.01) |
| B82Y 5/00 | (2011.01) |

(52) U.S. Cl.
CPC ............ *A61K 9/1075* (2013.01); *A61K 45/06* (2013.01); *A61K 47/10* (2013.01); *A61K 47/14* (2013.01); *A61K 47/186* (2013.01); *A61K 47/20* (2013.01); *B82Y 5/00* (2013.01)

(58) Field of Classification Search
CPC ...... A61K 9/1075; A61K 45/06; A61K 47/10; A61K 47/14; A61K 47/186; A61K 47/20; B82Y 5/00
See application file for complete search history.

(56) References Cited

U.S. PATENT DOCUMENTS

| | | | |
|---|---|---|---|
| 6,039,936 A | 3/2000 | Restle et al. | |
| 6,998,426 B2 | 2/2006 | L'alloret et al. | |
| 7,947,854 B2 | 5/2011 | Widmer et al. | |
| 8,546,609 B2 | 10/2013 | Watahiki et al. | |
| 8,900,562 B2 | 12/2014 | Mecozzi et al. | |
| 9,000,048 B2 | 4/2015 | Mecozzi et al. | |
| 9,278,134 B2 | 3/2016 | Rogers et al. | |
| 10,426,727 B2 | 10/2019 | Mecozzi et al. | |
| 10,758,483 B2 | 9/2020 | Mecozzi et al. | |
| 2010/0234228 A1 | 9/2010 | Lennon et al. | |
| 2013/0331305 A1* | 12/2013 | Aswath | ................ C10M 141/10 508/388 |
| 2016/0278375 A1 | 9/2016 | Wuest et al. | |
| 2018/0016510 A1 | 1/2018 | Kondo et al. | |
| 2020/0101014 A1 | 4/2020 | Mecozzi et al. | |

OTHER PUBLICATIONS

A. Hemsworth, The Pharmacological Actions of Some Polymethylene-Bis-(Hydroxyethyl)-Dimethyl-Ammonium Compounds on Cholinergic Transmission, 35 Eur. J Pharmacol. 127 (Year: 1976).*
Alvarez et al. (2016) "Reformlation of Fungizone by PEG-DSPE Micelles: Deaggregation and Detoxification of Amphotericin B." Pharm. Res. 33(9): 2098-2106.
Alvarez et al. (publicly available Fed. 2017) "Antifungal Efficacy of an Intravenous Formulation Containing Monomeric Amphotericin B, 5-Fluorocytosine, and Saline for Sodium Supplementation", Pharm. Res. (May 2017) 34(5): 1115-1124.
Aramwit et al. (2000) "The Effect of Serum Albumin on the Aggregation State and Toxicity of Amphotericin", B. J Pharm. Sci. 89(12): 1589-1593.
Asperguillus & Aspergillosis. https://www.aspergillus.org.uk/blogger/eucast-are-we-heading-towards-international-agreement/ (accessed Apr. 7, 2018).
Banerjee et al. (2017) "Transdermal Protein Delivery Using Choline and Geranate (CAGE) Deep Eutectic Solvent", Adv. Healthc. Mater. 6(15): 1-11.
Banerjee et al. (2018) "Ionic Liquids for Oral Insulin Delivery", Proc. Natl. Acad. Sci. 115(28): 7296-7301.
Barres et al. (2017) "Multicompartment Theranostic Nanoemulsions Stabilized by a Triphilic Semifluorinated Block Copolymer", Mol. Pharm 14: 3916-3926.
Bharmoria et al. (2016) "Unusually High Thermal Stability and Peroxidase Activity of Cytochrome c in Ionic Liquid Colloidal Formulation", Chem Commun. 52 (3): 497-500.

(Continued)

*Primary Examiner* — Sean M Basquill
(74) *Attorney, Agent, or Firm* — Leydig, Voit & Mayer, Ltd.

(57) ABSTRACT

The present invention discloses an ionic liquid composition comprising an at least partially hydrophobic ionic liquid, wherein the at least partially hydrophobic ionic liquid comprises a di cation comprising two monocationic groups linked by a bridging group wherein the bridging group provides an at least partially hydrophobic character. The composition may also include a hydrophilic ionic liquid. The hydrophobic ionic liquid may include a quaternary ammonium group which may be substituted or unsubstituted, saturated or unsaturated, linear, branched, cyclic or aromatic and the bridging group is a unsubstituted or substituted $C_3$-$C_{10}$ alkylene or $C_3$-$C_{10}$ alkoxy alkyl. Also disclosed is a nanoemulsion formulation which includes the ionic liquid compositions, at least one polymer, a hydrophobic liquid, an aqueous liquid, and a hydrophobic or hydrophilic therapeutic agent. Methods to deliver a therapeutic agent by delivering a nanoemulsion and methods to make a nanoemulsion are also disclosed.

16 Claims, 90 Drawing Sheets

(56) References Cited

OTHER PUBLICATIONS

Bhattacharyya et al. (2016) "Ether Functionalized Choline Tethered Amino Acid Ionic Liquids for Enhanced CO2 Capture" ACS Sustainable Chem. Eng. 4: 5441-5449.
Bingham et al. (2012) "Computational Study of Room-Temperature Ionic Liquids Interacting with a POPC Phospholipid Bilayer" J. Phys. Chem B 116(36): 11205-11216.
Blair, et al. (2015) "Albumin-Bound Paclitaxel: A Review in Non-Small Cell Lung Cancer" Drugs 75 (17): 2017-2024.
Bolard et al. (1991) "One-Sided Action of Amphotericin B on Cholesterol-Containing Membranes Is Determined by Its Self-Association in the Medium," Biochemistry 30(23): 5707-5715.
Brajtburg et al. (1990) "Amphotericin B: Delivery Systems", Antimicrob. Agents Chemother. 34(3): 381-384.
Browning et al. (2017) "Drug Delivery Strategies for Platinum-based Chemotherapy", ACS nano 11(9): 8560-8578.
Canongia Lopes et al. (2006) "Nanostructural Organization in Ionic Liquids" Phys. Chem. B 110: 3330-3335.
Centers for Disease Control and Prevention. "Invasive Candidiasis Statistics" https://www.cdc.gov/fungal/diseases/candidiasis/invasive/statistics.html.
Charlier et al. (2004) "Fatal Overdosage with Cisplatin" J Anal Toxicol. 28(2): 138-140.
Cybulska et al. (1985) "Effect of the Polar Head Structure of Polyene Macrolide Antifungal Antibiotics on the Mode of Permeabilization of Ergosterol- and Cholesterol-Containing Lipidic Vesicles Studied by 31P-NMR" Mol. Pharmacol. 29: 293-298.
Czerniak et al. (2017) "Synthesis and Antioxidant Properties of Dicationic Ionic Liquids", New J Chem. 41(2): 530-539.
Dai et al. (2017) "Ionic Liquids in Selective Oxidation: Catalysts and Solvents", Chem Rev. 117:6929-6983.
De Kruijiff et al. (1974) "Polyene Antibiotic-Sterol Interactions in Membranes of Acholeplasma-Laidlawii Cells and Lecithin Liposomes. 1. Specificity of Membrane-Permeability Changes Induced by Polyene Antibiotics" Biochim Biophys. Acta 339: 30-43.
Dobrucki et al. (2014) "Investigating the Optimal Size of Anticancer Nanomedicine" Proc. Natl. Acad. Sci. 111 (43): 15344-15349.
E Silva et al. (2014) "Sustainable Design for Environment-Friendly Mono and Dicationic Cholinium-Based Ionic Liquids", Ecotoxicol. Environ. Saf 108: 302-310.
Egorova et al. (publicly available Jan. 2017) "Biological Activity of Ionic Liquids and Their Application in Pharmaceutics and Medicine," Chem. Rev. (May 2017) 117(10): 7132-7189.
Einhorn, L. H. (2002) "Curing Metastatic Testicular Cancer" Proc. Natl. Acad. Sci. U. S. A. 99: 4592-4595.
Eriksson et al. (2002) "Comparison of Effects of Amphotericin B Deoxycholate Infused over 4 or 24 Hours: Randomised Controlled", Bmj 322(7286): 579-585.
Evaluate the Efficacy and Safety of Genexol®-PM Compared to Genexol® in Recurrent or Metastatic Breast Cancer. https://clinicaltrials.gov/ct2/show/NCT00876486 (accessed Jan. 30, 2016).
Fareghi-Alamdari et al. (2016) "Synthesis and Hypergolic Activity Evaluation of Some New Ammonium-lmidazolium Based Ionic Liquids," RSC Adv. 6(31): 26386-26391.
Florindo et al. (2014) "Cholinium-Based Ionic Liquids with Pharmaceutically Active Anions", RSC Adv. 4: 28126-28132.
Freire et al. (2007) "Mutual Solubilities of Water and Hydrophobic Ionic Liquids," J Phys. Chem. B III(45): 13082-13089.
Freire et al. (2010) "Hydrolysis of Tetrafluoroborate and Hexafluorophosphate Counter Ions in Imidazolium Based Ionic Liquids", J. Phys. Chem A 114(11): 3744-3749.
Gabbay (1966) "Topography of Nucleic Acid Helices in Solutions. I. The Nonidentity of Polyadenylic-Polyuridylic and Polyinosinic-Polycytidylic Acid Helices," Biochemistry 5(9): 3036-3043.
Goindi et al. (2014) "Development of a Novel Ionic Liquid-Based Microemulsion Formulation for Dermal Delivery of 5-Fluorouracil" AAPS PharmSciTech 15(4): 810-821.
Gong et al. (2012) "Polymeric micelles drug delivery system in oncology" Journal of Controlled Release 159 (3): 312-323.

Gothwal et al. (2016) "Polymeric Micelles: Recent Advancements in the Delivery of Anticancer Drugs" Pharmaceutical Research 33 (1): 18-39.
Goto, M. (2015) "Ionic Liquid-Mediated Transcutaneous Protein Delivery with Solid-in-Oil Nanodispersions." Med. Chem Commun. 6(12): 2124-2128.
Hiemenz, J. W. (2003) "Editorial Commentary: Amphotericin B Deoxycholate Administered by Continuous Infusion: Does the Dosage Make a Difference?" Clin. Infect. Dis. 36(8): 952-953.
Hill et al. (2005) "Zebrafish as a Model Vertebrate for Investigating Chemical Toxicity" Toxicol. Sci. 86(1): 6-19.
Hough et al. (2007) "The Third Evolution of Ionic Liquids: Active Pharmaceutical Ingredients" New J. Chem 31(8): 1429.
Hu et al. (2006) "Heterogeneity in a room-temperature ionic liquid: Persistent local environments and the red-edge effect" Proc. Natl. Acad. Sci. U. S. A. 103: 831-836.
Huang et al. (2002) "Ion Channel Behavior of Amphotericin B in Sterol-Free and Cholesterol- or Ergosterol-Containing Supported Phosphatidylcholine Bilayer Model Membranes Investigated by Electrochemistry and Spectroscopy" Biophys. J. 83(6): 3245-3255.
Imhof et al. (2003) "Continuous Infusion of Escalated Doses of Amphotericin B Deoxycholate: An Open-Label Observational Study", Clin. Infect. Dis. 36(8): 943-951.
Jameson et al. (2015) "Effect of Imidazolium Room-Temperature Ionic Liquids on Aggregation of Amphotericin B: A Circular Dichroism Study," RSC Adv. 5(98): 80325-80329.
Jhaveri et al. (2014) "Multifunctional polymeric micelles for delivery of drugs and siRNA" FPHAR 5: 1-26.
Jiang et al. (2007) "Phenomena and Mechanism for Separation and Recovery of Penicillin in Ionic Liquids Aqueous Solution" Ind. Eng. Chem Res. 46: 6303-6312.
Jing et al. (2016) "Interaction of Ionic Liquids with a Lipid Bilayer: A Biophysical Study of Ionic Liquid Cytotoxicity," J Phys. Chem. B 120(10): 2781-2789.
Juneidi et al. (2015) "Evaluation of Toxicity and Biodegradability for Cholinium-Based Deep Eutectic Solvents" RSC Adv. 5: 83636-83647.
Kabal'Nov et al. (1987) "Ostwald Ripening in Two-Component Disperse Phase Systems: Application to Emulsion Stability", Colloids and Surfaces 24: 19-32.
Kim et al. (2015) "Enhancement of Extraction Efficiency of Paclitaxel from Biomass Using Ionic Liquid-Methanol Co-Solvents under Acidic Conditions" Process Biochem 50(6): 989-996.
Kim et al. (2015) "Production of CNT-Taxol-Embedded PCL Microspheres Using an Ammonium-Based Room Temperature Ionic Liquid: As a Sustained Drug Delivery System" J. Colloid Interface Sci. 442: 147-153.
Kobayashi et al. (2014) "Improving Conventional Enhanced Permeability and Retention (EPR) Effects: What is the Appropriate Target?" Theranostics 4(1): 81-89.
Kuchlyan et al. (2016) "Ionic Liquids in Microemulsions: Formulation and Characterization" Curr. Opin. Colloid Interface Sci. 25: 27-38.
Langlet et al. (1994) "Theoretical Study of the Complexation of Amphotericin B with Sterols" Biochim Biophys. Acta 1191: 79-93.
Lau et al. (2010) "Hydrolysis of Cisplatin—a First-Principles Metadynamics Study" Phys. Chem. Chem. Phys. 12: 10348-10355.
Legrand et al. (1992) "Effects of Aggregation and Solvent on the Toxicity of Amphotericin B to Human Erythrocytes," Antimicrob. Agents Chemother 36(11): 2518-2522.
Lei et al. (2 017) "Introduction: Ionic Liquids," Chem. Rev. 2017, 117(10): 6633-6635.
Manic et al. (2012) "Solubility of Erythromycin in Ionic Liquids," J Chem. Thermodyn. 44(1): 102-106.
Marrucho et al. (2014) "Ionic Liquids in Pharmaceutical Applications," Annu. Rev. Chem. Biomol. Eng. 5(1): 527-546.
Matsumura, Y. (2008) "Poly (amino acid) micelle nanocarriers in preclinical and clinical studies" Adv. Drug Deliver. Rev. 60: 899-914.
McCrary et al. (2013) "Drug Specific, Tuning of an Ionic Liquid's Hydrophilic-Lipophilic Balance of to Improve Water Solubility of Poorly Soluble Active Pharmaceutical Ingredients," New J Chem. 37(11): 2196-2202.

(56) References Cited

OTHER PUBLICATIONS

Mehnert et al. (2002) "Supported Ionic Liquid Catalysis—A New Concept for Homogeneous Hydroformylation Catalysis" J. Am Chem Soc. 124: 12932-12933.
Miele et al. (2009) "Albumin-bound formulation of paclitaxel (Abraxane® ABI-007) in the treatment of breast cancer" Int. J. Nanomed. 4: 99-105.
Moniruzzaman et al. (2010) "Ionic Liquid in-Oil Microemulsion as a Potential Carrier of Sparingly Soluble Drug: Characterization and Cytotoxicity Evaluation," Int. J. Pharm 400(1-2): 243-250.
Moniruzzaman et al. (2010) "Ionic Liquid-Assisted Transdermal Delivery of Sparingly Soluble Drugs," Chem. Commun. 46(9): 1452-1454.
Moniruzzaman et al. (2011) "Ionic Liquids: Future Solvents and Reagents for Pharmaceuticals," J. Chem Eng of Japan 44(6): 370-381.
Muhammad et al. (2012) "Synthesis and Physical Properties of Choline Carboxylate Ionic Liquids" J. Chem Eng. Data 57(8): 2191-2196.
Noemi et al. (2009) "Amphotericin B: Side Effects and Toxicity" Rev. Iberoam Micol. 26(4): 223-227.
Palacios et al. (2011) "Synthesis-Enabled Functional Group Deletions Reveal Key Underpinnings of Amphotericin B Ion Channel and Antifungal Activities" PNAS, 108(17): 6733-6738.
Peleg et al. (2004) "Continuous and 4 h Infusion of Amphotericin B: A Comparative Study Involving High-Risk Haematology Patients", J Antimicrob. Chemother. 54(4): 803-808.
Peleteiro et al. (2016) "Furfural Production Using Ionic Liquids: A Review", Bioresour. Technol. 202: 181-191.
Pernak et al. (2012) "Synthesis and Properties of Ammonium Ionic Liquids with Cyclohexyl Substituent and Dissolution of Cellulose" RSC Adv. 2(22): 8429.
Petkovic et al. (2010) "Novel Biocompatible Cholinium-Based Ionic Liquids -Toxicity and Biodegradability," Green Chem. 12(4): 643-649.
Poole (2004) "Chromatographic and spectroscopic methods for the determination of solvent properties of room temperature ionic liquids," Journal of Chromatography A 1037(1-2): 49-82.
Poole et al. (2010) "Extraction of organic compounds with room temperature ionic liquids," Journal of Chromatography A 1217(16): 2268-2286.
Pretti et al. (2009) "Acute Toxicity of Ionic Liquids for Three Freshwater Organisms: *Pseudokirchneriella subcapitata*, *Daphnia magna* and *Danio rerio*" Ecotoxicol. Environ. Saf. 72: 1170-1176.
Rantamaki et al. (2017) "Impact of Surface-Active Guanidinium-, Tetramethylguanidinium-, and Cholinium-Based Ionic Liquids on Vibrio Fischeri Cells and Dipalmitoylphosphatidylcholine Liposomes," Sci. Rep. Apr. 7 46673: 1-12.
Raut et al. (2015) "A Morpholinium Ionic Liquid for Cellulose Dissolution," Carbohydr. Polym. 130: 18-25.
Rengstl et al. (2014) "Effect of Choline Carboxylate Ionic Liquids on Biological Membranes" Colloids Surfaces B Biointerfaces 123: 575-581.
Ruokonen et al. (2016) "Effect of Ionic Liquids on Zebrafish (*Danio rerio*) Viability, Behavior, and Histology; Correlation between Toxicity and Ionic Liquid Aggregation" Environ. Sci. Technol. 50: 7116-7125.
Sahbaz et al. (2017) "Ionic Liquid Forms of Weakly Acidic Drugs in Oral Lipid Formulations: Preparation, Characterization, in Vitro Digestion, and in Vivo Absorption Studies" Mol. Pharm 14(11): 3669-3683.
Santos et al. (2015) "Environmental Safety of Cholinium Based Ionic Liquids: Assessing Structure—Ecotoxicity Relationships" Green Chem 17(9): 4657-4668.
Schroeder et al. (1972) "Fluorometric Investigations of the Interaction of Polyene Antibiotics with Sterols" Biochemistry 11(16): 3105-3111.
Search Report and Written Opinion, dated Sep. 19, 2019, corresponding to International Application No. PCT/US2019/031773 (filed May 10, 2019), parent of the present application, 18 pp.
Singh et al. (2009) "Paclitaxel in cancer treatment: perspectives and prospects of its delivery challenges" Crit. Rev. Ther. Drug. 26: 333-372.
Smith et al. (2011) "Solubilities of Pharmaceutical Compounds in Ionic Liquids," J Chem. Eng. Data 56(5): 2039-2043.
Starzyk et al. (2014) "Self-Association of Amphotericin b: Spontaneous Formation of Molecular Structures Responsible for the Toxic Side Effects of the Antibiotic" J. Phys. Chem B 118(48): 13821-13832.
Takemoto et al. (2004) "Comparative Studies on the Efficacy of AmBisome and FUNGIZONE™ in a Mouse Model of Disseminated Aspergillosis" J. Antimicrob. Chemother. 53(2): 311-317.
Tang et al. (2014) "Investigating the Optimal Size of Anticancer Nanomedicine" Proc. Natl. Acad. Sci. 111: 15344-15349.
Torrado et al. (2008) "Amphotericin B Formulations and Drug Targeting" J. Pharm Sci. 97(7): 2405-2425.
Trimethyl-[3-(trimethylazaniumyl)propyl]azanium, (2005) PUBCHEM-CID: 25991. Available online at: https://pubchem.ncbi.nlm.nih.gov/compound/25991#section=Chemical-Vendors (modified Jun. 2019).
Ventura et al. (2017) "Ionic-Liquid-Mediated Extraction and Separation Processes for Bioactive Compounds: Past, Present, and Future Trends" So N. Chem Rev. 117:6984-7052.
Wakabayashi et al. (2018) "Ionic Liquid-Based Paclitaxel Preparation: A New Potential Formulation for Cancer Treatment" Mol. Pharm 15: 2484-2488.
Wang et al. (2018) "The Combined Use of a Continuous-Flow Microchannel Reactor and Ionic Liquid Cosolvent for Efficient Biocatalysis of Unpurified Recombinant Enzyme" J. Chem Technol. Biotechnol. 93: 2671-2680.
Wasserscheid et al. (2015) "Ionic Liquids in Catalysis" Catal. Lett. 145: 380-397.
Welton, T. (1999) "Room-Temperature Ionic Liquids. Solvents for Synthesis and Catalysis" Chem Rev. 99(8): 2071-2084.
Yamashita et al. (1995) "Micelle/Monomer Control over the Membrane-Disrupting Properties," J. Am. Chem. Soc. 117(23): 6249-6253.
Yerlikaya et al. (2013) "Effect of Bortezomib in Combination with Cisplatin and 5-Fluorouracil on 4T1 Breast Cancer Cells" Mol. Med. Rep. 8(1): 277-281.
Yoo et al. (2014) "Amphiphilic Interactions of Ionic Liquids with Lipid Biomembranes: A Molecular Simulation Study" Soft Matter 10(43): 8641-8651.
Yu et al. (1998) "In Vitro Dissociation of Antifungal Efficacy and Toxicity for Amphotericin B-Loaded Poly(Ethylene Oxide)-Block-Poly(β-Benzyl-L-Aspartate)" Micelles. J. Control. Release 56: 285-291.
Yu et al. (2002) "Mortality and Costs of Acute Renal Failure Associated with Amphotericin B Therapy" Clin. Infect. Dis. 32(5): 686-693.
Yu et al. (2016) "Application of albumin-based nanoparticles in the management of cancer" Journal of Materials Science—Materials in Medicine 27 (1): 1-10.
U.S. Appl. No. 11/946,174, filed Nov. 28, 2007.
U.S. Appl. No. 11/972,061, filed Jan. 10, 2008.
U.S. Appl. No. 15/306,714, filed Oct. 25, 2016.
U.S. Appl. No. 15/306,718, filed Oct. 25, 2016.
U.S. Appl. No. 16/494,719, filed Sep. 16, 2019.

* cited by examiner

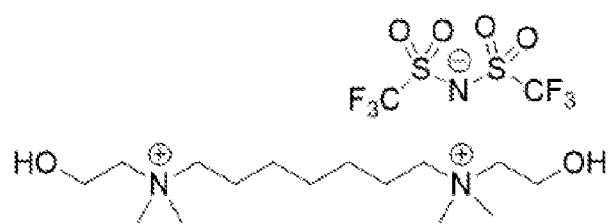
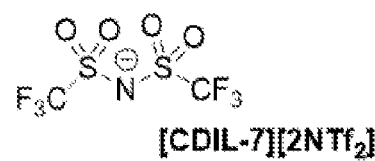
[CDIL-7][2NTf$_2$]
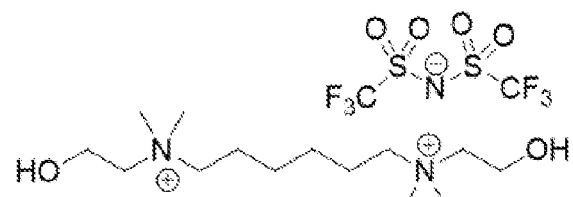
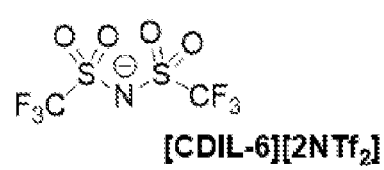
[CDIL-6][2NTf$_2$]
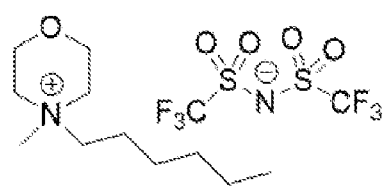
[Morph$_{1,6}$][NTf$_2$]
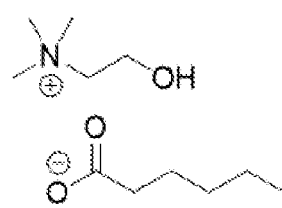
[Chol][Hex]
FIG. 3

- 10 mM M2DSG, 0.3 mL [CDIL-7][2NTf2], 0.2 mL [Chol][Hex], 1.5 mL MCT (ME-III-16)
- 10 mM M2DSG, 0.3 mL [CDIL-7][2NTf2], 0.2 mL [Chol][Hex], 1.5 mL MCT, 57 µg/mL AmB (ME-III-19)

- 1.2 mg/mL in 0.7mL [CDIL-7][2NTf$_2$] and 0.5mL [Chol][Hex]
- 1 mg/mL AmB in X-Gen
- 1 mg/mL AmB in DMSO
- 1 mg/mL AmB in 1mL [CDIL-6][2NTf$_2$] and 0.5mL [Chol][Hex]
- 1 mg/mL AmB in 1mL [Morph$_{1,6}$][NTf$_2$] and 0.5mL [Chol][Hex]

Most Common Cations and Anions in ILs

Cations
Imidazolium, Pyridinium, Pyrrolidinium, Piperidinium, Quinolinium, Quaternary ammonium, Quaternary phosphonium, Morpholinium, Cholinium

Anions
Tetrafluoroborate, Hexafluorophosphate, Methyl sulfate, Octyl sulfate, Acetate, Trifluoromethanesulfonate, Bis(trifluoromethylsulfonyl)imide, Halides

- Size of ions in ILs much larger than classical salts
  - Charge distributed over much larger volume → Delocalized in space
  - Charge density of ILs lower than classical salts
    - Reduces strength of electrostatic repulsion between similarly charged ions

FIG. 12

Challenges in drug delivery: Amphotericin B

- Highly potent polyene antifungal
  - Effective against *Aspergillus*, *Candida*, and *Cryptococcus* spp.
- Used to treat opportunistic infections
  - Affects persons with weakened immune systems
    - Undergoing chemotherapy, organ transplantation, HIV/AIDs, etc.
- Intravenous administration AmB serves as mainstay therapeutic for systemic and severe fungal infections
  - Severe adverse side-effects
  - Dose-limiting toxicity

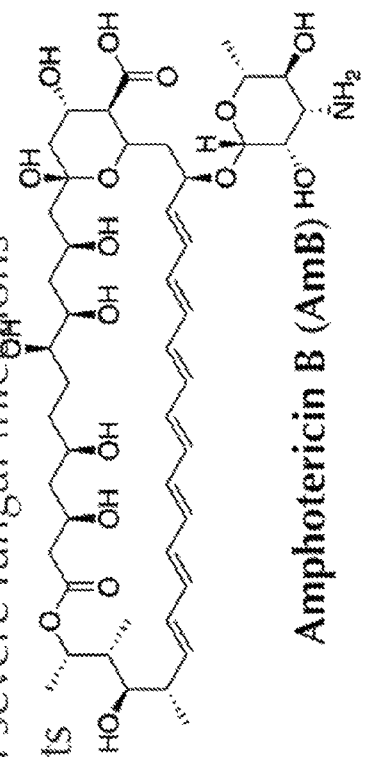

Amphotericin B (AmB)

FIG. 13

- AmB complexes associate and form transmembrane pores
  - Free diffusion (i.e. leakage) of components essential for cell life
- Aggregated form reduces selectivity towards ergosterol and leads to increased toxicity

Colloidal drug delivery vehicle: Nanoemulsion

- Immiscible components mixed and dispersed in continuous phase
- Non-equilibrium, thermodynamically unstable
- Meta-stable nanoparticles
  - Kinetically stabilized by polymer
  - Size varies
  - Typically larger than micelles
- FDA requires size < 500 nm
- Higher drug loading capacity

Cations
Cholinium 
Morpholinium 
Quaternary ammonium 
Anions
Bis(trifluoromethylsulfonyl)imide 
Acetate 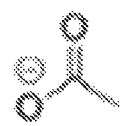
Octyl sulfate 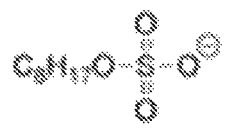
FIG. 19

Synthesis of Ionic Liquids
Cholinium based ILs
Synthesis of cholinium based ILs with carboxylate anions
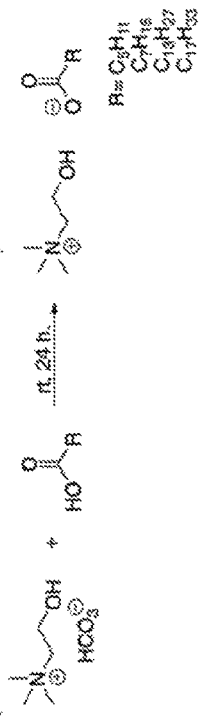
Synthesis of cholinium based ILs with bistrifluoromethylsulfonylimide anions
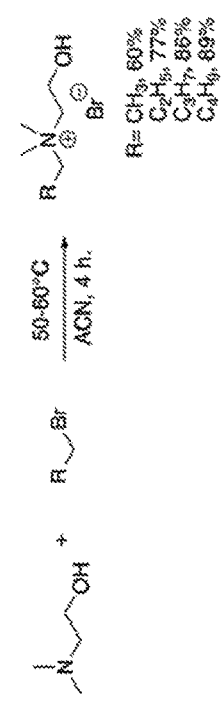
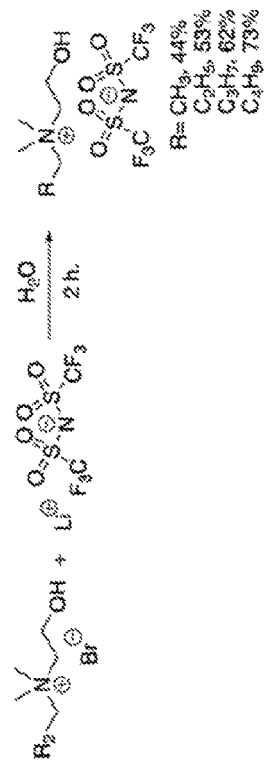
Bhattacharyya, S.; Shah, F. *ACS Sustainable Chem. Eng.* 2016, 4, 5441-5449.
FIG. 20

Solubilization of Drugs

Amphotericin B (AmB)

Itraconazole

Paclitaxel

| Ionic Liquid | Paclitaxel | Amphotericin B | Itraconazole |
|---|---|---|---|
| Water-soluble Cholinium based IL | 2 mg/mL | 6 mg/mL | 1 mg/mL |
| Dicholinium "A" | 25 mg/mL | 0.7 mg/mL | 1 mg/mL |
| Dicholinium "B" | 15 mg/mL | 0.5 mg/mL | Not tested |

FIG. 22

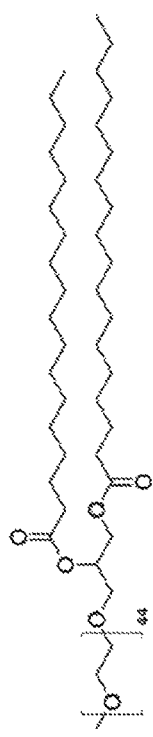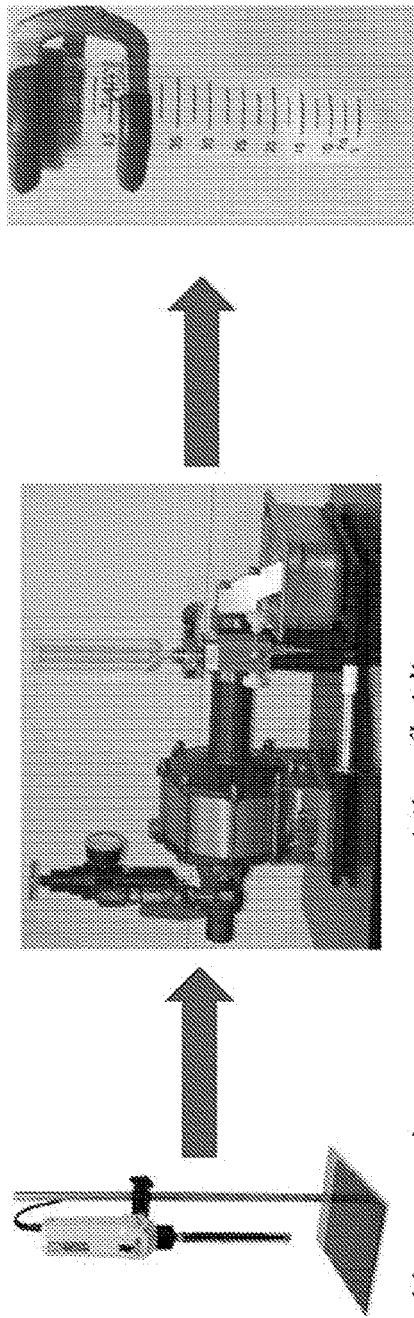
FIG. 25

• 10 mM M2DSG, 14 mL saline, 3 mL MCT, 1 mL [CDIL-7][2NTf$_2$],cisplatin

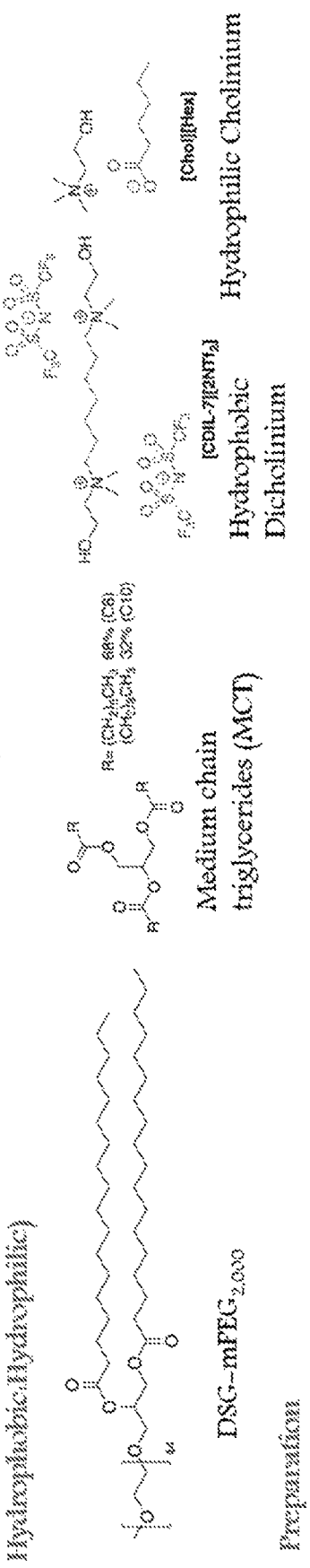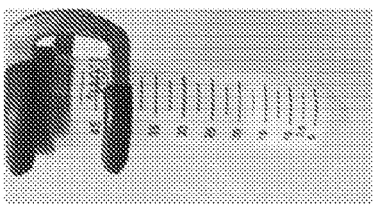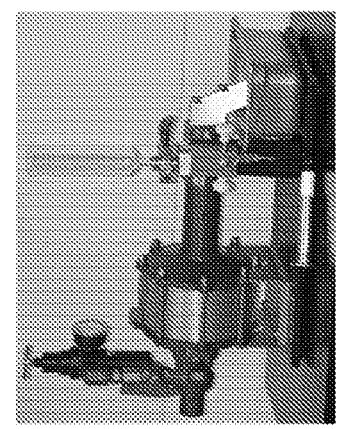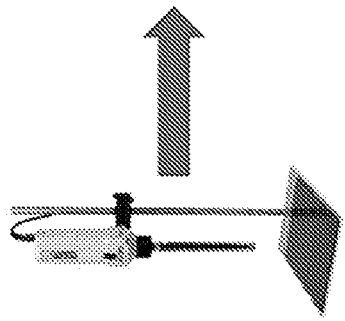
FIG. 33

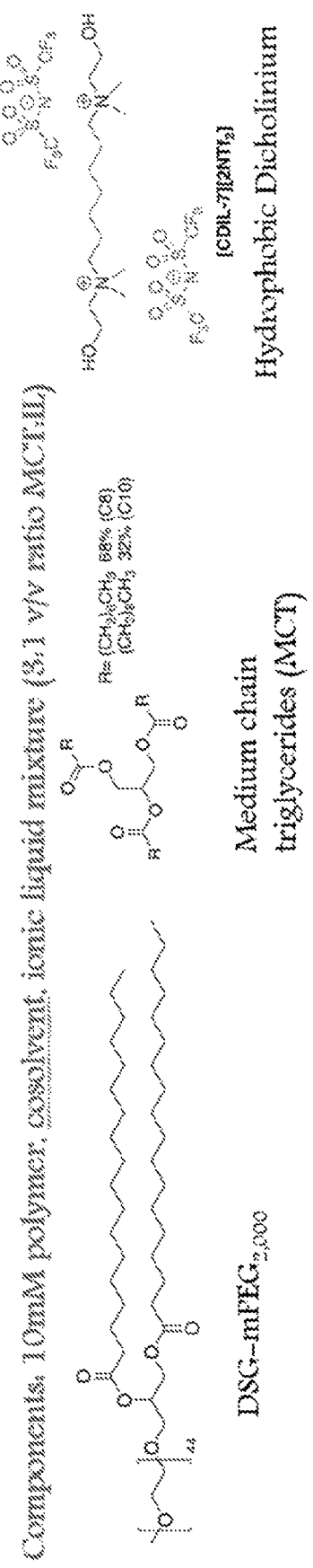
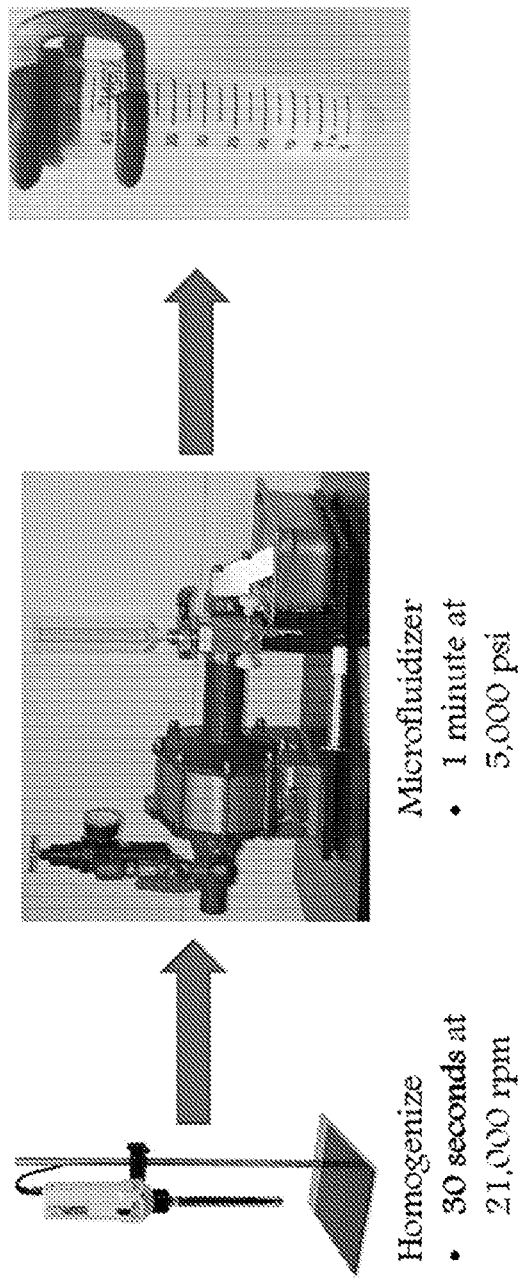
FIG. 34

- 15 mM M2DSG, 14 mL saline, 3 mL MCT, 1 mL IL mixture (1 : 0.67 v/v ratio [DC-ether][2NTf$_2$]:[Chol][Hex]) long term comparison
- 15 mM M2DSG, 14 mL saline, 3 mL MCT, 1 mL IL mixture (1 : 0.67 v/v ratio [DC-ether][2NTf$_2$]:[Chol][Hex]) *in vivo* study

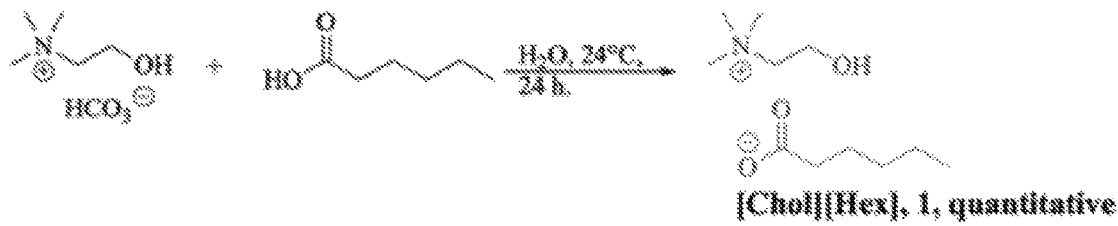
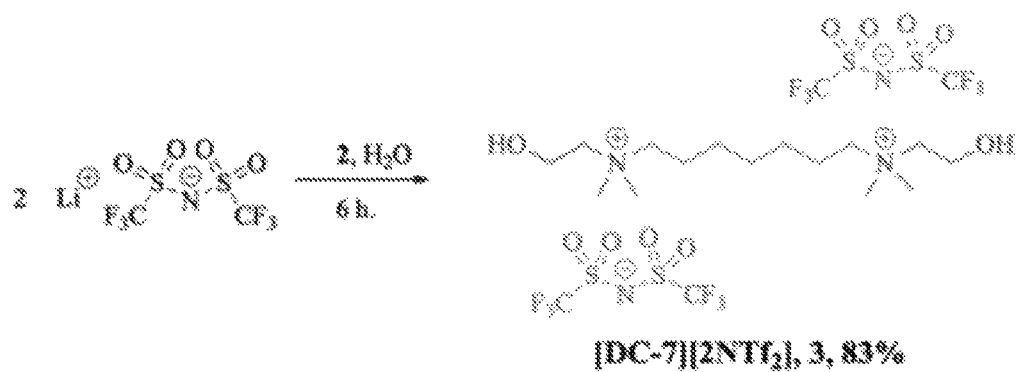
FIG. 46B

— 0.05 mg/mL AmB in DMSO

AmB nanoemulsion (10 mM M2DSG, 16 mL saline, 0.3 mL [DC-7][2NTf$_2$], 0.2 mL [Chol][Hex], 1.5 mL MCT), 57 µg/mL AmB, Day 42

— 0.01 mg/mL AmB in DMSO

• 2 mg/mL AmB in 1.5:1 v/v ratio [DC-7][2NTf$_2$]:[Chol][Hex]

- 10 mM M2DSG, 0.3 mL [DC-7][2NTf$_2$], 0.2 mL [Chol][Hex] 1.5 mL MCT, 57 μg/mL AmB
- Fungizone®

IONIC LIQUID-BASED NANOEMULSION FORMULATION FOR THE EFFICIENT DELIVERY OF HYDROPHILIC AND HYDROPHOBIC THERAPEUTIC AGENTS

CROSS-REFERENCE TO RELATED APPLICATIONS

This application is a U.S. National Stage Application under 35 U.S.C. § 371 of International Application No. PCT/US2019/031773, filed May 10, 2019, which claims the benefit of and priority to U.S. Provisional Patent Application Nos. 62/670,637 filed May 11, 2018, and 62/736,201 filed Sep. 25, 2018, each of which is hereby incorporated by reference in its entirety to the extent not inconsistent herein.

STATEMENT REGARDING FEDERALLY SPONSORED RESEARCH OR DEVELOPMENT

This invention was made with government support under EB021431 awarded by the National Institutes of Health. The government has certain rights in the invention.

BACKGROUND OF INVENTION

Ionic liquids (ILs) are a class of molecules composed of organic cations and anions whose melting point is below 100° C. ILs are customizable materials whose properties can be finely tuned through structural modifications within the cationic and anionic component. Because of the highly tunable nature of ILs, these compounds have been widely investigated for industrial applications as "task specific" designer solvent. More recently, the tunable nature and excellent solvation properties of ILs has created a burgeoning interest in the use of ILs as adjuvant components in drug delivery, namely as (1) cosolvents; (2) emulsifiers; and (3) solvents or antisolvents for design of crystalline substances. One study shows the effect of room temperature imidazolium based ionic liquids on the aggregation state of amphotericin B analyzed using circular dichroism. This study revealed that the nature of anion significantly affected the aggregation state of amphotericin B. Another study also demonstrated the ability to solubilize large amounts of amphotericin B in a specifically tuned IL. However, these findings could not be directly translated into increased therapeutic efficacy of amphotericin B as (1) both imidazolium based ILs and ammonium based ILs have been shown to exhibit toxicity; and (2) the inherent water solubility of both ILs (water solubility of imidazolium based ILs and the use of a water soluble acetate anion) increases the likelihood of concentration dependent aggregation of amphotericin B similar to FUNGIZONE™.

Amphotericin B (AmB) is a highly effective and potent polyene antifungal agent that is effective against a wide variety of fungi, including *Asperguillus, Candida*, and *Cryptococcus* spp. Intravenous administration of AmB serves as the mainstay therapeutic for systemic, severe fungal infections that are typically associated with high mortality. Amphotericin B has been cemented as the gold standard of antimycotics for decades, yet there are major limitations associated with the use of amphotericin B due to several adverse side-effects, including dose-dependent nephrotoxicity. These effects are primarily associated with the aggregation state of AmB in aqueous solution due to the hydrophobicity of AmB, which results in its aggregation in aqueous solution. This hydrophobicity is a result of the unique molecular structure of amphotericin B in which large hydrophilic and hydrophobic regions oppose one another. This self-aggregation results in a loss of binding specificity and consequential host toxicity.

The most widely used intravenous formulation of amphotericin B, termed FUNGIZONE™, is a mixture of amphotericin B, a detergent sodium deoxycholate (1:2 mole ratio), and a buffer. Despite the widespread use of FUNGIZONE™ the formulation suffers from concentration dependent aggregation and has severe adverse side-effects, most notably renal failure. One strategy that has been employed to improve the therapeutic index of amphotericin B is the use of carrier systems to modulate organ distribution and aggregation state.

It is also of interest to formulate hydrophilic drugs. For example, cisplatin is a highly potent, hydrophilic chemotherapeutic agent. Cisplatin (CP) is a chemotherapeutic in the platinum-based chemotherapy drug family, which accounts for approximately 50% of clinically used chemotherapeutics. Despite the widespread clinical use of this chemotherapeutic, the side-effects associated with this drug are significant and limit the maximum dose that can be administered. While toxic side-effects range from hearing loss to hemolysis, the most significant dose limiting side-effect includes nephrotoxicity. The use of nanoparticle-based delivery of cisplatin allows for the exploitation of passive targeting via the enhanced permeability and retention (EPR) effect for preferential delivery of drug to cancerous cells instead of healthy cells. The EPR effect refers to a passive targeting technique of fast growing cancerous tissue. This passive targeting takes advantage of the tumor vasculature abnormalities, specifically the aberrantly growing tumor vasculature that leaves the endothelial cells poorly aligned and with large fenestrations between them. This allows the penetration of appropriately sized nanoparticles into the tumor. Similarly, the growing tumor compresses the lymph vessels, which results in poor lymphatic drainage and accumulation of the nanoparticles. As such, the delivery of a water-soluble chemotherapeutic in a nanoemulsion based delivery vehicle would decrease the off-target side-effects associated with the drug. Some past attempts at mitigating cisplatin side effects typically have relied on chemical synthesis to add hydrophobic chains to cisplatin so as to make the molecule hydrophobic. However, the efficacy of the hydrophobic cisplatin is reduced as compared to that of the free water-soluble molecule. Various mechanisms for cleaving the hydrophobic chains only at the site of the tumor also did not provide great benefits. Other attempts of mitigating cisplatin side effects include liposomal formulation and micellar formulations. Neither of these strategies have provide formulations with suitable efficacy Thus, there remains a need in the art for formulations for hydrophobic drugs, for example, amphotericin B and for hydrophilic drugs, for example, cisplatin, as well as other hydrophobic and hydrophilic therapeutics.

SUMMARY OF THE INVENTION

In an aspect, the invention provides a non-toxic and hydrophobic ionic liquid that is miscible with a biocompatible cholinium-based (hydrophilic) ionic liquid. The abbreviation "CDIL" refers to cholinium-based dicationic ionic liquids and the abbreviation "DC" refers to dicholinium-based ionic liquids, wherein each of these abbreviations is used interchangeably through the present description. In embodiments, the inventive compositions comprising at least partially hydrophobic ionic liquids may be used to solubilize and deliver hydrophobic therapeutics to a patient.

In an embodiment, the invention provides an ionic liquid composition comprising an at least partially hydrophobic ionic liquid, wherein the at least partially hydrophobic ionic liquid comprises at least one dication comprising two monocationic groups linked by a bridging group, wherein the bridging group provides an at least partially hydrophobic character.

In an embodiment, each monocationic group is independently a quaternary ammonium group which may be substituted or unsubstituted, saturated or unsaturated, linear, branched, cyclic or aromatic; and the bridging group is a unsubstituted or substituted $C_3$-$C_{10}$ alkylene or $C_3$-$C_{10}$ alkoxyalkylene.

In an embodiment, the invention provides an ionic liquid composition comprising an at least partially hydrophobic ionic liquid, wherein the at least partially hydrophobic ionic liquid comprises at least one dication comprising two monocationic groups linked by a bridging group, wherein the bridging group provides an at least partially hydrophobic character, wherein the ionic liquid composition further comprises one or more components selected from a cosolvent (e.g., a hydrophobic liquid), a polymer (e.g. a surfactant), a hydrophobic compound (e.g., a hydrophobic therapeutic agent), a hydrophilic compound (e.g., a hydrophilic therapeutic agent), and combinations thereof.

In an embodiment, the ionic liquid composition comprises an at least partially hydrophobic ionic liquid comprising at least one dication, as described herein, a hydrophobic drug, and a hydrophobic liquid.

In an embodiment, the ionic liquid composition comprises an at least partially hydrophobic ionic liquid comprising at least one dication, as described herein, a hydrophobic drug, a hydrophobic liquid, and a polymer.

In an embodiment, the ionic liquid composition comprises an at least partially hydrophobic ionic liquid comprising at least one dication, as described herein, a hydrophilic drug, and a hydrophobic liquid.

In an embodiment, the ionic liquid composition comprises an at least partially hydrophobic ionic liquid comprising at least one dication, as described herein, a hydrophilic drug, a hydrophobic liquid, and a polymer.

In keeping with an aspect of the invention, the ionic liquid compositions further comprise one or more anions, as described herein.

In some embodiments, the ionic liquid composition comprises one or more dications characterized by Formula I:

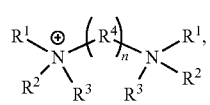
(Formula I)

wherein $R^1$-$R^4$ is as described herein.

In an embodiment, $R^1$, $R^2$, and $R^3$ are the same or different and are each independently substituted or unsubstituted $C_1$-$C_5$ alkyl, substituted or unsubstituted $C_1$-$C_5$ hydroxyalkyl; or any two of $R^1$, $R^2$ or $R^3$ may together form a substituted or unsubstituted $C_5$-$C_7$ cyclic group or heterocyclic group; wherein each $R^4$ is independently unsubstituted or substituted $C_3$-$C_8$ alkylene, $C_3$-$C_{10}$ alkoxyalkylene or —$R^5OR^5$—, wherein each $R^5$ is independently unsubstituted or substituted $C_1$-$C_3$ alkylene; and wherein n is 1, 2, 3, 4, 5, 6, 7 or 8. In some embodiments, the invention provides an ionic liquid composition comprising one or more dications characterized by Formula I, wherein n is 1 or 2 or 3, and optionally wherein n is 1 or 2 and optionally wherein n is 0.

In some embodiments, the bridging group $R^4$ is $C_3$-$C_{10}$ alkylene or $C_3$-$C_{10}$ alkoxyalkylene and n is 1, and optionally $C_4$-$C_8$ alkylene or $C_4$-$C_8$ alkoxyalkylene and n is 1.

In some embodiments, the quaternary ammonium group is cholinium or morpholinium.

In some embodiments, the ionic liquid composition comprises one or more dications characterized by Formula Ia:

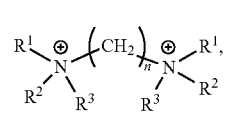
(Ia)

wherein $R^1$-$R^3$ is as described herein. In an embodiment, the ionic liquid composition is characterized by Formula Ia wherein n is 4, 5, 6, or 7

In some embodiments, the ionic liquid composition comprises one or more dications characterized by Formula Ib:

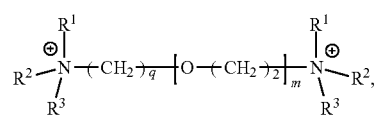
(Ib)

wherein $R^1$-$R^3$, q, and m are as described herein. In an embodiment, the ionic liquid composition is characterized by formula Ib wherein q is 1 or 2 and m is 1, 2 or 3. In keeping with certain embodiments of the invention, q is 1, 2 3, or 4 and m is 0, 1, 2 or 3.

In some embodiments of the invention, each of $R^1$-$R^3$ is independently H, $C_1$-$C_4$ alkyl or —$(CH_2)_mOR^6$, wherein each $R^6$ is independently —$CH_3$, $C_2H_5$, or H, and wherein m is 1, 2, 3 or 4. In some embodiments of the invention, at least one of $R^1$-$R^3$ is —$(CH_2)_mOR^6$. In some embodiments of the invention, m is 1, 2, or 3. In some embodiments of the invention, m is 1 or 2. In some embodiments of the invention, $R^6$ is —$CH_3$. In some embodiments of the invention, $R^6$ is —$C_2H_5$. In some embodiments of the invention, $R^6$ is H.

In some embodiments of the invention, each dication is characterized by formula 1, 2, 3, 4, or 5:

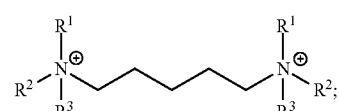
(1)

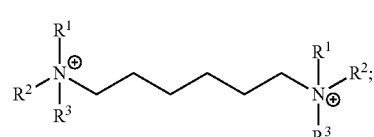
(2)

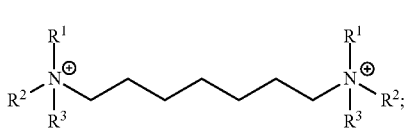
(3)

-continued

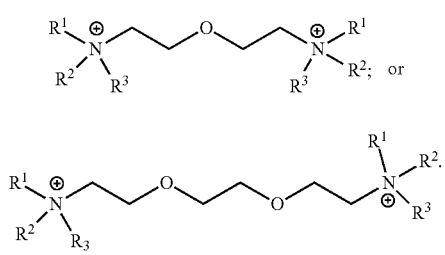

In some embodiments of the invention, the ionic liquid composition comprises one or more dications characterized by Formula 6, 7, 8, 9, 10, 1, 12, 13, 14 or 15:

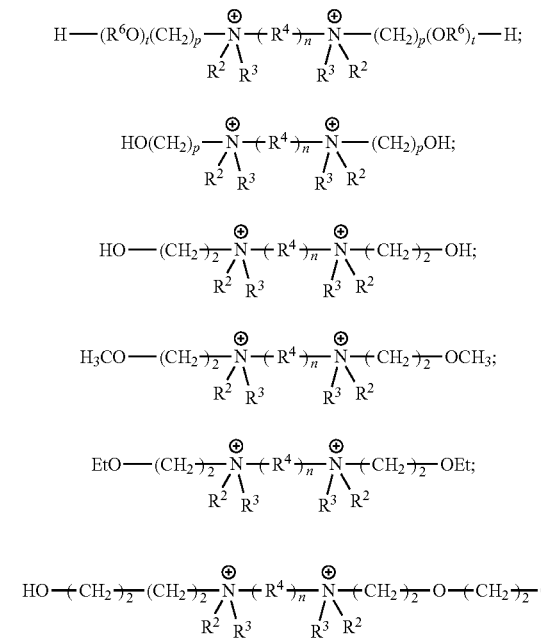

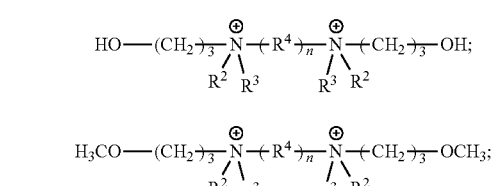

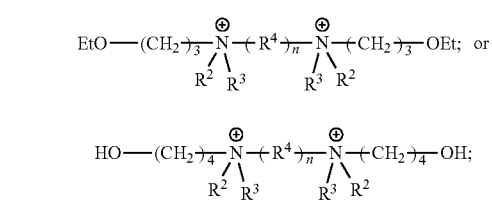

wherein each $R^6$ independently is $C_1$-$C_4$ alkylene or a bond, and each p and t independently is 1, 2, 3 or 4.

In some embodiments, the ionic liquid composition comprises one or more dications characterized by Formula 16, 17, 18, 19, 20, 21, 22, 23, 24, or 25:

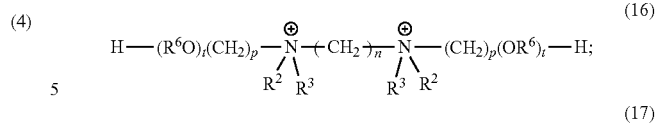

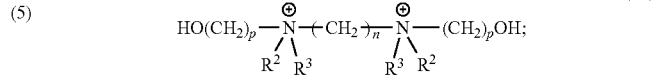

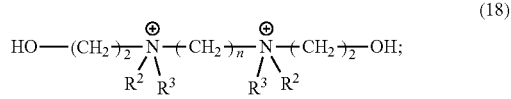

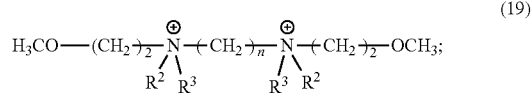

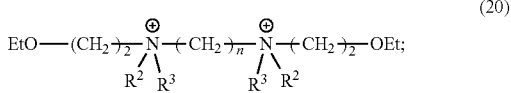

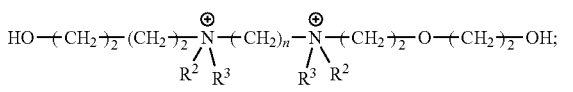

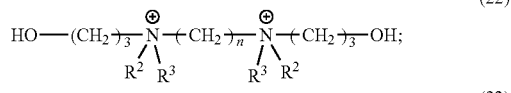

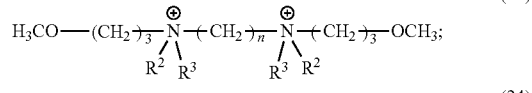

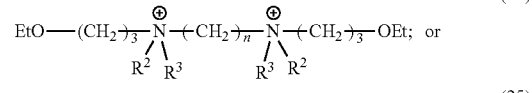

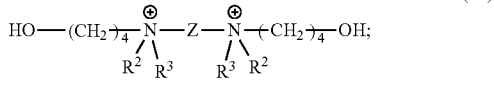

wherein Z has the formula:

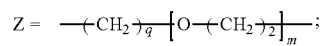

wherein each p, m and t independently is 1, 2, 3 or 4, wherein q is 0, 1, 2, or 3.

In some embodiments, the ionic liquid composition comprises one or more dications characterized by 26, 27, 28, 29, 30, 31, 32, 33, 34 or 35:

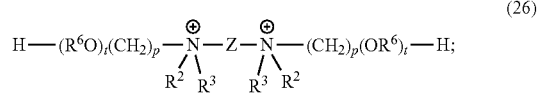

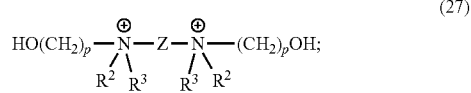

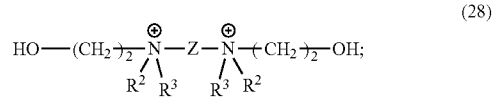

-continued

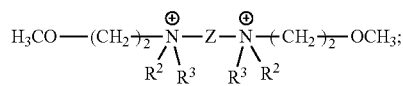 (29)

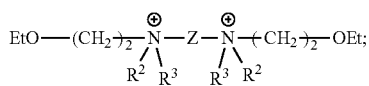 (30)

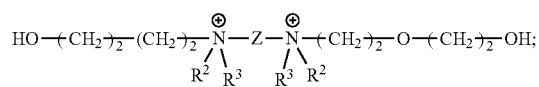 (31)

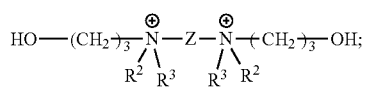 (32)

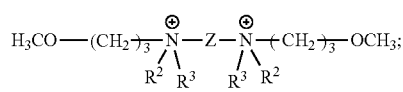 (33)

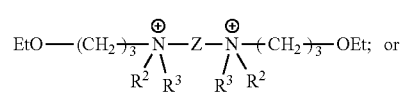 (34)

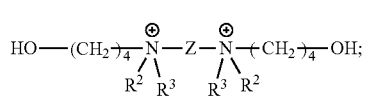 (35)

wherein Z has the formula:

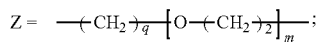

wherein each p, m and t independently is 1, 2, 3 or 4, wherein q is 0, 1, 2, or 3.

In some embodiments of the invention, each of $R^2$ and $R^3$ independently is substituted or unsubstituted $C_1$-$C_4$ alkyl. In some embodiments of the invention, each of $R^2$ and $R^3$ independently is —$CH_3$ or —$C_2H_5$. In some embodiments of the invention, the ionic liquid composition further comprises at least one anion.

In an embodiment of the invention, the anion has at least a partially hydrophobic character. In some embodiments of the invention, the anion is a substituted or unsubstituted acetate, alkyl sulfate, or bis(trifluoromethylsulfonyl)imide.

In some embodiments of the invention, the ionic liquid composition further comprises one or more anions characterized by Formula II:

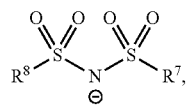 (II)

wherein each of $R^7$ and $R^8$ is independently a substituted or unsubstituted $C_1$-$C_{10}$ alkyl, substituted or unsubstituted $C_2$-$C_{10}$ hydroxyalkyl, or $C_1$-$C_{10}$haloalkyl. In some embodiments, the ionic liquid composition further comprises one or more anions characterized by Formula II wherein each of $R^7$ and $R^8$ is independently a substituted or unsubstituted $C_1$-$C_4$ alkyl, substituted or unsubstituted $C_2$-$C_4$ hydroxyalkyl, or $C_1$-$C_4$haloalkyl.

In an embodiment of the invention, at least one of $R^7$ and $R^8$, and optionally both of $R^7$ and $R^8$, is halomethyl, trifluoromethyl or is characterized by the formula:

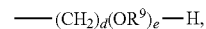

wherein each $R^9$ independently is $C_1$-$C_4$ alkylene or a bond, and each d and e independently is 1, 2, 3 or 4, and optionally each d and e independently is 1 or 2.

In an embodiment, the anion is characterized by formula 36:

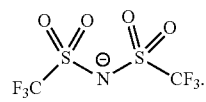 (36)

In some embodiments of the invention, the anion is characterized by formula 36, 37, 38, 39, 40, 41, 42, 43 or 44:

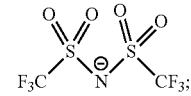 (36)

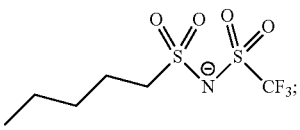 (37)

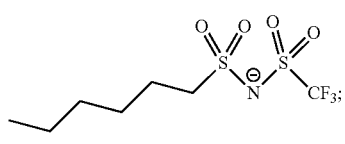 (38)

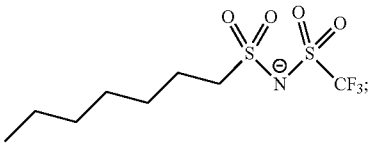 (39)

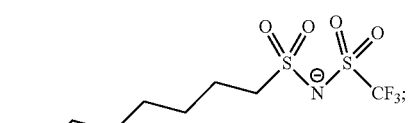 (40)

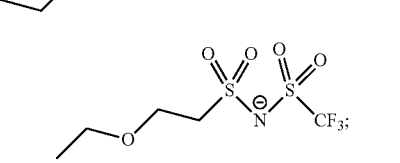 (41)

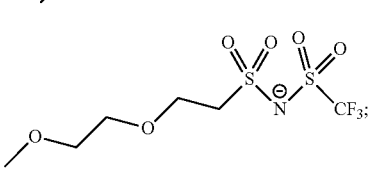 (42)

-continued
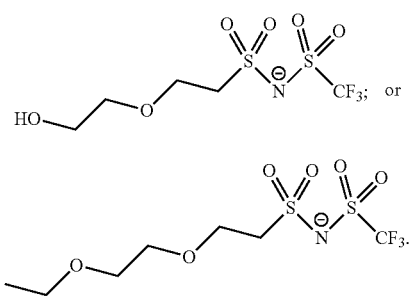
(43) or
(44)
In some embodiments of the invention, the anion is bis(trifluoromethylsulfonyl)imide characterized by the formula:
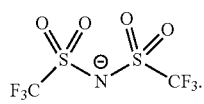
In some embodiments of the invention, the dication is characterized by formula 64, 65, 66, 67, 68, 69, 70, 71, 72 or 73:
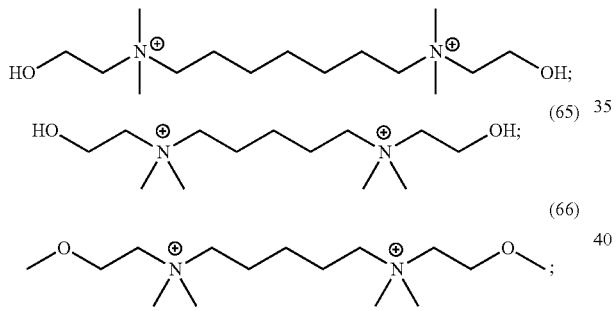
(64)
(65)
(66)
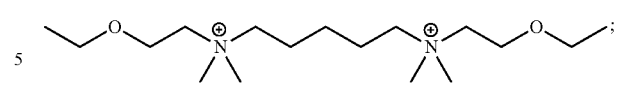
(67)
(68)
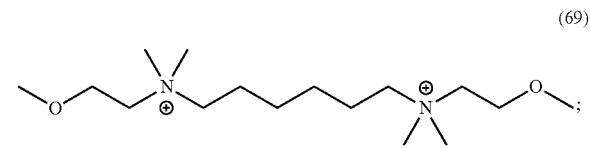
(69)
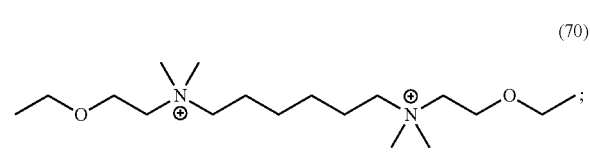
(70)
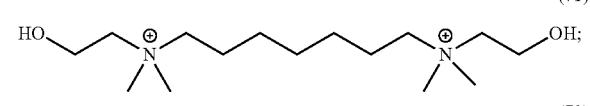
(71)
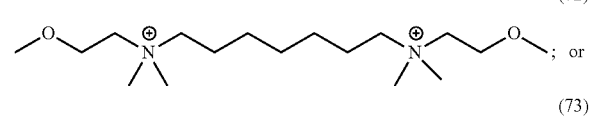
(72); or
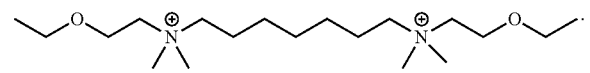
(73)
In some embodiments of the invention, the dication is characterized by a formula 74, 75, 76, 7, 78, 79, 80, 81, 82, 83, 84, 85, 86, 87 or 88:
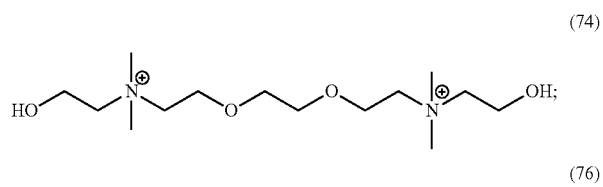
(74)
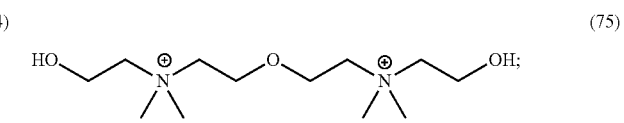
(75)
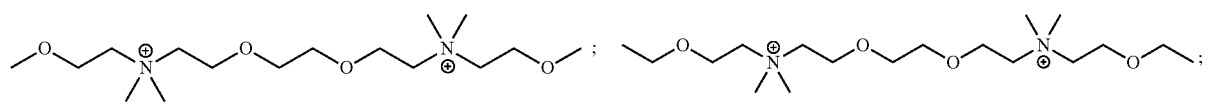
(76)
(77)
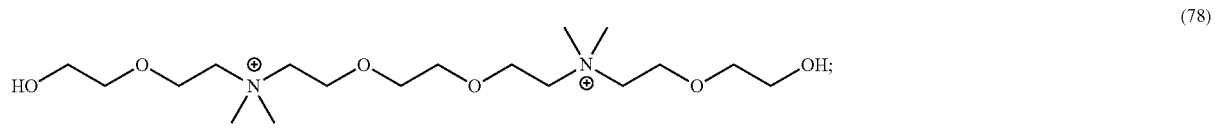
(78)
(79)
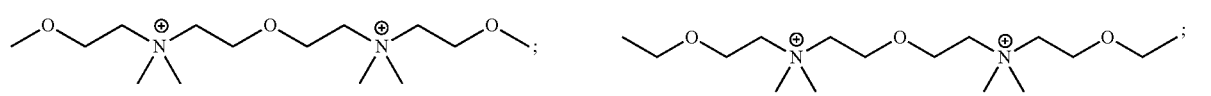
(80)

-continued

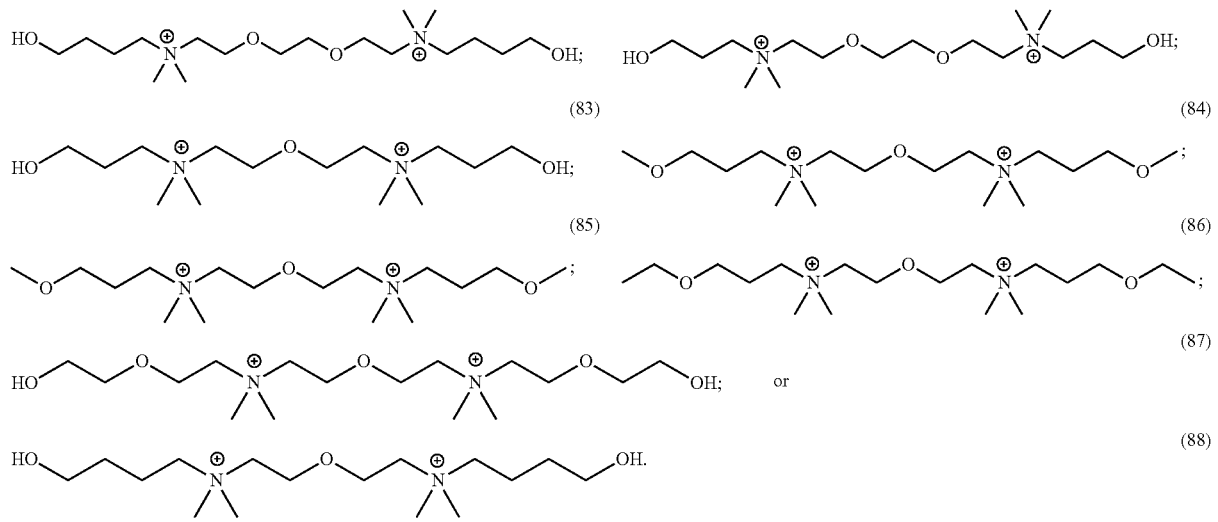

In some embodiments, the ionic liquid comprises dication and anions characterized by the formulas:

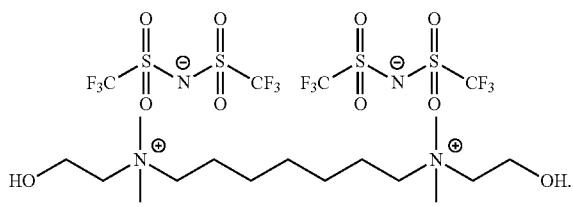

In some embodiments of the invention, the ionic liquid comprises dication and anions characterized by the formulas:

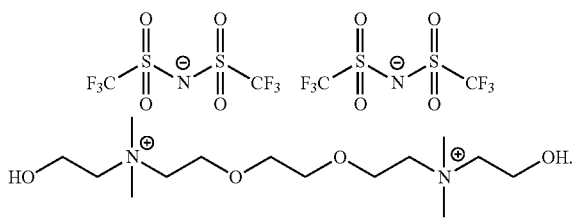

In some embodiments of the invention, the hydrophilic ionic liquid comprises choline and alkyl acetate. In some embodiments of the invention, the alkyl acetate is hexanoate.

In an embodiment of the invention, the ratio of the hydrophilic ionic liquid to the at least partially hydrophobic ionic liquid is between 1:1 to 1:10 (v/v). In an embodiment of the invention, the ratio of hydrophilic ionic liquid to the at least partially hydrophobic ionic liquid is 1:1.2 to 1:1.5 (v/v).

In some embodiments of the invention, the ionic liquid composition further comprises a therapeutic agent. In an embodiment, the therapeutic agent is a hydrophilic therapeutic agent or a hydrophobic therapeutic agent. In an embodiment, the therapeutic agent is an anticancer agent or antifungal agent. In an embodiment, the therapeutic agent is paclitaxel, doxorubicin, retinoic acid series, camptothecin, docetaxel, tamoxifen, anasterozole, itraconazole, topotecan, amphotericin B, belotecan, irinotecan, gleevec or vincristine, cisplatin or 5-fluorouracil (5-FU).

In another aspect, the invention provides nanoemulsions suitable for delivery of hydrophobic compounds and hydrophilic compounds. In some embodiments, the invention provides a nanoemulsion comprising an ionic liquid composition, as described herein. In keeping with aspects of the invention, the nanoemulsions provided herein can be suitable for delivery of hydrophobic compounds (e.g., hydrophobic therapeutic agent) and/or hydrophilic a hydrophilic compound (e.g., hydrophilic therapeutic agent).

In an embodiment, the invention provides a nanoemulsion comprising an ionic liquid composition comprising an at least partially hydrophobic ionic liquid, wherein the at least partially hydrophobic ionic liquid comprises at least one dication comprising two monocationic groups linked by a bridging group, wherein the bridging group provides an at least partially hydrophobic character, wherein the ionic liquid composition further comprises one or more components selected from a cosolvent (e.g., a hydrophobic liquid), a polymer (e.g. a surfactant), a hydrophobic compound (e.g., a hydrophobic therapeutic agent), a hydrophilic compound (e.g., a hydrophilic therapeutic agent), and combinations thereof, wherein the hydrophobic therapeutic agent or the hydrophilic agent is in the dispersed phase of the nanoemulsion.

In an embodiment, the hydrophobic liquid, ionic liquid and therapeutic agent are at least partially present in the dispersed phase and the aqueous solution is the continuous phase. In some embodiments, the hydrophobic liquid and ionic liquid are in the dispersed phase of the nanoemulsion but are at least partially separated from, such as exhibiting at least partial immiscibility.

In an embodiment, the invention provides a nanoemulsion comprising an ionic liquid composition comprising an at least partially hydrophobic ionic liquid comprising at least one dication, as described herein, a hydrophobic drug, and a hydrophobic liquid, wherein the hydrophobic drug is in the dispersed phase of the nanoemulsion.

In an embodiment, the invention provides a nanoemulsion comprising an ionic liquid composition comprising an at least partially hydrophobic ionic liquid comprising at least one dication, as described herein, a hydrophobic drug, a hydrophobic liquid, and a polymer, wherein the hydrophobic drug is in the dispersed phase of the nanoemulsion.

In an embodiment, the invention provides a nanoemulsion comprising an ionic liquid composition comprising an at least partially hydrophobic ionic liquid comprising at least one dication, as described herein, a hydrophilic drug, and a hydrophobic liquid, wherein the hydrophilic drug is in the dispersed phase of the nanoemulsion.

In an embodiment, the invention provides a nanoemulsion comprising an ionic liquid composition comprising an at least partially hydrophobic ionic liquid comprising at least one dication, as described herein, a hydrophilic drug, a hydrophobic liquid, and a polymer, wherein the hydrophilic drug is in the dispersed phase of the nanoemulsion.

In an embodiment, the invention provides a nanoemulsion for delivery of a therapeutic agent, said emulsion comprising an oil in water emulsion comprising a hydrophobic liquid; an aqueous solution; said therapeutic agent; an ionic liquid composition comprising an at least partially hydrophobic ionic liquid and a polymer; wherein said ionic liquid composition is capable of at least partially solubilizing the therapeutic agent.

In some embodiments, the invention provides a nanoemulsion for delivery of a therapeutic agent, said emulsion comprising an oil in water emulsion comprising a hydrophobic liquid; an aqueous solution; said therapeutic agent; an ionic liquid composition comprising a mixture of a hydrophilic ionic liquid and an at least partially hydrophobic ionic liquid, as described herein, and a polymer; wherein said ionic liquid composition is capable of at least partially solubilizing the therapeutic agent.

In some embodiments, the aqueous solution of the inventive nanoemulsion is a continuous phase of said nanoemulsion and said ionic liquid composition and hydrophobic liquid is a dispersed phase of said nanoemulsion.

In some embodiments, the ionic liquid has a solubility in water selected from the range of 1 µM and 15 mM. In some embodiments, ionic liquids are only sparingly miscible or not miscible, with MCT, although there is potentially for small MCT solubility in the ionic liquid and viceversa. The following references provide description of hydrophobic ionic liquids being fully or partially miscible with polar organic solvents: (i) Chromatographic and spectroscopic methods for the determination of solvent properties of room temperature ionic liquids; Colin F. Poole, Journal of Chromatography A, 1037 (2004) 49-82 and (ii) Extraction of organic compounds with room temperature ionic liquids, Colin F. Poole, Salwa K. Poole, Journal of Chromatography A, 1217 (2010) 2268-2286. Biphasic systems may formed with ionic liquids and organic solvents of low polarity (e.g. hexane, alkyl ethers).

In some embodiments, the therapeutic agent is a hydrophilic therapeutic agent or a hydrophobic therapeutic agent.

In some embodiments, the hydrophobic liquid and ionic liquid form two phases with aqueous solutions. In some embodiments of the invention, the hydrophobic liquid is one or more glycerides, such as MCT.

In some embodiments of the invention, the hydrophobic liquid is one or more medium-chain triglycerides characterized by 5 to 15 carbons per carbon chain and optionally 5 to 15 carbons per carbon chain, and optionally 8 to 10 carbons per carbon chain. In an embodiment, for example, the hydrophobic liquid is one or more medium-chain triglycerides grade used (Neobee M-5) contains a range of eight to ten carbon units per chain.

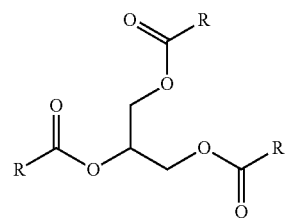

R = (CH$_2$)$_6$CH$_3$ 66% (C8)
(CH$_2$)$_8$CH$_3$ 32% (C10)

In an embodiment, the medium-chain triglycerides are characterized by a percentage of C8 and C10 chains that includes anything between 20% and 80% of each of the two kind of chains.

In some embodiments of the invention, the hydrophobic liquid is a cosolvent. In some embodiments, the hydrophobic liquid is a cosolvent in a dispersed phase of the nanoemulsion. In some embodiments, the hydrophobic liquid forms two phase with aqueous solution.

In some embodiments, the hydrophobic liquid is completely miscible with hydrophobic solvents such as diethyl ether or chloroform or ethyl acetate.

In some embodiments of the invention, the polymer comprises an amphiphilic polymer having a hydrophilic region and a hydrophobic region.

In an embodiment, the polymer comprises polyethylene glycol-polylactic acid (PEG-PLA) and polyethylene glycol-poly lactic acid-co-glycolic acid (PEG-PLGA) or any pegylated amphiphilic copolymer In some embodiments, the polymer comprises an ionic or neutral polyethylene glycol (PEG)-coupled lipid having a lipid moiety comprising a single chain or double chain $C_{10}$-$C_{24}$ alkyl and a polyethylene glycol moiety characterized by a molecular weight of 1,000 Da to 12,000 Da.

In some embodiments of the invention, the lipid portion comprises distearoyl.

In an embodiment of the invention, the polymer of the inventive nanoemulsion is selected from the group consisting of

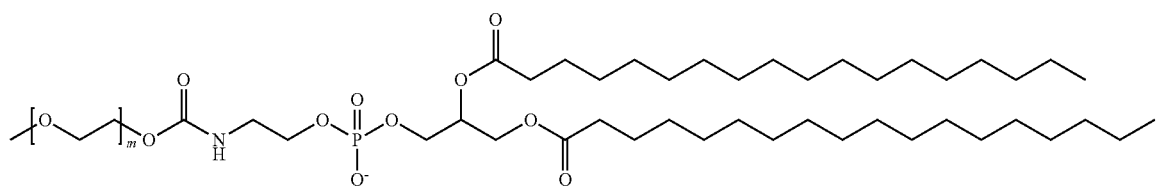

M2DSPE and

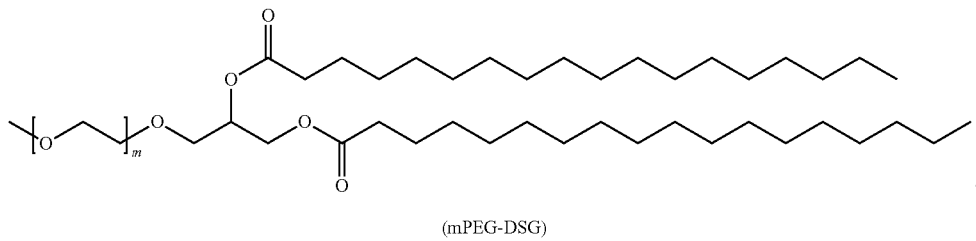

(mPEG-DSG)

In an embodiment, the polymer has a concentration of 1 mM to 50 mM, optionally 2 mM to 30 mM, optionally 10 mM to 20 mM.

In some embodiments, the ratio of hydrophobic liquid to ionic liquid composition of the inventive nanoemulsion is between 1:0.1 to 1:0.8 (v/v), and wherein the polymer has a concentration of 0.01 mM to 100 mM.

In some embodiments, the hydrophobic liquid:ionic liquid composition of the inventive nanoemulsion has a ratio of 1:0.2 to 1:0.6 (v/v), and wherein the polymer has a concentration of 1 mM to 50 mM, optionally 2 mM to 30 mM, and optionally 1 mM to 10 mM.

In some embodiments, the inventive nanoemulsion comprises a therapeutic agent that is a hydrophobic therapeutic agent and, optionally has a concentration selected from the range of 0.105 mg/mL to 50 mg/mL in the nanoemulsion, optionally selected from the range of 0.05 mg/mL to 3 mg/mL in the nanoemulsion, optionally selected from the range of 0.1 mg/mL to 2 mg/mL in the nanoemulsion. Useful concentrations of hydrophobic therapeutic agent in nanoemulsions for intravenous delivery include, for example, 0.05 mg/mL to 10 mg/mL.

In some embodiments, the inventive nanoemulsion comprises a therapeutic agent that is an anticancer agent or antifungal agent.

In some embodiments, the therapeutic agent is selected from the group consisting of paclitaxel, doxorubicin, retinoic acid series, camptothecin, docetaxel, tamoxifen, anasterozole, itraconazole, topotecan, amphotericin B, belotecan, irinotecan, gleevec and vincristine.

In some embodiments, the therapeutic agent in the nanoemulsion is amphotericin B and said amphotericin B has a concentration of between 0.05 mg/mL to 3 mg/mL relative to the hydrophobic liquid in said emulsion.

In some embodiments of the invention, the aqueous solution of the nanoemulsion comprises a saline solution.

In some embodiments of the invention, the emulsions contain individual oil droplet core particles having an average diameter less than or equal to 500 nanometers.

In an embodiment, the droplets have an average diameter less than or equal to 400 nanometers.

In some embodiments, the inventive nanoemulsion comprises a therapeutic agent that is amphotericin B and said nanoemulsion provides reduced toxicity effects upon administration to a mammalian subject as compared to an emulsion in the absence of the ionic liquid composition.

In some embodiments, the reduced toxicity effect is due to reduced aggregation of amphotericin B upon storage in said nanoemulsion and/or upon administration of said nanoemulsion to the mammalian subject.

In some embodiments of the invention, the nanoemulsion further comprises pharmaceutical excipients for administration to a subject via intravenous injection.

In some embodiments of the invention, the nanoemulsion further comprises a hydrophilic therapeutic agent and optionally has a concentration selected from the range of 0.05 mg/mL to 50 mg/mL in the nanoemulsion, optionally selected from the range of 0.05 mg/mL to 3 mg/mL in the nanoemulsion and optionally selected from the range of 0.1 mg/mL to 10 mg/mL in the nanoemulsion. Useful concentrations of hydrophilic therapeutic agent in nanoemulsions for intravenous delivery include, for example, 0.05 mg/mL to 10 mg/mL.

In some embodiments, the hydrophilic therapeutic agent is an anticancer agent or antifungal agent.

In an embodiment, the therapeutic agent is cisplatin or 5-fluorouracil (5-FU).

In an embodiment, the therapeutic agent is cisplatin and said cisplatin has a concentration of between 0.05 mg/mL to 3 mg/mL relative to the hydrophobic liquid in said emulsion.

In some embodiments comprising a hydrophilic therapeutic agent, the aqueous solution comprises a saline solution.

In some embodiments comprising a hydrophilic therapeutic agent, the emulsions contain individual oil droplet core particles having an average diameter less than or equal to 500 nm. In some embodiments comprising a hydrophilic therapeutic agent, the droplets have an average diameter less than or equal to 400 nm.

In some embodiments, the therapeutic agent is cisplatin and said nanoemulsion provides reduced toxicity effects upon administration to a mammalian subject as compared to an emulsion in the absence of the ionic liquid composition.

In some embodiments comprising a hydrophilic therapeutic agent, the emulsion further comprises pharmaceutical excipients for administration to a subject via intravenous injection.

In yet another aspect, the invention provides a method of delivering a therapeutic agent. In an embodiment, the invention provides a method of delivering a therapeutic agent to a mammalian subject in need thereof, said method comprising the steps of (a) providing an inventive nanoemulsion and (b) administering an effective amount of said emulsion to said subject. In embodiments of the invention, the therapeutic agent is released from said emulsion after delivery to the subject. In embodiments of the invention, the therapeutic agent is released and provides a therapeutic effect to the subject.

In embodiments of the invention, the method exhibits reduced toxicity effects of the therapeutic agent in the mammalian subject as compared administration of the therapeutic agent in the absence of a nanoemulsion comprising the ionic liquid composition.

In some embodiments, the invention provides a method of making a nanoemulsion comprising a hydrophilic therapeutic agent, said method comprising the steps of: (a) providing a composition comprising (i) a hydrophobic liquid; (ii) an aqueous solution; (iii) an ionic liquid composition comprising an at least partially hydrophobic ionic liquid as described herein; (iv) a hydrophilic therapeutic agent; and (iv) a polymer; and (b) emulsifying said composition to create the emulsion.

In some embodiments, the invention provides a method of making a nanoemulsion comprising a hydrophobic therapeutic agent, said method comprising the steps of: (a) providing a composition comprising (i) a hydrophobic liquid; (ii) an aqueous solution; (iii) an ionic liquid composition comprising a mixture of a hydrophilic ionic liquid and an at least partially hydrophobic ionic liquid as described herein; (iv) a hydrophobic therapeutic agent; and (iv) a polymer; and (b) emulsifying said composition to create the emulsion.

In some embodiments, the hydrophobic liquid is present at a percentage volume higher than a percentage volume of said ionic liquid. In some embodiments, the hydrophobic liquid is present at a percentage volume at least 2 times higher than a percentage volume of said ionic liquid. In some embodiments, the hydrophobic liquid is present at a percentage volume at least 3 times higher than a percentage volume of said ionic liquid. In some embodiments, the invention provides a nanoemulsion for delivery of a therapeutic agent, said emulsion comprising an oil in water emulsion comprising a hydrophobic liquid comprising one or more medium-chain triglycerides, an aqueous solution comprising a saline solution, an amphiphilic polymer, the therapeutic agent comprising amphotericin B, and an ionic liquid composition comprising at least one dication characterized by the formula:

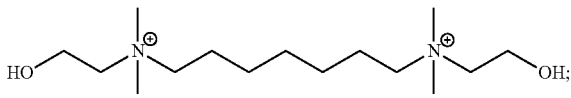 [SMILES: C[N+](C)(CCO)CCCCCCC[N+](C)(C)CCO]

wherein said ionic liquid composition is capable of at least partially solubilizing the therapeutic agent.

In some embodiments, the invention provides a nanoemulsion for delivery of a therapeutic agent, said emulsion comprising an oil in water emulsion comprising a hydrophobic liquid comprising one or more medium-chain triglycerides, an aqueous solution comprising a saline solution, an amphiphilic polymer, the therapeutic agent comprising cisplatin, and an ionic liquid composition comprising at least one dication characterized by the formula:

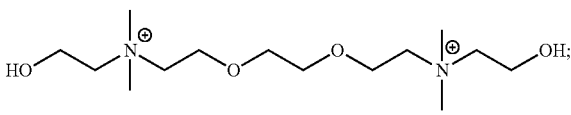 [SMILES: C[N+](C)(CCO)CCOCCOCC[N+](C)(C)CCO]

wherein said ionic liquid composition is capable of at least partially solubilizing the therapeutic agent.

In some embodiments, ionic liquid composition further comprises bis(trifluoromethylsulfonly)imide. In some embodiments, the amphiphilic polymer is ionic or neutral polyethylene glycol (PEG)-coupled lipid having a lipid moiety comprising a single chain or double chain $C_{10}$-$C_{24}$ alkyl and a polyethylene glycol moiety characterized by a molecular weight of 1,000 Da to 12,000 Da. In some embodiments, the ionic liquid composition further comprises a hydrophilic ionic liquid.

In some embodiments, the hydrophilic ionic liquid comprises choline and alkyl acetate.

In another aspect, the invention provides a method of delivering a therapeutic agent comprising administering the inventive nanoemulsions. In one embodiment, a composition comprising an ionic liquid mixture is described that provides high solubilization of AmB for use in a novel oil-in-water nanoemulsion based delivery system of AmB.

In an aspect, the present invention provides an ionic liquid composition comprising an at least partially hydrophobic ionic liquid, wherein the at least partially hydrophobic ionic liquid comprises a dication comprising two monocationic groups linked by a bridging group wherein the bridging group provides an at least partially hydrophobic character. The composition may also comprise a hydrophilic ionic liquid. The hydrophobic ionic liquid may include a quaternary ammonium group which may be substituted or unsubstituted, saturated or unsaturated, linear, branched, cyclic or aromatic and the bridging group is a unsubstituted or substituted $C_3$-$C_{10}$ alkylene or $C_3$-$C_{10}$ alkoxyalkyl.

The invention also provides a nanoemulsion formulation which includes the ionic liquid compositions, at least one polymer, a hydrophobic liquid, an aqueous liquid, and a hydrophobic or hydrophilic therapeutic agent.

For example, in an aspect the present invention provides a nanoemulsion for delivery of a hydrophobic therapeutic agent, said emulsion comprising an oil in water emulsion comprising: a hydrophobic liquid; an aqueous solution; an ionic liquid composition comprising a mixture of a hydrophilic ionic liquid and an at least partially hydrophobic ionic liquid; and a polymer; wherein said ionic liquid composition is capable of at least partially solubilizing the therapeutic agent. The nanoemulsion may further include a hydrophobic therapeutic agent.

For example, the present invention includes a nanoemulsion for delivery of a hydrophilic therapeutic agent, said emulsion comprising an oil in water emulsion comprising: a hydrophobic liquid; an aqueous solution; an ionic liquid composition comprising an at least partially hydrophobic ionic liquid; and a polymer; wherein said ionic liquid composition is capable of at least partially solubilizing the therapeutic agent. The nanoemulsion may further include a hydrophilic therapeutic agent.

In an embodiment, the present invention also provides a method of delivering a therapeutic agent to a subject in need thereof which includes providing a nanoemulsion of the present invention and administering an effective amount of the nanoemulsion to the subject.

In an embodiment, the invention also provides a method to make a nanoemulsion according to the present invention are also disclosed.

BRIEF DESCRIPTION OF THE DRAWINGS

FIG. 3. Structures of ILs studied for solubilization of AmB.

FIG. 12. Cations and anions in ILs.

FIG. 13. An overview of the challenges in delivering AmB.

FIG. 19 provides an overview of cations and anions in ionic liquids preferred for some applications.

FIG. 20 provides a sample synthesis of cholinium based IL component.

FIG. 22 provides an overview of paclitaxel, AmB, and itraconazole in ionic liquids of the present invention.

FIG. 25 shows nanoemulsion formulation with polymer and medium chain trigylcerides (MCT).

FIG. 33 shows the process for production of a composition for solubilizing and delivering a hydrophobic therapeutic in accordance with an embodiment of the invention.

FIG. 34 shows the process for production of a composition for solubilizing and delivering a hydrophilic therapeutic in accordance with an embodiment of the invention.

DETAILED DESCRIPTION OF THE INVENTION

Figure 1A:
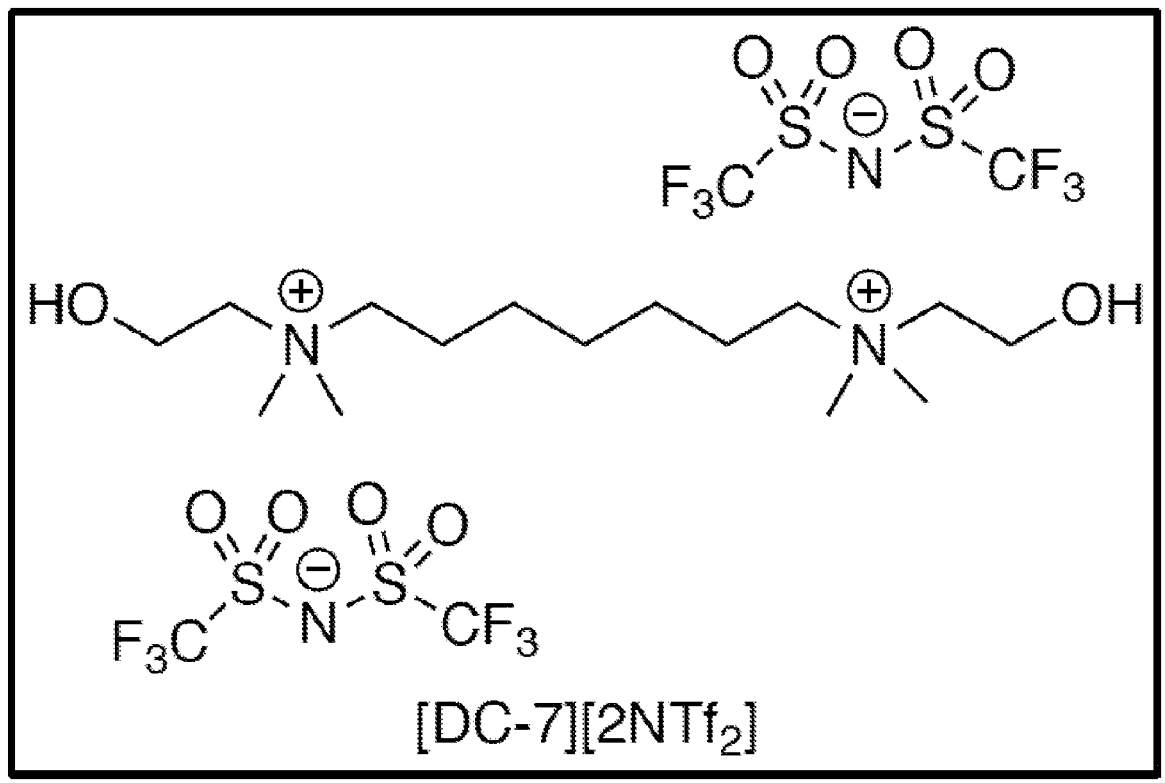
FIG. 1A. Structure of dicationic cholinium based ionic liquid [DC-7][2NTf$_2$]. The description "DC" or "CDIL" is used herein interchangeably.

"Emulsion" generally refers to a mixture of two or more immiscible substances, such as a mixture of two at least partially, optionally completely, immiscible liquids. Emulsions are a type of colloid that comprise at least one dispersed phase dispersed in a continuous phase. Emulsions are broadly defined as two immiscible phases in which a first phase is dispersed within a second continuous phase, such as a two-phase system in which one liquid is dispersed throughout a second liquid in the form of small droplets. This energy can either be supplied by mechanical equipment or the chemical potential inherent within the components. The two phases of an emulsion are generally referred to as the continuous phase and the dispersed phase, with the dispersed phase typically present as a smaller volume percentage. A dispersion of oil in water is referred to as an oil-in-water (o/w) emulsion. For o/w emulsions the emulsifying agent is typically more soluble in the aqueous phase. The reverse emulsion, water-in-oil, is abbreviated w/o and is stabilized by surfactants that are more stable in the oil phase. In an aqueous emulsion, the continuous phase is an aqueous solution.

Emulsions are not thermodynamically stable, but the stability can be improved by additives such as surfactants. As non-equilibrium systems, the formation of nanoemulsions generally requires an input of energy. High-energy emulsification methods commonly involve the introduction of mechanical shear through such equipment as high-shear stirrers, high-pressure homogenizers, microfluidizers or ultrasound generators. A microfluidizer is the piece of equipment used in the pharmaceutical industry for the production of emulsions that works by dividing a stream of liquid into two parts, passing each through a narrow opening and then colliding the streams under high pressure. The high shear forces created by the collision provide very fine emulsions with generally narrow particle size distributions. In typical usage, a coarse emulsion (diameter>1 µm) is first formed by some other method, and the size of that larger emulsion is reduced in the microfluidizer. The final droplet size and distribution shape will be dependent upon both the emulsion components (surfactant amount, oil volume percent, etc.) and the processing parameters (time, temperature, pressure etc.). As the desired droplet size decreases, the energy required for formation increases. Ultrasonic emulsification is also effective to reduce the size of emulsion droplets into the nanoscale. Emulsions can also be formed by changing the temperature of a mixture of immiscible liquids, for example by rapid cooling or heating to produce kinetically stable emulsions with small droplet sizes and narrow size distributions.

Emulsions include nanoemulsions comprising nanoscale droplets of one immiscible liquid dispersed within another. As used herein a nanoemulsion is a heterogeneous system composed of one immiscible liquid dispersed as droplets within another liquid, where the average droplet diameter is equal to or below 1000 nm.

As used herein "hydrophilic" refers to molecules, ions and/or components (e.g., functional groups, blocks of block polymers, etc.) of molecules or ions having at least one hydrophilic group, and "hydrophobic" refers to molecules and/or components (e.g., functional groups of polymers, and blocks of block copolymers etc.) of molecules having at least one hydrophobic group. Hydrophilic molecules, ions or components thereof tend to have ionic and/or polar groups, and hydrophobic molecules, ions or components thereof tend to have nonionic and/or nonpolar groups. Hydrophilic molecules, ions or components thereof tend to participate in stabilizing interactions with an aqueous solution, including hydrogen bonding and dipole-dipole interactions. Hydrophobic molecules, ions or components tend not to participate in stabilizing interactions with an aqueous solution and, thus often cluster or otherwise aggregate together in an aqueous solution to achieve a more stable thermodynamic state.

In the context of the present invention the term patient is intended to include a subject such as an animal. Patient or subject includes a mammal, for example human subject. Patient or subject includes a subject undergoing a medical procedure, such as undergoing the administration of a therapeutic or diagnostic agent.

A high percentage of pharmaceutical agents on the market and in the pipeline exhibit significant hydrophobic character, requiring careful formulation to translate therapeutic effect into the clinic. To overcome this problem, the inventors have rationally designed an ionic liquid-in-water nanoemulsion drug delivery system that harnesses the unique properties of ionic liquids. Ionic liquids are salts comprising organic cations and anions whose melting point is below 100° C.; some of which are remarkably liquid at room temperature. These unique molecules have exceptional physicochemical properties, namely negligible vapor pressure and excellent solvation capabilities. Moreover, nanoemulsions are attractive drug delivery vehicles in that the nanoparticle can lessen side effects, target specific tissues or pathologies, and the nanoparticle core can solubilize high concentrations of drugs. The present invention concerns rationally designed and synthesized novel hydrophobic dicationic ionic liquids as a component in a nanoemulsion system for use in systemic delivery of pharmaceutical agents. To demonstrate the versatility of the system, several pharmaceutical agents were selected for emulsification: the poorly water-soluble polyene antifungal agent Amphotericin B, the hydrophobic chemotherapeutic paclitaxel, and the water-soluble chemotherapeutic cisplatin and 5-fluorouracil.

Figure 11:
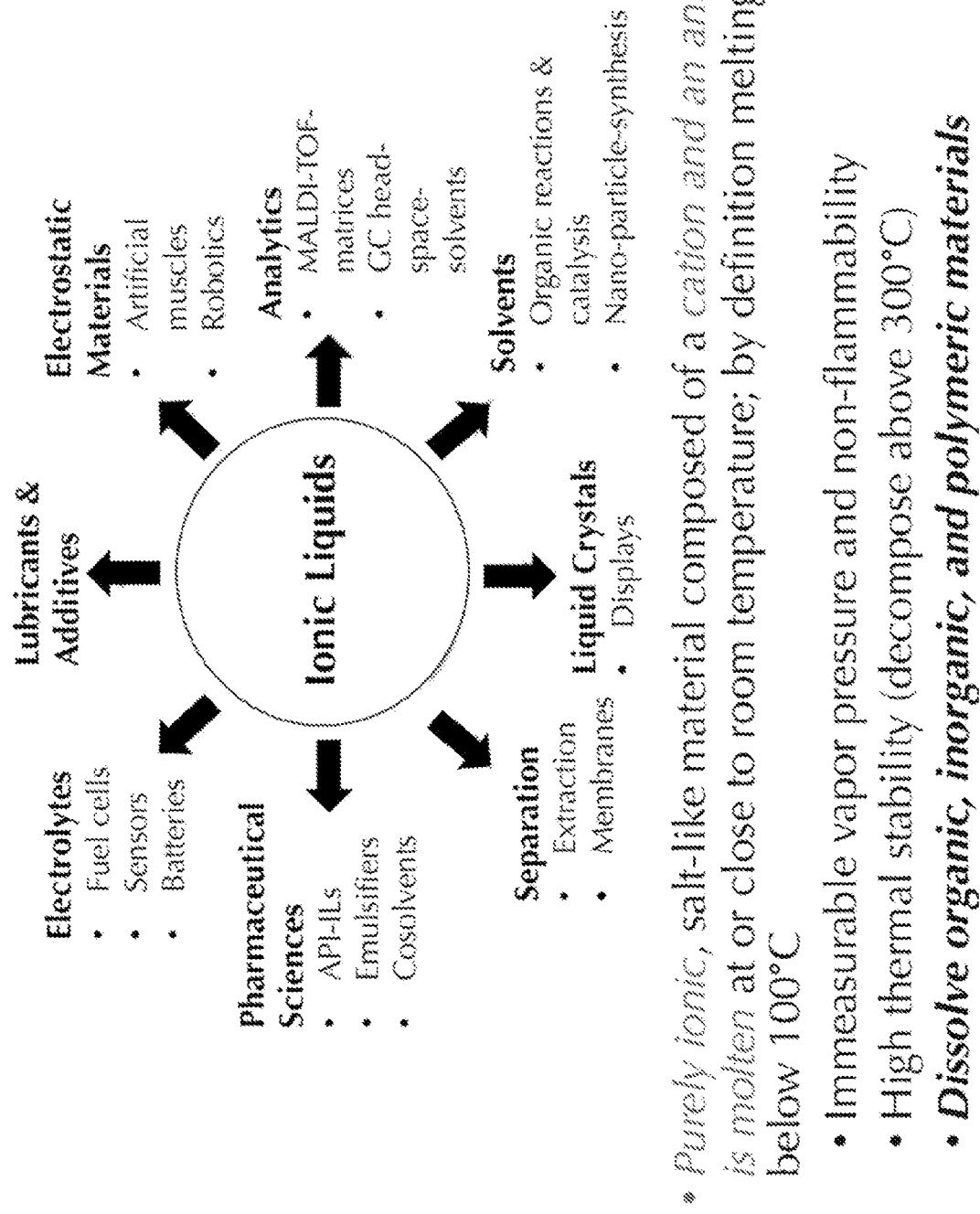
FIG. 11. An overview of ILs.

FIG. 11 provides an overview of ionic liquids (ILs). As shown in FIG. 11, ionic liquids are a versatile class of materials with potential to support a wide variety of applications including as formulation and delivery agents for pharmaceutical sciences. An ionic liquid is typically understood to include purely ionic, salt-like materials composed of a cation and an anion that is molten at or close to room temperature; by definition melting point below 100° C. These materials often characterized by an immeasurable vapor pressure and non-flammability, and high thermal stability (decompose above 300° C.). Ionic liquids may be used to dissolve organic, inorganic, and polymeric materials.

Figure 16:
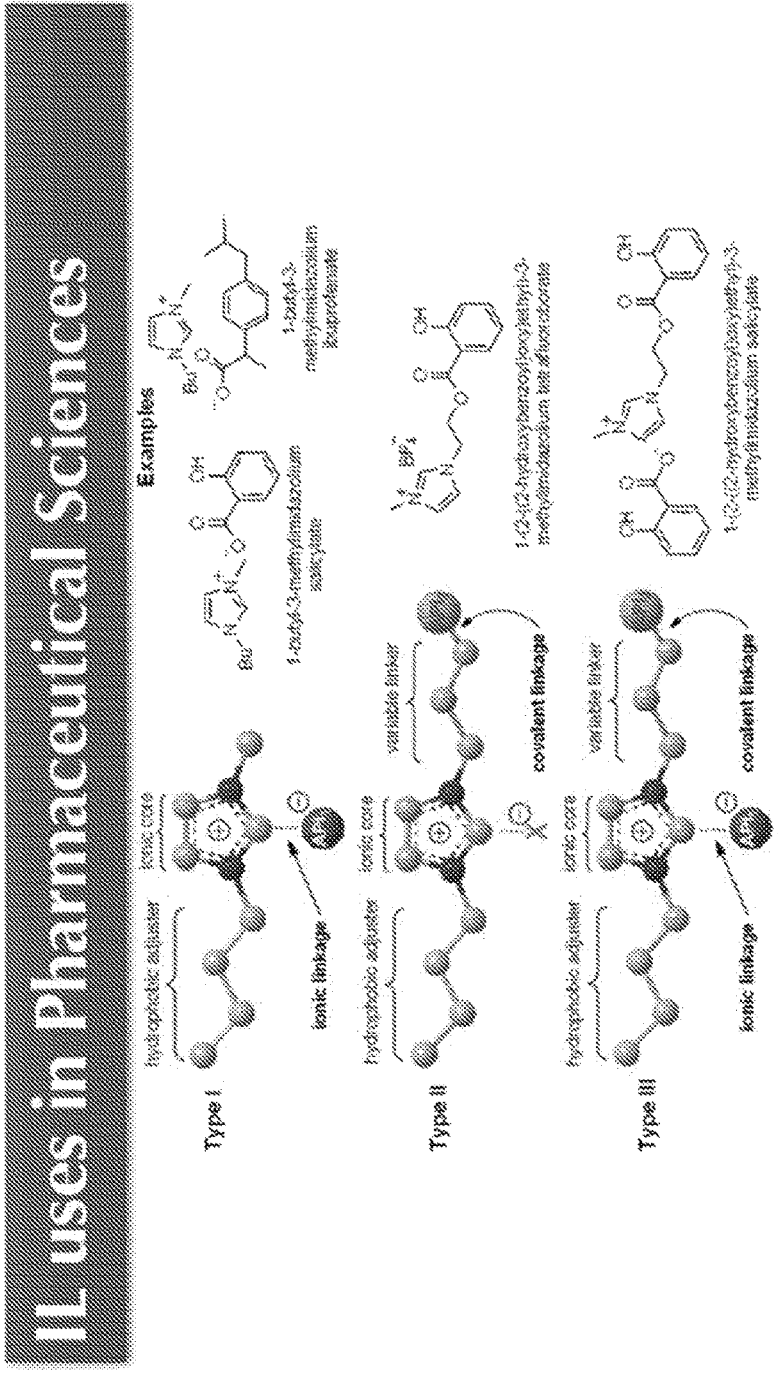
FIG. 16. An overview of the uses of ILs in pharmaceutical formulations.
Figure 17:
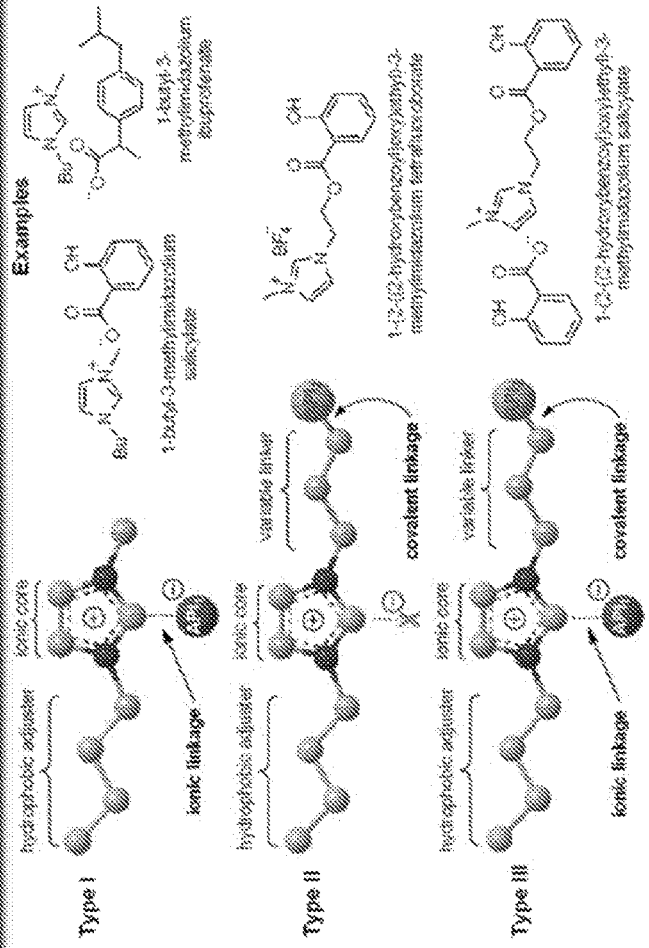
FIG. 17 provides an overview of the uses of ILs in pharmaceutical formulations.
Figure 21:
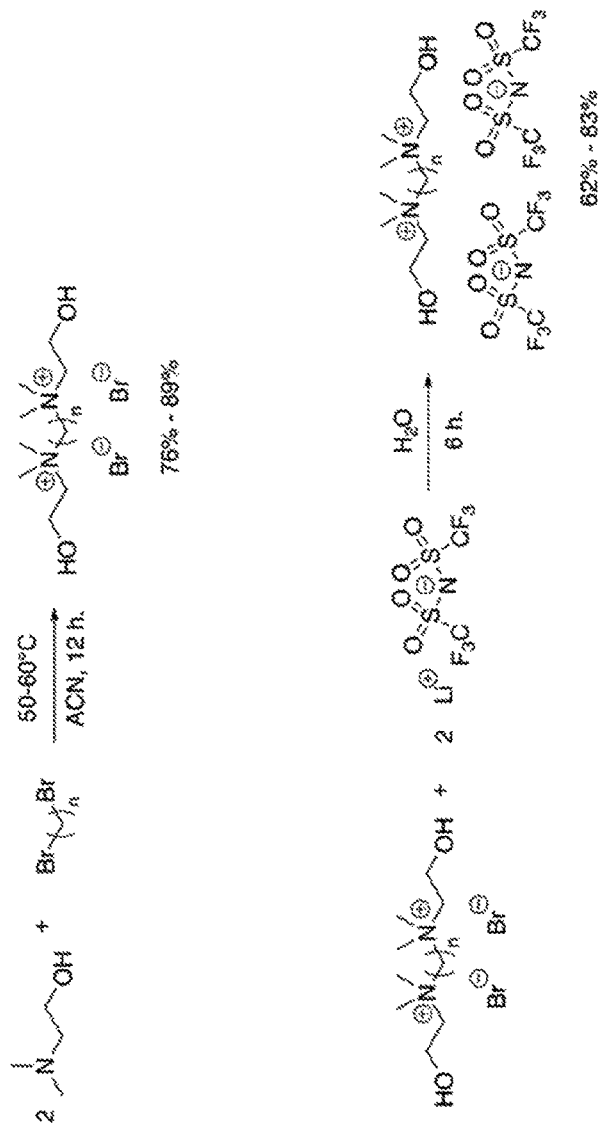
FIG. 21 provides a sample synthesis of cholinium based dicationic ILs.
Figure 24:
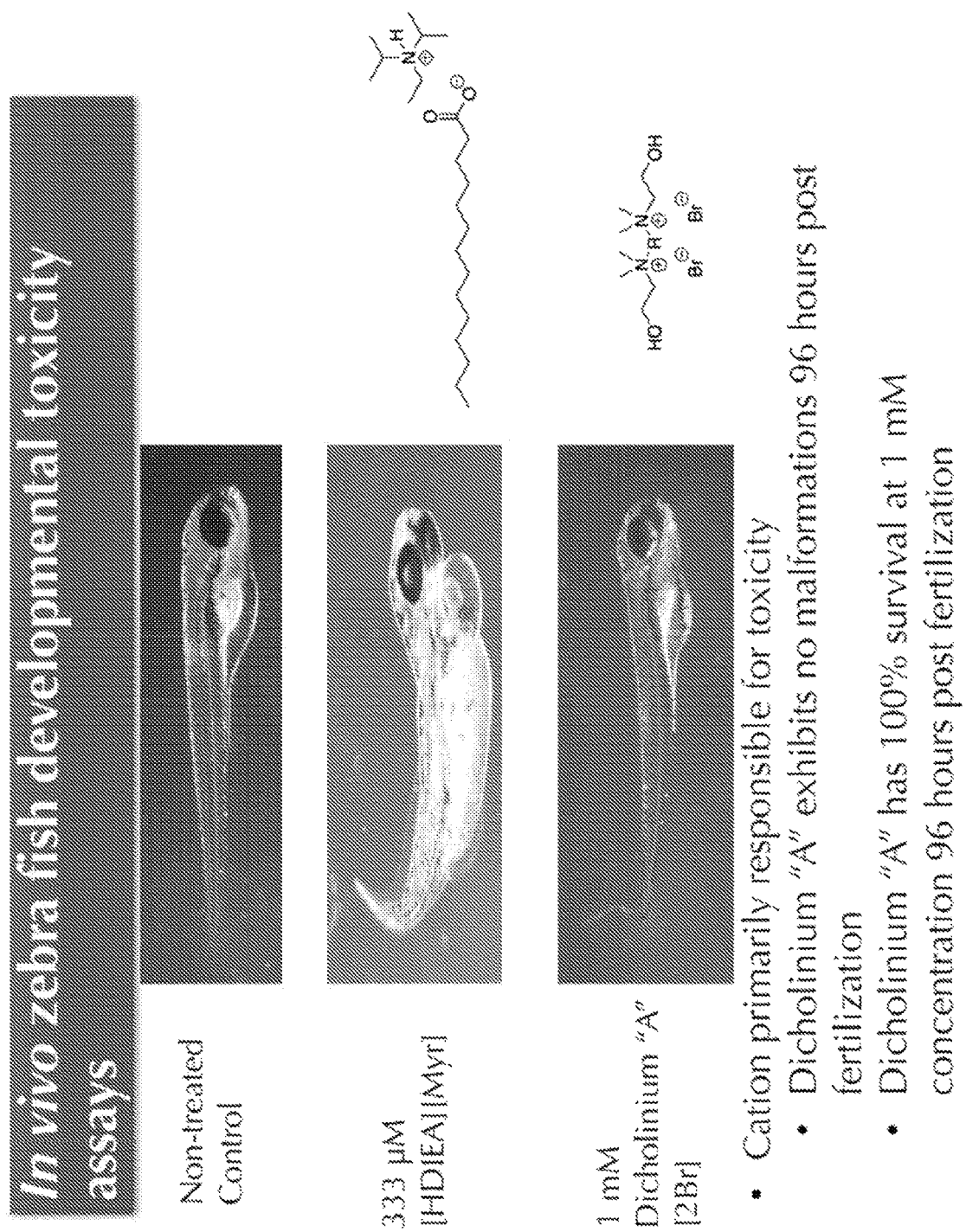
FIG. 24 shows that dicholinium ionic liquids show little toxicity in a zebrafish developmental assay.

FIG. 12 provides names and formulas of example cations and anions in exemplary ionic liquids. Size of ions in ILs are often larger than classical salts, for example, via ions asymmetric. Charge in ILs is often distributed over a larger volume than classical salts, for example, due to delocalized charge in space. Charge density of ILs is often lower than classical salts, for example, via reduced strength of electrostatic repulsion between similarly charged ion FIG. 16 provides an overview of the uses of ionic liquids in pharmaceutical formulations. ILs may be used as cosolvents, emulsifiers, copolymers and solvents or antisolvents for design of crystalline substances, for example, active-pharmaceutical ingredient (API) containing ILs and components in microemulsions for transdermal drug delivery. FIG. 17 provides an overview of the uses of ionic liquids in pharmaceutical formulations. FIG. 19 provides an overview of the most common cations and anions in ionic liquids, with the less preferred anions and cations shown in lined out format. FIG. 20 provides a sample synthesis of cholinium based ionic liquid component. FIG. 21 provides a sample synthesis of cholinium based dicationic ionic liquids. FIG. 24 shows that dicholinium ionic liquids show little toxicity in a zebrafish developmental assay.

Figure 18:
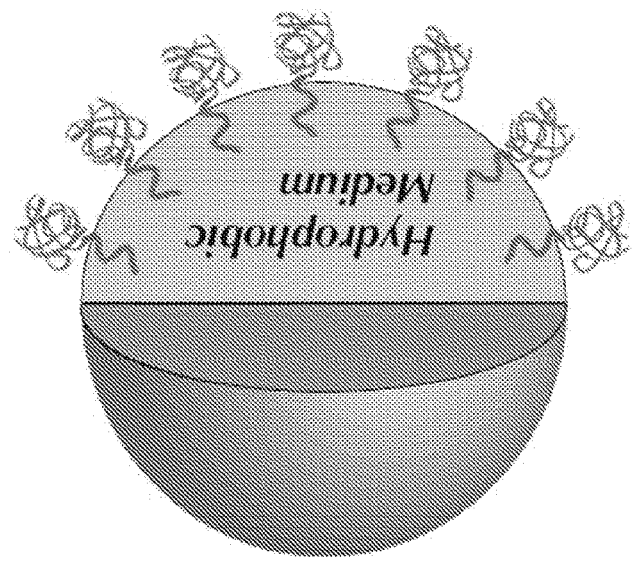
FIG. 18 provides an overview of nanoemulsions for pharmaceutical formulations.

FIG. 18 provides an overview of nanoemulsions for pharmaceutical formulations. In some embodiments, immiscible components are mixed and dispersed in continuous phase. Nanoemulsions are typically non-equilibrium, thermodynamically unstable. The dispersed phase may be provided as meta-stable nanoparticles, for example, kinetically stabilized by a polymer component. The FDA recommended stability is 11 months. The particle size of the dispersed phase varies, and typically is larger than micelles. For some applications, the FDA requires average particle size remain below 500 nm. Nanoemulsions often provides a delivery platform for high drug loading capacity. FIG. 25 shows an exemplary nanoemulsion formulation having mPEG polymer$_{2,000}$-DSG, medium chain triglyceride (MCT) cosolvent, an ionic liquid and a therapeutic agent component, such as a hydrophobic drug or hydrophilic drug.

In accordance with embodiments of the invention, high concentrations of drugs were solubilized in a hydrophilic ionic liquid, the novel hydrophobic dicationic ionic liquid, or in mixtures of the two. The in vivo biocompatibility of the novel hydrophobic ionic liquid was determined using a zebrafish viability assay. The ionic liquid-in-water nanoemulsion composition was tuned for each drug. All of the prepared nanoemulsions exhibit excellent stability, which was determined using dynamic light scattering. FIG. 22 provides an overview of of paclitaxel, Amphotericin B, and itraconazole in ionic liquids of the present invention.

Figure 23:
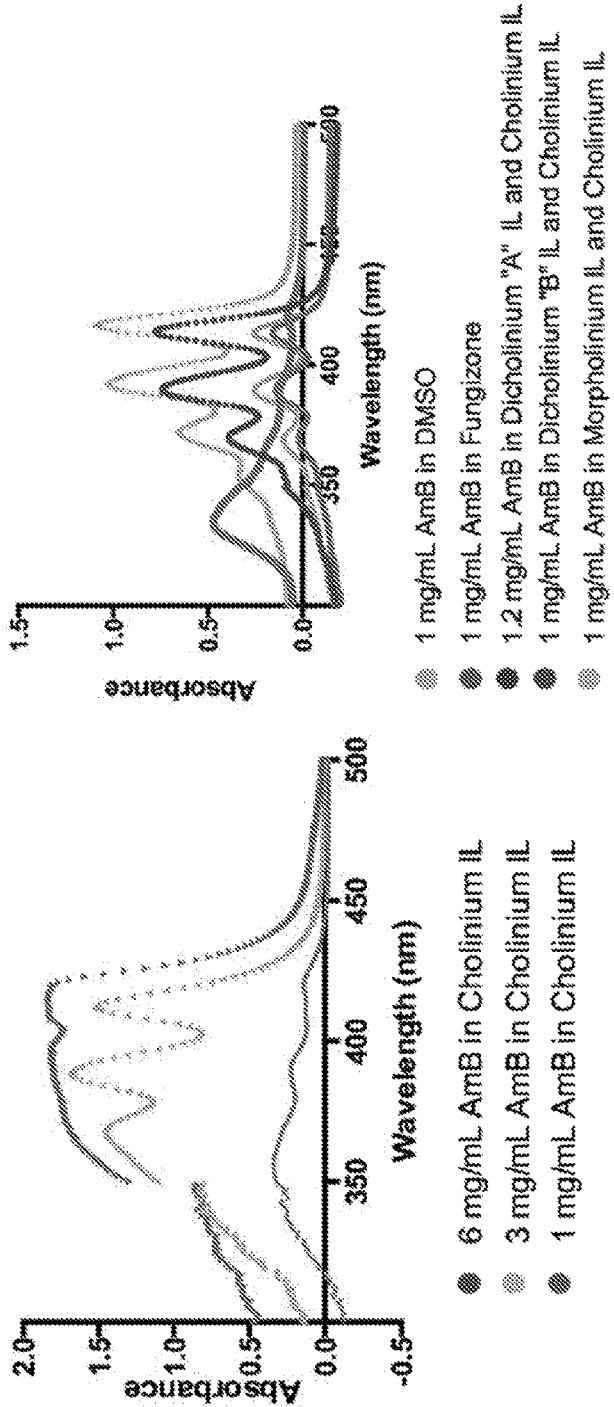
FIG. 23 shows aggregation studies of Amphotericin B in ionic liquids.
Figure 26:
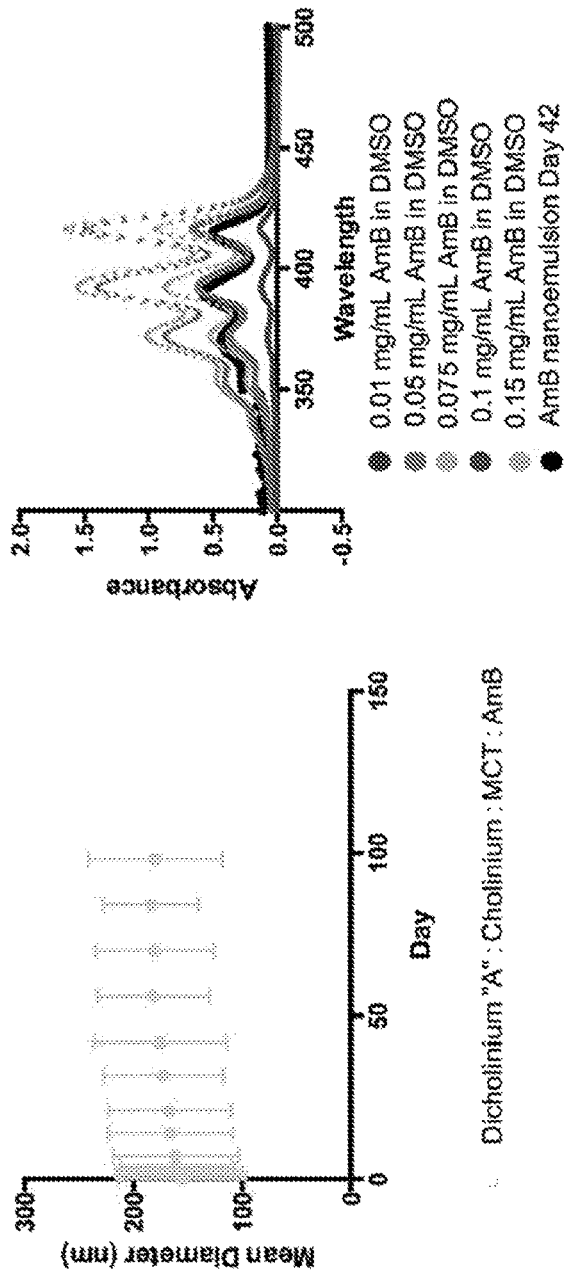
FIG. 26 shows long term stability of an AmB formulation of the present invention.
Figure 27:
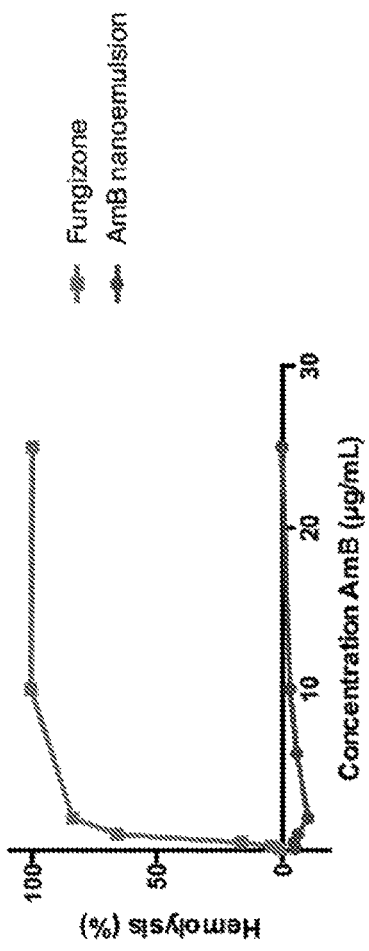
FIG. 27 Percent hemolysis of rabbit red blood cells with AmB containing nanoemulsion and FUNGIZONE™ after 1-hour incubation at 37° C.
Figure 28:
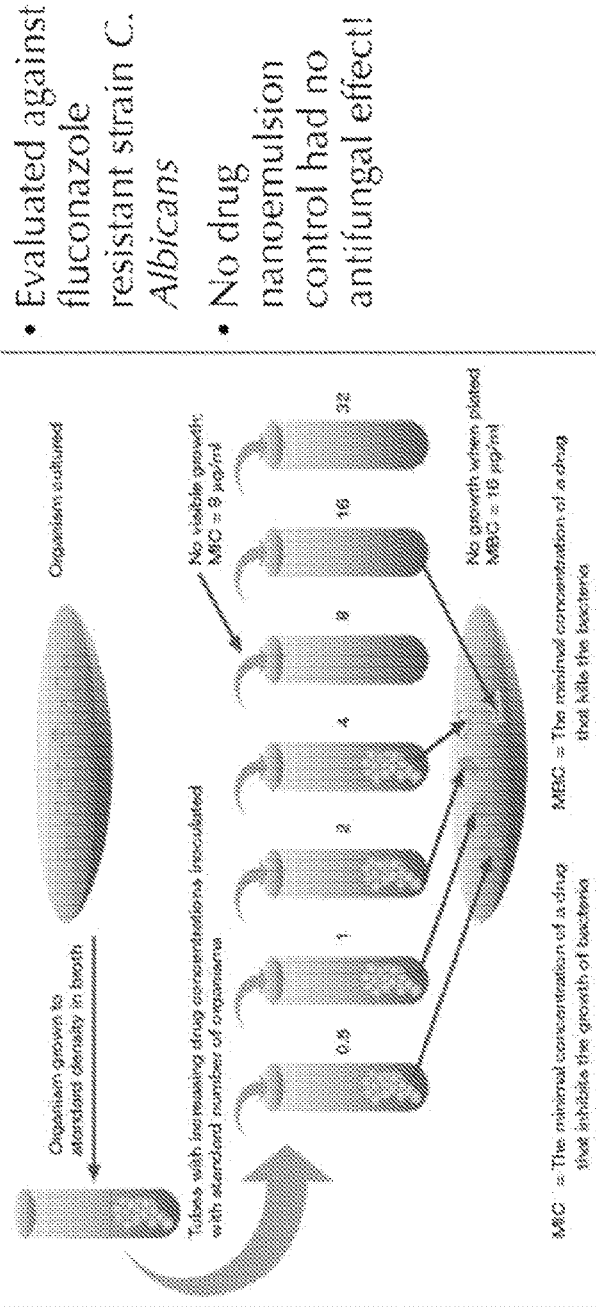
FIG. 28 shows process for determination of minimum inhibitory concentration (MIC).

Applicant has demonstrated that the absorption spectrum of Amphotericin B in an ionic liquid mixture and nanoemulsion indicates excellent monomerization. Hemolytic activity of the Amphotericin B in the ionic liquid nanoemulsion was negligible while maintaining antifungal activity against *Candida albicans* comparable to that of a commercial formulation. The in vitro drug release profile of a paclitaxel containing ionic liquid nanoemulsion was also characterized and exhibits a prolonged drug release. FIG. 23 shows aggregation studies of Amphotericin B in ionic liquids. FIG. 26 shows long term stability of an Amphotericin B formulation of the present invention. FIG. 27 shows percent hemolysis of rabbit red blood cells with AmB containing nanoemulsion and FUNGIZONE™ after 1-hour incubation at 37° C. FIG. 28 shows determination of minimum inhibitory concentration (MIC) including exemplary values of MIC (μg/mL) for AmB nanoemulsion (0.22-0.44) and FUNGIZONE™ (0.25-0.5)

The inventors have also shown that the hydrophilic drug cisplatin can be dissolved in a novel hydrophobic ionic liquid and this solution can be used to formulate a nanoemulsion when the standard polymeric surfactant PEG-DSG is used. In turn, the nanoemulsion can be used for the controlled delivery of the drug through IV infusion. This formulation is the first of its kind able to trap hydrophilic cisplatin inside a hydrophobic nanoemulsions particle composed of a new ionic liquid. The properties and structure of the new ionic liquid allow the complexation of both hydrophilic and hydrophobic molecules. Therefore, this class of new hydrophobic ionic liquids is very promising for the delivery of most small molecule drugs.

Without wishing to be bound to any particular theory, Applicant has demonstrated that an aqueous emulsion of cisplatin in an ionic liquid advantageously maintains the hydrophilic drug inside the nanoemulsions particles and the drug is then slowly released. This type of controlled delivery has never been achieved before for hydrophilic drugs and represents an objective advantage for any cancer therapy comprising administering cisplatin. The advantages are twofold—1) due to controlled delivery, the side effects of cisplatin on healthy tissues are reduced and 2) as a consequence of the reduced toxicity, the therapeutic index of cisplatin will most likely increase, allowing a more efficacious therapy.

Some conventional efforts to mitigate cisplatin side effects have relied on chemical synthesis (i.e., derivatization) to add hydrophobic chains to cisplatin to increase the hydrophobicity of the cisplatin molecule. However, the efficacy of the hydrophobic cisplatin is reduced as compared to that of the free water-soluble molecule (i.e., underivatized molecule). Cleavage of the hydrophobic chains only at the site of the tumor also does not provide suitable benefits. The inventive formulation is the first of its kind able to trap hydrophilic cisplatin inside a hydrophobic nanoemulsions particle composed of a new ionic liquid. The features of the inventive ionic liquid allow the complexation of both hydrophilic and hydrophobic molecules. Therefore, this class of new hydrophobic ionic liquids is very promising for the delivery of most small molecule drugs.

In general, the terms and phrases used herein have their art-recognized meaning, which can be found by reference to standard texts, journal references and contexts known to those skilled in the art. The following definitions are provided to clarify their specific use in the context of the invention.

In one embodiment, the present invention includes an ionic liquid composition. In an embodiment, the ionic liquid mixture includes an at least partially hydrophobic ionic liquid. As used herein, at least partially partially hydrophobic ionic liquid refers to on ionic liquid exhibiting at least a partially hydrophobic characteristic. In an embodiment, for example, an at least partially partially hydrophobic ionic liquid at least partially provides the dispersed phase of an emulsion having an aqueous solution as the continuous phase. In an embodiment, for example, an at least partially partially hydrophobic ionic liquid at least partially provides the dispersed phase in an oil in water emulsion or nanoemulsion.

A hydrophobic ionic liquid composition according to the invention is a salt formed between a dication as described herein and two anions. As used herein, the term "dication" is not meant to embrace a single species that has a $^+2$ or $^-2$ charge such as $Mg^{+2}$ or $SO_4^{2}$. Rather it contemplates a single molecule with two discreet mono-cationic groups, typically separated by a bridging group. In some embodiments, the mono-cationic groups may be different types of monocationic groups. In some embodiments, the dicationic liquid salts are preferably "germinal," which means both ionic groups are not only the same charge, but also the same structure. A hydrophobic ionic liquid in accordance with embodiments of the present invention is a liquid salt comprised of the dicationic and anionic species, and may be referred to herein as IL (ionic liquid). Thus, ILs exist in liquid form at the temperatures indicated herein. A "dicationic ionic liquid" (used synonymously with "liquid salts of a dication") in accordance with embodiments of the present invention is a liquid comprised of molecules which are salts of dicationic species. The salt forming counter-anions may be mono-ionic. Any dicationic ionic liquid, which is stable and has a solid/liquid transformation temperature of about 400° C. or less is contemplated.

Preferably, an ionic liquid of the invention will not substantially decompose or volatilize (or remain substantially non-volatile) as measured by being immobilized as a thin film in a fused silica capillary or on a silica solid support as described herein, at a temperature of about 200° C. or less. "Substantially" in this context means less than about 10% by weight will decompose or volatilize at about 200° C. inside a capillary over the course of about one hour. Moreover, the hydrophobic ionic liquid in accordance with this embodiment will preferably have either a solid/liquid transformation temperature at about 100° C. or less or a liquid range (the range of temperatures over which it is in a liquid form without burning or decomposing) of at least about 200° C.

As used herein, unless otherwise described, the term "about" refers to ±10% of the reported value.

The ionic liquids of the present invention are generally salts, comprising ion(s) with counter ion(s) resulting in a global net charge of zero. Thus, in most instances, each ion should have a counterion, one for each anion or cation. Charge should be preserved. In the case of an ionic liquid, two cations (including those identified as C' or C") (or one dication) (including those identified as C) are required and in the case of a dicationic ionic liquid, two anions (including those identified as C' or C") (or one dianion) (including those identified as C) are required. The choice of anion can have an effect of the properties of the resulting compound and its utility as a solvent. While anions and cations will be described in the context of a single species used, it is possible to use a mixture of cations to form salts with a dianionic species to form a dianionic ionic liquid. The reverse is true for dications. For clarity sake, the salt-forming ions will be referred to as counterions herein.

The ionic liquid mixture can include a hydrophilic ionic liquid with the at least partially hydrophobic ionic liquid. In general, ionic liquids are hydrophilic in view of the presence of a the polar charged cationic groups on the cationic species, including imidazolium, pyridinium, pyrrolidinium, piperidinium, quinolinium, quaternary ammonium, quaternary phosphonium, morpholinium, and cholinium groups. However, in the instant invention, an at least partially hydrophobic liquid includes a dication which has partially hydrophobic structure by the presence of a hydrophobic bridging region, which can include long (e.g., $C_3$-$C_{10}$) alkylene linkers and (e.g., $C_3$-$C_{10}$) alkoxyalkyl linkers which impart a partially hydrophobic nature to the dication. As used herein, "$C_3$-$C_{10}$" includes $C_3$, $C_4$, $C_5$, $C_6$, $C_7$, $C_8$, $C_9$, and $C_{10}$.

As such, ionic liquids of the invention can include wherein the monocationic group is a quaternary ammonium group which may be substituted or unsubstituted, saturated or unsaturated, linear, branched, cyclic or aromatic and the bridging group is a unsubstituted or substituted $C_3$-$C_{10}$ alkylene or $C_3$-$C_{10}$ alkoxyalkylene.

In embodiments, the dication may include two quaternary ammonium groups such as cholinium or morpholinium. Choline is a water-soluble vitamin-like nutrient and as such, its presence limits the toxicity of the synthesized dication.

Figure 5A:
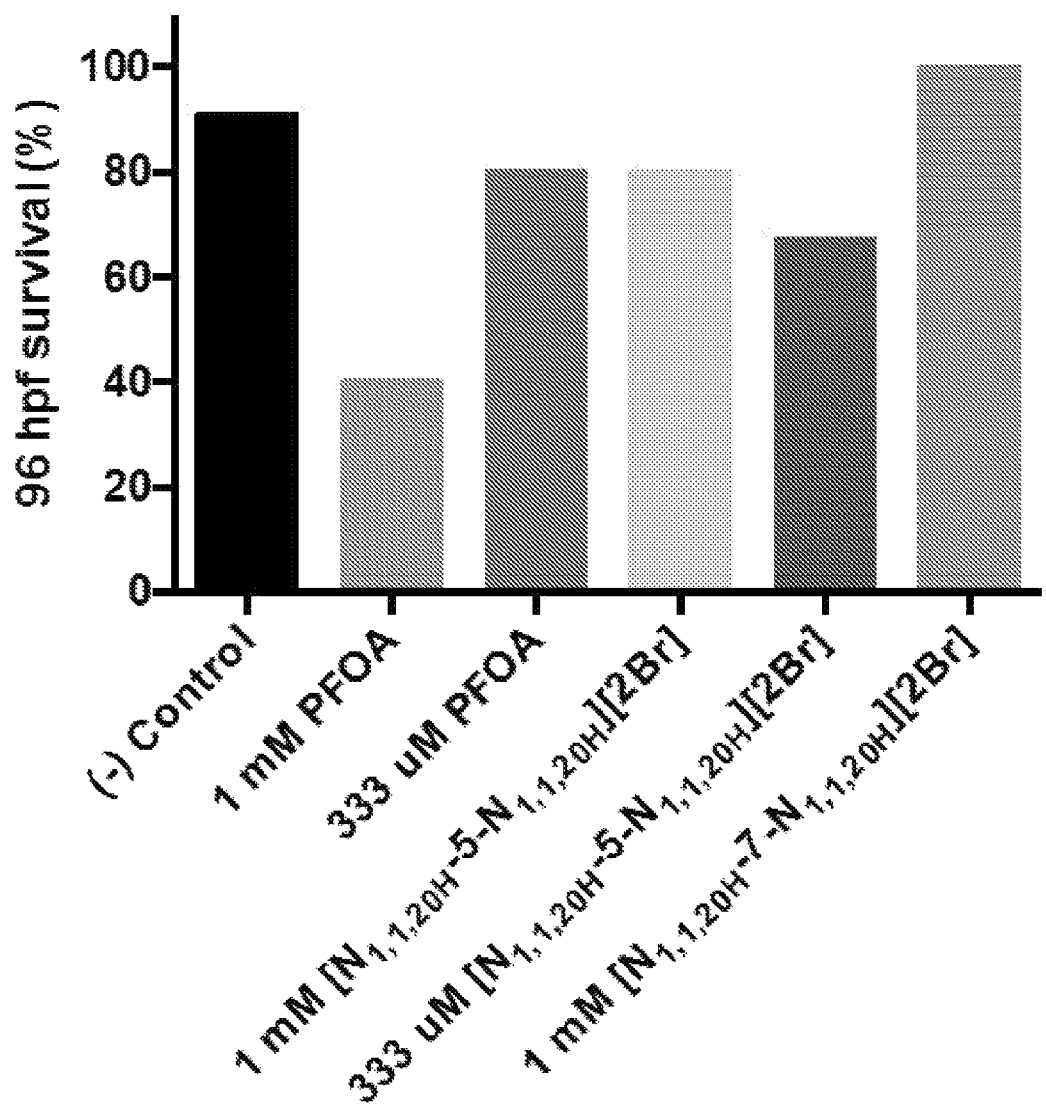
FIG. 5A. Zebrafish developmental toxicity assay for analysis of in vivo toxicity of [CDIL-7][2Br].
Figure 5B:
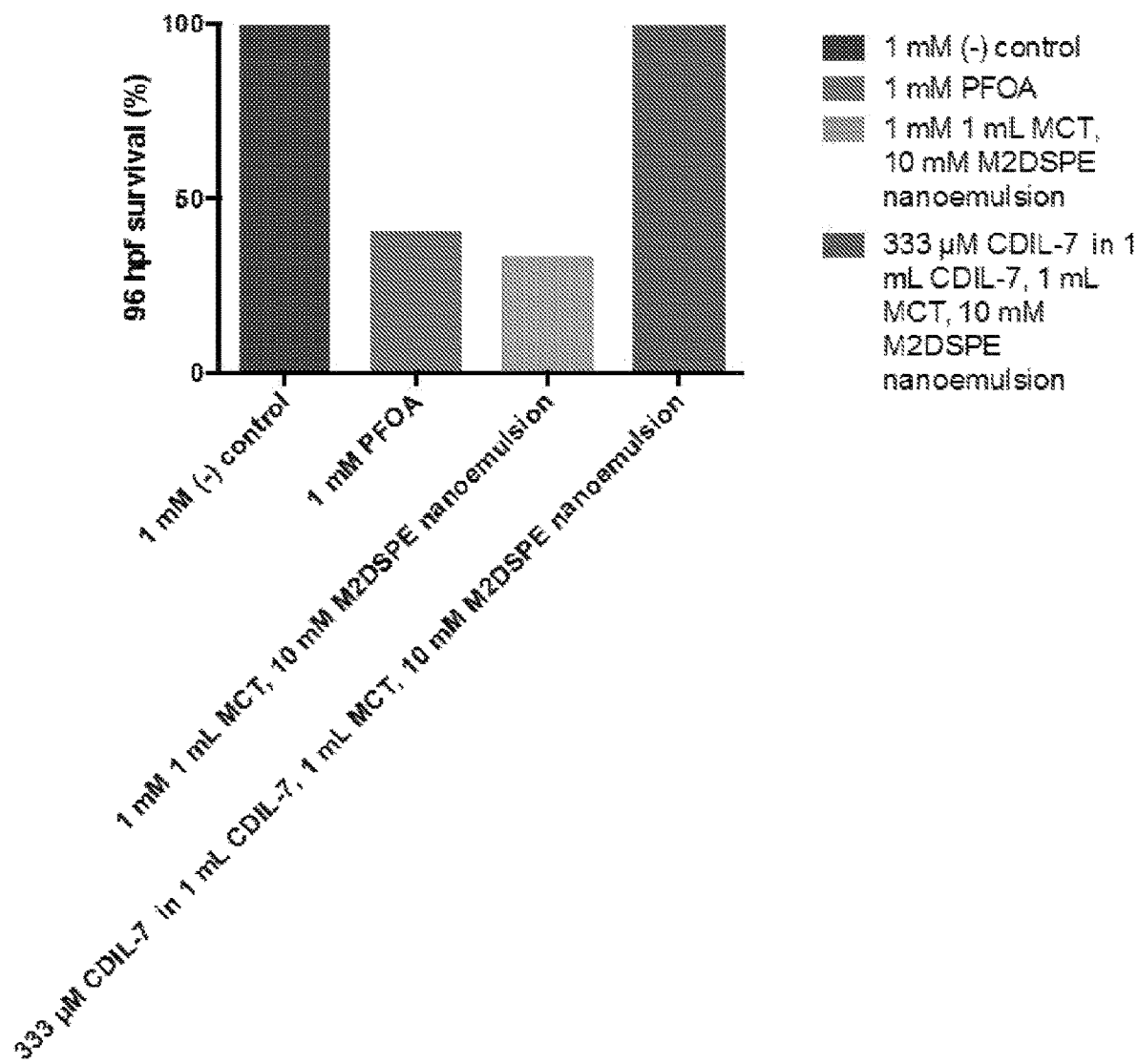
FIG. 5B. Zebrafish developmental toxicity assay for analysis of in vivo toxicity of [CDIL-7][2NTf$_2$].
Figure 6:
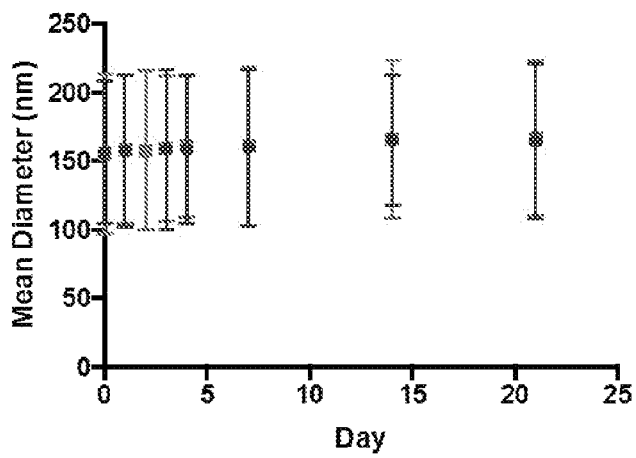
FIG. 6. Change in particle diameter of [CDIL-7][2NTf$_2$], [Chol][Hex], and MCT nanoemulsions with 10 mM M2DSG over time.
Figure 7:
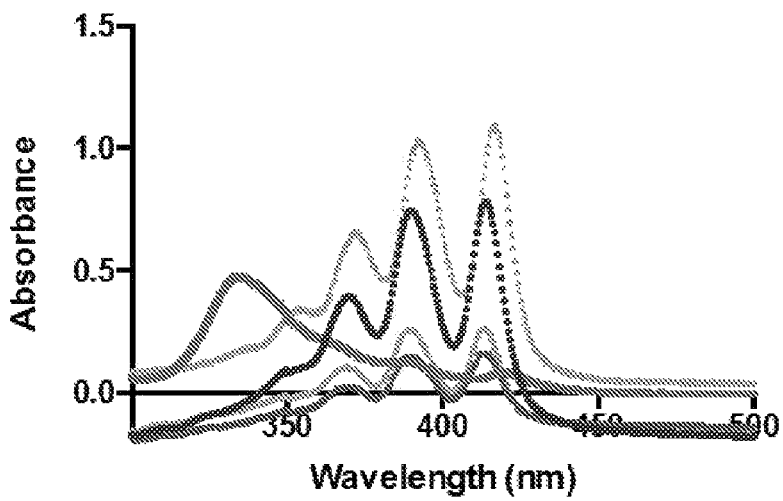
FIG. 7. UV/vis spectrum of the aggregation state of AmB in various IL mixtures, FUNGIZONE™ (X-Gen), or DMSO solvent.
Figure 8:
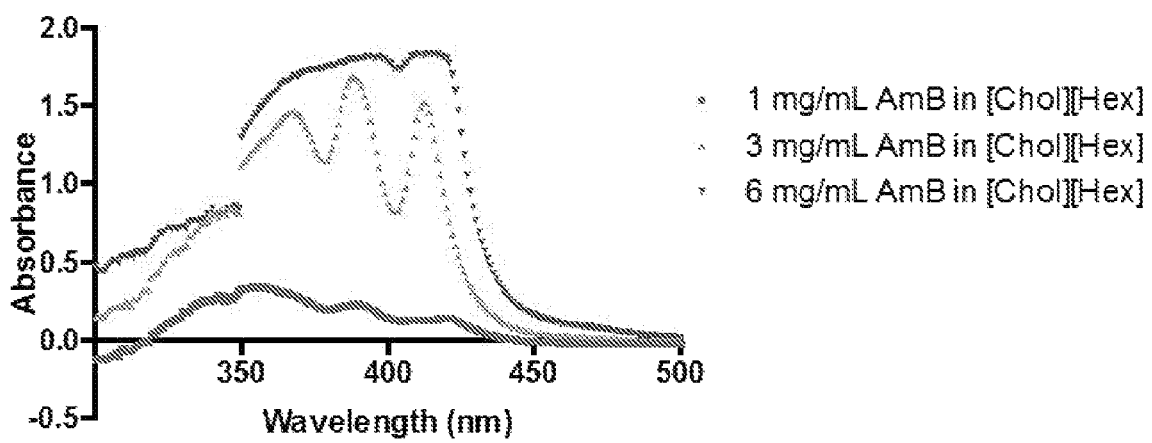
FIG. 8. UV/vis spectrum of the aggregation state of various concentrations of AmB in [Chol][Hex] with dilution using sterile saline.

Of note, the art teaches that hydrophobic ILs are typically toxic, often due to both the cationic and anionic structures. Hydrophobic ILs are formed from a combination of a hydrophobic anion and a cation with long alkyl chains. However, the alkyl chains can interact with lipid bilayer of the cell membrane, resulting in cell death. Applicant has surprisingly discovered that the presence of a second cationic group functions to limit the toxicity of the cations by eliminating or decreasing the potential to interact with the lipid bilayer. Indeed, the results presented herein at FIG. 5A, FIG. 5B and FIG. 24 show that the in vivo toxicity of the novel hydrophobic ionic liquids disclosed herein are extremely low.

In the at least partially hydrophobic ionic liquid compositions of the invention, the anion is an anion with at least a partially hydrophobic character. A non-limiting list of at least partially hydrophobic anions include acetate, alkyl sulfate, such as octyl sulfate, bis(trifluoromethylsulfonyl) imide, and mixtures thereof.

In the ionic liquid compositions of the invention, the ionic liquid also includes a hydrophilic ionic liquid. Hydrophilic ionic liquids include those conventionally known in the art, such as monocations formed from imidazolium, pyridinium, pyrrolidinium, piperidinium, quinolinium, quaternary ammonium, quaternary phosphonium, morpholinium, and cholinium head groups. Hydrophilic anions include, without limitation, tetrafluoroborate, hexafluorophosphate, methyl sulfate, alkyl acetates, halides, and trifluoromethanesulfonates.

In embodiments, the hydrophilic ionic liquid is selected for hydrophilicity as well as lack of toxicity in a mammalian subject. In one embodiment, the hydrophilic ionic liquid may comprise choline and an $C_2$ to $C_{10}$ alkyl acetate, such as hexanoate.

The present invention includes ionic liquid compositions, which are a mixture of hydrophobic ionic liquids of the present invention as described herein, and hydrophilic ionic liquids as are known in the art. Mixtures of hydrophobic ionic liquids and hydrophilic ionic liquids can be used with both hydrophobic or hydrophilic therapeutics, but the mixtures are most advantageously used with hydrophobic therapeutics. For solubilizing hydrophobic therapeutic agents, the ratio of the hydrophobic to hydrophilic ionic liquids may be tuned depending on the desired solubility of the target therapeutic in the ionic liquid. For example, if a target therapeutic has less solubility in the hydrophobic ionic liquid, additional amounts of hydrophilic ionic liquid may be added to increase solubility, or vice-versa. The relative proportions of hydrophobic to hydrophilic ionic liquids may also be determined by other characteristics, such as the ability to minimize the aggregation state of the target therapeutic in the mixture, or in dilutions of the mixture. In some embodiments, the ionic liquid composition of the invention include wherein the ratio of the hydrophilic ionic liquid to the at least partially hydrophobic ionic liquid is between about 50:1 to 1:50 (v/v). The ratio of hydrophilic ionic liquid to hydrophobic ionic liquid, in some embodiments, can be between about 20:1 to about 1:20, between about 10:1 and about 1:10, between about 5:1 and about 1:5, between about 2:1 and about 1:2. In some embodiments, the ratio is about 1.5:1.0 (v/v). For example, the hydrophilic ionic liquid can be present in an amount of 0.3 mL and the hydrophobic ionic liquid can be present in an amount of 0.2 mL.

In some embodiments, the ionic liquid composition comprises, consists essentially of, or consists of hydrophobic ionic liquid compositions of the invention as described herein. In embodiments, where the ionic liquid composition comprises or consists essentially of hydrophobic ionic liquid compositions is appropriate where the therapeutic is a hydrophilic therapeutic.

The present invention also includes a nanoemulsion for delivery of a hydrophobic or a hydrophilic therapeutic agent. The emulsion may include an oil in water emulsion which has one or more of the following components: a hydrophobic liquid; an aqueous solution; an ionic liquid composition comprising a mixture of a hydrophilic ionic liquid and an at least partially hydrophobic ionic liquid according the present invention; or an ionic liquid composition that comprises or consists essentially of a hydrophobic ionic liquid according to the invention; and a polymer. In embodiments, the ionic liquid composition is capable of solubilizing the therapeutic agent.

As used herein, "emulsion" refers to a mixture of two or more immiscible substances, such as a mixture of two immiscible liquids. Emulsions are a type of colloid that comprise at least one dispersed phase dispersed in a continuous phase. Emulsions are broadly defined as two immiscible phases in which a first phase is dispersed within a second phase, such as a two-phase system in which one liquid is dispersed throughout a second liquid in the form of small droplets. The two phases of an emulsion are generally referred to as the continuous phase and the dispersed phase, with the dispersed phase typically present as a smaller volume percentage. A dispersion of oil in water is preferred to as an oil-in-water (o/w) emulsion. For o/w emulsions, the emulsifying agent is typically more soluble in the aqueous phase. The reverse emulsion, water-in-oil, is abbreviated "w/o" and is stabilized by surfactants that are more stable in the oil phase. In an aqueous emulsion, the continuous phase is an aqueous solution.

Emulsions are not thermodynamically stable, but the stability can be improved by additives such as surfactants. As non-equilibrium systems, the formation of nanoemulsions generally requires an input of energy. High-energy emulsification methods commonly involve the introduction of mechanical shear through such equipment as high-shear stirrers, high-pressure homogenizers, microfluidizers or ultrasound generators. A microfluidizer is the piece of equipment used in the pharmaceutical industry for the production of emulsions that works by dividing a stream of liquid into two parts, passing each through a narrow opening and then colliding the streams under high pressure. The high shear forces created by the collision provide very fine emulsions with generally narrow particle size distributions. In typical usage, a coarse emulsion (diameter>1 μm) is first formed by some other method, and the size of that larger emulsion is reduced in the microfluidizer. The final droplet size and distribution shape will be dependent upon both the emulsion components (surfactant amount, oil volume percent, etc.) and the processing parameters (time, temperature, pressure etc.). As the desired droplet size decreases, the energy required for formation increases. Ultrasonic emulsification is also effective to reduce the size of emulsion droplets into the nanoscale. Emulsions can also be formed by changing the temperature of a mixture of immiscible liquids, for example by rapid cooling or heating to produce kinetically stable emulsions with small droplet sizes and narrow size distributions.

Emulsions include nanoemulsions comprising nanoscale droplets of one immiscible liquid dispersed within another. As used herein a nanoemulsion is a heterogeneous system composed of one immiscible liquid dispersed as droplets within another liquid, where the average droplet diameter is below 1000 nm.

In an aspect, an emulsion of the invention includes a hydrophobic liquid in which the hydrophobic or hydrophilic therapeutic agent is solubilized and/or dispersed, together with an ionic liquid composition as described herein and a polymer as described herein. Systems for solubilizing solid hydrophobic drugs include solubilization in an oil phase as known in the art. Saturated solutions of the drug to be emulsified can be used as the hydrophobic and/or dispersed and/or oil phase. The hydrophobic liquid useful for the invention, in one embodiment, can include any FDA-approved oil, for example, 2-octyl-1-dodecanol (FDA approved) or pharmaceutical grade soybean oil. In one embodiment of the present invention, the hydrophobic liquid includes glycerides, which can include monoglycerides, diglycerides, or triglycerides comprising short, medium or long chain acyl groups. In one embodiment, the triglyceride is a medium chain triglyceride ("MCT"), or mixtures thereof, as known in the art.

In an embodiment, the MCT is characterized by Formula A:

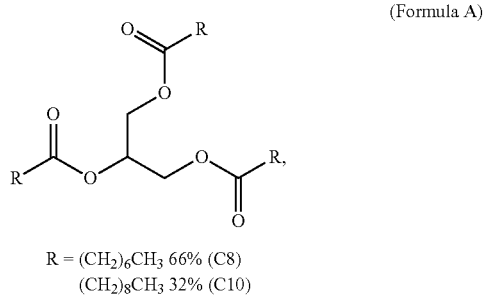

(Formula A)

R = $(CH_2)_6CH_3$ 66% (C8)
    $(CH_2)_8CH_3$ 32% (C10)

wherein each of the $C_8$ and $C_{10}$ acyl chains can be present in amounts from about 20% to about 80%. An illustrative MCT of Formula A is commercially available from Stepan (Northfield, Ill.) as NEOBEE™ M-5.

In an embodiment, a MCT in accordance with the invention includes the following Formula A1:

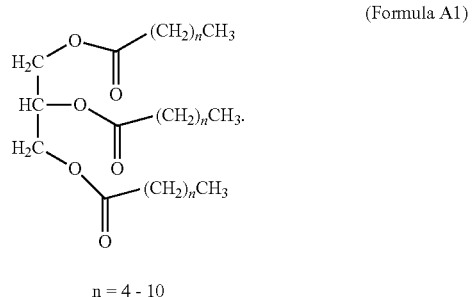

(Formula A1)

$n = 4 - 10$

Subsequent microfluidization can then lead to a nanoemulsion containing relatively large amounts of drug.

In keeping with an aspect of the invention, the exact size of the droplets may be "tuned" in accordance with the desired use or to maximize stability and/or delivery, as appropriate. For example, in an embodiment the emulsion is a nanoemulsion, for example, characterized by a dispersed phase comprising droplets as described elsewhere herein having cross sectional dimensions selected from the range of 20 nm to 1 micron, for example, 20 nm or more, 50 nm or more, 100 nm or more, 150 nm or more, 200 nm or more, 250 nm or more, 300 nm or more, 350 nm or more, 400 nm or more, 450 nm or more, or 500 nm or more. Alternatively, or in addition, the droplets having a cross sectional dimension selected from 1 micron or less, for example, 950 nm or less, 900 nm or less, 850 nm or less, 800 nm or less, 750 nm or less, 700 nm or less, 650 nm or less, 600 nm or less, or 550 nm or less. Thus, the droplets can have a cross sectional dimension bounded by any two of the aforementioned endpoints, for example, 50 nm to 950 nm, 100 nm to 900 nm, 150 nm to 850 nm, 200 nm to 800 nm, 250 nm to 750 nm, 300 nm to 700 nm, 350 nm to 650 nm, 400 nm to 600 nm, 450 nm to 550 nm, or 500 nm.

In an embodiment, the droplets have a cross sectional dimension selected from 100 nm to 1 micron, or 200 nm to 500 nm, or, alternatively, less than 500 nm, less than 400 nm, less than 300 nm, less than 200 nm, less than 100 nm.

In some embodiments of the invention, the nanoemulsion includes a polymer (e.g., one or more polymers) which is useful for stabilizing the emulsion. In embodiments, the polymer can include an amphiphilic polymer composed of a hydrophilic section and a hydrophobic section, such as an ionic or neutral polyethylene glycol (PEG)-coupled lipid, wherein the lipid comprises a single chain or double chain $C_{10}$-$C_{24}$ alkyl and the polyethylene glycol moiety has a molecular weight of 1,000 D to 12,000 D, for example, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000, 10,100, 10,200, 10,300, 10,400, 10,500, 10,600, 10,700, 10,800, 10,900, 11,000, 11,100, 11,200, 11,300, 11,400, 1 1,500, 11,600, 11,700, 11,800, or 11,900 D. The polyethylene glycol moiety can have a molecular weight bounded by any two of the aforementioned endpoints.

Exemplary and nonlimiting amphilic polymers include those with branched lipid groups, such as M2DSPE and mPEG-DSG shown below.

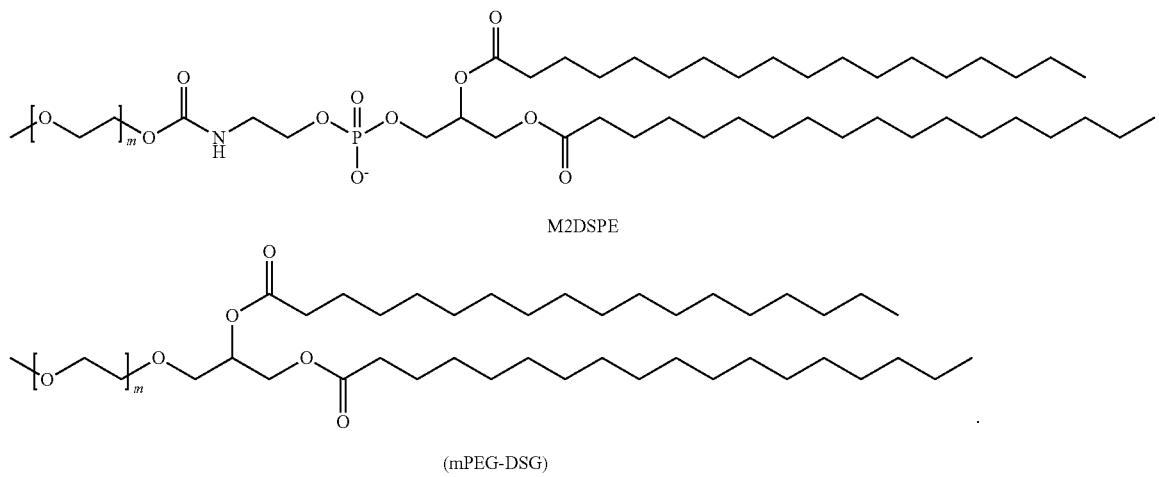

M2DSPE (mPEG-DSG)

Other nonlimiting amphiphilic polymers include any suitable pegylated amphiphilic copolymer. Illustrative examples of pegylated amphiphilic copolymers include copolymers of PEG-polylactic acid and PEG-poly(lactic-co-glycolic acid).

The nanoemulsion can comprise any suitable concentration of polymer. If the nanoemulsion comprises too little of the polymer, the nanoemulsion may not exhibit suitable stability. In contrast, if the nanoemulsion comprises too much polymer, the nanoemulsion may not exhibit suitable delivery of a therapeutic agent. Accordingly, the nanoemulsion can comprise 0.01 mM or more of polymer, for example, 0.05 mM or more, 0.1 or more, 0.5 mM or more, 1 mM or more, 5 mM or more, 10 mM or more, 15 mM or more, 20 mM or more, 25 mM or more, 30 mM or more, 35 mM or more, 40 mM or more, 45 mM, or 50 mM or more of polymer. Alternatively, or in addition, the nanoemulsion can comprise 100 mM or less of polymer, for example, 95 mM or less, 90 mM or less, 85 mM or less, 80 mM or less, 75 mM or less, 70 mM or less, 65 mM or less, 60 mM or less, or 55 mm or less of polymer. Thus, the nanoemulsion can comprise an amount of polymer bounded by any of the aforementioned amounts, for example, 0.01 mM to 100 mM of polymer, or 0.05 mM to 95 mM, 0.1 mM to 90 mM, 0.5 mM to 85 mM, 1 mM to 80 mM, 5 mM to 75 mM, 10 mM to 70 mM, 15 mM to 65 mM, 20 mM to 60 mM, 25 mM to 55 mM, 30 mM to 50 mM, 35 mM to 45 mM, or 40 mM of polymer.

In an embodiment, the nanoemulsion comprises a polymer at a concentration of 0.01 mM to 100 mM.

In a preferred embodiment, the nanoemulsion comprises a polymer at a concentration of between 2 mM and 30 mM. In a preferred embodiment, the nanoemulsion comprises a polymer concentration of 10 mM to 20 mM, for example, 11 mM, 12 mM, 13 mM, 14 mM, 15 mM 16 mM, 17 mM, 18 mM, or 19 mM.

In embodiments, the relative ratios of the hydrophobic liquid and ionic liquid compositions in the nanoemulsions can vary, although very generally it is desirable to have the hydrophobic liquid in excess to the ionic liquid compositions of the invention. In some embodiments, the ratio of hydrophobic liquid to ionic liquid composition of between 50:1 to 1:10 (v/v), for example, 49:1, 48:1, 47:1, 46:1, 45:1, 44:1, 43:1, 42:1, 41:1, 40:1, 39:1, 38:1, 37:1, 36:1, 35:1, 34:1, 33:1, 32:1, 31:1, 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10 (v/v). Alternatively, or in addition, the ratio of hydrophobic liquid to ionic liquid can be a range bounded by any of the aforementioned endpoints.

In a preferred embodiment, the ratio of hydrophobic liquid to ionic liquid composition, in some embodiments, can be between 20:1 to 1:5, between 10:1 and 1:1, between 5:1 and 2:1, or 3:1. In embodiments, the polymer has a concentration of 0.01 mM to 100 mM.

In an embodiment, the ratio of hydrophobic liquid to ionic liquid composition of 3:1 (v/v), and wherein the polymer has a concentration of 10 mM.

In embodiments, the nanoemulsion further comprises a hydrophobic or hydrophilic therapeutic agent. In certain embodiments, the therapeutic agent is a hydrophobic therapeutic agent. Use of hydrophobic therapeutic agents is beneficial as a variety of hydrophobic therapeutic agents exhibit reduced toxicity, increased therapeutic effectiveness or smaller required therapeutic dosages as compared to some non-hydrophobic therapeutic agents. In addition, therapeutic agents for a desired clinical application may only be available as a hydrophobic compound. In embodiments, emulsions of the invention are, thus, particularly useful for providing a therapeutically deliverable quantity of a hydrophobic therapeutic agent in order to achieve a desired clinical outcome, such as treatment of cancer or fungal infection.

The nanoemulsion can comprise any suitable amount of hydrophobic therapeutic agent. If the nanoemulsion comprises too little hydrophobic therapeutic agent, the nanoemulsion may not exhibit suitable activity. In contrast, if the nanoemulsion comprises too much hydrophobic agent, the nanoemulsion may exhibit undesirable properties (e.g., instability or increased toxicity). Typically, the nanoemulsion comprises 0.05 mg/mL or more of one or more hydrophobic therapeutic agent(s), for example, 0.1 mg/mL 0.2 mg/mL or more, 0.3 mg/mL or more, 0.4 mg/mL or more, 0.5 mg/mL or more, 0.6 mg/mL or more, 0.7 mg/mL or more, 0.8 mg/mL or more, 0.9 mg/mL or more, 1 mg/mL or more, 1.5 mg/mL or more, 2 mg/mL or more, 2.5 mg/mL or more, 3 mg/mL or more, 3.5 mg/mL or more, 4 mg/mL or more, 4.5 mg/mL or more, 5 mg/mL or more, 5.5 mg/mL or more, 6 mg/mL or more, 6.5 mg/mL or more, 7 mg/mL or more, 8 mg/mL or more, 8.5 mg/mL or more, or 9 mg/mL or more, 9.5 mg/mL or more, 10 mg/mL or more, 10.5 mg/mL or more, 11 mg/mL or more, 11.5 mg/mL or more, 12 mg/mL or more, 12.5 mg/mL or more, 13 mg/mL or more, 13.5 mg/mL or more, 14 mg/mL or more, 14.5 mg/mL or more, 15 mg/mL or more, 15.5 mg/mL or more, 16 mg/mL or more, 16.5 mg/mL or more, 17 mg/mL or more, 17.5 mg/mL or more, 18 mg/mL or more, 18.5 mg/mL or more, 19 mg/mL or more, 19.5 mg/mL or more, 20 mg/mL or more, 20.5 mg/mL or more, 21 mg/mL or more, 21.5 mg/mL or more, 22 mg/mL or more, 22.5 mg/mL or more, 23 mg/mL or more, 23.5 mg/mL or more, 24 mg/mL or more, 24.5 mg/mL or more, or 25 mg/mL or more of hydrophobic therapeutic agent(s). Alternatively, or in addition, the nanoemulsion can comprise 50 mg/mL or less of hydrophobic therapeutic agent(s), for example, 49.5 mg/mL or less, 49 mg/mL or less, 48.5 mg/mL or less, 48 mg/mL or less, 47.5 mg/mL or less, 47 mg/mL or less, 46.5 mg/mL or less, 46 mg/mL or less, 45.5 mg/mL or less, 45 mg/mL or less, 44.5 mg/mL or less, 44 mg/mL or less, 43.5 mg/mL or less, 43 mg/mL or less, 42.5 mg/mL or less, 42 mg/mL or less, 41.5 mg/mL or less, 41 mg/mL or less, 40.5 mg/mL or less, 40 mg/mL or less, 39.5 mg/mL or less, 39 mg/mL or less, 38.5 mg/mL or less, 38 mg/mL or less, 37.5 mg/mL or less, 37 mg/mL or less, 36.5 mg/mL or less, 36 mg/mL or less, 35.5 mg/mL or less, 35 mg/mL or less, 34.5 mg/mL or less, 34 mg/mL or less, 33.5 mg/mL or less, 33 mg/mL or less, 32.5 mg/mL or less, 32 mg/mL or less, 31.5 mg/mL or less, 31 mg/mL or less, 30.5 mg/mL or less, 30 mg/mL or less, 29.5 mg/mL or less, 29 mg/mL or less, 28.5 mg/mL or less, 28 mg/mL or less, 27.5 mg/mL or less, 27 mg/mL or less, 26.5 mg/mL or less, 26 mg/mL, or 25.5 mg/mL or less of hydrophobic therapeutic agent(s). Thus, the nanoemulsion can comprise hydrophobic therapeutic agent in a concentration bounded by any of the aforementioned values, for example, 0.1 to 50 mg/mL, 0.2 to 49.5 mg/mL, 0.3 to 49 mg/mL, 0.4 to 48.5 mg/mL, 0.5 to 48 mg/mL, 0.6 to 47.5 mg/mL, 0.7 to 47 mg/mL, 0.8 to 46.5 mg/mL, 0.9 to 46 mg/mL, 1.0 to 45.5 mg/mL, 1.5 to 45 mg/mL, 2 to 44.5 mg/mL, 2.5 to 44 mg/mL, 3 to 43.5 mg/mL, 3.5 to 43 mg/mL, 4 to 42.5 mg/mL, 4.5 to 42 mg/mL, 5 to 41.5 mg/mL, 5.5 to 41 mg/mL, 6 to 39.5 mg/mL, 6.5 to 39 mg/mL, 7 to 38.5 mg/mL, 7.5 to 38 mg/mL, 8 to 37.5 mg/mL, 8.5 to 37 mg/mL, 9 to 36.5 mg/mL, 9.5 to 36 mg/mL, 10 to 35.5 mg/mL, 10.5 to 35 mg/mL, 11 to 34.5 mg/mL, 11.5 to 34 mg/mL, 12 to 33.5 mg/mL, 12.5 to 33 mg/mL, 13 to 32.5 mg/mL, 13.5 to 32 mg/mL, 14 to 31.5 mg/mL, 14.5 to 31 mg/mL, 15 to 30.5 mg/mL, 15.5 to 30 mg/mL, 16 to 29.5 mg/mL, 16.5 to 29 mg/mL, 17 to 28.5 mg/mL, 17.5 to 28 mg/mL, 18 to 27.5 mg/mL, 18.5 to 27 mg/mL, 19 to 26.5 mg/mL, 19.5 to 26 mg/mL, 20 to 25.5 mg/mL, 20.5 to 25 mg/mL, 21 to 24.5 mg/mL, 21.5 to 24 mg/mL, 22 to 23.5 mg/mL, or 22.5 to 23 mg/mL of hydrophobic therapeutic agent(s).

In an embodiment, the nanoemulsion comprises a hydrophobic therapeutic agent in a concentration of 0.05 to 50 mg mL$^{-1}$. In another embodiment, the nanoemulsion comprises a hydrophobic therapeutic agent in a concentration of 0.05 to 3 mg mL$^{-1}$. In yet another embodiment, the nanoemulsion comprises a hydrophobic therapeutic agent in a concentration of 0.1 to 50 mg mL$^{-1}$. In still yet another embodiment, the nanoemulsion comprises a hydrophobic therapeutic agent in a concentration of 0.5 to 2 mg mL$^{-1}$. In yet another embodiment, the nanoemulsion comprises a hydrophobic therapeutic agent in a concentration of 0.1 to 3 mg mL$^{-1}$.

In another embodiment, the nanoemulsion comprises a hydrophobic therapeutic agent in a concentration of 0.5 to 2 mg mL$^{-1}$. In yet another embodiment, the nanoemulsion comprises a hydrophobic In keeping with an aspect of the invention, a variety of hydrophobic compounds are useful with the emulsions of the invention. In an embodiment, the hydrophobic compound comprises a hydrophobic drug (e.g., hydrophobic therapeutic agent). In an embodiment, the hydrophobic drug is an antifungal drug, for example, amphotericin B, or a polyene antifungal such as, for example, candicidin, filipin, hamycin, natamycin, nystatin, rimocidin; an imidazole antifungal, such as, for example, bifonazole, butoconazole, clotrimazole, econazole, fenticonazole, isoconazole, ketoconazole, luliconazole, miconazole, omoconazole, oxiconazole, sertaconazole, sulconazole, tioconazole; a triazole antifungal such as albaconazole, efinaconazole, epoxiconazole, fluconazole, isavuconazole, itraconazole, posaconazole, propiconazole, ravuconazole, terconazole, voriconazole; and others, such as thiazoles, griseofulvin, among others.

In a preferred embodiment, the hydrophobic drug is a polyene antifungal agent. In another preferred embodiment, the hydrophobic drug comprises, consists essentially of, or consists of amphotericin B.

In some embodiments, the inventive nanoemulsion can comprise more than one hydrophobic or hydrophilic compound (e.g., 2 or more, 3 or more, 4 or more, etc.). In an embodiment, the therapeutic agent is selected from an anticancer agent, an antifungal agent, and combinations thereof.

In another embodiment, the hydrophobic drug is a hydrophobic anticancer drug, such as, for example, paclitaxel, doxorubicin, retinoic acid series, camptothecin, docetaxel, tamoxifen, anasterozole, topotecan, belotecan, irinotecan, gleevec and vincristine, among others.

The nanoemulsion can comprise the therapeutic agent in any suitable concentration. If the nanoemulsion of the invention comprises too little of the therapeutic agent, the nanoemulsion may not exhibit desirable efficacy. In contrast, if the nanoemulsion comprise too much of the therapeutic agent, the nanoemulsion may be unstable.

In embodiments, the therapeutic agent has a concentration selected from the range of 0.1 mg mL$^{-1}$ to 50 mg mL$^{-1}$ in the nanoemulsion, or a concentration selected from a range of 0.05 mg mL$^{-1}$ to 3 mg mL$^{-1}$ in the nanoemulsion.

The nanoemulsion can comprise any suitable amount of hydrophilic therapeutic agent. If the nanoemulsion comprises too little hydrophilic therapeutic agent, the nanoemulsion may not exhibit suitable activity. In contrast, if the nanoemulsion comprises too much hydrophilic agent, the nanoemulsion may exhibit undesirable properties (e.g., instability or increased toxicity). Typically, the nanoemulsion comprises 0.05 mg/mL or more of one or more hydrophilic therapeutic agent(s), for example, 0.1 mg/mL 0.2 mg/mL or more, 0.3 mg/mL or more, 0.4 mg/mL or more, 0.5 mg/mL or more, 0.6 mg/mL or more, 0.7 mg/mL or more, 0.8 mg/mL or more, 0.9 mg/mL or more, 1 mg/mL or more, 1.5 mg/mL or more, 2 mg/mL or more, 2.5 mg/mL or more, 3 mg/mL or more, 3.5 mg/mL or more, 4 mg/mL or more, 4.5 mg/mL or more, 5 mg/mL or more, 5.5 mg/mL or more, 6 mg/mL or more, 6.5 mg/mL or more, 7 mg/mL or more, 8 mg/mL or more, 8.5 mg/mL or more, or 9 mg/mL or more, 9.5 mg/mL or more, 10 mg/mL or more, 10.5 mg/mL or more, 11 mg/mL or more, 11.5 mg/mL or more, 12 mg/mL or more, 12.5 mg/mL or more, 13 mg/mL or more, 13.5 mg/mL or more, 14 mg/mL or more, 14.5 mg/mL or more, 15 mg/mL or more, 15.5 mg/mL or more, 16 mg/mL or more, 16.5 mg/mL or more, 17 mg/mL or more, 17.5 mg/mL or more, 18 mg/mL or more, 18.5 mg/mL or more, 19 mg/mL or more, 19.5 mg/mL or more, 20 mg/mL or more, 20.5 mg/mL or more, 21 mg/mL or more, 21.5 mg/mL or more, 22 mg/mL or more, 22.5 mg/mL or more, 23 mg/mL or more, 23.5 mg/mL or more, 24 mg/mL or more, 24.5 mg/mL or more, or 25 mg/mL or more of hydrophilic therapeutic agent(s). Alternatively, or in addition, the nanoemulsion can comprise 50 mg/mL or less of hydrophilic therapeutic agent(s), for example, 49.5 mg/mL or less, 49 mg/mL or less, 48.5 mg/mL or less, 48 mg/mL or less, 47.5 mg/mL or less, 47 mg/mL or less, 46.5 mg/mL or less, 46 mg/mL or less, 45.5 mg/mL or less, 45 mg/mL or less, 44.5 mg/mL or less, 44 mg/mL or less, 43.5 mg/mL or less, 43 mg/mL or less, 42.5 mg/mL or less, 42 mg/mL or less, 41.5 mg/mL or less, 41 mg/mL or less, 40.5 mg/mL or less, 40 mg/mL or less, 39.5 mg/mL or less, 39 mg/mL or less, 38.5 mg/mL or less, 38 mg/mL or less, 37.5 mg/mL or less, 37 mg/mL or less, 36.5 mg/mL or less, 36 mg/mL or less, 35.5 mg/mL or less, 35 mg/mL or less, 34.5 mg/mL or less, 34 mg/mL or less, 33.5 mg/mL or less, 33 mg/mL or less, 32.5 mg/mL or less, 32 mg/mL or less, 31.5 mg/mL or less, 31 mg/mL or less, 30.5 mg/mL or less, 30 mg/mL or less, 29.5 mg/mL or less, 29 mg/mL or less, 28.5 mg/mL or less, 28 mg/mL or less, 27.5 mg/mL or less, 27 mg/mL or less, 26.5 mg/mL or less, 26 mg/mL, or 25.5 mg/mL or less of hydrophilic therapeutic agent(s). Thus, the nanoemulsion can comprise hydrophilic therapeutic agent in a concentration bounded by any of the aforementioned values, for example, 0.1 to 50 mg/mL, 0.2 to 49.5 mg/mL, 0.3 to 49 mg/mL, 0.4 to 48.5 mg/mL, 0.5 to 48 mg/mL, 0.6 to 47.5 mg/mL, 0.7 to 47 mg/mL, 0.8 to 46.5 mg/mL, 0.9 to 46 mg/mL, 1.0 to 45.5 mg/mL, 1.5 to 45 mg/mL, 2 to 44.5 mg/mL, 2.5 to 44 mg/mL, 3 to 43.5 mg/mL, 3.5 to 43 mg/mL, 4 to 42.5 mg/mL, 4.5 to 42 mg/mL, 5 to 41.5 mg/mL, 5.5 to 41 mg/mL, 6 to 39.5 mg/mL, 6.5 to 39 mg/mL, 7 to 38.5 mg/mL, 7.5 to 38 mg/mL, 8 to 37.5 mg/mL, 8.5 to 37 mg/mL, 9 to 36.5 mg/mL, 9.5 to 36 mg/mL, 10 to 35.5 mg/mL, 10.5 to 35 mg/mL, 11 to 34.5 mg/mL, 11.5 to 34 mg/mL, 12 to 33.5 mg/mL, 12.5 to 33 mg/mL, 13 to 32.5 mg/mL, 13.5 to 32 mg/mL, 14 to 31.5 mg/mL, 14.5 to 31 mg/mL, 15 to 30.5 mg/mL, 15.5 to 30 mg/mL, 16 to 29.5 mg/mL, 16.5 to 29 mg/mL, 17 to 28.5 mg/mL, 17.5 to 28 mg/mL, 18 to 27.5 mg/mL, 18.5 to 27 mg/mL, 19 to 26.5 mg/mL, 19.5 to 26 mg/mL, 20 to 25.5 mg/mL, 20.5 to 25 mg/mL, 21 to 24.5 mg/mL, 21.5 to 24 mg/mL, 22 to 23.5 mg/mL, or 22.5 to 23 mg/mL of hydrophilic therapeutic agent(s).

In an embodiment, the nanoemulsion comprises a hydrophilic therapeutic agent in a concentration of 0.05 to 50 mg mL$^{-1}$. In another embodiment, the nanoemulsion comprises a hydrophilic therapeutic agent in a concentration of 0.05 to 3 mg mL$^{-1}$. In yet another embodiment, the nanoemulsion comprises a hydrophilic therapeutic agent in a concentration of 0.1 to 50 mg mL$^{-1}$. In still yet another embodiment, the nanoemulsion comprises a hydrophilic therapeutic agent in a concentration of 0.5 to 2 mg mL$^{-1}$. In yet another embodiment, the nanoemulsion comprises a hydrophilic therapeutic agent in a concentration of 0.1 to 3 mg mL$^{-1}$.

In an embodiment, the nanoemulsion comprises a hydrophilic therapeutic agent in a concentration of 0.1 to 5 mg mL$^{-1}$, optionally for some applications a concentration of 0.5 to 2 mg mL$^{-1}$.

In one embodiment, a nanoemulsion of the invention includes wherein the therapeutic agent is amphotericin B and said amphotericin B has a concentration of between about 0.05 mg mL$^{-1}$ to 3 mg mL$^{-1}$ relative to the hydrophobic liquid in said emulsion.

As described above, the present invention provides emulsions, such as emulsions comprising a continuous phase and a dispersed phase. In certain embodiments, the aqueous solution of the continuous phase comprises a saline solution. In embodiments, for example, the aqueous solution of the continuous phase is isotonic to blood plasma. In an embodiment, the dispersed phase comprises a plurality of droplets dispersed in the continuous phase. In embodiments, for example, the droplets dispersed in the continuous phase comprise self-assembled supramolecular structures. Various emulsion embodiments do not include micelle-based solutions, but instead comprise droplets of the dispersed phase suspended in the continuous phase.

In embodiments, the nanoemulsions of the invention include where the therapeutic agent is amphotericin B and said nanoemulsion provides reduced toxicity effects of the nanoemulsion upon administration of the nanoemulsion to a mammalian subject as compared to an emulsion in the absence of the ionic liquid composition. The reduced toxicity effect may be due at least in part due to reduced aggregation of amphotericin B upon storage in said nanoemulsion and/or upon administration of said nanoemulsion to the mammalian subject.

In some embodiments, the nanoemulsion comprises a hydrophilic therapeutic agent. A hydrophilic therapeutic agent includes hydrophilic members of the group consisting of analgesics, anti-inflammatory agents, anthelmintics, anti-arrhythmic agents, anti-asthma agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, immunosuppressants, anti-protozoal agents, anti-thyroid agents, anti-tussives, anxiolytic, sedatives, hypnotics, neuroleptics, β-Blockers, cardiac inotropic agents, diuretics, anti-parkinsonian agents, gastro-intestinal agents, histamine H, -receptor antagonists, keratolytics, lipid regulating agents, muscle relaxants, anti-anginal agents, nutritional agents, analgesics, sex hormones, stimulants, cytokines, peptidomimetics, peptides, proteins, toxoids, sera, antibodies, and mixtures thereof.

Anticancer agents which are hydrophilic in nature include, cisplatin, carboplatin, oxaliplatin, vincristine, vinblastine, 5-fluorouracil (5-FU), mitomycin, cyclophosphamide, methotrexate, mitoxantron, topotecan, capecitabine, doxifluridine, irinotecan, tegafur, chlorambucil, belotecan, anasterozole, gleevec, floxuridine, leuprolide, flutamide, zoledronate, streptozocin, vinorelbine, hydroxyurea, retinoic acid, meclorethamine, busulfan, prednisone, mechlorethamine, dexamethasone, prednisolone, gemcitabine, and any combinations of the above or derivatives thereof.

The present invention also includes a pharmaceutical composition comprising a nanoemulsion of the invention to be administered to a mammal, e.g., a human. A pharmaceutical composition is "pharmaceutically acceptable" which refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk. In one embodiment of the invention, the pharmaceutical compositions of the present invention can be formulated into a variety of suitable formulations and administered orally, in aerosol form, parenterally, subcutaneously, intravenously, intramuscularly, intraperitoneally, interperitoneally, rectally, topically and vaginally.

The present invention also includes a method of delivering a hydrophobic therapeutic agent to a mammalian subject in need thereof. The method can include the steps of providing a nanoemulsion according to the invention, as a pharmaceutically acceptable formulation, and administering an effective amount of the emulsion to the subject. Preferably, the therapeutic agent is released from the emulsion after delivery to the subject. The method also includes wherein therapeutic agents administered via the methods of the invention exhibit reduced toxicity effects of the therapeutic agent in the mammalian subject as compared administration of the therapeutic agent in the absence of a nanoemulsion comprising the ionic liquid composition.

The present invention also includes a method of making a nanoemulsion, which may include the steps of: providing a composition according to the present invention, optionally including one or more of a hydrophobic liquid, an aqueous solution, an ionic liquid composition comprising a mixture of a hydrophilic ionic liquid and an at least partially hydrophobic ionic liquid according to the present invention; and emulsifying the composition to create the emulsion.

Compositions may be presented in unit dosage form, e.g., in ampules or vials, or in multi-dose containers, with or without an added preservative. The composition can be a solution, a suspension, or an emulsion in oily or aqueous vehicles, and may contain formulatory agents, such as suspending, stabilizing and/or dispersing agents. A suitable solution is isotonic with the blood of the recipient and is illustrated by saline, Ringer's solution, and dextrose solution. Alternatively, compositions may be in lyophilized powder form, for reconstitution with a suitable vehicle, e.g., sterile, pyrogen-free water or physiological saline. The compositions also may be in the form of a depot preparation. Such long-acting compositions may be administered by implantation (for example, subcutaneously or intramuscularly) or by intramuscular injection.

With respect to the administration of compositions of the invention, the terms "individual," "subject," "host," and "patient," used interchangeably herein, refer to any mammalian subject for whom diagnosis, treatment, or therapy is desired. In one preferred embodiment, the individual, subject, host, or patient is a human. Other subjects may include, but are not limited to, cattle, horses, dogs, cats, guinea pigs, rabbits, rats, primates, and mice.

Administration Schedules

In general, the compositions disclosed herein may be used at appropriate dosages defined by routine testing, to obtain optimal physiological effect, while minimizing any potential toxicity. The dosage regimen may be selected in accordance with a variety of factors including age, weight, sex, medical condition of the patient; the severity of the condition to be treated, the route of administration, and the renal and hepatic function of the patient.

Moreover, the dosage administration of the compositions may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile.

Specifically, the compositions may be administered at least once a week over the course of several weeks. In one embodiment, the compositions are administered at least once a week over several weeks to several months.

Statements Regarding Chemical Compounds and Nomenclature

In an embodiment, a composition or compound of the invention is isolated or purified. In an embodiment, an isolated or purified compound is at least partially isolated or purified as would be understood in the art. In an embodiment, the composition or compound of the invention has a chemical purity of 95%, optionally for some applications 99%, optionally for some applications 99.9%; optionally for some applications 99.99%, and optionally for some applications 99.999% pure.

As used throughout the present description, the expression "a group corresponding to" an indicated species expressly includes a radical (including a monovalent, divalent and trivalent radical) derived from that species.

The compounds of this invention and used with the methods or emulsions of the invention can contain one or more chiral centers. Accordingly, this invention is intended to include racemic mixtures, diasteromers, enantiomers, tautomers and mixtures enriched in one or more stereoisomer. The scope of the invention as described and claimed encompasses the racemic forms of the compounds as well as the individual enantiomers and non-racemic mixtures thereof.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

As used herein, the term "substituted" refers to a compound wherein a hydrogen is replaced by another functional group.

As used herein, the terms "alkylene" and "alkylene group" are used synonymously and refer to a divalent group derived from an alkyl group as defined herein. The invention includes compounds having one or more alkylene groups. Alkylene groups in some compounds function as attaching and/or spacer groups. For example, compounds of the invention may have substituted and/or unsubstituted $C_1$-$C_{50}$ alkylene, $C_1$-$C_{40}$ alkylene $C_1$-$C_{30}$ alkylene, $C_1$-$C_{20}$ alkylene, $C_1$-$C_{10}$ alkylene, $C_1$-$C_5$ alkylene, $C_1$-$C_4$ alkylene groups.

As used herein, the terms "cycloalkylene" and "cycloalkylene group" are used synonymously and refer to a divalent group derived from a cycloalkyl group as defined herein. The invention includes compounds having one or more cycloalkylene groups. Cycloalkyl groups in some compounds function as attaching and/or spacer groups. Compounds of the invention may have substituted and/or unsubstituted $C_3$-$C_{20}$ cycloalkylene, $C_3$-$C_{10}$ cycloalkylene and $C_3$-$C_5$ cycloalkylene groups.

As used herein, the term "halo" refers to a halogen group such as a fluoro (—F), chloro (—Cl), bromo (—Br), iodo (—I) or astato (—At).

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl(alkoxy)$_n$-alkoxy wherein n is an integer from 1 to 10, preferably 1 to 4, and more preferably for some embodiments 1 to 3.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, or 7-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkoxyalkyl group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein me refers to —CH$_3$, et refers to —C$_2$H$_5$, and MeO— refers to CH$_3$O—.

As to any of the groups described herein which contain one or more substituents, it is understood that such groups do not contain any substitution or substitution patterns which are sterically impractical and/or synthetically non-feasible. In addition, the compounds of this invention include all stereochemical isomers arising from the substitution of these compounds. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others: halogen, including fluorine, chlorine, bromine or iodine; pseudohalides, including —CN;

—COOR where R is a hydrogen or an alkyl group or an aryl group and more specifically where R is a methyl, ethyl, propyl, butyl, or phenyl group all of which groups are optionally substituted;

—COR where R is a hydrogen or an alkyl group or an aryl group and more specifically where R is a methyl, ethyl, propyl, butyl, or phenyl group all of which groups are optionally substituted;

—CON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—OCON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—N(R)$_2$ where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring which can contain one or more double bonds and can contain one or more additional carbon atoms;

—SR, where R is hydrogen or an alkyl group or an aryl group and more specifically where R is hydrogen, methyl, ethyl, propyl, butyl, or a phenyl group, which are optionally substituted;

—SO$_2$R, or —SOR where R is an alkyl group or an aryl group and more specifically where R is a methyl, ethyl, propyl, butyl, or phenyl group, all of which are optionally substituted;

—OCOOR where R is an alkyl group or an aryl group;

—SO$_2$N(R)$_2$ where each R, independently of each other R, is a hydrogen, or an alkyl group, or an aryl group all of which are optionally substituted and wherein R and R can form a ring which can contain one or more double bonds and can contain one or more additional carbon atoms;

—OR where R is H, an alkyl group, an aryl group, or an acyl group all of which are optionally substituted. In a particular example R can be an acyl yielding —OCOR" where R" is a hydrogen or an alkyl group or an aryl group and more specifically where R" is methyl, ethyl, propyl, butyl, or phenyl groups all of which groups are optionally substituted; and —NO$_2$.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

As to any of the above groups which contain one or more substituents, it is understood that such groups do not contain any substitution or substitution patterns which are sterically impractical and/or synthetically non-feasible. In addition, the compounds of this invention include all stereochemical isomers arising from the substitution of these compounds.

Pharmaceutically acceptable salts comprise pharmaceutically-acceptable anions and/or cations. As used herein, the term "pharmaceutically acceptable salt" can refer to acid addition salts or base addition salts of the compounds in the present disclosure. A pharmaceutically acceptable salt is any salt which retains at least a portion of the activity of the parent compound and does not impart significant deleterious or undesirable effect on a subject to whom it is administered and in the context in which it is administered. Pharmaceutically acceptable salts include metal complexes and salts of both inorganic and organic acids. Pharmaceutically acceptable salts include metal salts such as aluminum, calcium, iron, magnesium, manganese and complex salts. Pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, -32-cilexetil, citric, edetic, edisylic, estolic, esyl, esylic, formic, fumaric, gluceptic, gluconic, glutamic, glycolic, glycolylarsanilic, hexamic, hexylresorcjnoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalacturonic, propionic, salicylic, stearic, succinic, sulfamic, sulfanlic, sulfonic, sulfuric, tannic, tartaric, teoclic, toluenesulfonic, and the like. Pharmaceutically acceptable salts may be derived from amino acids, including but not limited to cysteine. Other pharmaceutically acceptable salts may be found, for example, in Stahl et al., Handbook of Pharmaceutical Salts: Properties, Selection, and Use, Wiley-VCH; Verlag Helvetica Chimica Acta, Zürich, 2002. (ISBN 3-906390-26-8). Pharmaceutically-acceptable cations include among others, alkali metal cations (e.g., Lit, Nat, K$^+$), alkaline earth metal cations (e.g., Ca$^{2+}$, Mg$^{2+}$), non-toxic heavy metal cations and ammonium (NH$_4^+$) and substituted ammonium (N(R')$_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Br), sulfate, acetates (e.g., acetate, trifluoroacetate), ascorbates, aspartates, benzoates, citrates, and lactate.

The compounds of this invention can contain one or more chiral centers. Accordingly, this invention is intended to include racemic mixtures, diasteromers, enantiomers, tautomers and mixtures enriched in one or more stereoisomer. The scope of the invention as described and claimed encompasses the racemic forms of the compounds as well as the individual enantiomers and non-racemic mixtures thereof.

The following examples further illustrate the invention but, of course, should not be construed as in any way limiting its scope.

EXAMPLES

Dicholinium based ionic liquid may be referred to as either "CDIL", or "DC". For purposes herein the designations are equivalent.

Particle Size Determinations. Particle size and overall long-term stability of the prepared nanoemulsions were monitored using dynamic light scattering (DLS). The mean particle diameter was measured approximately every seven to fourteen days.

The following abbreviations are used herein: [Chol][Hex] refers to cholinium hexanoate IL; CP refers to cisplatin; PTX refers to paclitaxel; ITX refers to itraconazole; [DC-7] refers to a dication characterized by formula (64); [DC-ether] refers to a dication characterized by formula (74);

Characterization Methods $^1$H, $^{13}$C, and $^{19}$F NMR spectroscopy. $^1$H, $^{13}$C, and $^{19}$F NMR spectra were measured using a Bruker Avance III HD 400 MHz spectrometer or the Varian UI 500 MHz spectrometer. All spectra were measured with either $(CD_3)_2CO$, $CD_3OD$, or $D_2O$ as the solvent.

Figure 71:
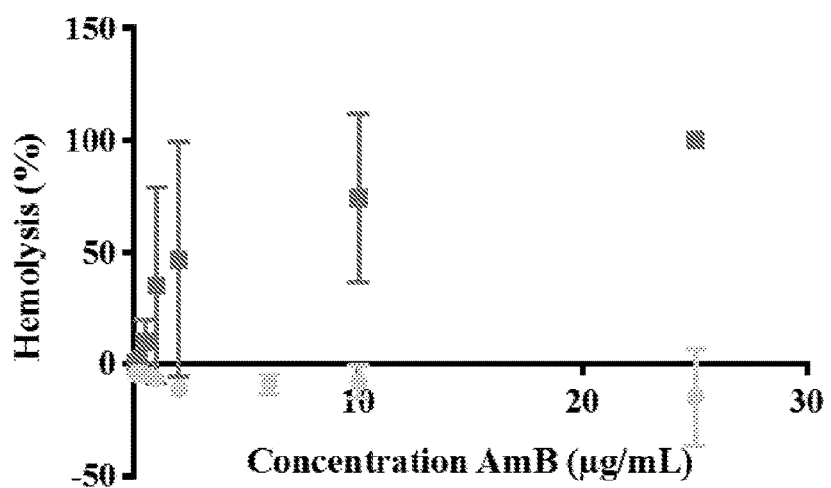
FIG. 71. In vitro hemolysis assay of AmB containing nanoemulsion after incubation with rabbit red blood cells at 37° C. for 1 hour. Error bars indicate standard deviation between two replicate trials.

Hemolysis Assay. A method to one previously described was adapted.[2] To determine the hemolytic activity of the ionic liquid nanoemulsion with amphotericin B, 10% suspended rabbit red blood cells (Lampire Biologic Laboratories, Inc. Pipersville, Pa.), were washed three times with PBS. For each wash, the cells were centrifuged at 2000 rpm for 4 min at 15° C. Cells were diluted 200-fold in PBS prior to analysis. The cell suspension was then further diluted 50:50 v/v with AmB-containing formulations. Samples were incubated at 37° C. with 200×g shaking for 1 hour. Samples were then removed and set on ice for 5 minutes to halt hemolysis. The samples were centrifuged at 2000 rpm for 4 minutes at 15° C. to settle intact cells and cell debris. 100 µL portions of supernatant from each sample were transferred to a 96 well plate in triplicate. Sample hemoglobin absorbances were measured at 540 nm. The percentage of hemolysis was calculated as: $100 \times Abs_{sample} - Abs_{negative}/Abs_{positive} - Abs_{negative}$, where $Abs_{sample}$, $Abs_{negative}$, and $Abs_{positive}$ refer to the absorbances of sample supernatants, negative control supernatant, and positive control supernatants incubated with rabbit red blood cells, respectively. The concentrations of AmB-containing formulations were 0.1 µg/mL, 0.25 µg/mL, 0.5 µg/mL, 2 µg/mL, 6 µg/mL, 10 µg/mL, and 25 µg/mL. The positive control sample, in which total lysis of cells was achieved was prepared with the rabbit red blood cells in the presence of 25 µg/mL AmB sodium deoxycholate (Amphotericin B for Injection USP, X-GEN Pharmaceuticals, Horseheads, N.Y.), also referred to as FUNGIZONE™. Amphotericin B for Injection USP was rehydrated according to the manufacturer's instructions. Nanoemulsion samples were prepared by dilution of nanoemulsion with phosphate buffered saline in sterile conditions. Incubation of red blood cells with phosphate buffered saline served as the negative control. All AmB containing samples were shielded from light during the analysis. To correct for scattering of nanoemulsion, nanoemulsion without drug was used as the background (FIG. 71).

Minimum Inhibitory Concentration (MIC) analysis. The following method was adapted from previously analyzed MIC studies of Amphotericin B.[2] A fluconazole resistant strain of *Candida albicans*, K1, was used in antifungal efficacy studies. The strain was subcultured on Sabouraund dextrose agar (SDA) plates and grown in YPD medium. To prepare the inoculum, fungal strains were cultured for approximately 24 hours on SDA plates. SDA plates were adjusted to $1 \times 10^3$ CFU/mL in RPMI 1640 buffered to pH 7.0 with MOPS. Fungi were added to serial dilutions of emulsion with drug concentrations of $55 \times 10^{-3}$-28.5 µg/mL in 96-well plates using the microdilution method. Plates were incubated at 37° C. throughout the study. Plates were analyzed by absorbance (OD600, 530 nm) at 24 h and 48 h using a Synergy H1 microplate reader (BioTek). The minimum inhibitory concentration is identified as the concentration range in which a low absorbance value (corresponding to minimal fungi) increases, indicating increased fungal growth. As 1 has previously been shown to exhibit antifungal activity, we conducted a control experiment with a nanoemulsion containing no drug. This did not exhibit any antifungal activity, demonstrating that all antifungal activity observed corresponded solely to the AmB.

Note: The increased absorbance values for higher concentrations of AmB with the AmB nanoemulsions and Fungizone® can be attributed to the scattering of the emulsion or sodium deoxycholate aggregated, increasing the absorbance.

TABLE S3

Absorbance at 530 nm of formulations incubated with K1 strain *Candida Albicans* at 37° C. for 24 h.

| | No fungi control | 28.5 µg/mL AmB | 14.25 µg/mL AmB | 7.125 µg/mL AmB | 3.5625 µg/mL AmB | 1.78 µg/mL AmB | 0.89 µg/mL AmB | 0.44 µg/mL AmB | 0.22 µg/mL AmB | 0.11 µg/mL AmB | 0.055 µg/mL AmB |
|---|---|---|---|---|---|---|---|---|---|---|---|
| AmB nano | 0.825 | 1.579 | 0.992 | 0.524 | 0.327 | 0.197 | 0.137 | 0.087 | 0.075 | 0.067 | 0.076 |
| AmB nano | 0.134 | 1.573 | 1.017 | 0.599 | 0.349 | 0.209 | 0.132 | 0.097 | 0.077 | 0.069 | 0.092 |
| AmB nano | 0.045 | 1.47 | 0.988 | 0.605 | 0.381 | 0.223 | 0.147 | 0.104 | 0.081 | 0.071 | 0.066 |
| No Drug nano | 0.038 | 1.488 | 0.782 | 0.453 | 0.271 | 0.167 | 0.119 | 0.209 | 0.269 | 0.267 | 0.26 |
| No Drug nano | 0.046 | 1.411 | 0.828 | 0.481 | 0.293 | 0.187 | 0.129 | 0.164 | 0.282 | 0.275 | 0.266 |
| No Drug nano | 0.056 | 1.45 | 0.852 | 0.484 | 0.294 | 0.179 | 0.13 | 0.155 | 0.275 | 0.263 | 0.268 |
| Fungizone control | 0.037 | 0.383 | 0.253 | 0.218 | 0.139 | 0.095 | 0.077 | 0.063 | 0.055 | 0.052 | 0.05 |
| Fungizone control | 0.037 | 0.359 | 0.239 | 0.249 | 0.153 | 0.106 | 0.083 | 0.067 | 0.058 | 0.054 | 0.052 |

TABLE S4

Absorbance at 530 nm of formulations incubated with K1 strain *Candida Albicans* at 37° C. for 48 h.

|  | No fungi control | 28.5 µg/mL AmB | 14.25 µg/mL AmB | 7.125 µg/mL AmB | 3.562 µg/mL AmB | 1.78 µg/mL AmB | 0.89 µg/mL AmB | 0.44 µg/mL AmB | 0.22 µg/mL AmB | 0.11 µg/mL AmB | 0.055 µg/mL AmB |
|---|---|---|---|---|---|---|---|---|---|---|---|
| AmB nano | 0.793 | 1.526 | 1.014 | 0.535 | 0.332 | 0.198 | 0.138 | 0.088 | 0.088 | 0.21 | 0.299 |
| AmB nano | 0.173 | 1.592 | 1.041 | 0.598 | 0.342 | 0.207 | 0.131 | 0.098 | 0.091 | 0.236 | 0.276 |
| AmB nano | 0.057 | 1.467 | 1.01 | 0.645 | 0.47 | 0.22 | 0.154 | 0.103 | 0.086 | 0.227 | 0.255 |
| No Drug nano | 0.188 | 1.099 | 0.88 | 0.522 | 0.307 | 0.208 | 0.223 | 0.347 | 0.411 | 0.392 | 0.364 |
| No Drug nano | 0.123 | 1.247 | 0.924 | 0.551 | 0.391 | 0.225 | 0.274 | 0.311 | 0.39 | 0.379 | 0.366 |
| No Drug nano | 0.166 | 1.295 | 0.938 | 0.584 | 0.328 | 0.216 | 0.236 | 0.305 | 0.386 | 0.369 | 0.352 |
| Fungizone control | 0.038 | 0.376 | 0.242 | 0.21 | 0.133 | 0.092 | 0.075 | 0.061 | 0.054 | 0.05 | 0.052 |
| Fungizone control | 0.036 | 0.359 | 0.233 | 0.246 | 0.149 | 0.103 | 0.08 | 0.065 | 0.057 | 0.051 | 0.053 |

In Vivo Developmental Toxicity Study. An embryo-larval zebrafish (*Danio rerio*) model was used to evaluate the toxicity of the novel dicationic cholinium-based ionic liquid. The following protocol was taken from previously published protocol, analyzing the toxicity of a novel triphilic polymers for use as a component in a nanoemulsion.[1] Zebrafish of the AB strain were obtained from Dr. Michael Taylor at the University of Wisconsin-Madison School of Pharmacy, where the fish were cultured until sexual maturation. Zebrafish were maintained in a light/dark cycle of 14:10 h at 28.5° C. in egg water (0.03% Instant Ocean, Blacksburg, Va., USA). The adult fish were fed *Anemia nauplii* twice daily. Embryos were obtained from adult fish with a ratio of 1:2 for female to male. Six breeding groups were placed in separate spawning aquariums, equipped with a mesh bottom to prevent the eggs from being cannibalized. Crossing was induced in the morning. After one hour, eggs free of macroscopically discernible symptoms of infection and disease were collected, rinsed with egg water, and transferred into Petri dishes until chemical exposure. The embryo-larval toxicity assay was subsequently carried out. 8 fertilized eggs at 2 hours post fertilization (hpf) stage were added to a 24-well plate. Each well was filled with eggs and contained 600 µL of egg water. Six concentrations plus two controls (negative and positive) were plated. For analysis of [DC-7][2Br], sodium bis(trifluoromethylsulfonyl)imide, and [DC-7][2NTf$_2$] containing nanoemulsion the concentrations analyzed were 1 mM, 333 µM, 111 µM, 37 µM, 12.3 µM, and 4.1 µM. 1.5 mL of [DC-7][2NTf$_2$] was added to a 15 mL conical centrifuge tube followed by 1.5 mL of egg water. The sample was allowed to sit for 6 days prior to use. Each day, the sample was sonicated at 40° C. for 6 hours and then allowed to remain at room temperature for 18 hours. After 6 days, the sample was centrifuged at 2000 rpm for 5 minutes to ensure complete sedimentation of the ionic liquid. 1.2 mL of egg water was removed and served as the stock solution. This served as the highest concentration sample. Integration of the internal standard and [DC-7][2NTf$_2$] in the QNMR sample allowed for quantitation of the concentration of [DC-7][2NTf$_2$] present in the stock solution used for the zebrafish viability assay. The concentrations analyzed for [DC-7][2NTf$_2$] sample were 7.11 mM, 3.56 mM, 1.78 mM, 889 µM, 444 µM, and 222 µM.

The plates were covered and incubated at 28.5° C. in a light/dark cycle of 14:10 throughout the 96 hpf exposure period. The observations of zebrafish development were made directly in the well using a stereomicroscope (Nikon SMZ18) every 24 hours. The end points that were selected to monitor the effects of [DC-7][2Br], sodium bis(trifluoromethylsulfonyl)imide, [DC-7][2NTf$_2$] saturated water solution and nanoemulsion included mortality, spontaneous movement, hatching success, pericardial edema, and curved body axis. Embryos and larvae were considered dead when no heartbeat was observed. The number of hatched embryos and a cumulative mortality tally were recorded every 24 h after 2 hpf. At 96 hpf, following the final observations, representative larvae for [DC-7][2Br] and [DC-7][2NTf$_2$] saturated egg water were anesthetized with 0.4% tricaine mesylate solution and mounted on Petri dishes using low melting point agarose. These larvae were then photographed using a high-definition color microscope camera (Nikon DSFi2). Finally, all larvae used for the analysis were euthanized following.

REFERENCES (1) Barres, A. R.; Wimmer, M. R.; Mecozzi, S. Multicompartment Theranostic Nanoemulsions Stabilized by a Triphilic Semifluorinated Block Copolymer. *Mol. Pharm.* 2017, 14, 3916-3926.
(2) Alvarez, C.; Hwan, D.; Kwon, G. S. Reformulation of Fungizone by PEG-DSPE Micelles: Deaggregation and Detoxification of Amphotericin B. *Pharm. Res.* 2016, 33 (9), 2098-2106.

Example 1

This example demonstrates a method of making a nanoemulsion in accordance with an embodiment of the invention.

Figure 14:
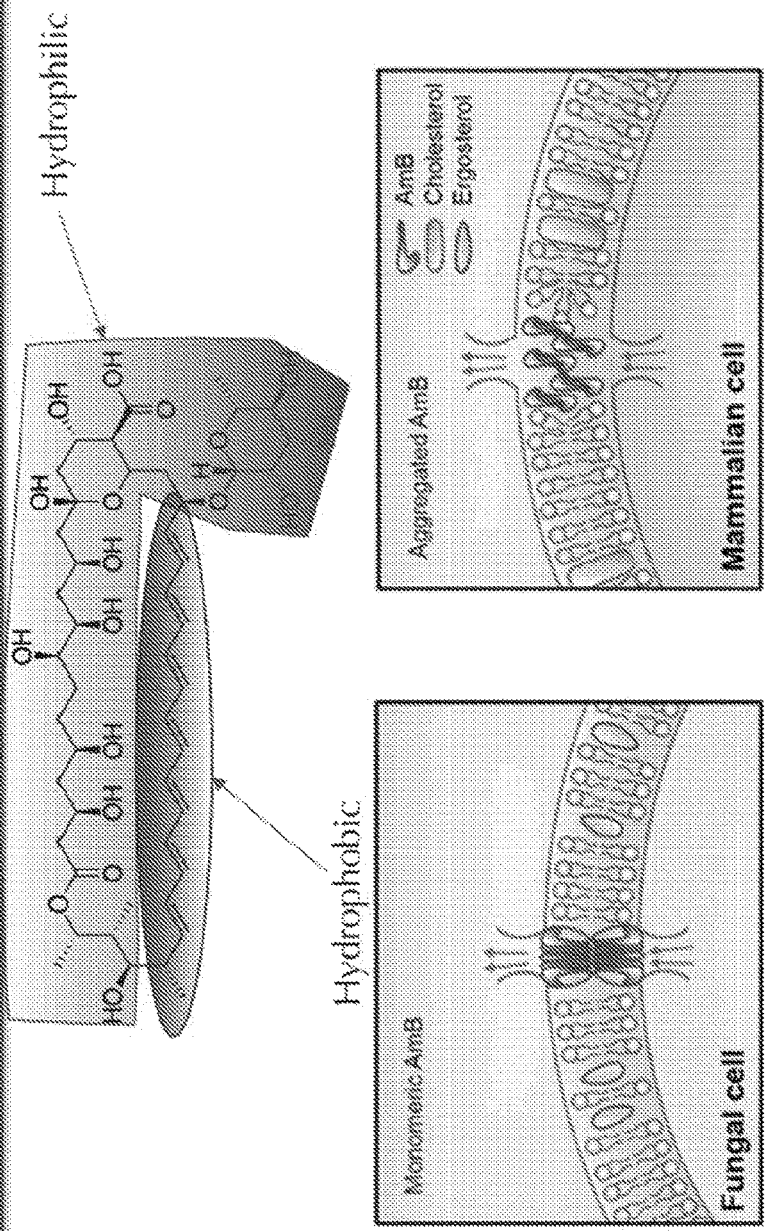
FIG. 14. An overview of the mechanism of action of AmB.
Figure 15:
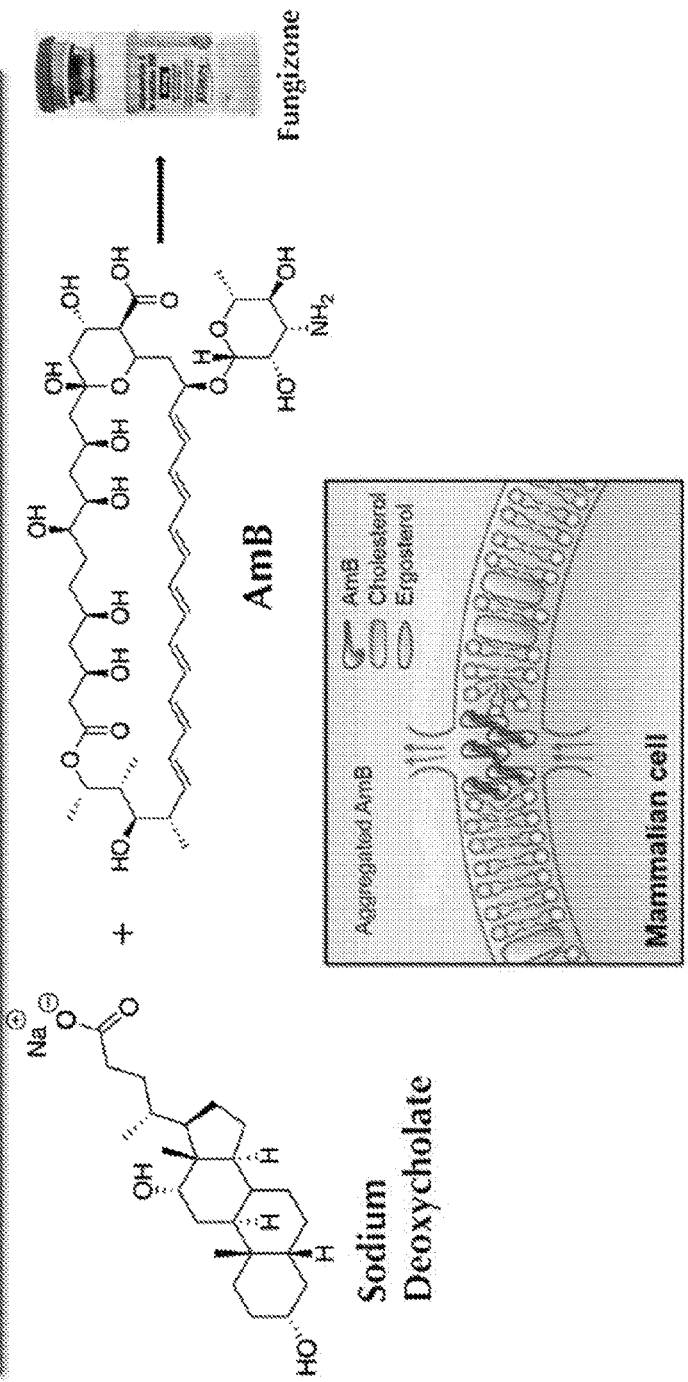
FIG. 15. An overview of the commercial formulation of AmB.

Example 1: Room-Temperature Ionic Liquid Based Nanoemulsions: Synthesis and Formulation for Delivery of Poorly Water Soluble Active Pharmaceutical Agents Amphotericin B (AmB) is a highly effective polyene antifungal agent typically used for invasive fungal infections. Despite the efficacy of this drug, there are major limitations to its use due to adverse side effects, including acute infusion-related febrile reactions and dose-dependent nephrotoxicity. These effects are attributed, at least in part, to the aggregation of AmB due to its poor water solubility. FIG. 13 provides an overview of the challenges in delivering Amphotericin B. FIG. 14 provides an overview of the mechanism of action of Amphotericin B. FIG. 15 provides an overview of the commercial formulation of Amphotericin B.

To overcome these problems, we have designed a novel potential drug delivery system that harnesses the unique properties of ionic liquids. Ionic liquids (ILs) are organic cations and anions whose melting point is below 100° C.; some of which are remarkably liquid at room temperature. ILs have been widely used in industrial applications due to their unique properties, namely negligible vapor pressure, low flammability, and excellent solvation capabilities. More recently, ILs have been explored in the pharmaceutical industry primarily as active pharmaceutical ingredient-ionic liquids (API-ILs).[1] However, there is burgeoning interest in the use of ILs as adjuvant components in drug delivery. Herein, we report the use of a mixture of a hydrophilic and a novel hydrophobic room temperature ionic liquid to serve as solvent for solubilization and deaggregation of AmB for use in an oil-in-water IL containing nanoemulsion drug delivery system.

High concentrations of AmB were solubilized in a hydrophilic cholinium room temperature ionic liquid, a novel hydrophobic dicationic cholinium-based ionic liquid, and in mixtures of the two. The absorption spectrum of AmB in the ionic liquid(s) and ionic liquid mixtures indicates excellent monomerization. In vivo biocompatibility of the novel dicationic cholinium-based ionic liquid ionic was analyzed using zebra-fish assays. The previously unstudied hydrophobic dicationic cholinium based ionic liquid was characterized using differential scanning calorimetry (DSC). In vitro biocompatibility of the nanoemulsions prepared with the hydrophobic dicationic-cholinium based ionic liquid were characterized using a cell viability assay. Nanoemulsions of the ionic liquid mixtures and ionic liquid mixtures with AmB were prepared and the hemolytic activity of these nanoemulsions were analyzed. AmB containing nanoemulsions exhibited negligible hemolytic activity. Antifungal activity of the AmB nanoemulsion formulation was evaluated against *Candida albicans* and antifungal activity of the AmB containing nanoemulsion was shown to be as effective as FUNGIZONE™ based on the minimum inhibitory concentration.

Relevant Background

Amphotericin B (AmB) is a highly effective and potent polyene antifungal agent that is effective against a wide variety of fungi, including *Asperguillus, Candida*, and *Cryptococcus* spp.[2-4] Intravenous administration of AmB serves as the mainstay therapeutic for systemic, severe fungal infections that are typically associated with high mortality.[5] While patient outcomes have improved remarkably over the past 50 years, opportunistic infections are still prevalent due to the increased number of persons with weakened immune systems (i.e. individuals undergoing chemotherapy, organ transplantation, and individuals with HIV/AIDS) and advancements and changes in healthcare practices. The precise mechanism of antifungal action of AmB is still not completely understood, yet the generally accepted mechanism includes: (1) cell sensitivity to polyene antibiotics is based on the presence of sterol in the membrane; (2) increased fungal cell sensitivity to AmB originates from its increased affinity for ergosterol-containing membranes (fungal cells) in comparison to cholesterol-containing membranes (mammalian cells); and (3) the mechanism of action is similar for both mammalian and fungal cells. AmB or AmB-sterol complexes form transmembrane pores. Such pores allow free diffusion of biologically necessary cell components, typically resulting in cell death.[2,4]

AmB has been cemented as the gold standard of antimycotics for decades, yet there are major limitations associated with the use of AmB due to several adverse side-effects, including dose-dependent nephrotoxicity. These effects are primarily associated with the aggregation state of AmB in aqueous solution due to the hydrophobicity of AmB, which results in its aggregation in aqueous solution. This hydrophobicity is a result of the unique molecular structure of AmB in which large hydrophilic and hydrophobic regions oppose one another. This self-aggregation results in a loss of binding specificity and consequential host toxicity.[6]

The most widely used intravenous formulation of AmB, termed FUNGIZONE™, is a mixture of AmB, a detergent sodium deoxycholate (1:2 mole ratio), and a buffer.[7] Despite the widespread use of FUNGIZONE™ the formulation suffers from concentration dependent aggregation and has severe adverse side-effects, most notably renal failure. One strategy that has been employed to improve the therapeutic index of AmB is the use of carrier systems to modulate organ distribution and aggregation state.

Ionic liquids are a class of molecules composed of organic cations and anions whose melting point is below 100° C.[8] ILs are customizable materials whose properties can be finely tuned through structural modifications within the cationic and anionic component. Because of the highly tunable nature of ILs, these compounds have been widely investigated for industrial applications as "task specific" designer solvent.[1,8] More recently, the tunable nature and excellent solvation properties of ILs has created a burgeoning interest in the use of ILs as adjuvant components in drug delivery, namely as (1) cosolvents; (2) emulsifiers; and (3) solvents or antisolvents for design of crystalline substances.[9-11] It has been demonstrated that a wide variety of pharmaceuticals can be solubilized extracted using in various ionic liquids.[1,10,12-14] One such pharmaceutical that has been analyzed includes AmB. Specifically, the effect of room temperature imidazolium based ionic liquids on the aggregation state of AmB has been analyzed using circular dichroism.[15] This study revealed that the nature of anion significantly affected the aggregation state of AmB.[15] Another study also demonstrated the ability to solubilize large amounts of AmB in a specifically tuned IL.[16] However, these findings could not be directly translated into increased therapeutic efficacy of AmB as (1) both imidazolium based ILs and ammonium based ILs have been shown to exhibit toxicity; and (2) the inherent water solubility of both ILs (water solubility of imidazolium based ILs and the use of a water soluble acetate anion) increases the likelihood of concentration dependent aggregation of AmB similar to FUNGIZONE™.[17] To prevent the inherent concentration dependent aggregation state of AmB, we designed a non-toxic and hydrophobic IL that is miscible with a biocompatible cholinium based IL that exhibited high solubilization of AmB for use in a novel oil-in-water nanoemulsion based delivery system of AmB.[18,19]

Data Summary: Rationale and Synthesis of Dicholinium Based IL

Figure 2:
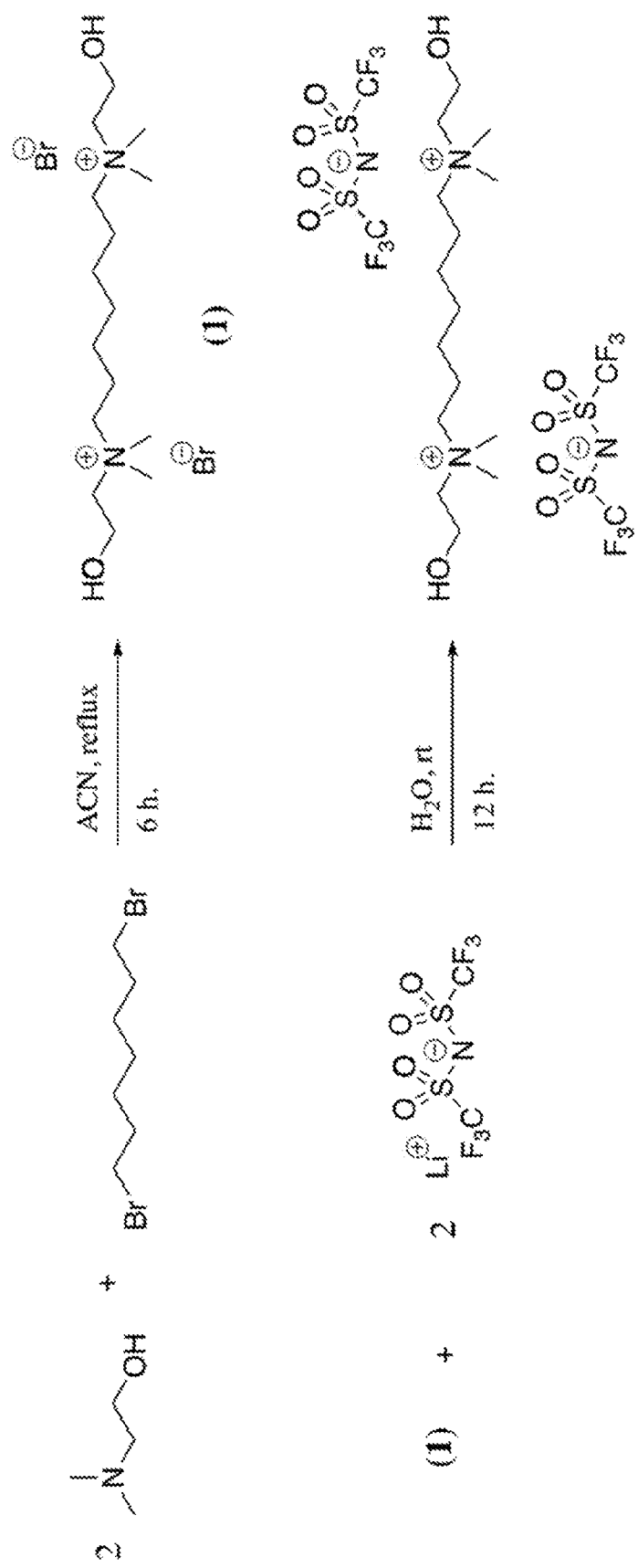
FIG. 2. Synthesis of dicationic cholinium based ionic liquid [DC-7][2NTf$_2$].
Figure 4:
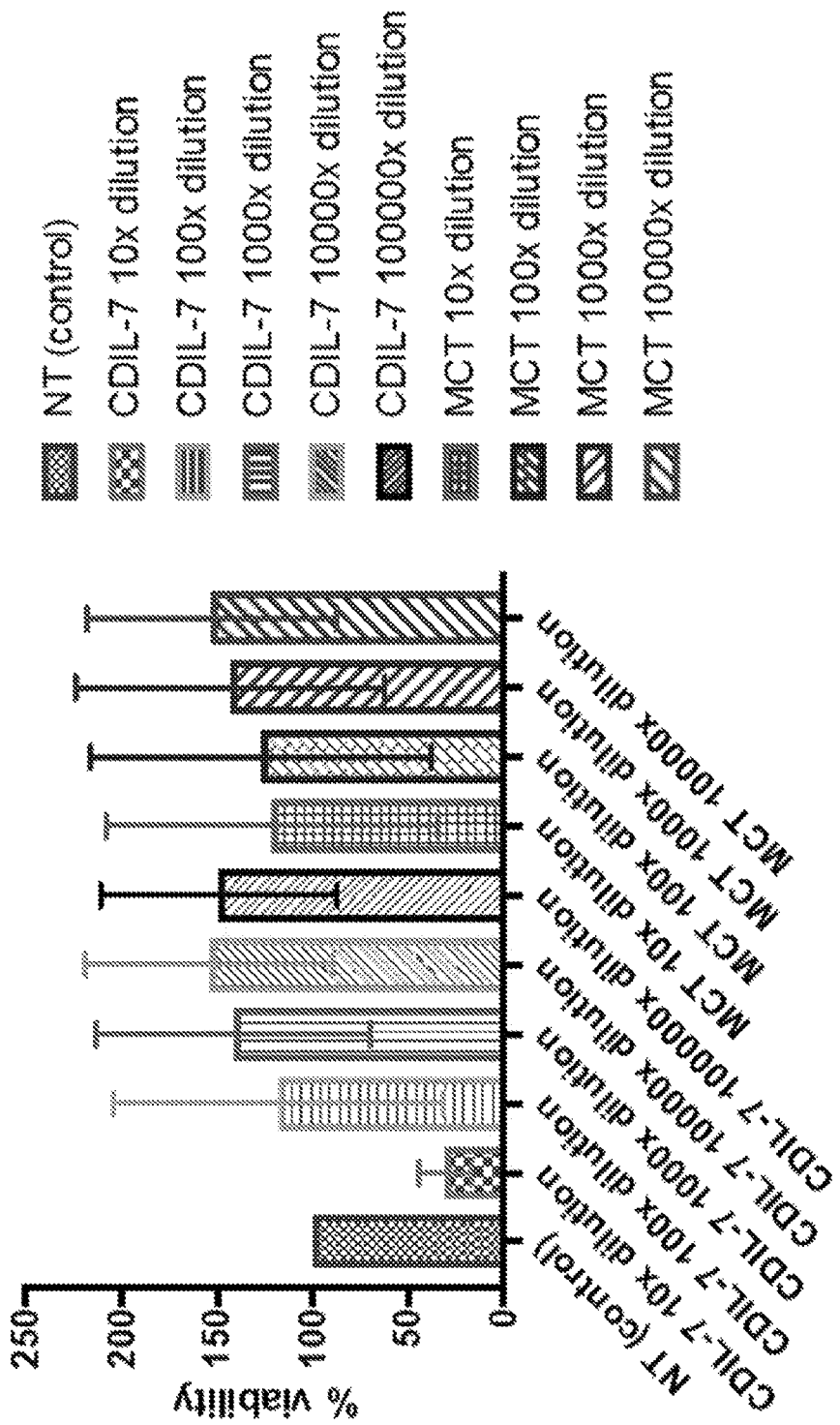
FIG. 4. Cell viability assay of [CDIL-7][2NTf$_2$] nanoemulsion with A549 human lung carcinoma cells after 24 hour incubation.

Hydrophobic ILs have characteristically been categorized as toxic. IL toxicity is predominantly related to the cationic structure. Specifically, hydrophobic ILs are typically formed from a combination of a hydrophobic anion and a cation with long-alkyl chains. These alkyl chains result in high toxicity due to interaction of these alkyl chains with the lipid bilayer of the cell membrane, resulting in cell death.[1,10,20] As such, it was thought that one method for decreasing the toxicity of a hydrophobic IL would be to eliminate the potential of the long-alkyl chains ability to interact with the lipid bilayer via tethering the long alkyl chain between two cationic headgroups. Recently, dicationic ILs have been garnering interest in a variety of research topics.[21-23] However, their use in pharmaceutical applications has been limited. Choline is a water-soluble vitamin-like nutrient. As such, it was selected as the cationic moiety head-group to limit the toxicity of the synthesized dication. This dicholinium cationic structure has only been mentioned once previously in the literature and was limited in scope with use of only water-soluble, halogen-based anions.[24] While choline is inherently water-soluble due to the hydrogen-bonding hydroxyl moiety, it was thought that introduction of two hydrophobic anions and the presence of a long alkyl linker would limit the water-solubility of the synthesized ILs. As such, the designed structure would allow for the solubilization of both hydrophobic and hydrophilic moieties due to the presence of both hydrophobic and hydrophilic regions. Bis(trifluoromethylsulfonly)imide was selected as the anion as it is both a hydrophobic anion and non-toxic. Dicationic precursor of the hydrophobic IL in the form of a bis (cholinium) dibromide was synthesized in a quaternization reaction using a modified method by Czerniak et. Al[21]. The hydrophobic dicholinium IL was afforded by using an anion-exchange metathesis reaction in water (FIG. 2).

Amphotericin B Solubility in ILs

Amphotericin B exhibited relatively high solubility in the novel dicholinium based ILs. Solubility of AmB in a morphilinium based ionic liquid was also relatively high. While the morphilinium based ionic liquid had been previously prepared, to the best of our knowledge, this ionic liquid had not been previously analyzed for the ability to solubilize hydrophobic drug and most certainly not AmB. This ionic liquid served as a comparison hydrophobic IL: (1) where the hydrophobicity was derived from a combination of both the bis(trifluoromethylsulfonyl)imide anion as well as the presence of a long, untethered alkyl chain with an expected increased toxicity; and (2) as a comparison hydrophobic monocationic IL.

TABLE 1

Loading of AmB and Paclitaxel in ILs

| Ionic Liquid | AmB (mg mL$^{-1}$) |
| --- | --- |
| [CDIL-7][2NTf$_2$] | 0.7 |
| [CDIL-6][2NTf$_2$] | 0.5 |
| [Morph$_{1,6}$][NTf$_2$] | 0.6 |
| [Chol][Hex] | 6 |

Characterization of [CDIL-7][2NTf$_2$]

Differential Scanning Calorimetry

Thermograms in a temperature range from −80° C. to 100° C. were recorded using a differential scanning calorimeter from Perkin Elmer, model DSC 7. The heating-cooling rate was 10° C. min$^{-1}$. The sample was equilibrated at 25° C. followed by heating to 100° C. An isothermal hold occurred for 10 minutes and then the sample was cooled to −80° C., followed by another isothermal hold for 10 minutes. The sample was then heated to 100° C. The melting point of [DC-7][2NTf$_2$] was determined to be 32° C. It was determined that [CDIL-7][2NTf$_2$] exhibits a freezing point at −8.78° C. and a melting point of 32.8° C. As such, the novel hydrophobic IL is indeed a room-temperature ionic liquid (FIGS. 61A-61D).

In Vitro Cell Viability Assays on A549 Human Lung Carcinoma Cells

In order to have a preliminary understanding on the toxicity profile of [CDIL-7][2NTf$_2$], cell viability assays of [CDIL-7][2NTf$_2$] containing nanoemulsion were analyzed using A549 human lung carcinoma cells. [CDIL-7][2NTf$_2$] itself could not be directly analyzed using an in vitro cell viability assay due to the hydrophobicity and density of [CDIL-7][2NTf$_2$]. The nanoemulsion studied was prepared with 10 mM N-(carbonyl-methoxypolyethyleneglycol 2000)-1,2-distearoyl-sn-glycero-3-phosphoethanolamine (M2DSPE) surfactant, 1 mL [CDIL-7][2NTf$_2$], and 1 mL medium chain triglycerides (MCT) from coconut oil. All three replicate trials show minimal toxicity. A control nanoemulsion containing only biocompatible MCT was also analyzed and similarly exhibited low toxicity.

In vitro studies were completed prior to completion of the hemolysis assays. [DC-7][2NTf$_2$] itself could not be directly analyzed using an in vitro cell viability assay due to the hydrophobicity and density of [DC-7][2NTf$_2$]. As such, a nanoemulsion containing the ionic liquid was analyzed. Three-day cytotoxicity studies were performed on A549 human lung adenocarcinoma cell line. The nanoemulsion studied was prepared with 10 mM N-(Carbonyl-methoxy-polyethyleneglycol 2000)-1,2-distearoyl-sn-glycero-3-phosphoethanolamine (M2DSPE) surfactant, 1 mL [DC-7][2NTf$_2$], and 1 mL medium chain triglycerides (MCT) from coconut oil with 16 mL saline (0.9% w/w sodium chloride). A nanoemulsion was prepared with 2 mL MCT, 10 mM M2DSPE as a control. A549 cells were cultured in RPMI-1640 media containing 10% (v/v) heat inactivated fetal bovine serum and 1% (v/v) penicillin-streptomycin. Cells were grown into a monolayer in tissue culture plates incubated at 37° C. in a 5% CO2 atmosphere and 90% relative humidity. For the viability assay, cells were added to a 96-well plate at a cell density of 3000 cells/well and incubated for 24 h. Both nanoemulsions were used from previous preparations (i.e. they were not prepared the day of plating). Nanoemulsion solutions at varying concentrations were prepared in RPMI 1640 immediately before plating. A 10 μL aliquot of each solution and 90 μL of the supplemented RPMI 1640 were added to each well. The cells were then incubated with the RPMI 1640 control and [DC-7][2NTf$_2$] containing nanoemulsion for 24 hrs. After 24 hrs of incubation, the assay was carried out following the manufacturers protocol (CellTiter-Blue® Cell Viability Assay). 100 μL of diluted CellTiter blue was added to each well after removing previous media. The fluorescence signal was measured 2 h after addition of the dye. A minimum of six wells was used for each sample. The fluorescence signals of the wells were averaged (n=6) and represented as percentages of cell viability determined using untreated cells as the control (100% viability).

In Vivo Zebra Fish Toxicity Studies

To determine the in vivo toxicity of the prepared dicholinium based ionic liquids, the water soluble [CDIL-7][2Br] and a [CDIL-7][2NTf$_2$] containing nanoemulsion were evaluated using a zebrafish developmental toxicity assay. The nanoemulsion was prepared with 10 mM M2DSPE as surfactant, 1 mL [CDIL-7][2NTf$_2$], and 1 mL MCT. Both the water-soluble salt and analyzed hydrophobic containing nanoemulsion exhibited minimal toxicity. [CDIL-7][2Br] had a 100% survival rate at 1 mM concentration 96 hours post fertilization (FIG. 5A) and exhibited no birth defects.

Similarly, 100% survival was observed 96 hours post fertilization at concentration of 333 μM [CDIL-7][2NTf$_2$] in a nanoemulsion (FIG. 5B). As such, the in vivo toxicity of the novel hydrophobic [CDIL-7][NTf$_2$] was established to be extremely low.

Particle Size Determination

Particle size was determined by dynamic light scattering (DLS). AmB containing nanoemulsion and nanoemulsion without AmB were prepared. Nanoemulsions were prepared with 10 mM 1,2-Distearoyl rac-glycerol, methoxypolyethylene glycol molecular weight 2000 (M2DSG), 0.3 mL [CDIL-7][2NTf$_2$], 0.2 mL [Chol][Hex], and 1.5 mL MCT.

The prepared nanoemulsions have a particle size of −166±59 nm after 21 days of stability. Nanoemulsions are still stable and will continuously be analyzed every 7 days until a particle size of 500 nm is reached or nanoparticles exhibit instability.

Deaggregation of AmB in IL and IL-Mixtures

As the aggregation state of AmB is directly related to the toxicity, the aggregation state of AmB was studied in the prepared IL and IL-mixtures to determine the potential for use as a novel drug delivery system. Measuring the absorbance of AmB using UV/vis spectroscopy provides insight into the aggregation state of AmB. In all of the ionic liquid mixtures analyzed, AmB is in the non-toxic monomeric form. However, due to the increased ability of [CDIL-7][2NTf$_2$] to solubilize AmB and anticipated decreased water solubility, [CDIL-7][2NTf$_2$] was selected as the hydrophobic ionic liquid for use in nanoemulsion formulation.

Due to the high solubility of AmB in [Chol][Hex] and the inherent water-solubility of [Chol][Hex], we analyzed AmB solely in [Chol][Hex]. However, similarly to the AmB deoxycholate formulation, this suffered from concentration dependent aggregation. Namely, above the critical aggregation concentration of AmB it is primarily in the monomeric form. However, upon dilution a substantial amount of AmB began to form aggregates. As such, the combination of [Chol][Hex] and [CDIL-7][2NTf$_2$] is required for (1) high AmB solubility (afforded primarily by [Chol][Hex]); (2) deaggregation of AmB (afforded by [CDIL-7][2NTf$_2$]); and (3) limited water solubility (afforded solely by [CDIL-7][2NTf$_2$]).

In Vitro Hemolysis Assay

Figure 9:
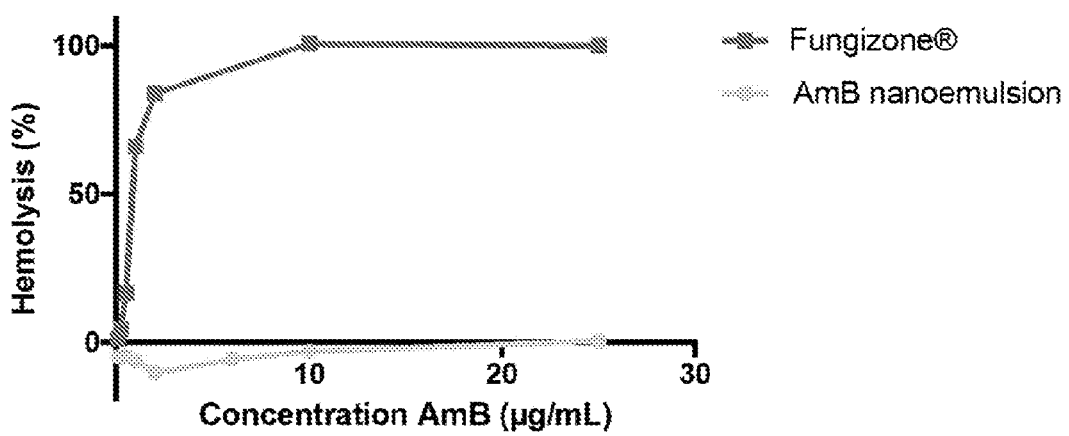
FIG. 9. Percent hemolysis of rabbit red blood cells with AmB containing nanoemulsion and FUNGIZONE™ after 1-hour incubation at 37° C.
Figure 10:
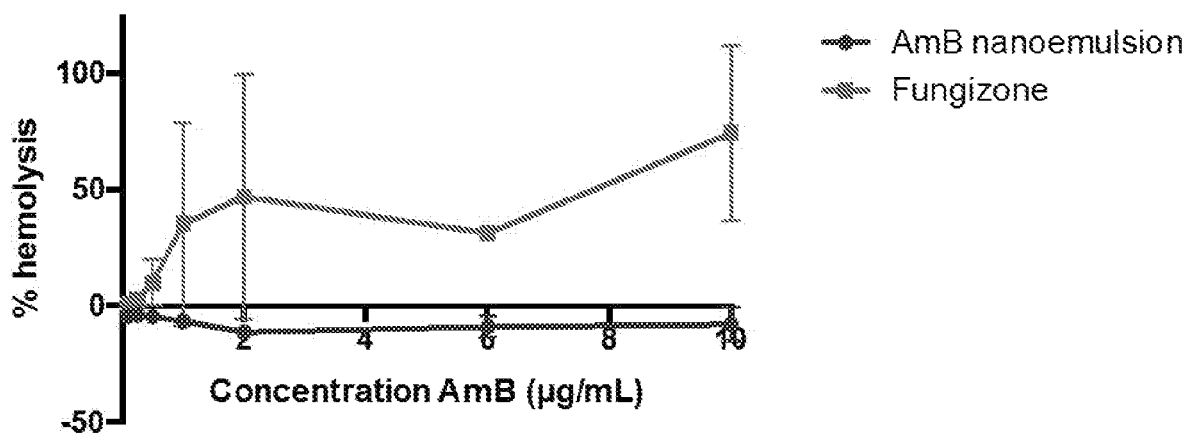
FIG. 10 shows hemolysis of rabbit red blood cells with AmB containing nanoemulsion and FUNGIZONE™ after 1-hour incubation at 37° C.

Hemolytic activity was used to assess the in vitro mammalian cell membrane toxicity of AmB containing nanoemulsion and FUNGIZONE™. The AmB containing nanoemulsion did not exceed 1% hemolysis at all analyzed concentrations (FIG. 9). In comparison, FUNGIZONE™ was highly hemolytic even at low concentrations (2 μg/mL).

Fungicidal Efficacy

Minimum Inhibitory Concentration (MIC)

The minimum inhibitory concentration, or the lowest concentration of AmB in a given formulation that considerably inhibited fungal growth, of the AmB containing nanoemulsion was evaluated against *Candida albicans* in order to verify the fungicidal activity of AmB in the prepared nanoemulsions. In six replicate studies, the MIC of AmB containing against *C. albicans* ranged from 0.22-0.44 μg/mL. This concentration range is consistent with FUNGIZONE™ (0.25-0.5 μg/mL).[5]

Conclusions:

A highly effective nanoemulsion based colloidal drug delivery system was rationally designed for delivery of amphotericin B. This drug delivery system is triphasic and comprised of a novel hydrophobic dicationic cholinium based ionic liquid that exhibited a remarkably toxicity profile. Through use of a cationic moiety coupled with a hydrophobic and non-toxic anion, we were successfully able to prepare a hydrophobic IL with negligible in vivo toxicity with combination of hydrophobic and hydrophilic regions. This hydrophobic IL was rationally designed for the solubilization of hydrophobic pharmaceutics, such as AmB. The use of a specifically selected anion further increased the hydrophobicity of the IL overall and assisted in the deaggreation of AmB. To our knowledge, for the first time a nanoemulsion containing a hydrophobic ionic liquid has demonstrated the ability to effectively deliver a hydrophobic pharmaceutical agent.

REFERENCES (1) Egorova, K. S.; Gordeev, E. G.; Ananikov, V. P. Biological Activity of Ionic Liquids and Their Application in Pharmaceutics and Medicine. *Chem. Rev.* 2017, 117 (10), 7132-7189.

(2) Bolard, J.; Legrand, P.; Heitz, F.; Cybulska, B. One-Sided Action of Amphotericin B on Cholesterol-Containing Membranes Is Determined by Its Self-Association in the Medium. *Biochemistry* 1991, 30 (23), 5707-5715.

(3) Legrand, P.; Romero, E. A.; Cohen, B. E.; Bolard, J. Effects of Aggregation and Solvent on the Toxicity of Amphotericin B to Human Erythrocytes. *Antimicrob. Agents Chemother.* 1992, 36 (11), 2518-2522.

(4) Yamashita, K.; Janout, V.; Bernard, E. M.; Armstrong, D.; Regen, S. L. Micelle/Monomer Control over the Membrane-Disrupting Properties. 1995, 6249-6253.

(5) Alvarez, C.; Andes, D. R.; Kang, J. Y.; Krug, C.; Kwon, G. S. Antifungal Efficacy of an Intravenous Formulation Containing Monomeric Amphotericin B, 5-Fluorocytosine, and Saline for Sodium Supplementation. *Pharm. Res.* 2017, 34 (5), 1115-1124.

(6) Aramwit, P.; Yu, B. G.; Lavasanifar, A.; Samuel, J.; Kwon, G. S. The Effect of Serum Albumin on the Aggregation State and Toxicity of Amphotericin B. *J. Pharm. Sci.* 2000, 89 (12), 1589-1593.

(7) Brajtburg, J.; Powderly, W. G.; Kobayashi, G. S.; Medoff, G. Amphotericin B: Delivery Systems. *Antimicrob. Agents Chemother.* 1990, 34 (3), 381-384.

(8) Lei, Z.; Chen, B.; Koo, Y. M.; Macfarlane, D. R. Introduction: Ionic Liquids. *Chem. Rev.* 2017, 117 (10), 6633-6635.

(9) Raut, D. G.; Sundman, O.; Su, W.; Virtanen, P.; Sugano, Y.; Kordas, K.; Mikkola, J. P. A Morpholinium Ionic Liquid for Cellulose Dissolution. *Carbohydr. Polym.* 2015, 130, 18-25.

(10) Elliott, G. D.; Kemp, R.; MacFarlane, D. R.; Fujita, K.; Forsyth, M. The Development of Ionic Liquids for Biomedical Applications. *Abstr. Pap. 236th ACS Natl. Meet.* Philadelphia, Pa., United States, Aug. 17-21, 2008 2008, IEC-180.

(11) Marrucho, I. M.; Branco, L. C.; Rebelo, L. P. N. Ionic Liquids in Pharmaceutical Applications. *Annu. Rev. Chem. Biomol. Eng.* 2014, 5 (1), 527-546.

(12) Manic, M. S.; Najdanovic-Visak, V. Solubility of Erythromycin in Ionic Liquids. *J. Chem. Thermodyn.* 2012, 44 (1), 102-106.

(13) Moniruzzaman, M.; Tahara, Y.; Tamura, M.; Kamiya, N.; Goto, M. Ionic Liquid-Assisted Transdermal Delivery of Sparingly Soluble Drugs. *Chem. Commun.* 2010, 46 (9), 1452-1454.

(14) Smith, K. B.; Bridson, R. H.; Leeke, G. A. Solubilities of Pharmaceutical Compounds in Ionic Liquids. *J. Chem. Eng. Data* 2011, 56 (5), 2039-2043.

(15) Jameson, L. P.; Dzyuba, S. V. Effect of Imidazolium Room-Temperature Ionic Liquids on Aggregation of Amphotericin B: A Circular Dichroism Study. *RSC Adv.* 2015, 5 (98), 80325-80329.

(16) Mccrary, P. D.; Beasley, P. A.; Gurau, G.; Narita, A.; Barber, P. S.; Cojocaru, O. A.; Rogers, R. D. Drug Specific, Tuning of an Ionic Liquid's Hydrophilic-Lipophilic Balance of to Improve Water Solubility of Poorly Soluble Active Pharmaceutical Ingredients †. *New J. Chem.* 2013, 37 (Il), 2196-2202.

(17) Freire, M. G.; Neves, C. M. S. S.; Carvalho, P. J.; Gardas, R. L.; Fernandes, A. M.; Marrucho, I. M.; Santos, L. M. N. B.; Coutinho, J. A. P. Mutual Solubilities of Water and Hydrophobic Ionic Liquids. *J. Phys. Chem. B* 2007, 111 (45), 13082-13089.

(18) Petkovic, M.; Ferguson, J. L.; Gunaratne, H. Q. N.; Ferreira, R.; Leitão, M. C.; Seddon, K. R.; Rebelo, L. P. N.; Pereira, C. S. Novel Biocompatible Cholinium-Based Ionic Liquids—toxicity and Biodegradability. *Green Chem.* 2010, 12 (4), 643.

(19) Rantamaki, A. H.; Ruokonen, S.-K.; Sklavounos, E.; Kyllonen, L.; King, A. W. T.; Wiedmer, S. K. Impact of Surface-Active Guanidinium-, Tetramethylguanidinium-, and Cholinium-Based Ionic Liquids on *Vibrio fischeri* Cells and Dipalmitoylphosphatidylcholine Liposomes. *Sci. Rep.* 2017, 7 (April), 46673.

(20) Jing, B.; Lan, N.; Qiu, J.; Zhu, Y. Interaction of Ionic Liquids with a Lipid Bilayer: A Biophysical Study of Ionic Liquid Cytotoxicity. *J. Phys. Chem. B* 2016, 120 (10), 2781-2789.

(21) Czerniak, K.; Walkiewicz, F. Synthesis and Antioxidant Properties of Dicationic Ionic Liquids. *New J. Chem.* 2017, 41 (2), 530-539.

(22) Fareghi-Alamdari, R.; Ghorbani-Zamani, F.; Zekri, N. Synthesis and Hypergolic Activity Evaluation of Some New Ammonium-Imidazolium Based Ionic Liquids. *RSC Adv.* 2016, 6 (31), 26386-26391.

(23) e Silva, F. A.; Siopa, F.; Figueiredo, B. F. H. T.; Gonçalves, A. M. M.; Pereira, J. L.; Gonçalves, F.; Coutinho, J. A. P.; Afonso, C. A. M.; Ventura, S. P. M. Sustainable Design for Environment-Friendly Mono and Dicationic Cholinium-Based Ionic Liquids. *Ecotoxicol. Environ. Saf.* 2014, 108, 302-310.

(24) Gabbay, E. J. Topography of Nucleic Acid Helices in Solutions. I. The Nonidentity of Polyadenylic-Polyuridylic and Polyinosinic-Polycytidylic Acid Helices. *Biochemistry* 1966, 5 (9), 3036-3043.

Example 2

This example demonstrates a nanoemulsion comprising hydrophilic therapeutic agent, in accordance with an embodiment of the invention.

Figure 1B:
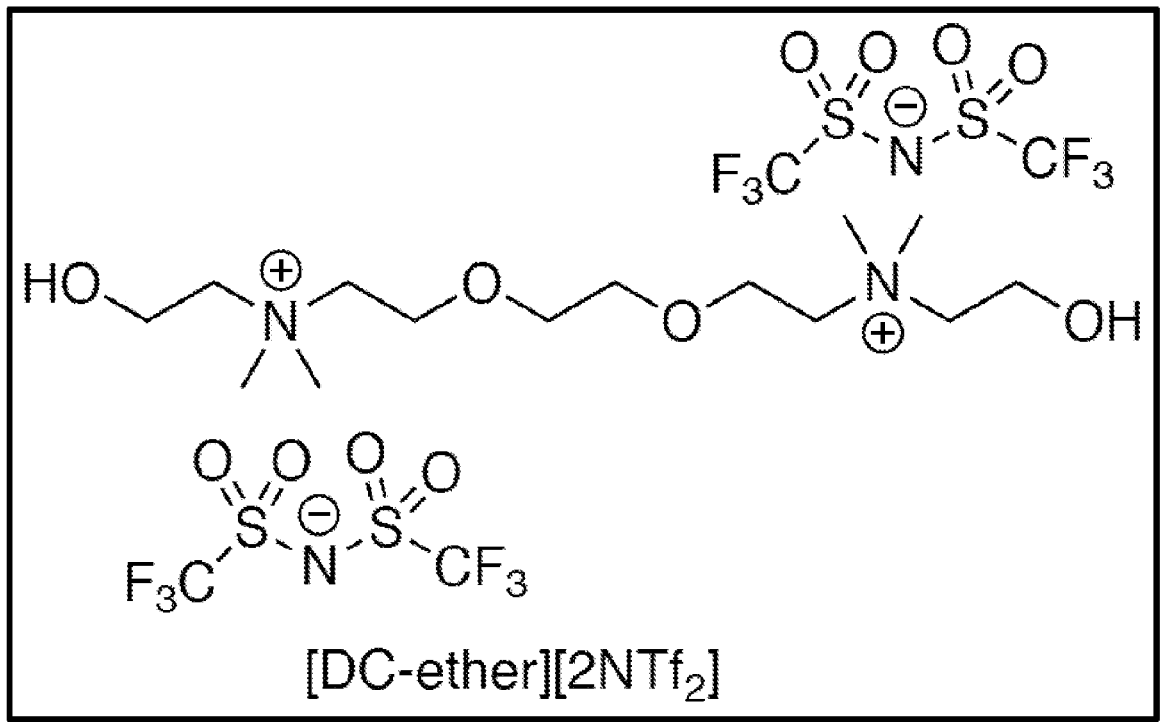
FIG. 1B. Structure of dicationic cholinium based ionic liquid [DC-ether][2NTf$_2$].
Figure 29A:
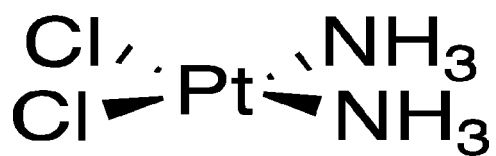
FIG. 29A shows the structure of cisplatin.

Cisplatin is a highly potent, hydrophilic chemotherapeutic agent. Cisplatin (CP, FIG. 1) is a chemotherapeutic in the platinum-based chemotherapy drug family, which accounts for approximately 50% of clinically used chemotherapeutics. Despite the widespread clinical use of this chemotherapeutic, the side-effects associated with this drug are significant and limit the maximum dose that can be administered. Structure, FIG. 29A. While toxic side-effects range from hearing loss to hemolysis, the most significant dose limiting side-effect includes nephrotoxicity.[1] The use of nanoparticle-based delivery of cisplatin allows for the exploitation of passive targeting via the enhanced permeability and retention (EPR) effect for preferential delivery of drug to cancerous cells instead of healthy cells. The EPR effect refers to a passive targeting technique of fast-growing cancerous tissue. This passive targeting takes advantage of the tumor vasculature abnormalities, specifically the aberrantly growing tumor vasculature that leaves the endothelial cells poorly aligned and with large fenestrations between them. This allows the penetration of appropriately sized nanoparticles into the tumor. Similarly, the growing tumor compresses the lymph vessels, which results in poor lymphatic drainage and accumulation of the nanoparticles.[2,3] As such, the delivery of a water-soluble chemotherapeutic in a nanoemulsion based delivery vehicle would decrease the off-target side-effects associated with the drug.

In a preliminary attempt to deliver cisplatin in a more controlled manner, we solubilized 1 mg/mL of CP in the ionic liquid mixture (i.e. 0.6 mL [CDIL-7][2NTf$_2$] and 0.4 mL [Chol][Hex]). This mixture was able to stably solubilized (i.e. no drug precipitation) for over 1 week. However, given the water-solubility of the CP, it was decided that preparation of a nanoemulsion would require use of solely a hydrophobic ionic liquid ([CDIL-7][2NTf$_2$], FIG. 2), as opposed to an ionic liquid mixture, to prevent: (1) dissociation of drug out of the ionic liquid mixture during the emulsification process, or (2) burst release of the drug with release of [Chol][Hex].

Figure 29B:
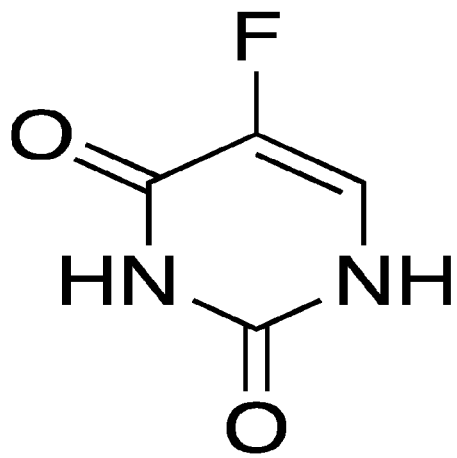
FIG. 29B shows the structure of 5-fluorouracil.
Figure 30:
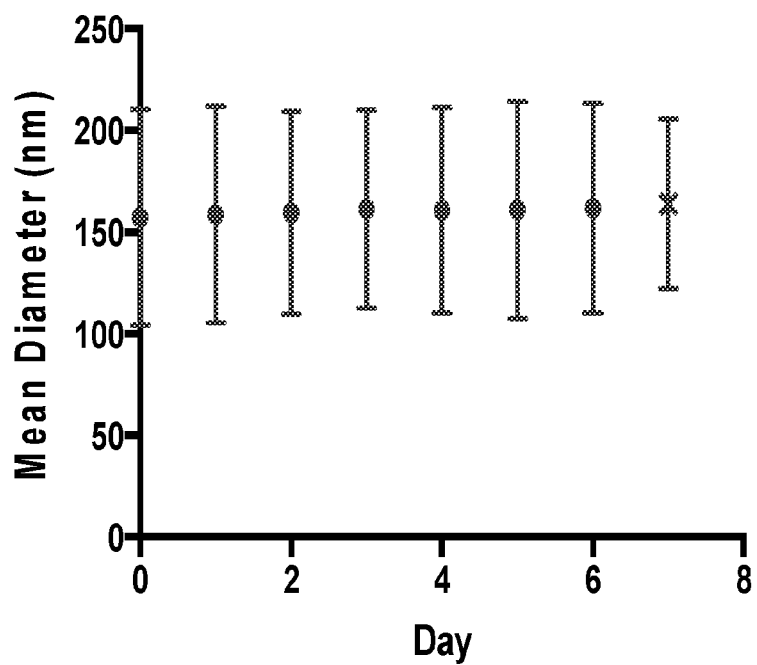
FIG. 30. Change in particle diameter of [CDIL-7][2NTf$_2$], and MCT nanoemulsion with 10 mM M2DSG over time.

Cisplatin and 5-Fluorouracil Solubility in Hydrophobic Ionic Liquid 5-fluorouracil is a highly effective, hydrophilic chemotherapeutic used intravenously for a wide variety of cancers, including pancreatic and breast cancers. 5-fluorouracil (5-FU) is a halogenated pyrimidine, with a fluorine at position 5 (FIG. 29B). This water-soluble BCS III class drug is a thymidylate synthase enzyme inhibitor. 5-FU is converted to into 5-fluorodeoxyuridylates, which also disrupts RNA synthesis along with inhibiting the enzyme. 5-FU has previously been investigated in an ionic-liquid microemulsion for use in dermal drug delivery. Here, a water-soluble imidazolium based ionic liquid was used in an ionic liquid in oil microemulsion to increase the skin permeation of 5-FU. Given the composition of this microemulsion, it could not be used intravenously.

Both cisplatin and 5-FU were solubilized at relatively high concentrations in the hydrophobic ionic liquid as depicted in Table 2.

TABLE 2

Solubility of cisplatin and 5-FU

| Ionic Liquid | Cisplatin (mg mL$^{-1}$) | 5-fluorouracil (mg mL$^{-1}$) |
|---|---|---|
| [CDIL-7][2NTf$_2$] | 3 | 1 |

Particle Size Determination: cisplatin nanoemulsion. The cisplatin nanoemulsion was prepared with 10 mM 1,2-Distearoyl rac-glycerol, methoxypolyethylene Glycol molecular weight 2000 (M2DSG), 1 mL [CDIL-7][2NTf$_2$] and 3 mL MCT with a concentration of 0.1 mg/mL cisplatin.

The particle size of the cisplatin nanoemulsion had a mean diameter of 164±42 nm and was stable for 7 days. After 7 days, the hydrophobic ionic liquid could be observed to have sedimented.

UV/vis analysis of cisplatin. An initial study using UV/vis spectroscopy was completed in order to determine a potential analytical method for differentiating whether cisplatin is solubilized stably in a nanoemulsion, or if the cisplatin partitions into the water component during emulsification.

Figure 31:
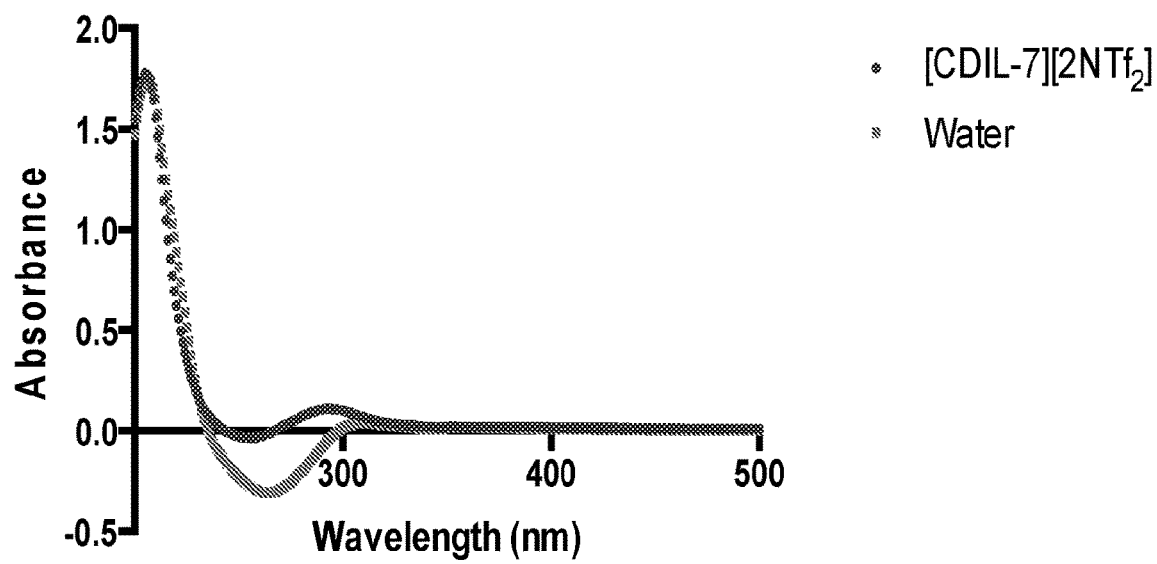
FIG. 31. UV/vis absorption spectrum of cisplatin solubilized in [CDIL-7][2NTf$_2$] (top line, blue) and in water (lower line, red).

It was determined that there is a slight blue-shift for both of the observed peaks of cisplatin in [CDIL-7][2NTf$_2$] as compared to water. A more pronounced shift is observed for the weak intensity peak observed at ~280 nm. However, the highest intensity peak is also blue shifted by ~3 nm (FIG. 31)

Figure 32:
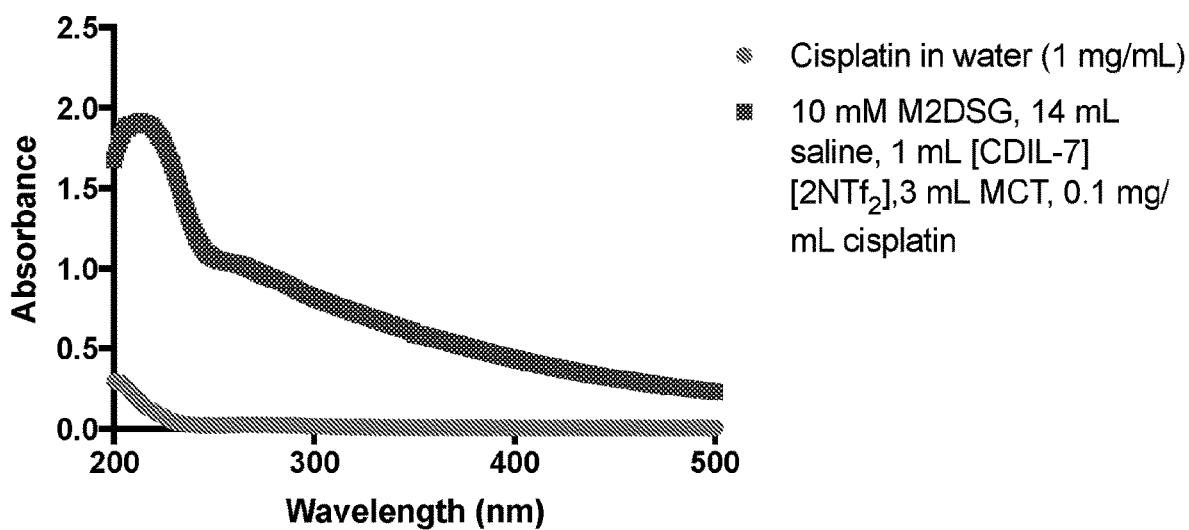
FIG. 32. UV/vis absorption spectrum of cisplatin present in the prepared nanoemulsion (top line, blue) and in water (bottom line, red).

Immediately after preparation of a cisplatin nanoemulsion, a similar analysis was completed. It appears the slight blue-shift for both of the observed peaks of cisplatin in [CDIL-7][2NTf$_2$] as compared to water is maintained in the nanoemulsion. This indicates that at least some of the cisplatin remains in the ionic liquid and can be successfully emulsified (FIG. 32).

REFERENCES (1) Browning, R. J.; Reardon, P.; Parhizkar, M.; Pedley, R. B.; Edirisinghe, M.; Knowles, J. C.; Stride, E. Drug Delivery Strategies for Platinum-based Chemotherapy. *ACS nano* 2017, 11, 8560-8578.
(2) Tang, L.; Yang, X.; Yin, Q.; Cai, K.; Wang, H.; Chaudhury, I.; Yao, C.; Zhou, Q.; Kwon, M.; Hartman, J. A.; Dobrucki, L. W.; Borst, L. B.; Lezmi, S.; Helferich, W. G.; Ferguson, A. L.; Fan, T. M.; Cheng, J. Investigating the Optimal Size of Anticancer Nanomedicine. *Proc. Natl. Acad. Sci.* 2014, 111, 15344-15349.
(3) Kobayashi, H.; Watanabe, R.; Choyke, P. L. Improving Conventional Enhanced Permeability and Retention (EPR) Effects: What is the Appropriate Target? *Theranostics* 2014, 4 (1), 81-89.
(4) Goindi, S.; Arora, P.; Kumar, N.; Puri, A. Development of a Novel Inoic Liquid-Based Microemulsion Formulation for Dermal Delivery of 5-Fluorouracil. *AAPS PharmSciTech* 2014, 15, 810-821.

Example 3

This example demonstrates a nanoemulsion comprising therapeutic agents, in accordance with an embodiment of the invention.

Room-Temperature Ionic Liquid Based Nanoemulsions: Synthesis and Formulation for Delivery of Poorly Water Soluble Active Pharmaceutical Agents.

Paclitaxel Solubility in Ionic-Liquids. After the successful solubilization of AmB, paclitaxel (PTX) was solubilized in the dicholinium ILs in order to analyze the potential of solubilizing a broad range of hydrophobic drugs. PTX is a highly-hydrophobic chemotherapeutic agent. Despite the efficacy of this drug, its clinical use remains a challenge due to the potential for hemolysis, local precipitation, and off-target toxicity. The current formulations for PTX are TAXOL™, ABRAXANE™, and GENEXOL™. TAXOL™ is formulated with Cremophor EL and ethanol. It is delivered intravenously after dilution, but serious side effects ascribed to Cremophor EL have been reported with Taxol™, including strong immunogenicity, nephrotoxicity and neurotoxicity.[1,2] ABRAXANE™ is an albumin-bound paclitaxel nanoparticle formulation for injectable suspension using an infusion set incorporating a 15 µm filter. Although this formulation mitigates some side effects seen with solvent-bound paclitaxel, serious side effects still include neutropenia and thrombocytopenia.[3,4] Lastly, GENEXOL® is a micelle formulation of paclitaxel with PEG-b-PLA.[5,6] It is currently being used in phase III clinical trials. While GENEXOL® relieves some of the side effects of general systemic administration of paclitaxel, it suffers from a quick burst release of the drug and from dissociation in blood:4 PTX exhibited a relatively high solubility in the novel dicholinium based ILs.

Itraconazole Solubility in Ionic-Liquids. Itraconazole is an antifungal agent in the triazole class of antifungals. Azole antifungal mechanism of action includes interference with ergosterol synthesis by inhibiting the enzyme CYP51 in the ergosterol biosynthetic pathway. As such, this disrupts the membrane processes necessary for growth and proliferation. Triazoles are typically used to treat both superficial and more severe systemic fungal infections. Itraconazole was also able to be solubilized in the dicholinium and cholinium based IL, demonstrating the broad anti-fungal potential of the IL nanoemulsion systems. See Table 3.

TABLE 3

| Ionic Liquid | AmB (mg/mL) | PTX (mg/mL) | ICA (mg/mL) | Cisplatin (mg/mL) |
| --- | --- | --- | --- | --- |
| [CDIL-7][2NTf$_2$] | 0.7 | 25 | 1 | 3 |
| [CDIL-6][2NTf$_2$] | 0.5 | 15 | Not tested | Not tested |
| [Chol][Hex] | 6 | 2 | 1 | Not tested |

The PTX nanoemulsion was prepared with 10 mM 1,2-Distearoyl rac-glycerol, methoxypolyethylene glycol molecular weight 2000 (M2DSG), 0.3 mL [CDIL-7][2NTf2], 0.2 mL [Chol][Hex], and 1.5 mL MCT. The particle size of the PTX nanoemulsion had a mean diameter of 154±49 nm. After 21 days, a small amount of hydrophobic IL was observed to have sedimented at the bottom of the nanoemulsion tube. Subsequently, drug precipitation was observed and the nanoemulsion was no longer monitored. The precipitation of PTX can be attributed to the release of PTX from the destabilized nanoemulsion. A method that could be employed to increase nanoparticle stability includes (1) decreasing the volume of ionic liquid used in the formulation overall; or (2) emulsification of solely the hydrophobic ionic liquid.

Figure 35:
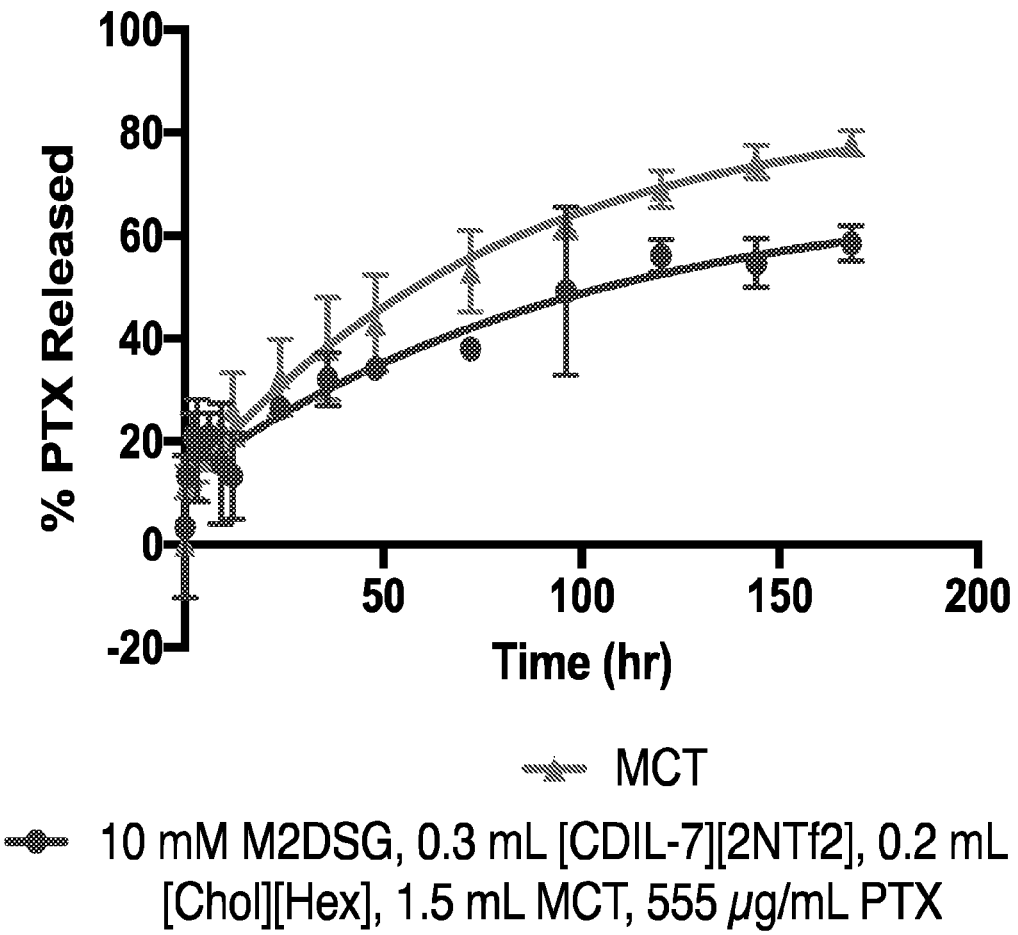
FIG. 35 shows a time course for release of PTX from a nanoemulsion in accordance with an embodiment of the present invention.

An in vitro time-release study was performed in which the emulsion was dialyzed under sink conditions (Phosphate buffered saline solution at 37° C.) in two replicate trials for one week to simulate physiological conditions and a time-release profile was constructed (FIG. 35). Aliquots of the emulsion solutions were obtained at various time points and the amount of PTX remaining was quantified using HPLC. The time-release profile demonstrates that the IL nanoemulsion is able to stably emulsify and release PTX for one week in pseudo-physiological conditions. This system exhibits a remarkably high half-life of 68.70 hours. Most notably, the half-life is larger than that of a nanoemulsion prepared with 10 mM M2DSPE and 2 mL of MCT, which exhibited a half-life of 54.66 hours. As such, the time-release profile can be easily adjusted by altering the ratio of the ionic liquid to MCT for the desired release.

Example 4

This example demonstrates a nanoemulsion comprising AmB as a hydrophobic therapeutic agent, in accordance with an embodiment of the invention.

Figure 36A:
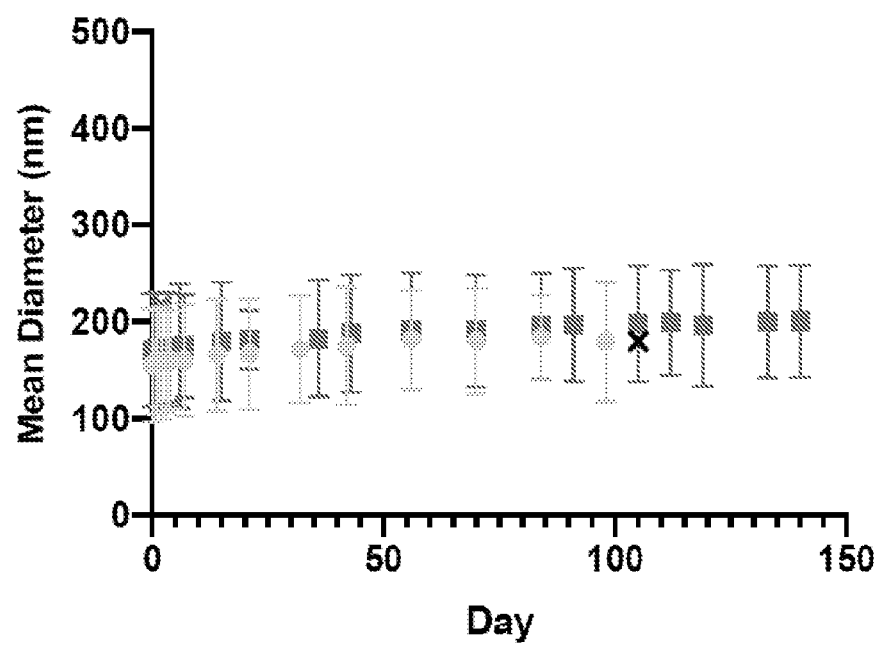
FIG. 36A. Comparison of average particle size over time of nanoemulsions prepared with [DC-7][2NTf$_2$] as the hydrophobic ionic liquid (yellow) or [DC-ether][2NTf$_2$] as the hydrophobic ionic liquid (red).

Given the lower viscosity of [DC-ether][2NTf$_2$] as compared to [DC-7][2NTf2], it was thought that use of this hydrophobic ionic liquid would result in nanoemulsions with greater long-term stability. In order to verify this potentially increased stability, a nanoemulsion was prepared with the same formulation used for Amphotericin B (AmB) delivery with [DC-7][2NTf$_2$] (FIG. 36A). Use of [DC-ether]

[2NTf$_2$] has produced a nanoemulsion with increased long-term stability, resulting in a nanoemulsion that is still stable after 140 days in comparison to the [DC-7][2NTf$_2$] nanoemulsion that was stable for 98 days. The size of these nanoemulsions is comparable, with the [DC-7][2NTf$_2$] and [DC-ether][2NTf$_2$] containing nanoemulsion having a size of 180±62 nm on day 98 and 197±59 on day 91, respectively.

Figure 36B:
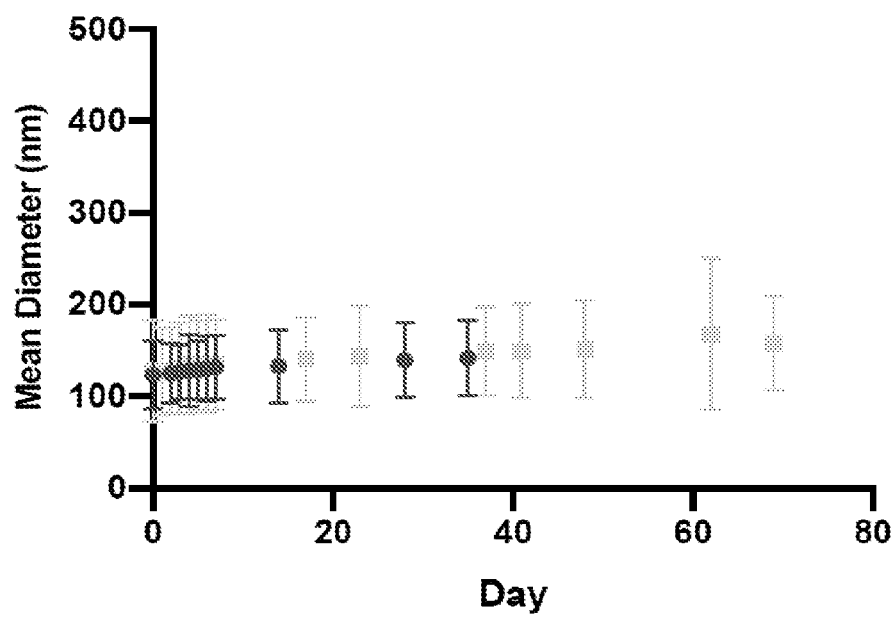
FIG. 36B. Average particle size over time of nanoemulsions prepared with 15 mM M2DSG, 3 mL MCT, and 1 mL ionic liquid mixture.

In order to increase the concentration of AmB that could be delivered intravenously, the overall volume of ionic liquid mixture present in the nanoemulsion formulation was also increased. Nanoemulsions were prepared with 15 mM M2DSG, 3 mL MCT, and 1 mL of ionic liquid mixture. A larger concentration of polymer was chosen in order to ensure long-term stability of the prepared nanoemulsions as the overall total volume of hydrophobic media had increased (i.e. changed from 2 mL to 4 mL). Two nanoemulsions were prepared, containing either [DC-7][2NTf$_2$] or [DC-ether][2NTf$_2$] as the hydrophobic ionic liquid (FIG. 36B). Despite having a higher volume of ionic liquid mixture present in the nanoemulsion formulation, the prepared nanoemulsions are exhibiting excellent stability. The [DC-ether][2NTf$_2$] containing nanoemulsion and [DC-7][2NTf$_2$] containing nanoemulsion have a particle size of 158±51 nm on day 69 and 142±41 nm on day 35, respectively.

Example 5

This example demonstrates a nanoemulsion comprising cisplatin as a hydrophilic therapeutic agent, in accordance with an embodiment of the invention.

Figure 37A:
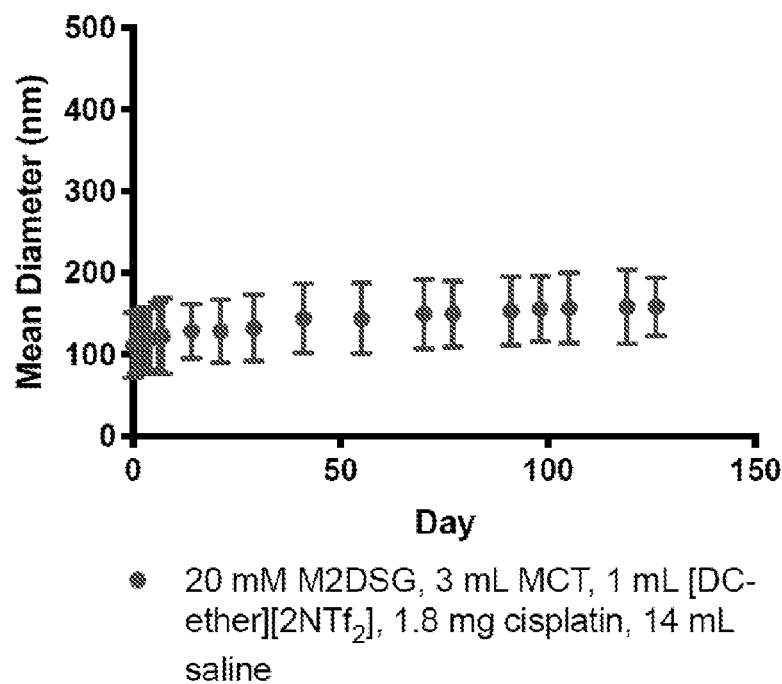
FIG. 37A. Average particle size of cisplatin containing nanoemulsion with [DC-ether][2NTf$_2$] as the hydrophobic ionic liquid.
Figure 37B:
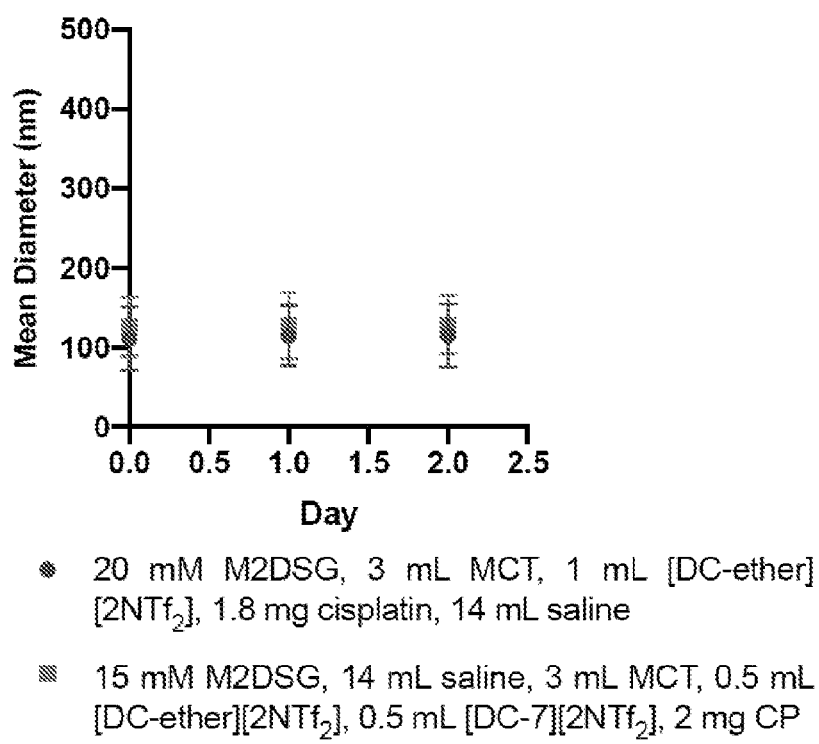
FIG. 37B. Comparison of average particle size over 2 days of [DC-ether][2NTf$_2$] only nanoemulsion (blue) and nanoemulsion prepared with mixture of [DC-ether][2NTf$_2$] and [DC-7][2NTf$_2$].

Due to only a seven-day shelf life of the nanoemulsion prepared with 10 mM M2DSG, 1.5 mL MCT, 0.5 mL [DC-7][2NTf$_2$], and cisplatin, an alternative nanoemulsion was prepared with [DC-ether][2NTf$_2$] in an attempt to increase the stability of the nanoemulsion overall. Similar to the nanoemulsions prepared with AmB, the overall volume of the ionic liquid in the formulation was increased in order to increase the concentration of cisplatin in the nanoemulsion. An initial nanoemulsion was prepared with 20 mM M2DSG, 3 mL MCT, and 1 mL [DC-ether][2NTf$_2$] (FIG. 37A). Alteration of the ionic liquid from [DC-7][2NTf$_2$] to [DC-ether][2NTf$_2$] resulted in a marked increase in stability of the nanoemulsion, resulting in a particle size of 159±36 nm on day 126. While [DC-ether][2NTf$_2$] has a decreased viscosity as compared to [DC-7][2NTf$_2$], this ionic liquid has an increased water-solubility. As such, a cisplatin containing nanoemulsion was prepared with a mixture of [DC-ether][2NTf$_2$] and [DC-7][2NTf$_2$] (FIG. 37B). The presence of the [DC-ether][2NTf$_2$] would decrease the viscosity of the ionic liquid mixture overall, while incorporation of the more hydrophobic [DC-7][2NTf$_2$] would prevent partition of cisplatin from the nanoemulsion. This nanoemulsion has remained stable for over one week and has a comparable average particle size to the nanoemulsion prepared with only [DC-ether][2NTf$_2$] as the hydrophobic ionic liquid (FIG. 37B). The sizes were compared over the first two days of stability, as this was the time frame the nanoemulsions were analyzed using an in vitro time-release study.

Example 6

This example demonstrates determining the aggregation state of AmB in ILs in accordance with an embodiment of the invention.

Figure 38A:
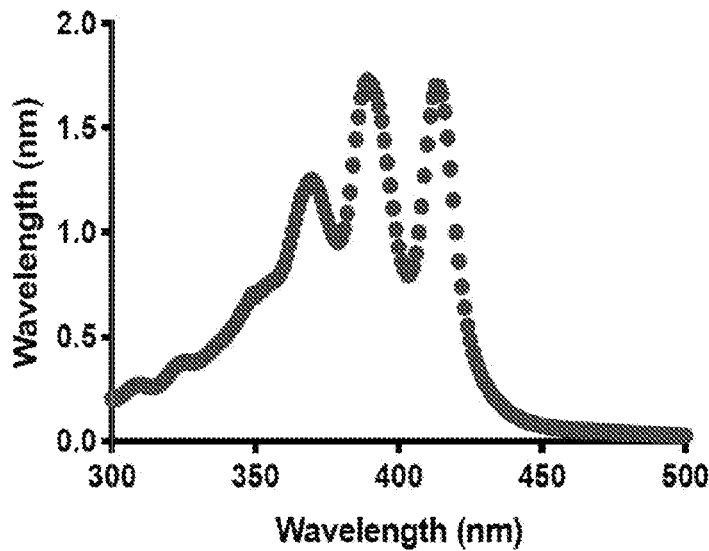
FIG. 38A. UV/vis spectrum of AmB in a mixture of [DC-ether][2NTf$_2$] and [Chol][Hex].
Figure 38B:
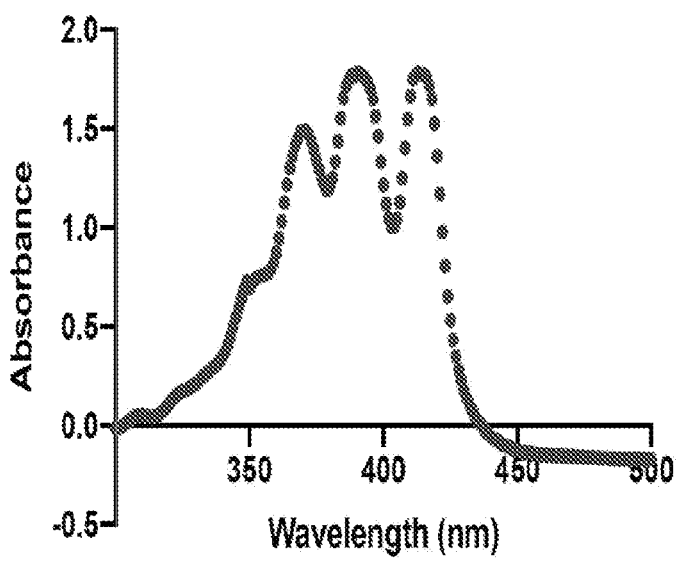
FIG. 38B. UV/vis spectrum of AmB in an IL mixture of [DC-7][2NTf$_2$] and [Chol][Hex] used for in vitro time-release study.
Figure 38C:
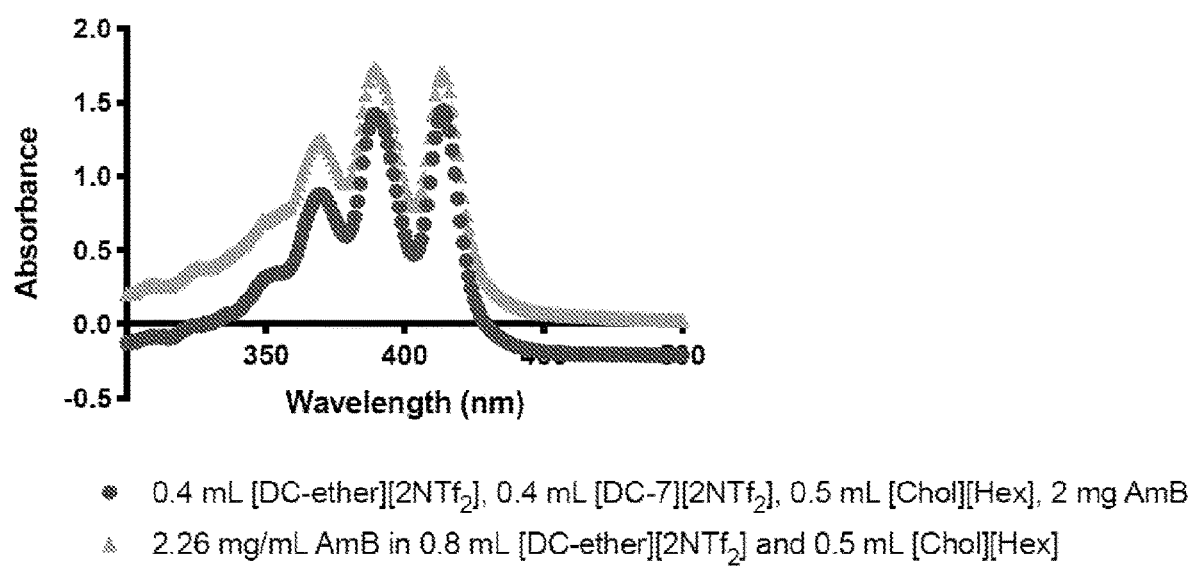
FIG. 38C. UV/vis spectrum of AmB in IL mixtures.

While the aggregation state of AmB had previously been evaluated in a mixture of [DC-7][2NTf$_2$] and [Chol][Hex], the aggregation state had not been evaluated in [DC-ether] [2NTf$_2$] containing nanoemulsions. Given the increased long-term stability of the prepared nanoemulsions using [DC-ether][2NTf$_2$] as compared to [DC-7][2NTf$_2$], the aggregation state of AmB was evaluated in these media prior to emulsification. AmB remains in the non-toxic, monomeric form in both ionic liquid mixtures analyzed (FIGS. 38A-38B). As such, [DC-ether][2NTf$_2$] can be used as the hydrophobic ionic liquid for emulsification of AmB.

Example 7

This example demonstrates the in vitro time release of AmB and cisplatin from ILs in accordance with an embodiment of the invention.

In vitro time-release studies were completed for both AmB containing nanoemulsions and cisplatin containing nanoemulsions. In these studies, the nanoemulsion was dialyzed under sink conditions to simulate physiological conditions. The release profile was then constructed using a one-phase exponential association, which was then used to calculate the first order rate constant ($t_{1/2}$).

Example 7A: Amphotericin B

Figure 39A:
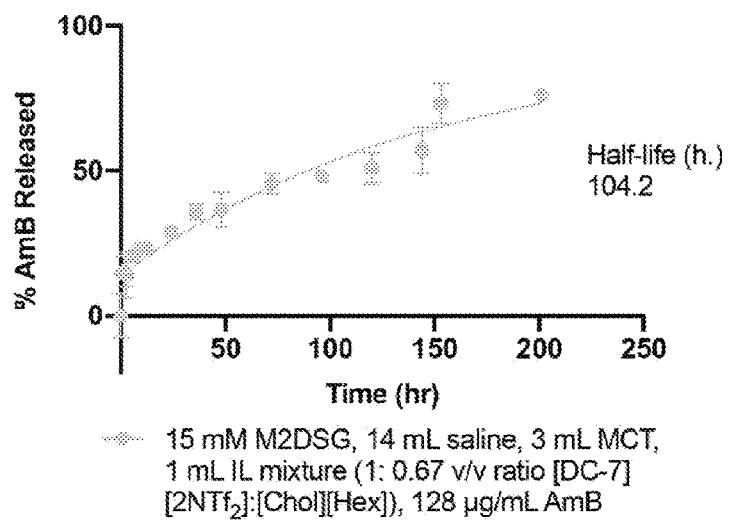
FIG. 39A. In vitro nanoemulsion drug release profile of AmB monitored for 201 hours.
Figure 39B:
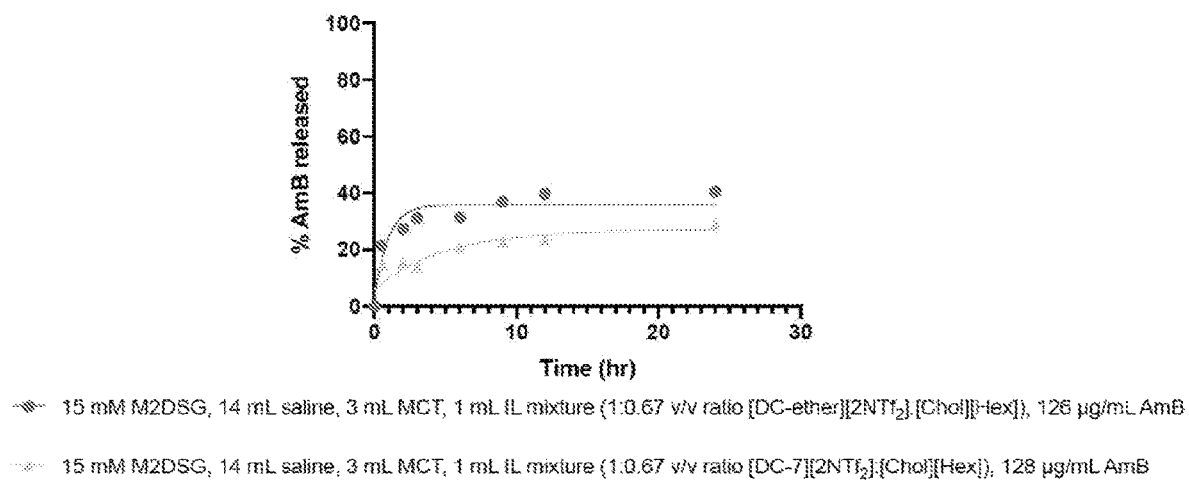
FIG. 39B. Comparison of in vitro AmB drug release of nanoemulsions containing [DC-7][2NTf$_2$] (yellow) or [DC-ether][2NTf$_2$] (red) monitored for 24 hours.

A prolonged, sustained release of AmB in the monomeric form is desired as clinical studies have shown that a continuous infusion of AmB over 24 hours is better tolerated than a 2-4 hour infusion.[1-3] The dose-limiting nephrotoxicity of AmB precludes higher dosages of AmB or longer therapies, indicating that prolonged release is the best route to circumvent AmB's inherent toxicity.[4,5] A nanoemulsion prepared with [DC-7][2NTf$_2$] as the hydrophobic ionic liquid exhibits a prolonged release, with a half-life of 104 hours (FIG. 39A). Despite the presence of a water-soluble ionic liquid, not all AmB is immediately released within the first 24 hours. For the [DC-ether][2NTf$_2$] nanoemulsion time-release study, only one bath was analyzed for 24 hours. After 24 hours less than 40% of AmB was released from [DC-ether][2NTf$_2$] containing nanoemulsion (FIG. 39B). In comparison, after 24 hours less than 25% AmB was released from the [DC-7][2NTf$_2$] (FIG. 39B). The faster release of AmB from the [DC-ether][2NTf$_2$] nanoemulsion is unsurprising, given the increased water-solubility of [DC-ether][2NTf$_2$] as compared to [DC-7][2NTf$_2$]. This indicates that the release profile can be modulated through altering ratios of [DC-ether][2NTf$_2$] and [DC-7][2NTf$_2$].

Example 7B: Cisplatin

Similar to AmB, prolonged release of chemotherapeutics is desired. Sustained release of chemotherapeutics allows for the exploitation of passive targeting via the enhanced permeability and retention (EPR) effect for preferential delivery of drug to cancerous cells instead of healthy cells. The EPR effect refers to a passive targeting technique of fast-growing cancerous tissue. This passive targeting takes advantage of the tumor vasculature abnormalities, specifically the abnormally growing tumor vasculature that leaves the endothelial cells poorly aligned with large fenestrations between them. This allows the penetration of appropriately sized nanoparticles into the tumor. Further, the growing tumor compresses the lymph vessels, which results in poor lymphatic drainage and accumulation of the nanoparticles.[6,7] As such, sustained release of cisplatin allows for increased time for the nanoparticles to accumulate at the solid cancerous tissue and deliver a higher concentration of drug payload directly at the tumor site. In comparison, when the drug is directly delivered systemically, a large portion of the drug fails to reach the tumor site. In this way, the delivery of a water-soluble chemotherapeutic in a nanoemulsion-based delivery vehicle would also significantly decrease the off-target side-effects associated with the drug. This selectively is not unattainable for a drug when delivered systemically in an aqueous solution. Despite the widespread clinical use of cisplatin, the side-effects associated with this drug are significant and limit the maximum dose that can be administered. While toxic side-effects range from hearing loss to hemolysis, the most significant dose limiting side-effect includes nephrotoxicity.[8] These severe side effects can be attributed to the mode of action of cisplatin. Cisplatin is activated inside of cells through the hydrolysis of the Pt—Cl bonds. The hydrolyzed cisplatin complexes bind subsequently bind to DNA. As such, affecting cell division is the primary mechanism of anticancer activity.[9] The delivery of cisplatin in a nanoemulsion, therefore, allows for an increased concentration of drug can be delivered to cancerous tissue while preventing hydrolysis of the drug and subsequent off-target effects.

Figure 40A:
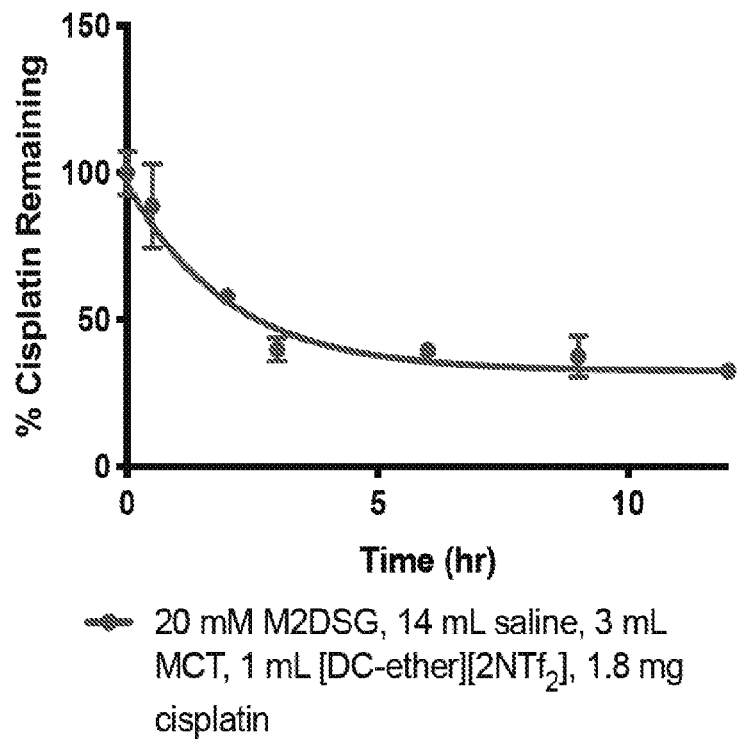
FIG. 40A. In vitro nanoemulsion drug release profile of cisplatin for the first 12 hours of analysis.
Figure 40B:
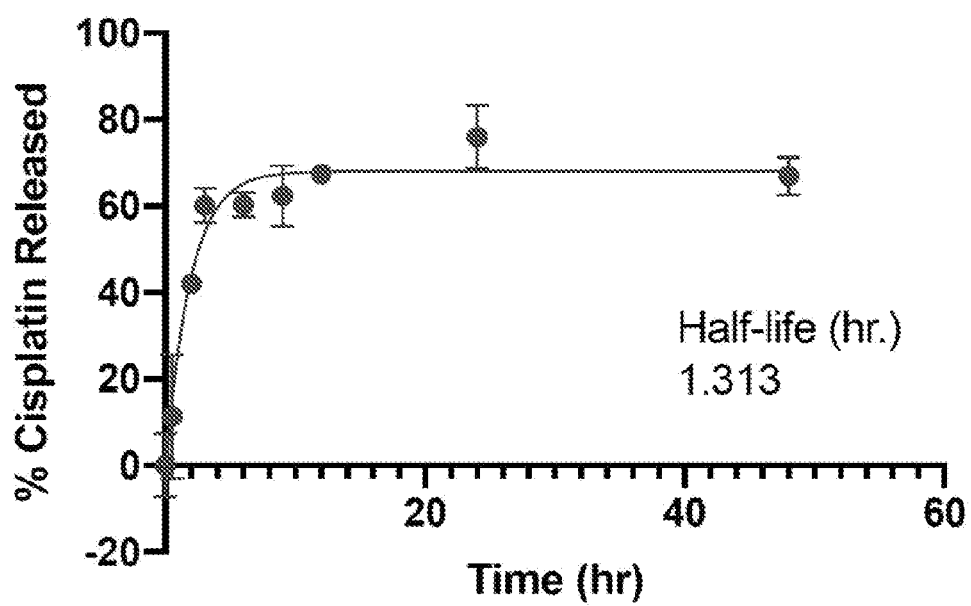
FIG. 40B. In vitro nanoemulsion drug release profile of cisplatin from a nanoemulsion composed of 20 mM M2DSG, 1 mL [DC-ether][2NTf$_2$], 3 mL MCT and 1.8 mg cisplatin monitored for 48 hours.

Previously, UV/vis spectroscopy was used to verify the successful emulsification of cisplatin (i.e. cisplatin remains in the ionic liquid and does not immediately partition into the 80 aqueous phase). However, due to the low molar absorptivity of cisplatin, the use of UV/vis spectroscopy resulted in only subtle changes between free cisplatin and emulsified cisplatin. An in vitro time-release study provides more quantitative information about the efficiency of emulsification of cisplatin, while also providing the drug release profile of cisplatin. Any cisplatin present solely in the aqueous phase of the nanoemulsion will be released immediately after the cassette is dialyzed. Comparison of time-point at 0 hours (prior to dialysis) and time-point at 0.5 hours (0.5 hours of dialysis) indicates that 88% of the cisplatin was retained in the ionic liquid during emulsification (FIG. 40A). After 48 hours, only 67% of the drug had been released. Despite the fact the nanoemulsion has a half-life of 1.3 hours (FIG. 40B), this is a marked improvement from systemic administration of a water-soluble chemotherapeutic. Given that 67% is released over the course of 48 hours this indicates that the cisplatin containing nanoemulsion exhibits prolonged drug release and may take advantage of the EPR effect.

Figure 40C:
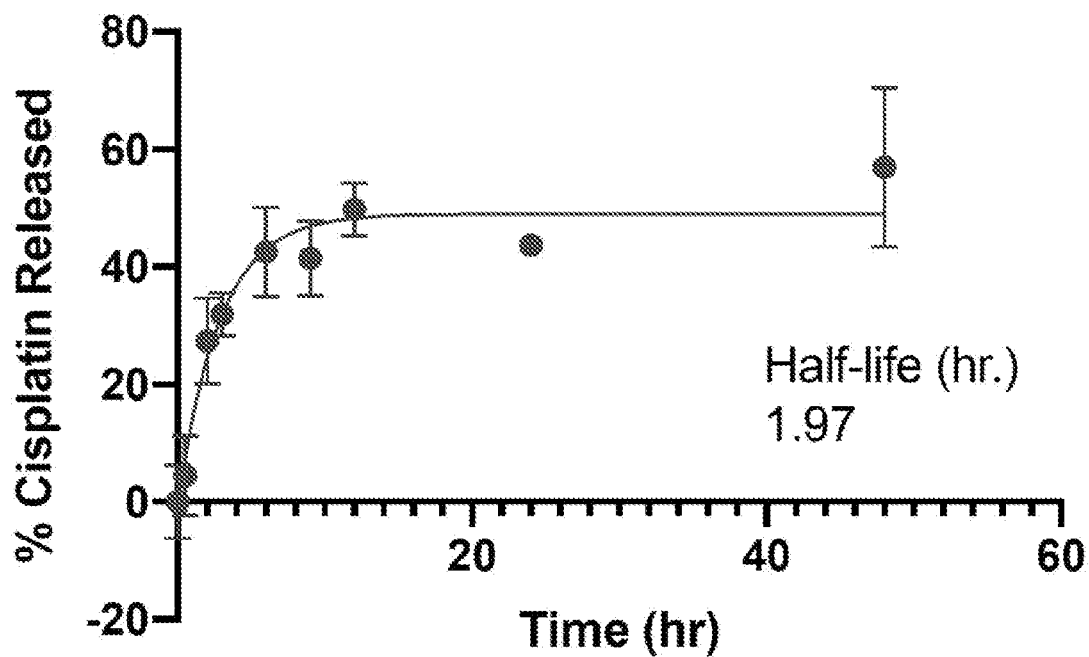
FIG. 40C. In vitro drug release profile of cisplatin from a nanoemulsion composed of 15 mM M2DSG, 0.5 mL [DC-ether][2NTf$_2$], 0.5 mL [DC-7][2NTf$_2$], 3 mL MCT, and 2 mg cisplatin monitored over 48 hours.
Figure 40D:
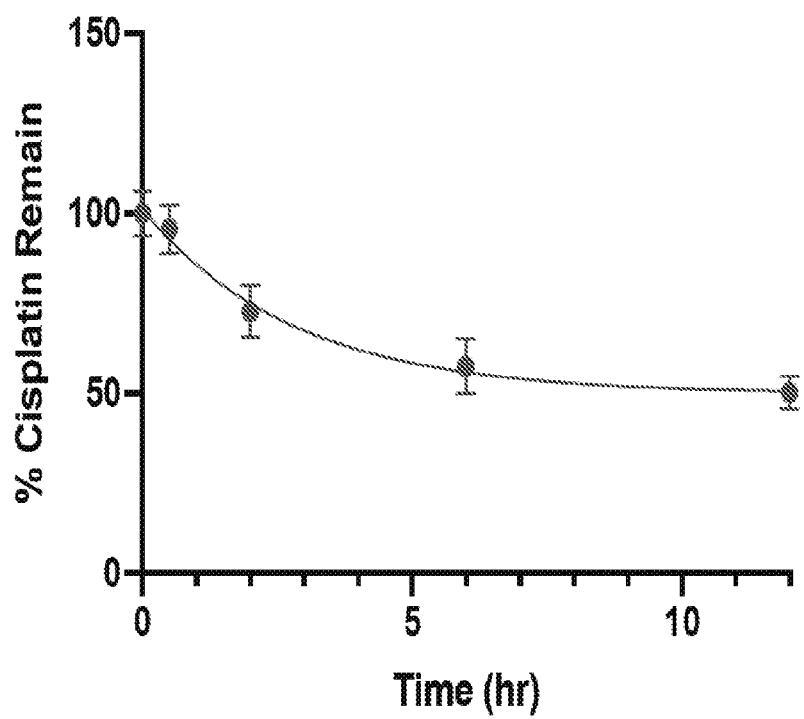
FIG. 40D. In vitro drug release profile of cisplatin from a nanoemulsion prepared with 15 mM M2DSG, 0.5 mL [DC-ether][2NTf$_2$], 0.5 mL [DC-7][2NTf$_2$] and 3 mL MCT over the first 12 hours of analysis.

Due to the difference in drug release of AmB in a nanoemulsion composed of [DC-7][2NTf$_2$] and [DC-ether][2NTf$_2$], it was thought that the drug release of cisplatin could be prolonged through incorporation of [DC-7][2NTf$_2$] into the nanoemulsion. A nanoemulsion was formulated with 15 mM 1,2-Distearoyl-rac-glycero-3-methylpolyoxyethylene with an average molecular weight of 2000 g/mol for the PEG (M2DSG) as surfactant, 0.5 mL [DC-ether][2NTf$_2$], 0.5 mL [DC-7][2NTf$_2$], 3 mL MCT, and 2 mg cisplatin. This nanoemulsion was then immediately analyzed using an in vitro time-release study. Use of a mixture of [DC-7][2NTf$_2$] and [DC-ether][2NTf$_2$] resulted in a prolonged drug-release, with a half-life of 1.97 hours (FIG. 40C). Similarly, the capacity of the nanoemulsion to successfully incorporate cisplatin in the hydrophobic media of the nanoemulsion as opposed to the aqueous phase improved. This nanoemulsion exhibited a 96% retention of cisplatin during emulsification (FIG. 40D). The improved half-life as well as increased emulsification efficiency can be attributed to the fact [DC-7][2NTf$_2$] is more hydrophobic than [DC-ether][2NTf$_2$]. As such, an optimal formulation can be achieved by using a mixture of [DC-ether][2NTf$_2$] and a more hydrophobic ionic liquid.

Example 8

This example demonstrates the in vitro cell viability assays on 4T1 murine breast cancer cells of ILs comprising cisplatin in accordance with an embodiment of the invention.

Figure 41A:
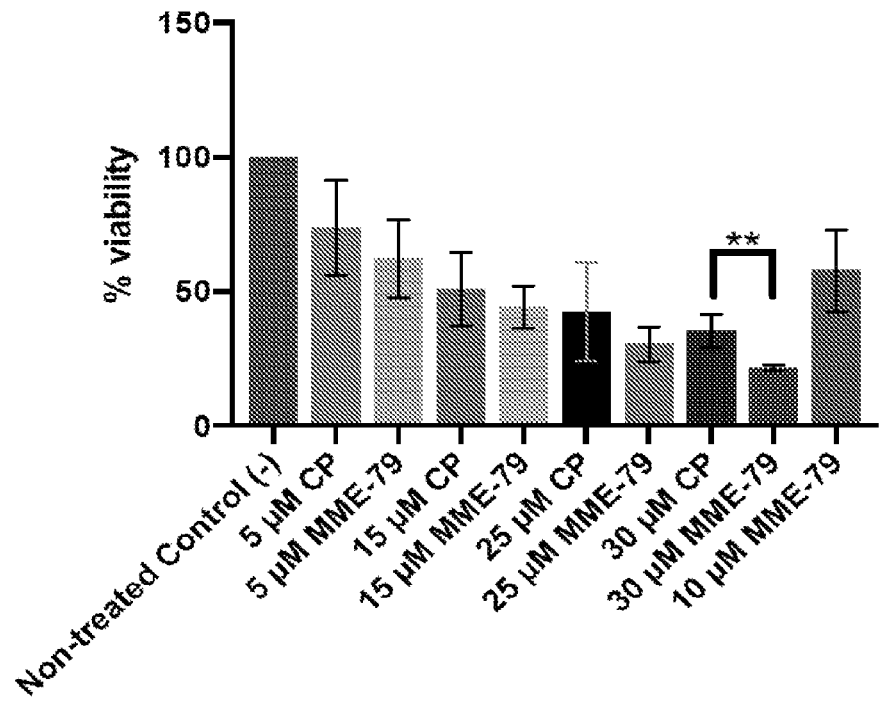
FIG. 41A. 4T1 cell viability study of non-treated control, cisplatin controls, and a nanoemulsion prepared with 15 mM M2DSG, 0.5 mL [DC-ether][2NTf$_2$], 0.5 mL [DC-7][2NTf$_2$], 3 mL MCT, and cisplatin. Data is presented as a mean±standard deviation (n=3) (** indicates p<0.05).
Figure 41B:
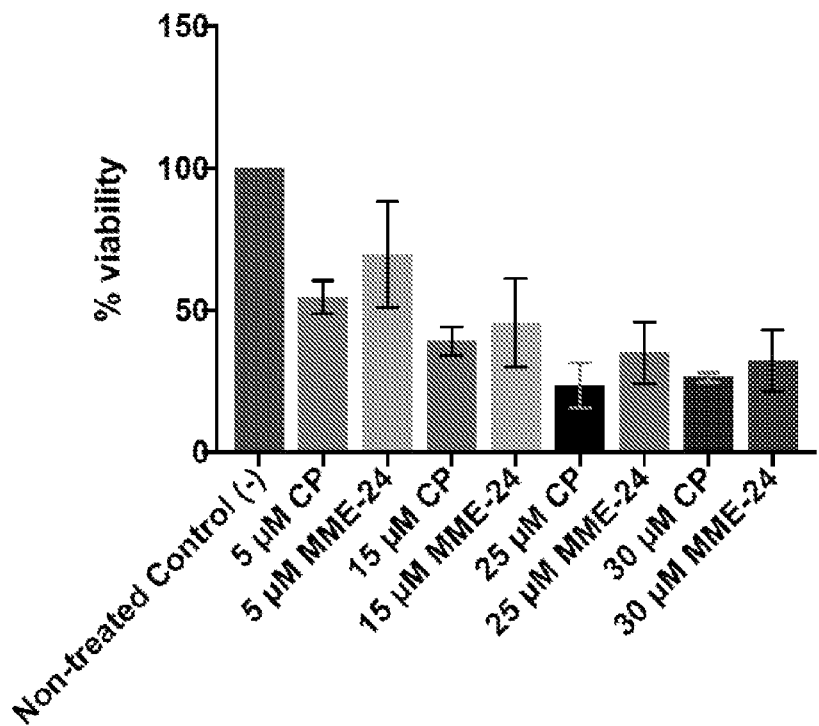
FIG. 41B. 4T1 cell viability study of non-treated control, cisplatin in cell culture media, and a nanoemulsion prepared with 20 mM M2DSG, 1 mL [DC-ether][2NTf$_2$], 3 mL MCT, and cisplatin. Data is presented as a mean±standard deviation (n=3).
Figure 41C:
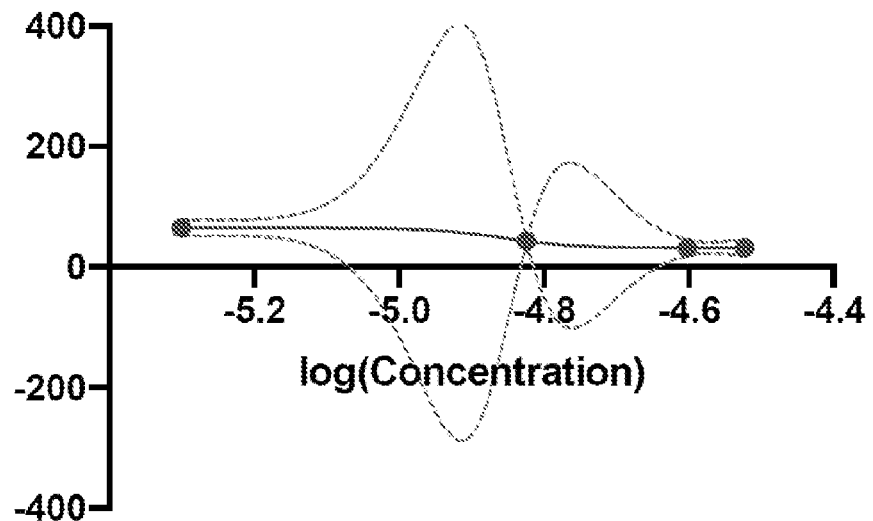
FIG. 41C. Calculation of the IC$_{50}$ of cisplatin in a nanoemulsion formulated with 15 mM M2DSG, 0.5 mL [DC-7][2NTf$_2$], 0.5 mL[DC-ether][2NTf$_2$], 3 mL MCT and 14 mL saline. The calculation was performed using graphpad Prism using a least squares ordinary fit.

In order to verify that cisplatin retains its efficacy in the ionic liquid nanoemulsions, cell viability assays of [DC-7][2NTf$_2$] and [DC-ether][2NTf$_2$] containing nanoemulsions were analyzed using a 4T1 murine breast carcinoma cell line. The nanoemulsions used for the cell viability assays were the same nanoemulsions used to construct a time-release profile of cisplatin. Specifically, the nanoemulsions analyzed were composed of: (1) 15 mM M2DSG 0.5 mL [DC-ether][2NTf$_2$], 0.5 mL [DC-7][2NTf$_2$], 3 mL MCT, 2 mg cisplatin, and 14 mL saline (MME-79); (2) 20 mM M2DSG, 1 mL [DC-ether][2NTf$_2$], 3 mL MCT, 1.8 mg cisplatin, and 14 mL saline (MME-24). MME-79 was analyzed on day 7, day 8, and day 11 of its stability, while MME-24 was analyzed on day 133, day 134, and day 137 of its stability. This allowed for determination of long-term efficacy of cisplatin in the nanoemulsions. Both nanoemulsions containing cisplatin are effective against 4T1 cells (FIGS. 41A-41B), indicating that cisplatin retains its efficacy after emulsification even when stored for an extended period of time. At the highest concentration analyzed (30 μM), the nanoemulsion containing a mixture of [DC-ether][2NTf$_2$] and [DC-7][2NTf$_2$] is more effective than that of cisplatin alone (FIG. 41A), demonstrating the benefit of a nanoemulsion based cisplatin drug delivery system. The IC$_{50}$ value of cisplatin in the nanoemulsion prepared with 15 mM M2DSG, 0.5 mL [DC-ether][2NTf$_2$], 0.5 mL [DC-7][2NTf$_2$], 3 mL MCT and 14 mL saline was also calculated. The IC$_{50}$ value of the nanoemulsion was found to be 14 μM, which is consistent with previously reported values of cisplatin for the 4T1 cell line.

Example 9

This example demonstrates In vivo Zebrafish toxicity studies in accordance with an embodiment of the invention.

Previously, the water-soluble ionic liquid precursor ([DC-7][2Br]), the water-soluble anion (sodium bis(trifluoromethylsulfonyl)imide) and a nanoemulsion containing the hydrophobic ionic liquid were analyzed using a zebrafish developmental toxicity assay. The hydrophobic ionic liquid in of itself had not been analyzed. This was due to the fact this hydrophobic ionic liquid has a greater density than water and it was thought this factor would result in cytotoxic effects, not necessarily from the inherent toxicity of the ionic liquid. For instance, toxic effects could be observed from various factors, including changes in surface tension to the zebrafish embryo. While the nanoemulsion was evaluated, analysis of the nanoemulsion does not directly analyze the toxicity of the hydrophobic ionic. To circumvent this issue, a water-solution saturated with the hydrophobic ionic liquid was analyzed using a zebrafish developmental toxicity assay. Quantitative NMR studies were used in order to determine the concentration of [DC-7][2NTf$_2$] in a saturated water solution. This allowed for direct analysis of the toxicity of the hydrophobic ionic liquid, [DC-7][2NTf$_2$]. The water-soluble precursor of the hydrophobic ionic liquid with an ether linkage as opposed to an alkyl linkage was also analyzed ([DC-ether][2Cl]) in order to determine the effect of an ether-linkage on the toxicity of the cationic moiety. Both the water-soluble precursor as well as the hydrophobic ionic liquid saturated ionic liquid exhibited minimal toxicity.

Figure 42A:
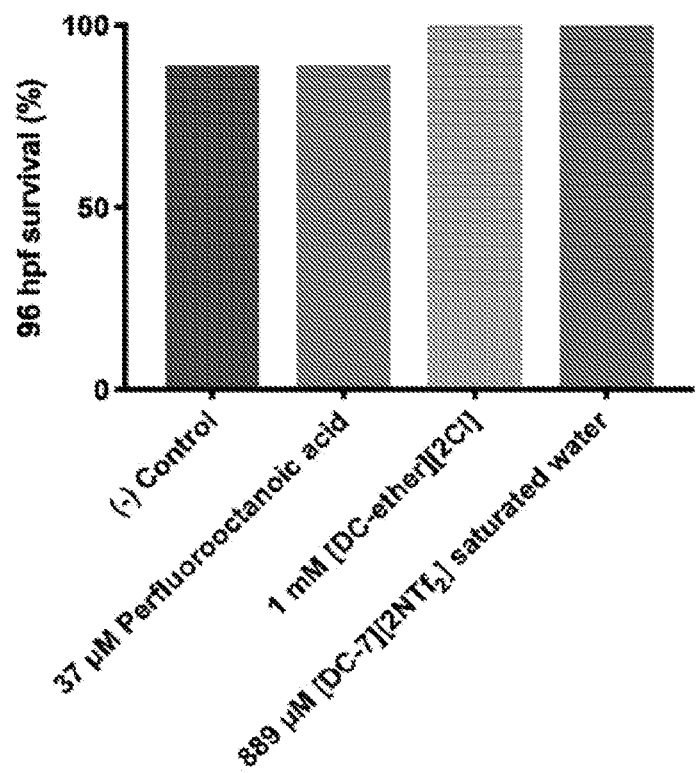
FIG. 42A. Zebrafish developmental toxicity assay for analysis of the in vivo toxicity of [DC-7][2NTf$_2$] and [DC-ether][2Cl].
Figure 42B:
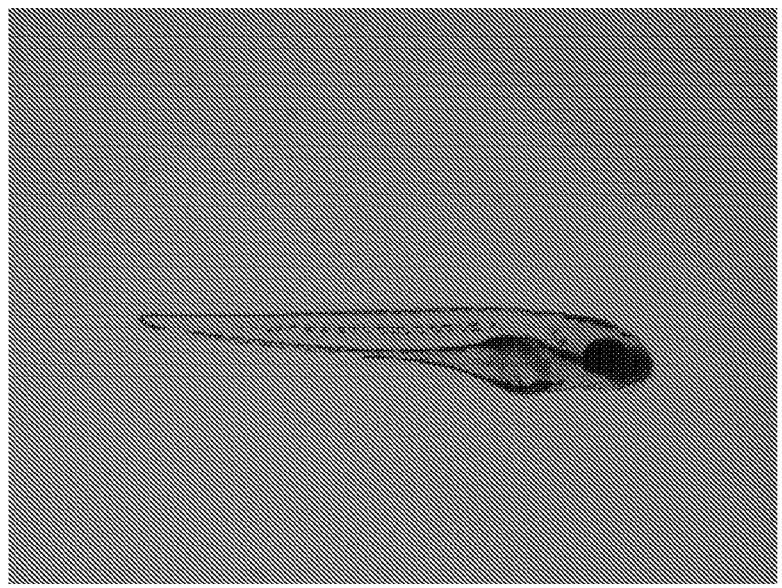
FIG. 42B. Zebrafish developmental toxicity image at 96 hours post-fertilization for analysis of in vivo toxicity of [DC-7][2NTf$_2$] at 889 µM.
Figure 42C:
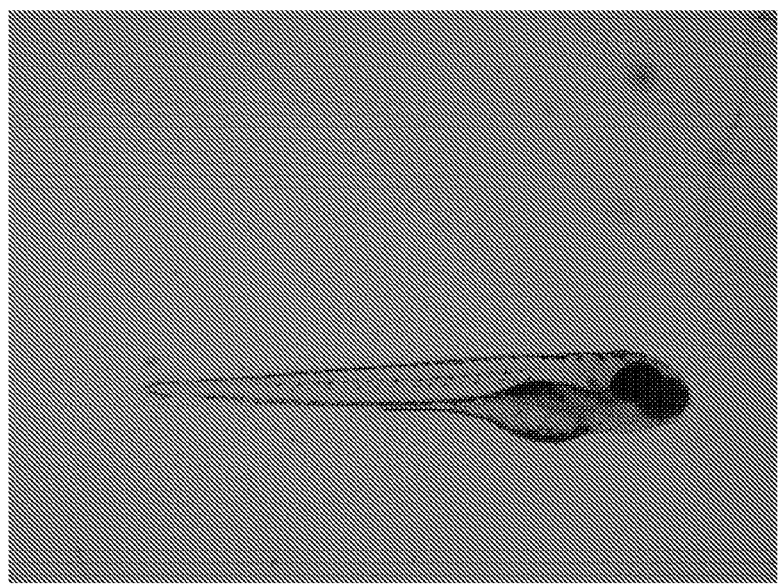
FIG. 42C. Zebrafish developmental toxicity image at 96 hours post-fertilization for analysis of in vivo toxicity of [DC-ether][2Cl] at 1 mM.

[DC-7][2NTf$_2$] saturated water had a 100% viability (FIG. 42A) at 96 hours post fertilization with no malformations at a concentration of 889 μM (FIG. 42B). This further verifies the biocompatibility of the novel hydrophobic ionic liquids. [DC-ether][2Cl] had 100% viability (FIG. 42A) and no malformations (FIG. 42C) 96 hours post fertilization at a concentration of 1 mM. This is consistent with the previous analysis of [DC-7][2Br], indicating that the presence of an ether-linkage does not affect the cationic moieties toxicity.

Example 10

This example demonstrates In vivo preliminary mouse studies studies in accordance with an embodiment of the invention.

A preliminary study was completed with six female Balb/C mice that had been used for a previous in vivo study. Ionic liquid containing nanoemulsions, without the presence of drug, were intravenously administered via the tail vein in order to evaluate the toxicity of the ionic liquids present in the nanoemulsions when administered systemically. Two nanoemulsions containing ionic liquids were analyzed, while one emulsion containing MCT only was analyzed in order to evaluate the toxicity of the polymer only. The nanoemulsions containing ionic liquid analyzed were (1) 15 mM M2DSG, 14 ml saline, 3 mL MCT, 1 mL [DC-ether][2NTf$_2$], and (2) 15 mM M2DSG, 14 mL saline, 3 mL MCT, 0.6 mL [DC-ether][2NTf$_2$], 0.4 mL [Chol][Hex]. Nanoemulsion (1) is representative of a formulation for delivery of cisplatin while (2) is representative of a formulation for delivery of AmB. Two different concentrations for each nanoemulsion were analyzed, mimicking the formulation for delivery of 0.2 mg/kg AmB and 0.4 mg/kg AmB. All mice survived 1 week after injection, prior to euthanization. While not enough mice were used in order to publish this study, it demonstrates the ability to use these ionic liquid nanoemulsions intravenously.

Example 11

This example demonstrates the change in average particle size over time of nanoemulsions in accordance with an embodiment of the invention.

Figure 43A:
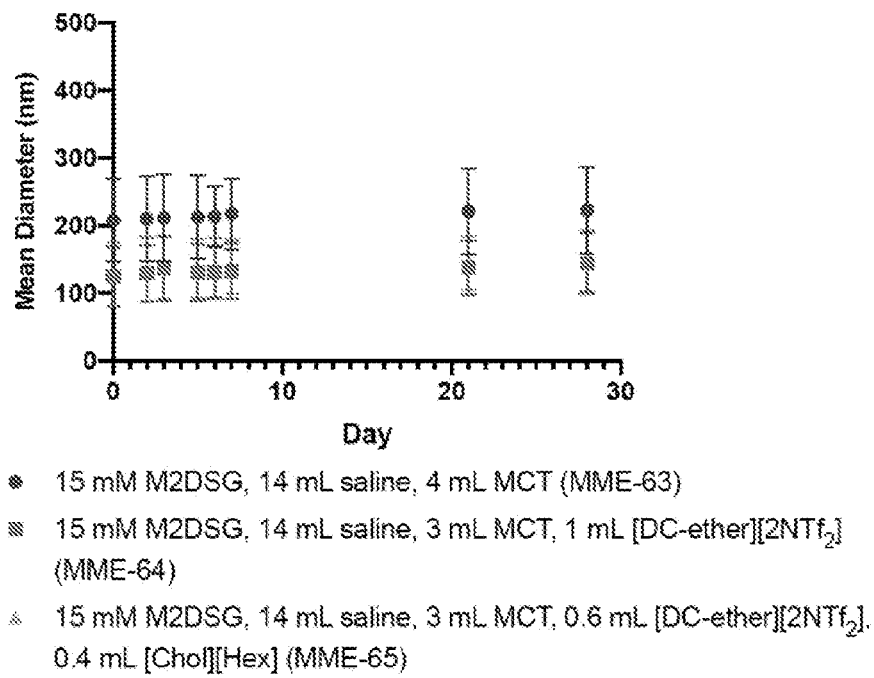
FIG. 43A. Average particle size over time of nanoemulsions used for preliminary in vivo study.
Figure 43B:
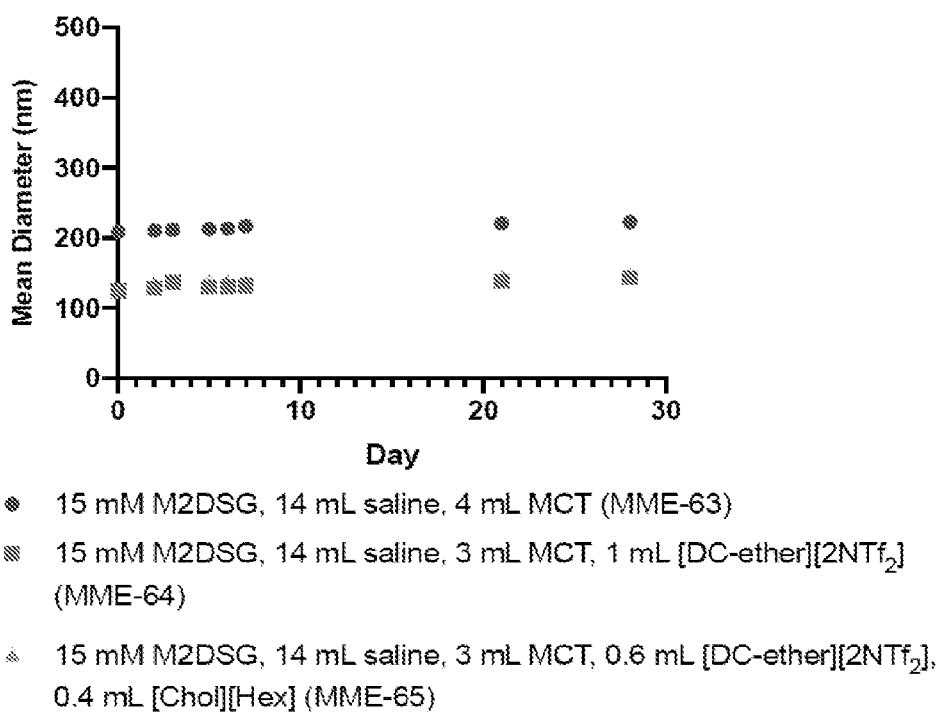
FIG. 43B. Average particle size over time of nanoemulsions used for preliminary in vivo studies with error bars omitted for clarity.
Figure 44:
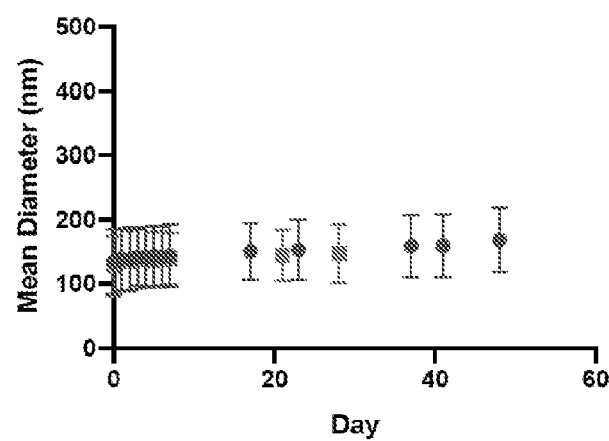
FIG. 44. Comparison of the average particle size over time of two nanoemulsions prepared with the same composition in order to demonstrate the reproducibility of these nanoemulsions.

Two nanoemulsions were prepared using the same composition in order to demonstrate the reproducibility of these nanoemulsions. FIGS. 43A, 43B, and 44.

REFERENCES (1) Eriksson, U. Comparison of Effects of Amphotericin B Deoxycholate Infused over 4 or 24 Hours: Randomised Controlled. *Bmj* 2002, 322 (7286), 579-579.
(2) Imhof, A.; Walter, R. B.; Schaffner, A. Continuous Infusion of Escalated Doses of Amphotericin B Deoxycholate: An Open-Label Observational Study. *Clin. Infect. Dis.* 2003, 36 (8), 943-951.
(3) Peleg, A. Y.; Woods, M. L. Continuous and 4 h Infusion of Amphotericin B: A Comparative Study Involving High-Risk Haematology Patients. *J. Antimicrob. Chemother.* 2004, 54 (4), 803-808.
(4) Yu, D. T.; Chertow, G. M.; Dasbach, E. J.; Bates, D. W.; Seger, D. L.; Platt, R.; Gomes, D. R. J.; Su, L. Mortality and Costs of Acute Renal Failure Associated with Amphotericin B Therapy. *Clin. Infect. Dis.* 2002, 32 (5), 686-693.
(5) Hiemenz, J. W. Editorial Commentary: Amphotericin B Deoxycholate Administered by Continuous Infusion: Does the Dosage Make a Difference? *Clin. Infect. Dis.* 2003, 36 (8), 952-953.
(6) Dobrucki, L. W.; Dobrucki, I. T.; Yao, C.; Lezmi, S.; Ferguson, A. L.; Tang, L.; Helferich, W. G.; Chaudhury, I.; Zhou, Q.; Yin, Q.; et al. Investigating the Optimal Size of Anticancer Nanomedicine. *Proc. Natl. Acad. Sci.* 2014, 111 (43), 15344-15349.
(7) Kobayashi, H.; Watanabe, R.; Choyke, P. L. Improving Conventional Enhanced Permeability and Retention (EPR) Effects; What Is the Appropriate Target? *Theranostics* 2014, 4 (1), 81-89.
(8) Browning, R. J.; James, P.; Reardon, T.; Parhizkar, M.; Pedley, R. B.; Edirisinghe, M.; Knowles, J. C.; Stride, E. Drug Delivery Strategies for Platinum-Based Chemotherapy. 2017.
(9) Lau, J. K.; Ensing, B. Hydrolysis of Cisplatin—a First-Principles Metadynamics Study. *Phys. Chem. Chem. Phys.* 2010, 12, 10348-10355.
(10) Yerlikaya, A.; Altikat, S.; Irmak, R.; Cavga, F. Z.; Kocacan, S. A.; Boyaci, I. Effect of Bortezomib in Combination with Cisplatin and 5-Fluorouracil on 4T1 Breast Cancer Cells. *Mol. Med. Rep.* 2013, 8 (1), 277-281.

Example 12

Example 12: Chemical-Physical-Biological Characterization

MATERIALS. Cisplatin was purchased from Santa Cruz Biotechnology (Dallas, Tex.). Sodium trifluoroacetate, 97%, was purchased from VWR International (Radnor, Pa.). 1,6-dibromohexane, 98% was purchased from Fisher Scientific (Hampton, N.H.). Solvents and all other reagents were purchased from Sigma-Aldrich Co. (Milwaukee, Wis.) and Spectrum (Gardena, Calif.) and used as received, unless otherwise mentioned.

Normal saline (AirLife sterile 0.9% sodium chloride for irrigation USP) and Amphotericin B for injection USP (Gen-X pharmaceuticals) were purchased from the University of Wisconsin-Madison Hospital Pharmacy. Amphotericin B powder was purchased from Sigma-Aldrich Co, stored at 4° C., and shielded from light during storage. Rabbit red blood cells were purchased from Lampire Biologic Laboratories, Inc (Pipersville, Pa.) and stored at 4° C. The rabbit red blood cells were used within 2 weeks of receipt. Phosphate buffered saline (pH 7.4) (PBS) was purchased from Cellgro (Mediatech Inc., Manassas, Va.). N-(Methylpolyoxyethyleneoxycarbonyl)-1,2-distearoyl-sn-glycero-3-phosphoethanolamine, sodium salt (DSPE-PEG, 2000 g/mol average molecular weight PEG) and 1,2-Distearoyl-rac-glycero-3-methylpolyoxyethylene (DSG-PEG, 2,000 g/mol average molecular weight of PEG) were purchased from NOF America Corporation (White plains, NY) and stored at −20° C. 1,2-Distearoyl-rac-glycero-3-methylpolyoxyethylene (DSG-PEG, 2,000 g/mol average molecular weight of PEG) was also purchased from Avanti® Polar Lipids, Inc (Alabaster, Ala.) and stored at −20° C. 1,7-dibromohexane, 98% was purchased from Fisher Scientific (Hampton, N.H.). Solvents and all other reagents were purchased from Sigma-Aldrich Co. (Milwaukee, Wis.) and Spectrum (Gardena, Calif.) and used as received, unless otherwise mentioned.

Synthetic Methods.

Synthesis of cholinium hexanoate. Cholinium hexanoate ([Chol][Hex]) was synthesized via an acid-base neutralization reaction between choline bicarbonate (~80% in water) and hexanoic acid. Hexanoic acid was added dropwise to the aqueous solution of choline bicarbonate. The reaction mixture was stirred at room temperature open to atmosphere for 24 hours. Water was subsequently removed using rotary evaporation under reduced pressure at 60° C. The isolated ionic liquid was further dried under high vacuum for 2 hours at 60° C. The ionic liquid was then further dried under high vacuum for 48 hours at room temperature.

Synthesis of dicationic cholinium-based bromide salt. Dicationic cholinium-based bromide salt ([DC-7][2Br]) was prepared via a quaternization reaction. Dimethylaminoethanol (0.078 mol) and alkyl dibromide (0.039 mol) were added to a glass reaction flask containing acetonitrile (100 mL). The reaction mixture was refluxed overnight. After this time, the reaction was cooled to room temperature. The white precipitate was filtered off and rinsed three times with acetone (60 mL acetone). The salt was dried under reduced pressure for a minimum of 24-hours before use.

Synthesis of cholinium-based dicationic ionic liquid. Dicationic cholinium-based ionic liquid ([DC-7][2NTf$_2$]) was prepared via an anion-exchange metathesis reaction. Cholinium-based dicationic bromide salt (0.034 mol) was dissolved in Millipore water (500 mL). Lithium bis(trifluoromethylsulfonyl)imide (0.068 mol) was then added to the reaction mixture. The reaction mixture was stirred until phase separation was observed (between 6 and 12 hours). The ionic liquid layer was isolated and washed with deionized water until no bromide was observed using the silver nitrate test (1M silver nitrate in water).

Characterization Methods

Example 12A. $^1$H, $^{13}$C, and $^{19}$F NMR spectroscopy. $^1$H, $^{13}$C, and $^{19}$F NMR spectra were measured using a Bruker Avance III HD 400 MHz spectrometer or the Varian UI 500 MHz spectrometer. All spectra were measured with either (CD$_3$)$_2$CO, CD$_3$OD, or D$_2$O as the solvent.

Example 12A: Quantitative $^{19}$F NMR spectroscopy (QNMR) for determination of concentration of hydrophobic ionic liquids in a water-solution for comparison of water-solubility of hydrophobic ionic liquids.

$^{19}$F NMR spectra was measured using a Varian UI 500 MHz spectrometer equipped with a Nalorac Quad Nucleus DD probe (qn6121, 5 mm). The internal temperature of the NMR spectrometer was maintained at 25° C. Sodium trifluoroacetate was used as an internal standard was employed in order to determine the concentration of [DC-7][2NTf$_2$]. The internal standard was prepared in D$_2$O and the stock solution was allowed to sonicate at 30° C. for 4 hours prior to use in order to ensure complete dissolution of sodium trifluoroacetate. Prior to quantitative study, the T$_1$ value of both [DC-7][2NTf$_2$] and sodium trifluoroacetate were determined using an inversion recover experiment acquired with 12 independent quadratically spaced variable (tau) values (values from 0.06944-10). The T$_1$ value was calculated in order to ensure that both signals fully relaxed between pulses. The following parameters were employed for acquisition of T$_1$ spectra: 500 MHz; spectra width, 107962.2 Hz; acquisition time, 1.004 s; number of points, 216688; relaxation delay, 18.996 s; number of transients, 1; 90° pulse width, 17.1 µs. X-Win32 software was used to calculate the T$_1$ value and processing included a line broadening of 1 Hz.

Figure 58:
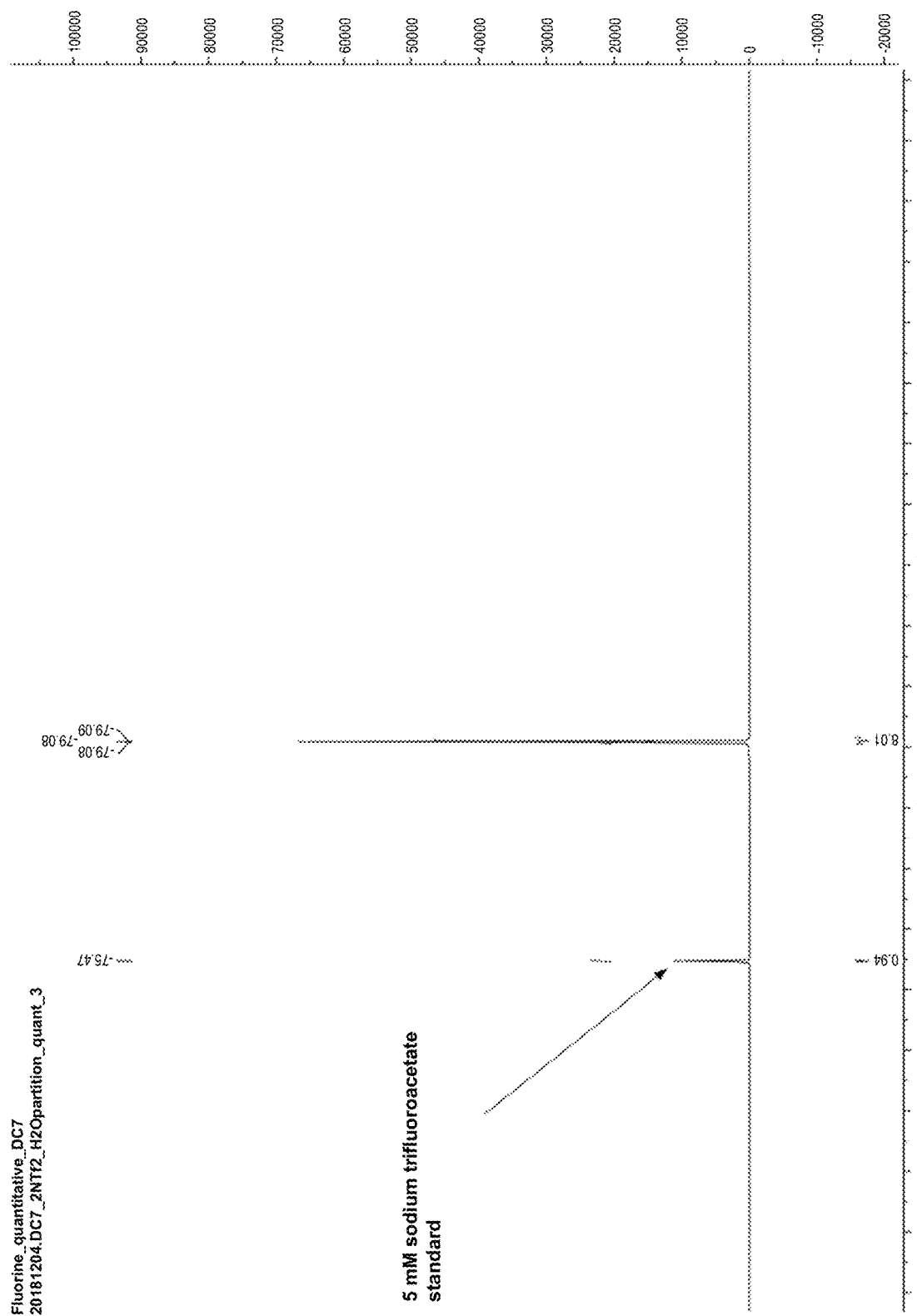

The T$_1$ value of the sodium trifluoroacetate and [DC-7][2NTf$_2$] was determined to be 2.76±0.172 seconds and 2.69±0.0885 seconds, respectively. After determination of T$_1$, the QNMR study was completed on an optimized spectrum. The following parameters were employed for acquisition of QNMR spectrum: 500 MHz; spectral width, 107962.2 Hz; acquisition time, 2.00 s; number of points, 431848; relaxation delay, 28.00 s; number of transients, 32; 90° pulse width, 17.1 is. The acquired spectrum has a signal to noise ratio of 4700, which exceeded the desired 3000 needed for quantitation. Sample preparation was as follows and exactly mimicked samples preparation for in vivo toxicity study to ensure accurate representation of concentration: 1.5 mL of [DC-7][2NTf$_2$] was added to a 15 mL conical centrifuge tube followed by 1.5 mL of D$_2$O (FIG. 58). The sample was allowed to sit for 6 days prior to use. Each day, the sample was sonicated at 40° C. for 6 hours and then allowed to remain at room temperature for 18 hours. After 6 days, the sample was centrifuged at 2000 rpm for 5 minutes to ensure complete sedimentation of the ionic liquid. 0.5 mL of D$_2$O was removed and then subsequently analyzed. Integration of the internal standard and [DC-7][2NTf$_2$] allowed for quantitation of the concentration of [DC-7][2NTf$_2$] present in the stock solution used for the zebrafish viability assay. The concentration of [DC-7][2NTf$_2$] in the D$_2$O sample was found to be 10.66 mM using the following formula:

$$\text{Concentration } IL = \frac{\left(\frac{\text{Integration DC} - 7}{12}\right)(\text{Concentration Standard})}{\left(\frac{\text{Integration Standard}}{3}\right)}$$

TABLE 4

Water-solubility of synthesized hydrophobic ionic liquids

| Ionic Liquid | Ionic Liquid Concentration in D$_2$O (mM) |
| --- | --- |
| [DC-6][2NTf$_2$] | 10 |
| [DC-7][2NTf$_2$] | 6 |
| [DC-ether][2NTf$_2$] | 13 |

Example 12B: Electrospray Ionization Mass Spectrometry (ESI)

Figure 59:
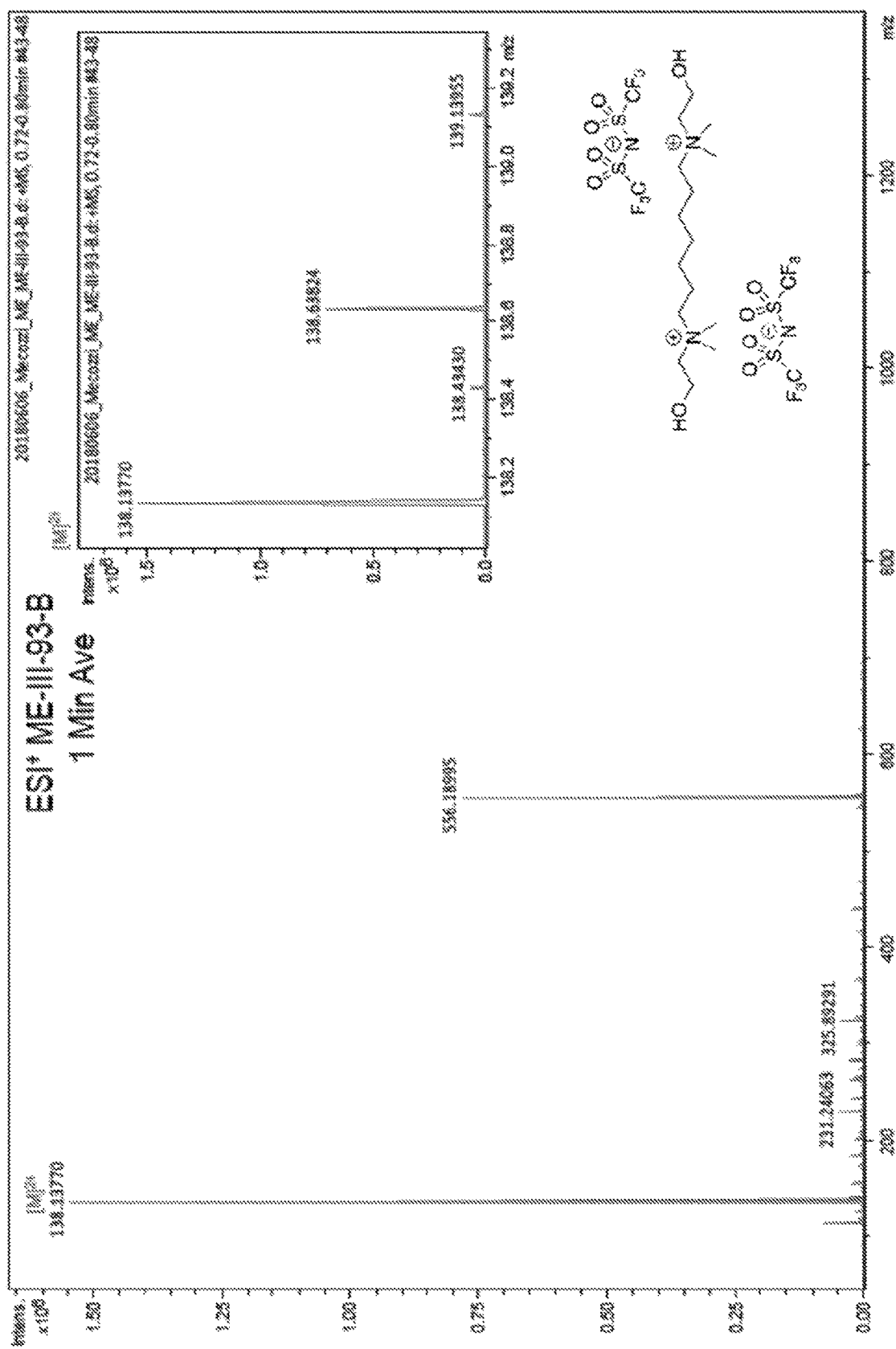
Figure 60:
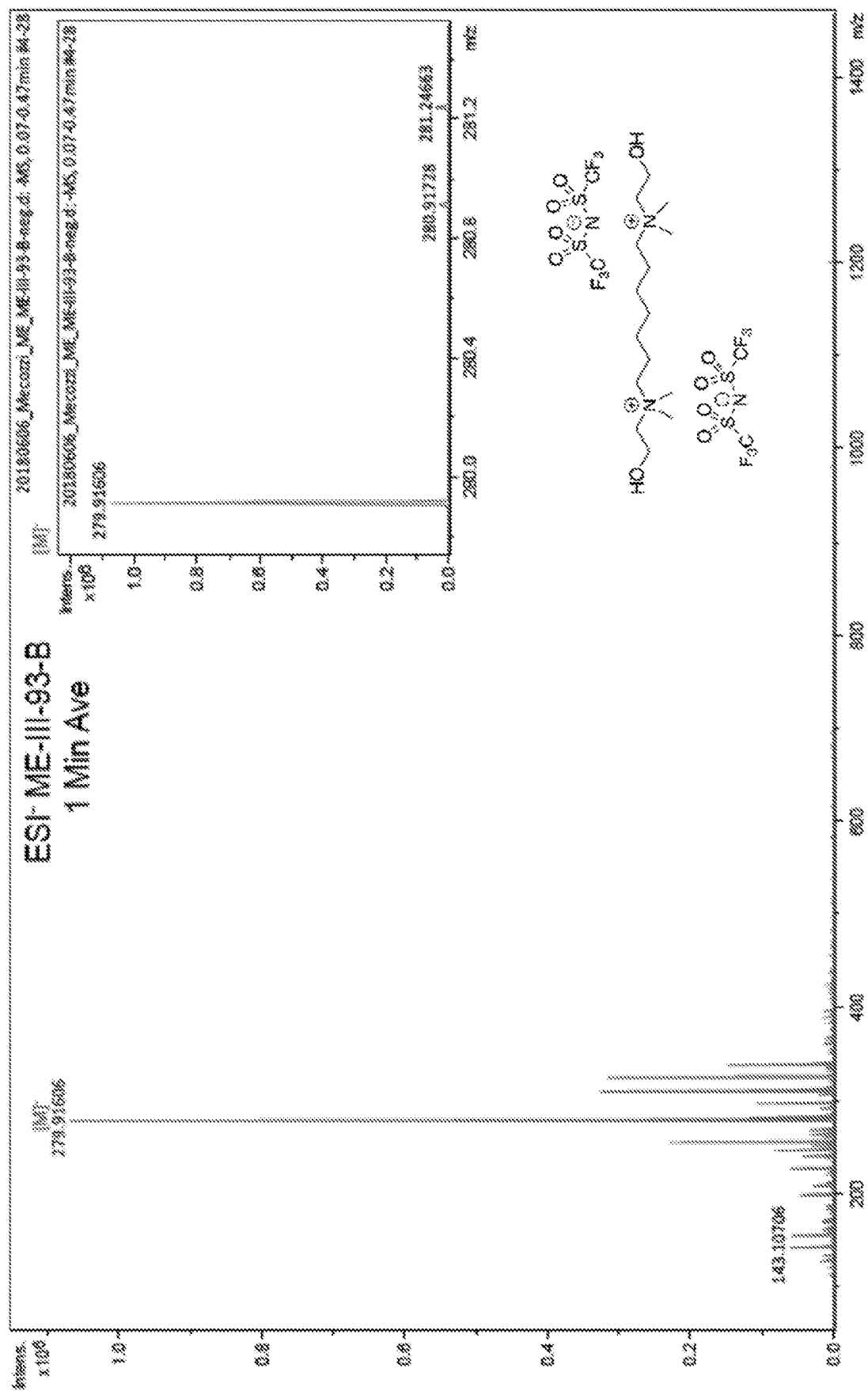
Figure 61A:
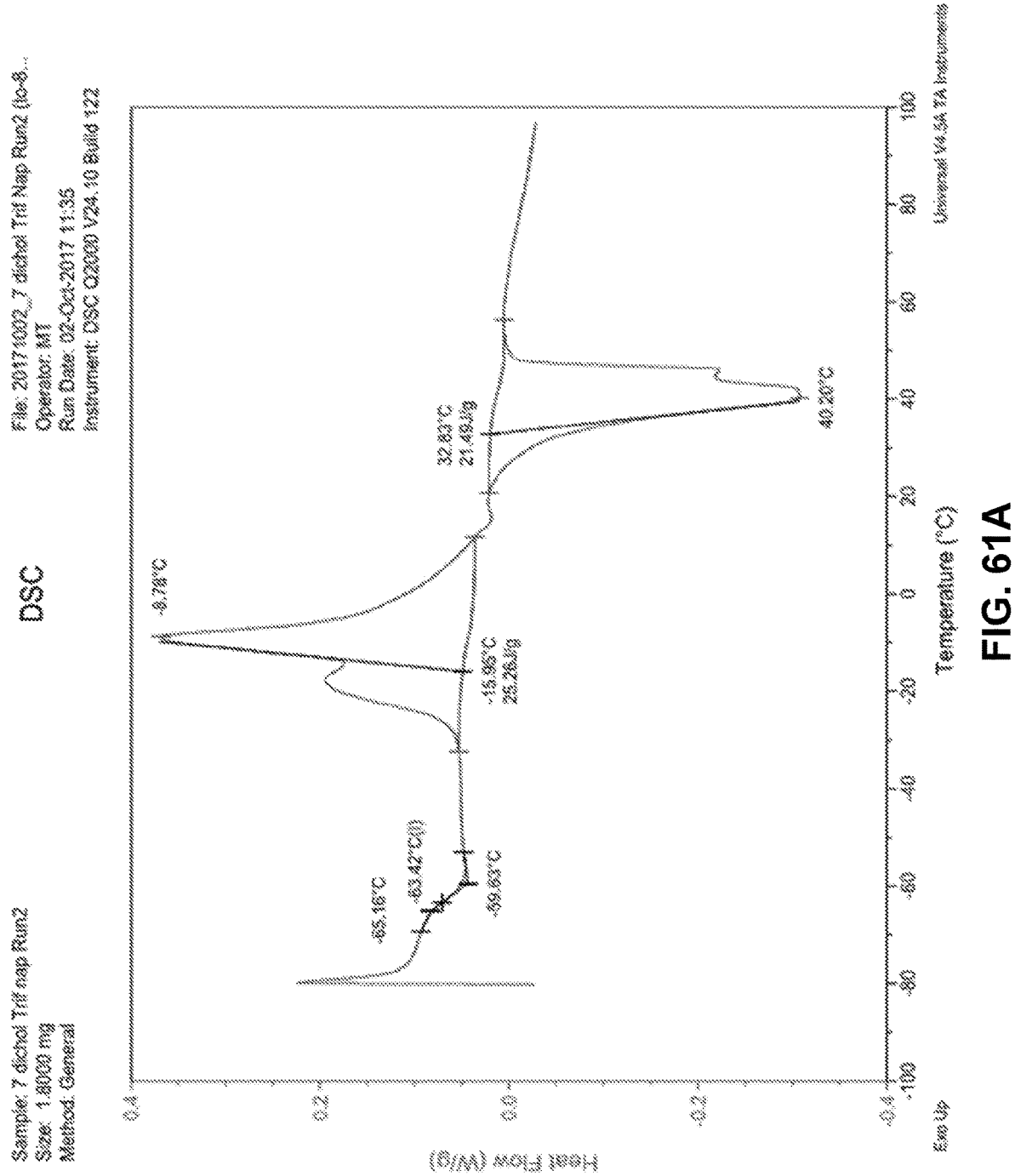
Figure 61B:
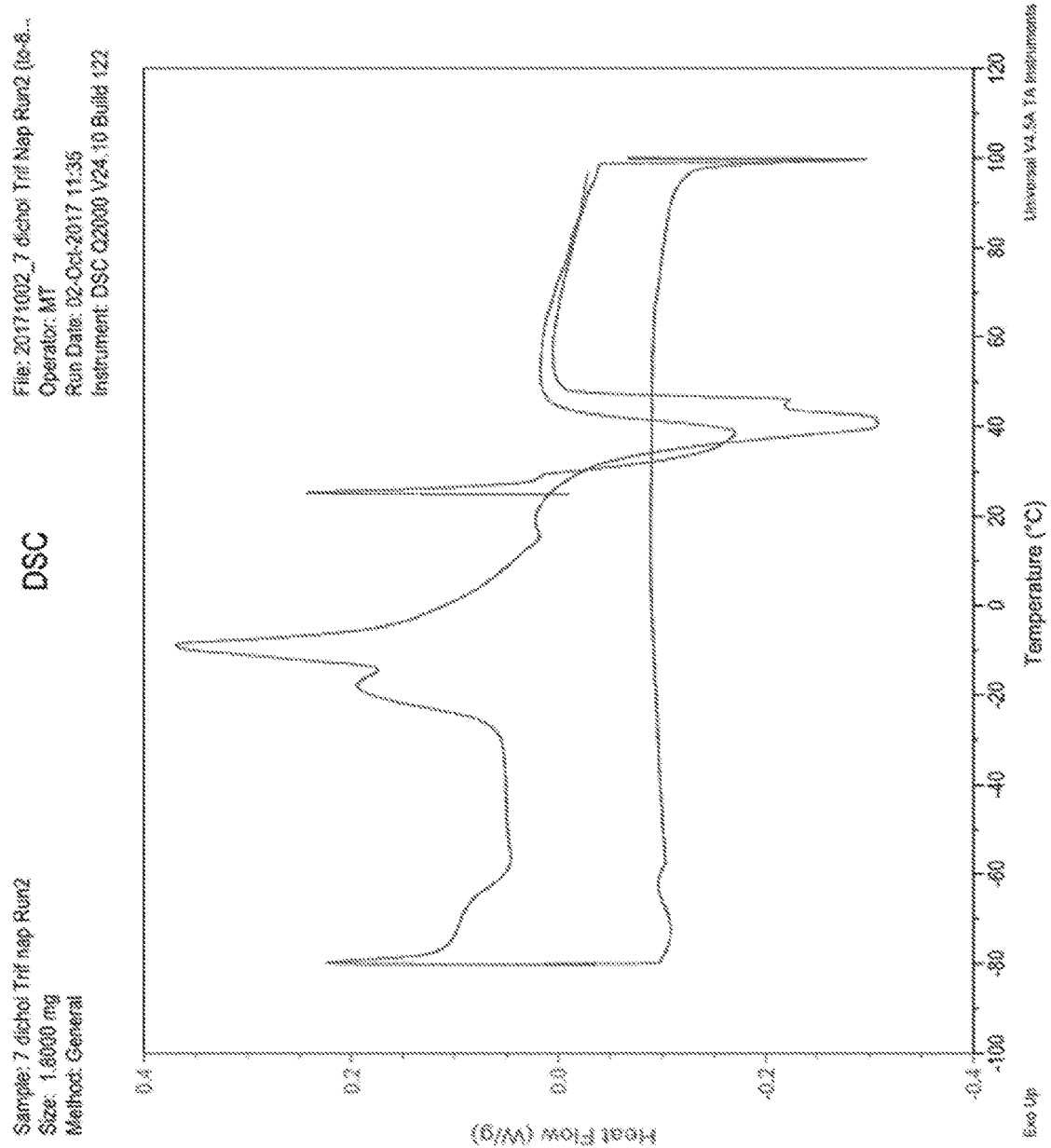
Figure 61C:
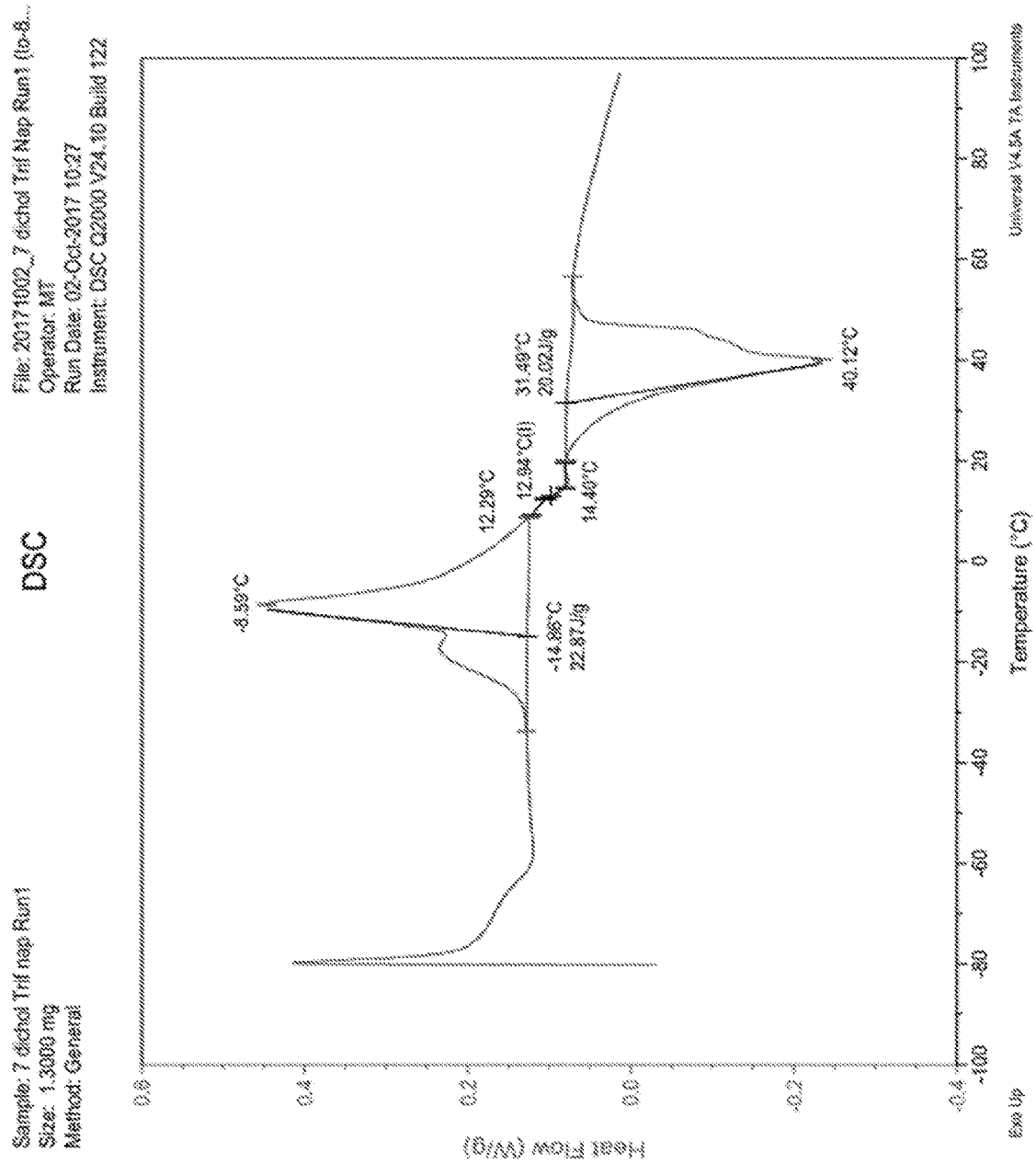
Figure 61D:
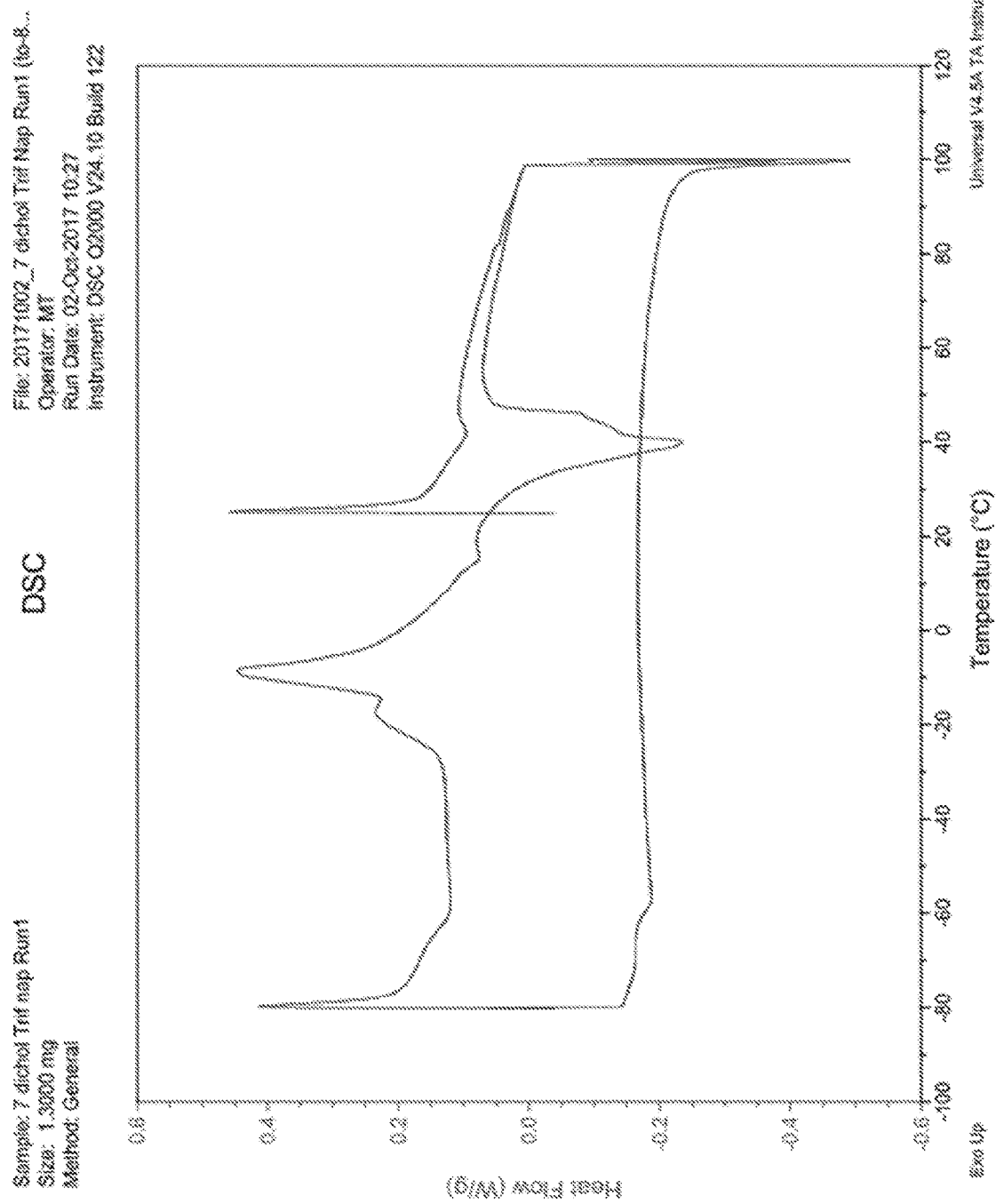

Sample was analyzed using ESI ultra high resolution QTOF MS (MaXis 4G) with ESI infusion on positive ion mode and negative ion mode. Sample was prepared with a 1:1,000 dilution in methanol for the positive ion mode and 1:100,000 in methanol for the negative ion mode (FIGS. 59 and 60).

| Compound formula | Theoretical (monoisotopic) Mass | 5 ppm | Range | Observed Mass | Mass Accuracy (ppm) | Resolution (FWHM) | Intensity |
| --- | --- | --- | --- | --- | --- | --- | --- |
| [C$_{15}$H$_{36}$N$_2$O$_2$]$^{2+}$ | 138.138291 | 138.1376003 | 138.1389817 | 138.13770 | -4.278 | 16,189 | 1,539,372 |
| [C$_2$F$_6$N$_1$O$_4$S$_2$]$^-$ | 279.916745 | 279.9153454 | 279.9181446 | 279.91606 | -2.447 | 49,005 | 1,065,709 |

Example 12C: Physical Characterization—Viscosity

A Brookfield viscometer (Model RVDV-1) was used to analyze the ionic liquids at 30° C. The spindle used on the instrument was CPA-41Z. After addition of 2 mL of sample to the instrument cup, the cup was warmed until all IL samples were completely transparent before beginning the measurement. The RPM was adjusted per sample in order to ensure the percent torque applied per sample was in a consistent range.

TABLE 5

Viscosity of dicationic cholinium-based ionic liquids

| Ionic Liquid | Temperature (° C.) | RPM* | Torque (%) | Viscosity (cP) |
|---|---|---|---|---|
| [DC-6][2NTf$_2$] | 30.2 | 5 | 72.8 | 1788 |
| [DC-ether][2NTf$_2$] | 30.2 | 10 | 72.6 | 891.5 |

Example 12D: UV-Visible Spectroscopy

Measuring absorbance of Amphotericin B (AmB) at distinct wavelengths using UV/vis spectroscopy provides insight into its degree of self-aggregation. Absorption spectra were obtained on a Varian Cary 100Bio UV-vis spectrometer (Varian, Palto Alto, Calif.) at 25° C. using a quartz coverslip with a 0.1 mm pathlength (Starna Cells, Inc., Atascadero, Calif.) or a 1 mm pathlength quartz cuvette (Starna Cells, Inc., Atascadero, Calif.). Absorbance was measured from 300 nm to 500 nm. Samples were prepared by direct addition of AmB powder to neat ionic liquids. Ionic liquids solid at room temperature were first melted using a water bath at 60° C. prior to addition of AmB powder. After addition of solid drug, (1) 100 µL of methanol was then added to the IL mixture and the mixture was stirred at room temperature for 1 hour. (2) The drug/IL mixture was then placed under rotary evaporation in a water bath with at a temperature of 60° C. for 1 hour. (3) The drug/IL mixture was then placed under high vacuum for 1 hour. (4) The drug/IL mixture was then allowed to stir for 1 hour. This process (steps 1-4) was repeated until all drug visibly was solubilized. The drug/IL mixture was then placed under rotary evaporation at 60° C. for an additional hour and then under high vacuum for 24 hours prior to use to ensure removal of all methanol. Samples were shielded from light prior to analysis. Neat ionic liquids served as the baseline for AmB samples solubilized in ionic liquid. Dilution samples were performed using 1×PBS for dilution. Analysis of AmB nanoemulsion required a nanoemulsion without drug as the baseline to correct for inherent scattering of the prepared nanoemulsion.

UV/visible spectroscopy Amphotericin B water partition study. The ionic liquid mixture was prepared by direct addition of AmB powder to neat ionic liquids. Ionic liquids solid at room temperature were first melted using a water bath at 60° C. prior to addition of AmB powder. After addition of solid drug, (1) 100 µL of methanol was then added to the IL mixture and the mixture was stirred at room temperature for 1 hour. (2) The drug/IL mixture was then placed under rotary evaporation in a water bath with at a temperature of 60° C. for 1 hour. (3) The drug/IL mixture was then placed under high vacuum for 1 hour. (4) The drug/IL mixture was then allowed to stir for 1 hour. This process (steps 1-4) was repeated until all drug visibly was solubilized. Prior to the partition study, the IL mixture was stirring for 5 minutes, followed by 25 minutes of rotation on rotary evaporator at 60° C. to remove any residual water. 200$\mu$L of this sample was removed and saved for later UV/vis analysis. 500 $\mu$L of water was added to the remaining 500 µL of the IL mixture (at a temperature of –60° C. as was used immediately after stirring) in a 1.5 mL centrifuge tube. The sample was vortexed for 30 seconds, and sonicated for 1 min. The sample was then centrifuged at 2000 rpm for 2 minutes. The water layer was immediately removed after centrifugation. Water of a mixture of [DC-7][2NTf$_2$] and [Chol][Hex] was used as the baseline. Samples were analyzed using a quartz microscope slide with a 0.1 mm pathlength and were analyzed from 300 nm to 500 nm. 200 µL of sample was placed on the microscope slide for each analysis for uniformity.

Measuring absorbance of cisplatin (CP) using UV/vis spectroscopy provides insight into its emulsification efficacy. Absorption spectra were obtained on a Varian Cary 100Bio UV-vis spectrometer (Varian, Palto Alto, Calif.) at 25° C. using a quartz coverslip with a 0.1 mm pathlength (Starna Cells, Inc., Atascadero, Calif.). Absorbance was measured from 200 nm to 500 nm. For analysis completed in [DC-7][2NTf$_2$] only, IL without drug was used as baseline. Samples were shielded from light prior to analysis.

Example 12E: In Vitro Cytotoxicity on 4T1 Murine Breast Carcinoma Cells

Figure 70:
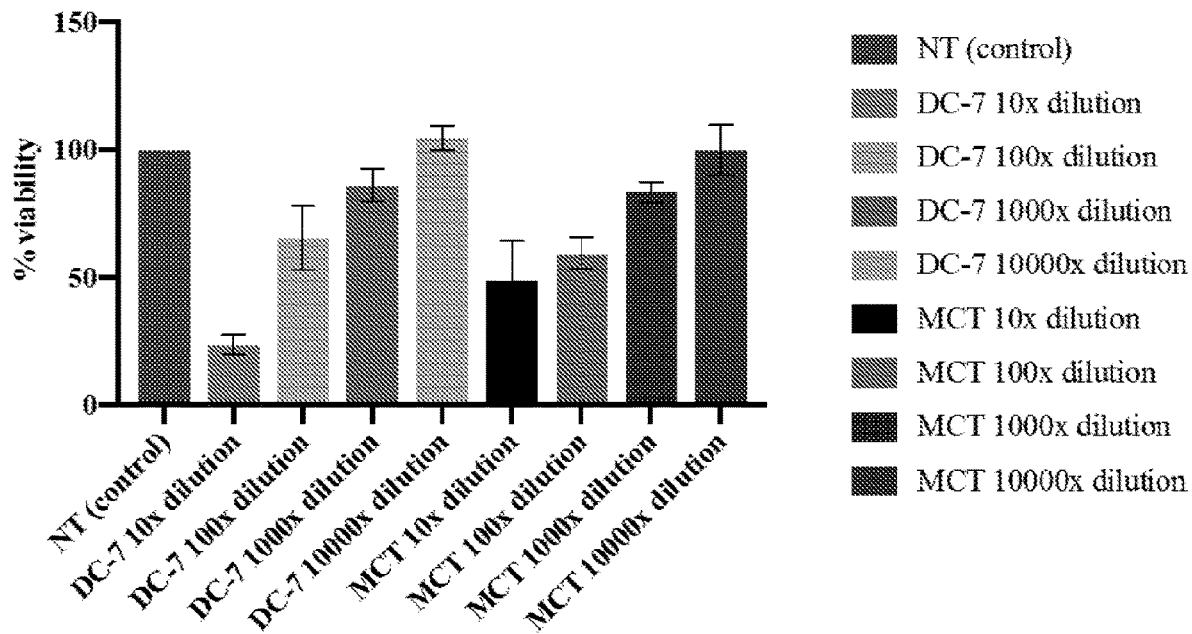
FIG. 70. In vitro cell viability assay of two replicate trials of [DC-7][2NTf$_2$] containing nanoemulsion with A549 human lung carcinoma cells after 24-hour incubation.

In vitro studies were completed to verify that the activity of the chemotherapeutic cisplatin was maintained after emulsification. Three-day cytotoxicity studies were performed on 4T1 murine breast carcinoma cell line. The two nanoemulsions that were studied were formulated as follows: (1) 20 mM 1,2-distearoyl-rac-glycerol-methoxypolyethyleneglycol 2000 (M2DSG) surfactant, 1 mL [DC-ether] [2NTf$_2$], and 1 mL medium chain triglycerides (MCT) from coconut oil with 14 mL saline (0.9% w/w sodium chloride); (2) 15 mM 1,2-distearoyl-rac-glycerol-methoxypolyethyleneglycol 2000 (M2DSG) surfactant, 0.5 mL [DC-ether] [2NTf$_2$], 0.5 mL [DC-7][2NTf$_2$] and 1 mL medium chain triglycerides (MCT) from coconut oil with 14 mL saline (0.9% w/w sodium chloride). 4T1 cells were cultured in DMEM media containing 10% (v/v) heat inactivated fetal bovine serum and 1% (v/v) penicillin-streptomycin. Cells were grown into a monolayer in tissue culture plates incubated at 37° C. in a 5% CO$_2$ atmosphere and 90% relative humidity. For the viability assay, cells were added to a 96-well plate at a cell density of 3000 cells/well and incubated for 24 h. Both nanoemulsions were used from previous preparations (i.e. they were not prepared the day of plating). Nanoemulsion solutions at varying concentrations were prepared in DMEM media (+) immediately before plating. 100 µL of nanoemulsion solution were directly added to the wells. The cells were then incubated with the DMEM control, cisplatin controls prepared in DMEM media (+), and cisplatin containing nanoemulsions for 24 hours. After 24 h of incubation, the assay was carried out following the manufacturers protocol (CELLTITER-BLUE™ Cell Viability Assay). 100 μL of diluted CellTiter blue was added to each well after removing previous media. The fluorescence signal was measured 2 h after addition of the dye. A minimum of six wells was used for each sample. The fluorescence signals of the wells were averaged (n=6) and represented as percentages of cell viability determined using untreated cells as the control (100% viability) (FIG. 70).

Example 12F: Nanoemulsion Preparation

Aqueous polymer solutions were prepared freshly (10-20 mM) in sterile, normal saline and sonicated at 40° C. until fully dissolved (approximately 2 hours). Saline was composed of 0.9% (w/w) sodium chloride USP. Drug/IL mixture solutions were prepared freshly, being allowed to sit for no more than 48 hours. Solid drug was directly added to the IL mixture. (1) 100 μL of methanol was then added to the IL mixture and the mixture was stirred at room temperature for 1 hour. (2) The drug/IL mixture was then placed under rotary evaporation in a water bath with at a temperature of 60° C. for 1 hour. (3) The drug/IL mixture was then placed under high vacuum for 1 hour. (4) The drug/IL mixture was then allowed to stir for 1 hour. This process (steps 1-4) was repeated until all drug was visibly dissolved. The drug/IL mixture was then placed under rotary evaporation at 60° C. for an additional hour and then under high vacuum for 24 h prior to use to ensure removal of all methanol. During solubilization of cisplatin and Amphotericin B, the IL mixture was shielded from light to prevent degradation. The homogenizer and microfluidizer were first cleaned with 100% and 70% ethanol followed by 100% and 70% methanol and finally three rinses with Millipore water to remove all traces of any previous nanoemulsions. For PTX drug/IL mixture solution and medium chain triglycerides (MCT) from coconut oil were added to the polymer solution. Certain AmB containing nanoemulsions are prepared using both processes (i.e. where IL mixture and MCT is homogenized with polymer solution and also where IL mixture and MCT are homogenized alone (no polymer solution). To ensure all of the drug/IL mixture was added to the polymer solution, the drug/IL mixture was warmed to 60° C. to allow for ease of pouring. The prepared mixture was then homogenized with the high-speed homogenizer (Power Gen 500, Fisher Scientific, Hampton, N.H.) for 1 min at 21,000 rpm at room temperature. The resulting crude emulsion was then further mixed with the microfluidizer (model M-110S, Microfluidics Corp., Newton, Mass.) for 1 min under 5,000 psi with the cooling bath kept at 0° C. The final emulsion was then filtered with a 0.45 μm nylon filter and stored in a sterile, plastic centrifuge tube (Corning Inc., Corning, N.Y.) at 4° C.

For IL nanoemulsions containing cisplatin, IL and MCT were homogenized with the high-speed homogenizer (Power Gen 500, Fisher Scientific, Hampton, N.H.) for 1 min at 21,000 rpm at room temperature. The polymer solution was then added to the microfluidizer and subsequently the IL/MCT mixture was added. The polymer solution and IL/MCT mixture were mixed with the microfluidizer (model M-110S, Microfluidics Corp., Newton, Mass.) for 1 min under 5,000 psi with the cooling bath kept at 0° C. The final emulsion was then filtered with a 0.45 μm nylon filter and stored in a sterile, plastic centrifuge tube (Corning Inc., Corning, N.Y.) at 4° C. Nanoemulsions prepared with cisplatin were shielded from light during storage. An excess of MCT was used in all nanoemulsions (PTX, CP, and AmB) in an attempt to prevent partition of IL into the aqueous phase, which would result in destabilization of the nanoemulsion.

Particle Size Determination by dynamic light scattering (DLS). Particle sizes of emulsions were analyzed by dynamic light scattering (NICOMP 380ZLS, Particle Sizing Systems, Santa Barbara, Calif.). The emulsions were diluted at the intensity factor of 500 KHz by adding 1-100 μL of the emulsion to 3.00 mL of Millipore water. Each particle size analyzing was run for 5 minutes at room temperature and repeated three times. The data was analyzed using Gaussian analysis and reported as volume weighted average diameters.

TABLE 6

Nanoemulsion particle size and standard deviation monitored over time using dynamic light scattering for ionic liquid nanoemulsions with cisplatin.

| | 20 mM M2DSG, 1 mL [DC-ether][2NTf$_2$], 3 mL MCT, 1.8 mg cisplatin, 14 mL saline | | | 15 mM M2DSG, 0.5 mL [DC-7][2NTf$_2$], 0.5 mL [DC-ether][2NTf$_2$], 3 mL MCT, 2 mg cisplatin, 14 mL saline | |
|---|---|---|---|---|---|
| Day | Particle Size (nm) | Standard Deviation (nm) | Day | Particle Size (nm) | Standard Deviation (nm) |
| 0 | 110.9 | 40.3 | 0 | 126.2 | 37.4 |
| 1 | 114.9 | 38.1 | 1 | 127.1 | 41.3 |
| 2 | 114.6 | 39.9 | 2 | 128.2 | 36.9 |
| 3 | 117.2 | 40.2 | 3 | 128.2 | 35.8 |
| 4 | 119.1 | 38.7 | 4 | | |
| 5 | | | 5 | | |
| 6 | 120.9 | 42.9 | 6 | | |
| 7 | 122.2 | 46.7 | 7 | 131.9 | 40.1 |
| 14 | 128.4 | 33.4 | | | |
| 21 | 128.4 | 38.8 | | | |
| 29 | 132.4 | 40.4 | | | |
| 41 | 144.4 | 42.5 | | | |
| 55 | 143.9 | 43.5 | | | |
| 70 | 149.4 | 42.6 | | | |
| 77 | 149.4 | 40.0 | | | |
| 91 | 153.0 | 42.4 | | | |
| 98 | 155.8 | 40.0 | | | |
| 105 | 156.4 | 43.3 | | | |
| 119 | 158.2 | 45.6 | | | |
| 126 | 158.6 | 35.5 | | | |
| 133 | 162.4 | 47.1 | | | |

TABLE 7

Nanoemulsion particle size and standard deviation monitored over time using dynamic light scattering for ionic liquid nanoemulsions with Amphotericin B.

| | 15 mM M2DSG, 14 mL saline, 3 mL MCT, 1 mL IL mixture (1:0.67 v/v ratio [DC7][2NTf$_2$]:[Chol][Hex]) 128 μg/mL AmB | | 15 mM M2DSG, 14 mL saline, 3 mL MCT, 1 mL IL mixture (1:0.67 v/v ratio DCether][2NTf$_2$]:[Chol][Hex]) 126 μg/mL AmB | |
|---|---|---|---|---|
| Day | | | | |
| 0 | 123.4 | 37.524 | 128 | 55.556 |
| 1 | | | 127.3 | 47.615 |
| 2 | 125.3 | 32.335 | 128.4 | 47.243 |
| 3 | 126.7 | 30.405 | 131 | 48.876 |
| 4 | 128.1 | 39.449 | 134.4 | 53.358 |
| 5 | 128.6 | 32.281 | 133.7 | 49.193 |
| 6 | 130.1 | 35.783 | 135.5 | 53.116 |
| 7 | 131.5 | 34.728 | 134.8 | 49.619 |
| 14 | 132.8 | 40.224 | | |
| 17 | | | 140.5 | 45.669 |
| 23 | | | 144 | 54.592 |
| 28 | 139.3 | 40.803 | | |

TABLE 7-continued

Nanoemulsion particle size and standard deviation monitored over time using dynamic light scattering for ionic liquid nanoemulsions with Amphotericin B.

| Day | 15 mM M2DSG, 14 mL saline, 3 mL MCT, 1 mL IL mixture (1:0.67 v/v ratio [DC7][2NTf$_2$]:[Chol][Hex]) 128 µg/mL AmB | | 15 mM M2DSG, 14 mL saline, 3 mL MCT, 1 mL IL mixture (1:0.67 v/v ratio DCether][2NTf$_2$]:[Chol][Hex]) 126 µg/mL AmB | |
|---|---|---|---|---|
| 35 | 142 | 40.886 | | |
| 37 | 142 | | 149.3 | 48.238 |
| 41 | | | 149 | 51.992 |
| 48 | | | 151 | 53.773 |
| 62 | | | 168.3 | 82.63 |
| 69 | | | 158.2 | 51.103 |
| 76 | | | 158.2 | |

TABLE 8

Nanoemulsion particle size and standard deviation monitored over time using dynamic light scattering for ionic liquid nanoemulsions with Paclitaxel.
10 mM M2DSG, 0.3 mL [DC-7][2NTf$_2$], 0.2 mL [Chol][Hex], 1.5 mL MCT, 556 µg/mL PTX

| Day | Particle Size (nm) | Standard Deviation (nm) |
|---|---|---|
| 0 | 140.0 | 52.5 |
| 1 | 141.3 | 50.3 |
| 2 | 142.1 | 54.0 |
| 3 | 143.7 | 48.6 |
| 4 | 144.0 | 51.8 |
| 5 | 145.9 | 48.5 |
| 7 | 145.0 | 47.1 |
| 14 | 153.9 | 55.7 |
| 21 | 154.6 | 49.2 |

TABLE 9

Nanoemulsion particle size and standard deviation monitored over time using dynamic light scattering for ionic liquid nanoemulsions used for preliminary in vivo study.

| Day | 15 mM M2DSG, 14 mL saline, 4 mL MCT (MME-63) | | 15 mM M2DSG, 14 mL saline, 3 mL MCT, 1 mL [DC-ether][2NTf$_2$] (MME-64) | | 15 mM M2DSG, 14 mL saline, 3 mL MCT, 0.6 mL [DC-ether][2NTf$_2$], 0.4 mL [Chol][Hex] (MME-65) | |
|---|---|---|---|---|---|---|
| 0 | 208.1 | 61.817 | 124.4 | 43.526 | 127.9 | 46.924 |
| 2 | 210.1 | 62.821 | 129.2 | 41.606 | 135 | 47.254 |
| 3 | 211.6 | 64.336 | 136.4 | 47.872 | 138 | 46.504 |
| 5 | 212.8 | 61.726 | 130.1 | 41.375 | 136.8 | 43.651 |
| 6 | 213.3 | 44.788 | 130.9 | 39.543 | 137.8 | 43.966 |
| 7 | 217.4 | 52.619 | 132.4 | 40.789 | 138.9 | 40.138 |
| 21 | 220.9 | 63.401 | 138.2 | 40.627 | 144.4 | 39.411 |
| 28 | 222.8 | 64.401 | 143.9 | 44.74 | 147.1 | 45.743 |

TABLE S2

Nanoemulsion particle size and standard deviation monitored over time using dynamic light scattering for ionic liquid nanoemulsions with Amphotericin B and no drug.

| | 10 mM M2DSG, 16 mL saline, 0.3 mL [DC-7][2NTf$_2$], 0.2 mL [Chol][Hex], 1.5 mL MCT, 57 µg/mL AmB | | | 15 mM M2DSG, 14 mL saline, 0.6 mL [DC-7][2NTf$_2$], 0.4 mL [Chol][Hex], 3 mL MCT, 128 µg/mL | | | 10 mM M2DSG, 16 mL saline, 0.3 mL [DC-7][2NTf$_2$], 0.2 mL [Chol][Hex], 1.5 mL MCT | | |
|---|---|---|---|---|---|---|---|---|---|
| Day | Particle Size (nm) | Standard Deviation (nm) | Day | Particle Size (nm) | Standard Deviation (nm) | Day | Particle Size (nm) | Standard Deviation (nm) | |
| 0 | 155.2 | 58.7 | 0 | 123.4 | 37.5 | 0 | 156.6 | 52.2 | |
| 1 | 158.4 | 54.3 | 1 | | | 1 | 157.1 | 55.6 | |
| 2 | 158.1 | 58.2 | 2 | 125.3 | 32.3 | 2 | | | |
| 3 | 159.2 | 53.0 | 3 | 126.7 | 30.4 | 3 | 158.4 | 58.1 | |
| 4 | 160.8 | 51.6 | 4 | 128.1 | 39.4 | 4 | 158.7 | 54.1 | |
| 5 | | | 5 | 128.6 | 32.3 | 5 | | | |
| 6 | | | 6 | 130.1 | 35.8 | 6 | | | |
| 7 | 160.8 | 57.9 | 7 | 131.5 | 34.7 | 7 | 159.6 | 56.821 | |
| 14 | 166.1 | 57.5 | 14 | 132.8 | 40.2 | 14 | 165.3 | 47.3 | |
| 21 | 166.7 | 56.7 | 21 | | | 21 | 164.2 | 56.7 | |
| 28 | | | 28 | 139.3 | 40.8 | 28 | | | |
| 32 | 172.0 | 55.4 | 35 | 142.0 | 40.9 | | | | |
| 42 | 175.1 | 61.5 | | | | 42 | 172.8 | 53.7 | |
| 56 | 181.6 | 51.8 | | | | | | | |
| 70 | 180.4 | 54.7 | | | | | | | |
| 84 | 183.6 | 44.1 | | | | | | | |
| 98 | 179.8 | 62.0 | | | | | | | |

Example 12G: In Vitro Drug Release—Paclitaxel

The nanoemulsion was initially diluted by a factor of 20 (0.125 mL of nanoemulsion plus 2.375 mL of Millipore Milli-Q water). A time-zero time point was established by diluting 100 μL of diluted nanoemulsion mixture above in 900 μL of acetonitrile (ACN). A 3 mL capacity SlideA-Lyzer Dialysis cassette (G2 2,000 MWCO from Thermo Fisher Scientific Inc., Fitchburg, Wis.) was hydrated by stirring for 12 h in a 3 L PBS bath (300 mL of 10×PBS and 2,700 mL of Millipore Milli-Q water) at 37° C. After this time, the remaining diluted nanoemulsion solution and 100 μL of PBS (1×) were added to the cassette, which was then returned to the PBS bath and stirred for 1 week at 37° C.; this was performed twice. Time points were taken at 0.5, 2, 3, 6, 9, 12, 24, 36, 48, 72, 96, 120, 144, and 168 h. At each time point a long-stemmed glass pipet was used to mix the contents of the cassette three times. Then a 100 μL aliquot of nanoemulsion was removed from the cassette and diluted with 900 μL of ACN. The nanoemulsion aliquot was then replaced in the cassette by 100 μL of fresh PBS (1×). Sink conditions were maintained by replacing the 3 L PBS baths at the 3, 6, 9, and 12 h time points and every 12 h thereafter. The paclitaxel concentration remaining in the nanoemulsion at each time point was quantified by reverse phase HPLC. The HPLC system used was a Shimadzu prominence HPLC system (Shimadzu, Japan) equipped with an LC-20AT pump, SIL-20 AC HT autosampler, CTO-20 AC column oven, and an SPD-M20A diode array detector. For each time point sample, 20 μL was injected into a C18 column (Agilent XDB-C18, 4.6 Å×150 mm) and eluted with an isocratic mixture of 25% water and 75% ACN. The run time was 7 min, the flow rate was 1.0 mL/min, and the detection was set at 227 nm. Paclitaxel eluted at 4.15 min. Concentration of paclitaxel was determined by integrating the area of the peak and extrapolation from a standard calibration curve (500, 100, 50, 25, 10, 5, 2.5 μg/mL).

In vitro time-release profile of PTX nanoemulsion, exhibiting a half-life of 68.7 hours. Emulsion was dialyzed at 37° C. under sink conditions for 1-week. Concentration of PTX was measured using HPLC. Error bars represent standard deviation between two separate samples.

In Vitro Drug Release—Cisplatin nanoemulsion 15 mM M2DSG, 0.5 mL [DC-ether][2NTf$_2$], 0.5 mL [DC-7][2NTf$_2$], 3 mL MCT, 14 mL saline, 2 mg cisplatin. A t=0 time point was established by diluting 100 μL nanoemulsion in 900 μL acetonitrile (ACN). A 3 mL capacity Slide-A-Lyzer Dialysis cassette G2 2,000 MWCO from Thermo Fisher Scientific Inc. (Fitchburg, Wis.) was hydrated by stirring for 12 hours in a 3 L PBS bath (300 mL 10×PBS and 2,700 mL Milli-Q water) at 37° C. After this time, 2.5 mL of nanoemulsion was added to the cassette, in triplicate, which was then returned to the PBS bath and allowed to stir for 1 week at 37° C. Time points were taken at 0.5, 2, 6, 12, 24, 48, and 72 hours. For each time point a 100 μL aliquot of nanoemulsion was removed from the cassette and diluted with 900 μL ACN. The nanoemulsion aliquot was then replaced in the cassette by 100 μL of fresh PBS solution (10×PBS). Sink conditions were maintained by replacing the 3 L PBS baths at the 3, 6, 9, and 12-hour time points and every 12-hours following.

The cisplatin concentration remaining in the nanoemulsion was quantified by reverse phase HPLC. The HPLC system used was a Shimadzu prominence HPLC system (Shimadzu, Japan) equipped with an LC-20AT pump, SIL-20 AC HT autosampler, CTO-20 AC column oven, and an SPD-M20A diode array detector. For each time point sample, 20 μL was injected into a C18 column (Agilent XDB-C18, 4.6 Å×150 mm) and eluted with an isocratic mixture of 75% of a water/methanol mixture (50:50 water:methanol) with 25% acetonitrile. The run time was 7 minutes, the flow rate was 1.0 mL min$^{-1}$, and the detection was set at 254 nm. Cisplatin eluted after 2.6 minutes.

In Vitro Drug Release—Cisplatin nanoemulsion 20 mM M2DSG, 1 mL [DC-ether][2NTf$_2$], 3 mL MCT, 14 mL saline, 1.8 mg cisplatin. A t=0 time point was established by diluting 100 μL nanoemulsion in 9004 acetonitrile (ACN). A 3 mL capacity Slide-A-Lyzer Dialysis cassette G2 2,000 MWCO from Thermo Fisher Scientific Inc. (Fitchburg, Wis.) was hydrated by stirring for 12 hours in a 3 L PBS bath (300 mL 10×PBS and 2,700 mL Milli-Q water) at 37° C. After this time, 2.5 mL of nanoemulsion was added to the cassette, in triplicate, which was then returned to the PBS bath and allowed to stir for 1 week at 37° C. Time points were taken at 0.5, 2, 3, 6, 9, 12, 24, 36, 48, 72, 96, 120, 144, 168 hours. For each time point a 100 μL aliquot of nanoemulsion was removed from the cassette and diluted with 900 μL ACN. The nanoemulsion aliquot was then replaced in the cassette by 100 μL of fresh PBS solution (10×PBS). Sink conditions were maintained by replacing the 3 L PBS baths at the 3, 6, 9, and 12-hour time points and every 12 hours following.

The cisplatin concentration remaining in the nanoemulsion was quantified by reverse phase HPLC. The HPLC system used was an Agilent HPLC system (Santa Clara, Calif.) equipped with an LC-20AT pump, SIL-20 AC HT autosampler, CTO-20 AC column oven, and an SPD-M20A diode array detector. For each time point sample, 20 μL was injected into a C18 column (Agilent XDB-C18, 4.6 Å×150 mm) and eluted with an isocratic mixture of 50% water in ACN. The run time was 5 minutes, the flow rate was 1.0 mL min$^{-1}$, and the detection was set at 227 nm. Cisplatin eluted after 2.3 minutes.

In Vitro Drug Release. A 3 mL capacity SlideA-Lyzer Dialysis cassette (G2 2,000 MWCO from Thermo Fisher Scientific Inc., Fitchburg, Wis.) was hydrated prior to use by stirring for 12 h in a 3 L PBS bath (300 mL of 10×PBS and 2,700 mL of Millipore Milli-Q water) at 37° C. After this time, 2.5 mL nanoemulsion was directly added to the cassette. A time-zero time point was established by diluting 100 μL of the nanoemulsion mixture above in 900 μL of methanol (MeOH). 100 μL of PBS was then added to the cassette, which was then returned to the PBS bath and stirred for 201 hours at 37° C. Three cassettes were used in the experiment. Time points were taken at 0.5, 2, 3, 6, 9, 12, 24, 36, 48, 72, 96, 120, 144, 153, and 201 h. To ensure uniform analysis, at each time point a long-stemmed glass pipet was used to mix the contents of the cassette three times before the nanoemulsion aliquot was removed. Then a 100 μL aliquot of nanoemulsion was removed from the cassette and diluted with 900 μL of MeOH. The nanoemulsion aliquot was then replaced in the cassette by 100 μL of PBS. Sink conditions were maintained by replacing the 3 L PBS baths at the 3, 6, 9, and 12 h time points and every 12 h thereafter. To ensure no degradation of Amphotericin B in the methanol, 20 μg/mL propyl gallate was added to time point samples 0, 0.5, 2, 3, 6, 9, 12, 24, 36, 48, 72, 96 and 120 h. 200 μg/mL propyl gallate was added to time point samples 144, 153 and 201 h.

The Amphotericin B concentration remaining in the nanoemulsion was quantified by reverse phase HPLC. The HPLC system used was a Shimadzu prominence HPLC system (Shimadzu, Japan) equipped with an LC-20AT pump, SIL-20 AC HT autosampler, CTO-20 AC column over, and an SPD-M20A diode array detector. For each time point sample, 20 µL was injected into a C8 column (Agilent XDB-C8, 4.6 Å×150 mm) and eluted with an isocratic mixture of 10% water (with 5% acetic acid) and 90% MeOH (with 5% acetic acid). The for samples 0, 0.5, 2, 3, 6, 9, 12, 24, 36, 48, 72, 96 and 120 h the run time was 4 minutes, the flow rate was 0.8 mL min$^{-1}$, and the detection was set at 406 nm. Amphotericin B eluted at 2.4 minutes. For samples 144, 153 and 201 h the run time was 7 minutes, the flow rate was 0.8 mL min$^{-1}$, and the detection was set at 406 nm. Amphotericin B eluted at 5.1 minutes. Concentration of Amphotericin B was determined by integrating the area of the peak and extrapolation from a standard calibration curve (500, 100, 50, 25, 10, 5, 1 µg). Curve fitting analysis using a one-phase exponential association was used to calculate the half-life ($t_{1/2}$).

Example 13

Example 13: Preparation, Characterization, and Formulation Optimization of Ionic Liquid in Water Nanoemulsions for Systemic Delivery of Amphotericin B ABSTRACT: Amphotericin B (AmB) is an extremely active polyene antifungal agent that poses a challenge for intravenous drug delivery due to the drug's dose-limiting toxicity. Current intravenous formulations of AmB suffer from severe side effects that are attributed to the self-aggregation of AmB in aqueous solutions. To overcome this problem, we have rationally designed an ionic liquid-in-water nanoemulsion drug delivery system that harnesses the unique properties of ionic liquids. High concentrations of AmB were solubilized in a hydrophilic cholinium-based ionic liquid and a new hydrophobic dicationic cholinium-based ionic liquid. The absorption spectrum of AmB in the ionic liquids, ionic liquid mixtures, and prepared nanoemulsion indicates excellent monomerization. The hydrophobic ionic liquid exhibits high in vivo biocompatibility determined using a zebra-fish viability assay. Hemolytic activity of the ionic liquid nanoemulsion containing AmB was negligible, yet this nanoemulsion maintained antifungal activity against *Candida albicans*. The system also exhibits a sustained in vitro drug release, ideal for systemic delivery of the antifungal agent. The preliminary results presented in this Communication indicate that rationally designed ionic liquid-in-water nanoemulsions may allow for the delivery of a variety of pharmaceuticals intravenously, broadening the scope of ionic liquids in the pharmaceutical sciences.

Opportunistic fungal infections are still a prevalent disease worldwide due to the number of people with weakened immune systems. The CDC estimates that in the United States alone 46,000 people are affected by invasive candidiasis each year and approximately 30% will succumb to their infection.[1] Amphotericin B (AmB), is a potent antifungal agent that is effective against a wide variety of fungi.[2-6] Intravenous administration of AmB serves as the mainstay treatment of systemic, severe fungal infections. Despite the efficacy of AmB, there are significant limitations to its use due to adverse side effects, including dose-dependent nephrotoxicity.[7] These severe adverse side-effects are primarily attributed to the self-association of AmB in aqueous solution due to its unique amphiphilic molecular structure (FIG. 1A).[2,3,8] AmB acts by forming transmembrane pores, resulting in a severe electrolyte imbalance and subsequent cell death (FIG. 1A).[2,7-9] A common strategy to overcome the issues associated with aggregation have taken advantage of AmB's affinity for sterol structures and include the commercial formulation, FUNGIZONE™.[5,6,10] FUNGIZONE™ is both a commercially and clinically important formulation of AmB. FUNGIZONE™ broad spectrum of activity led to significantly decreased mortality rate after its introduction, yet it still suffers from severe side effects.

Ionic liquids (ILs) are asymmetric organic cations and anions whose melting point is below 100° C. that have unique physicochemical properties, notably excellent solvation capabilities.[11-16] This versatile property has rendered ILs as advantageous components in biomedical applications, such as solvents for separation and use in biocatalysis.[17-26] ILs have more recently been explored in the pharmaceutical sciences primarily as active pharmaceutical ingredient-ionic liquids and IL-in-oil microemulsions for transdermal drug delivery.[27-34] The remarkable property of ILs to serve as solvating agents for pharmaceutical compounds has been well documented.[15,23,25,35-39]

However, the ILs that have been previously used for solubilization of drugs can be characterized as water-soluble, toxic if administered systemically, or both.[40-45] While these ILs can be considered for transdermal or oral drug delivery, these ILs could not be considered for use in intravenous administration, thus limiting the scope of pharmaceuticals that could be delivered.

Due to the unique properties of ILs, we wondered whether a rationally designed IL could be: (1) hydrophobic; (2) non-toxic; (3) and a liquid at or close to room-temperature. In this way, we could systemically deliver AmB without the severe side-effects associated with aggregated AmB. Most importantly, the preparation of such a hydrophobic IL would allow for systemic delivery of a variety of pharmaceuticals. In this Communication, we report polymeric nanoemulsions formulated with a mixture of ILs and a commercially available mixture of medium chain triglycerides as the interior dispersed in water. We demonstrate the potential versatility of the system using the complex drug Amphotericin B, which has opposing hydrophobic and hydrophilic domains. A further complicating factor for formulation is AmB's low water solubility (<1.0 µg/mL).[5,46] As such, AmB serves as an ideal model pharmaceutical as it demonstrates the potential of these IL-in-water nanoemulsions to be used with both hydrophobic and potentially hydrophilic pharmaceuticals.

Figure 46A:
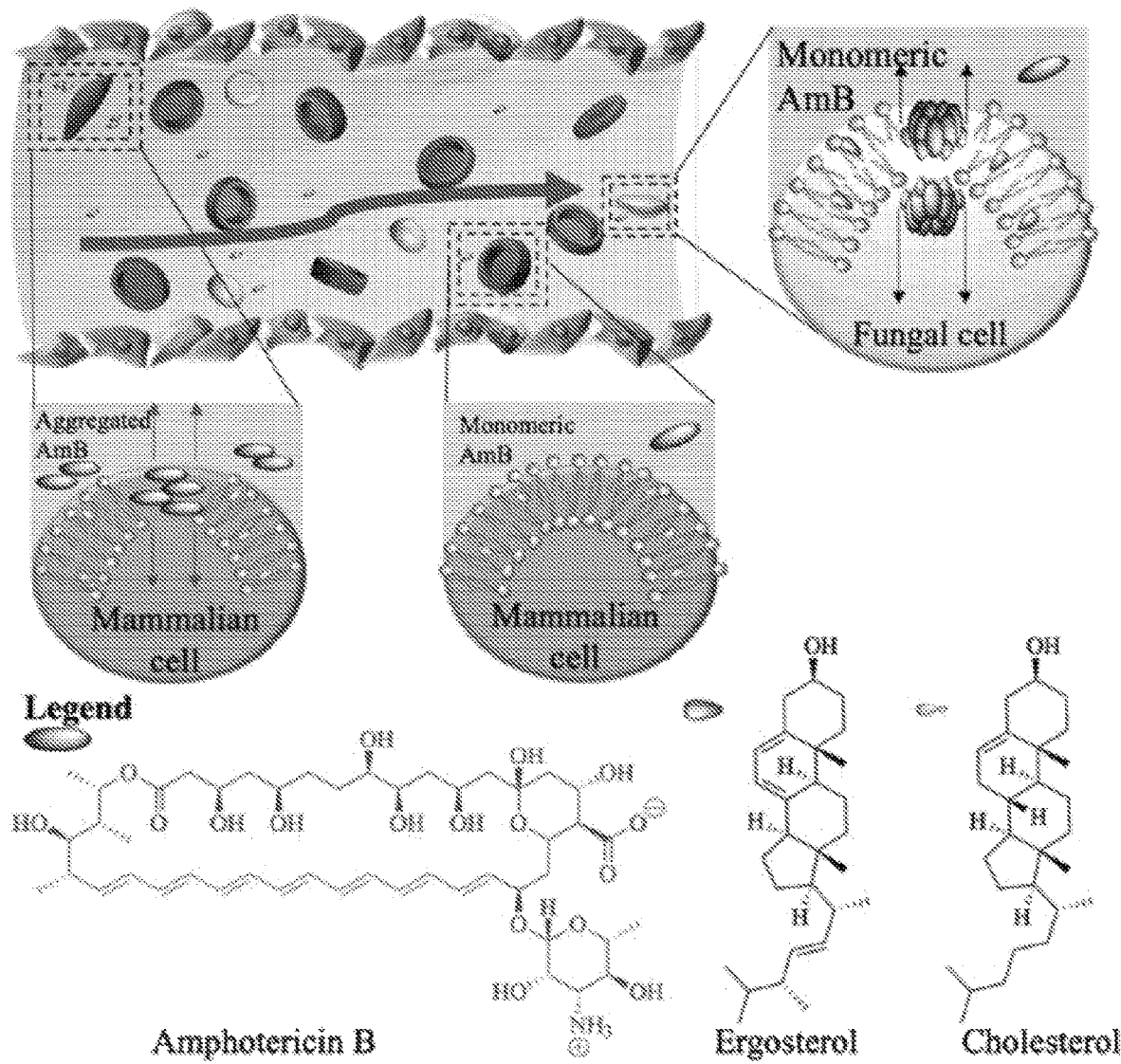

We focused our efforts on cholinium-based ILs as previous studies have shown the biocompatibility of cholinium-based ILs.[45,47,48] Furthermore, we selected cholinium-based ILs for the solubilization and deaggregation of AmB due to the presence of a hydroxy moiety on the cation (FIG. 46B). One structural feature of sterols that is required for AmB-sterol interactions to occur is a 3β-OH for hydrogen-bonding with the polar head group of AmB (FIG. 46A).[49-53] We rationally considered a cationic moiety with the same hydrogen-bonding capabilities to facilitate solubilization and deaggregation of AmB.

Figure 52:
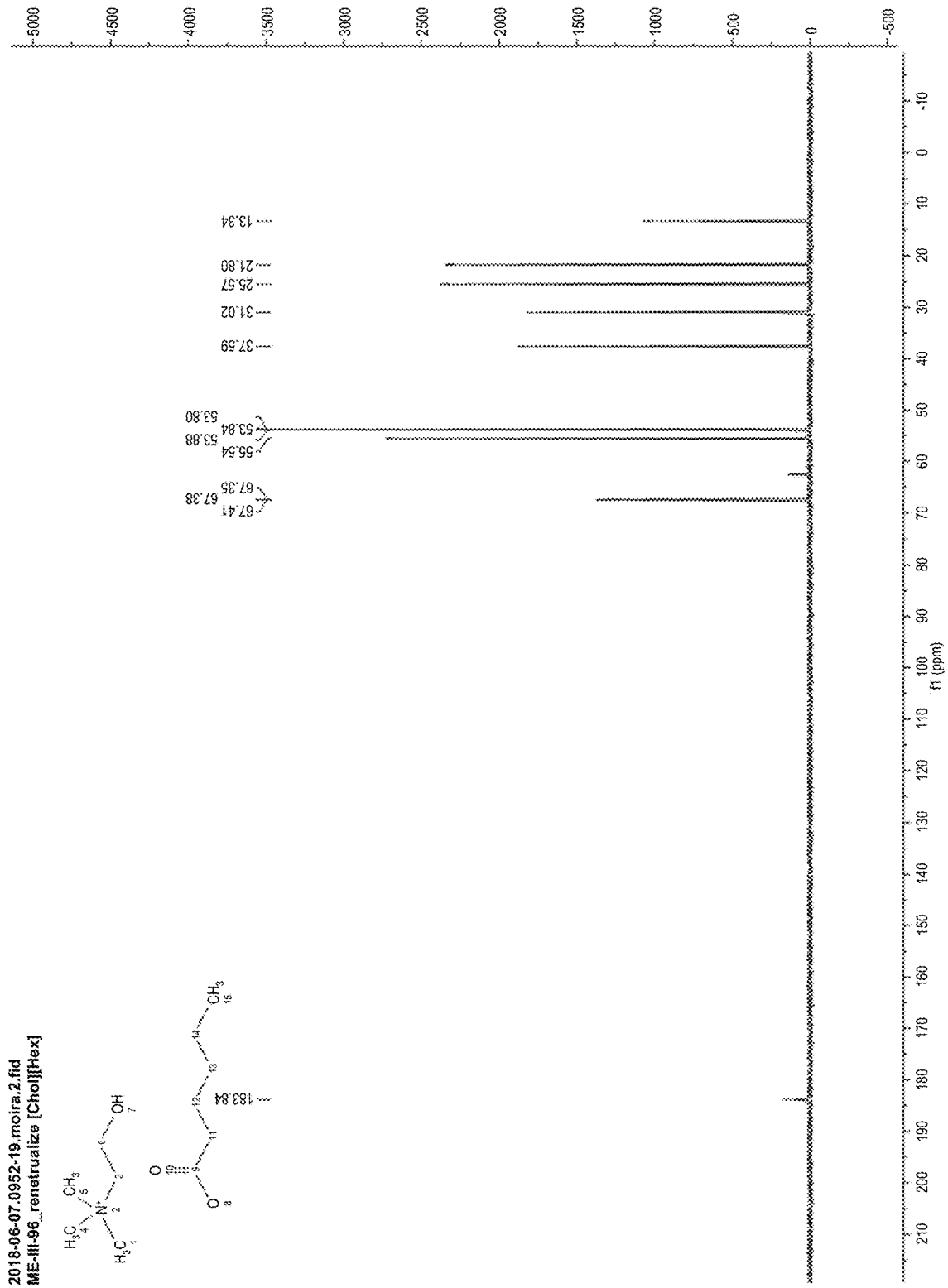
Figure 53:
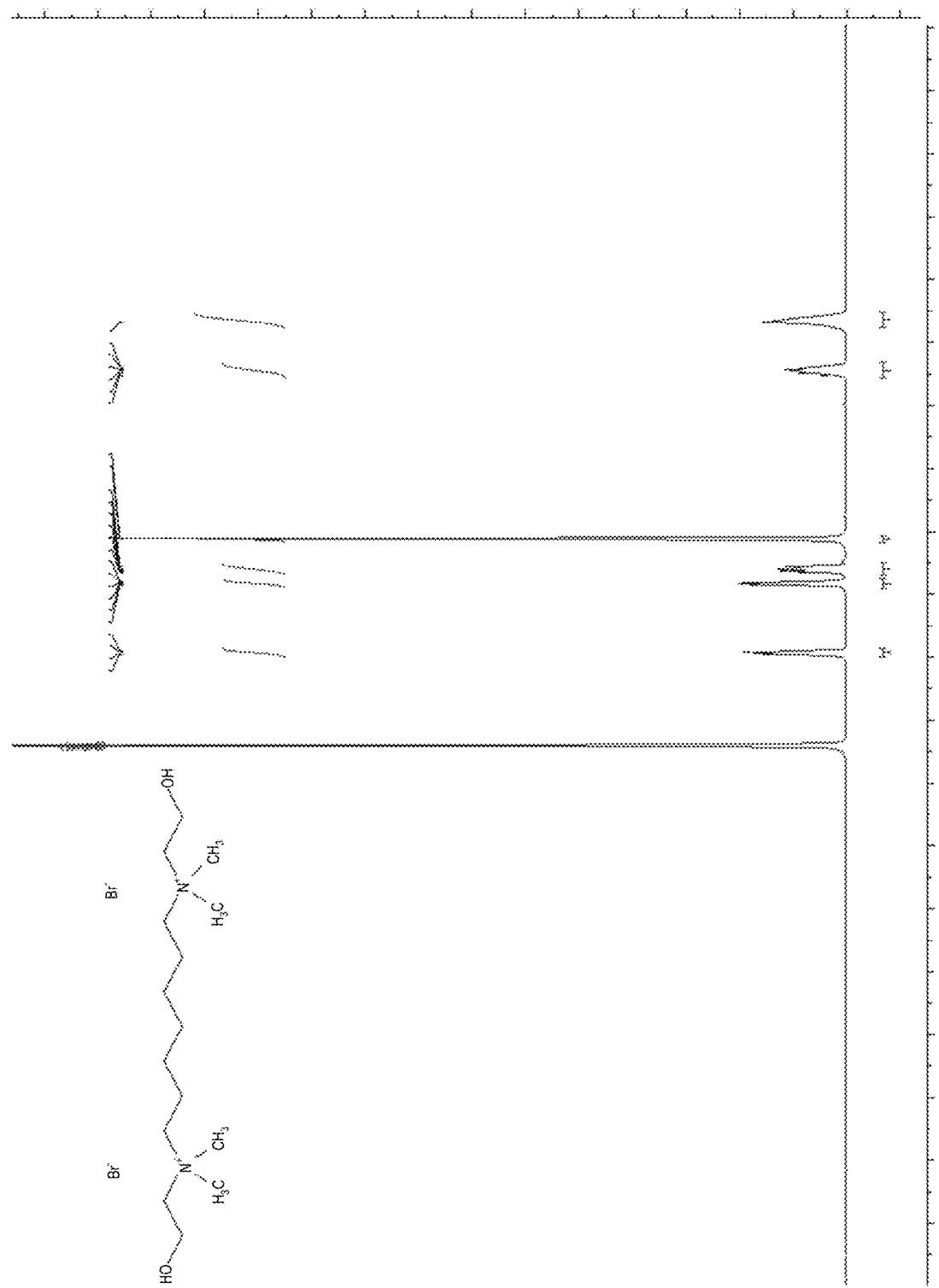
Figure 54:
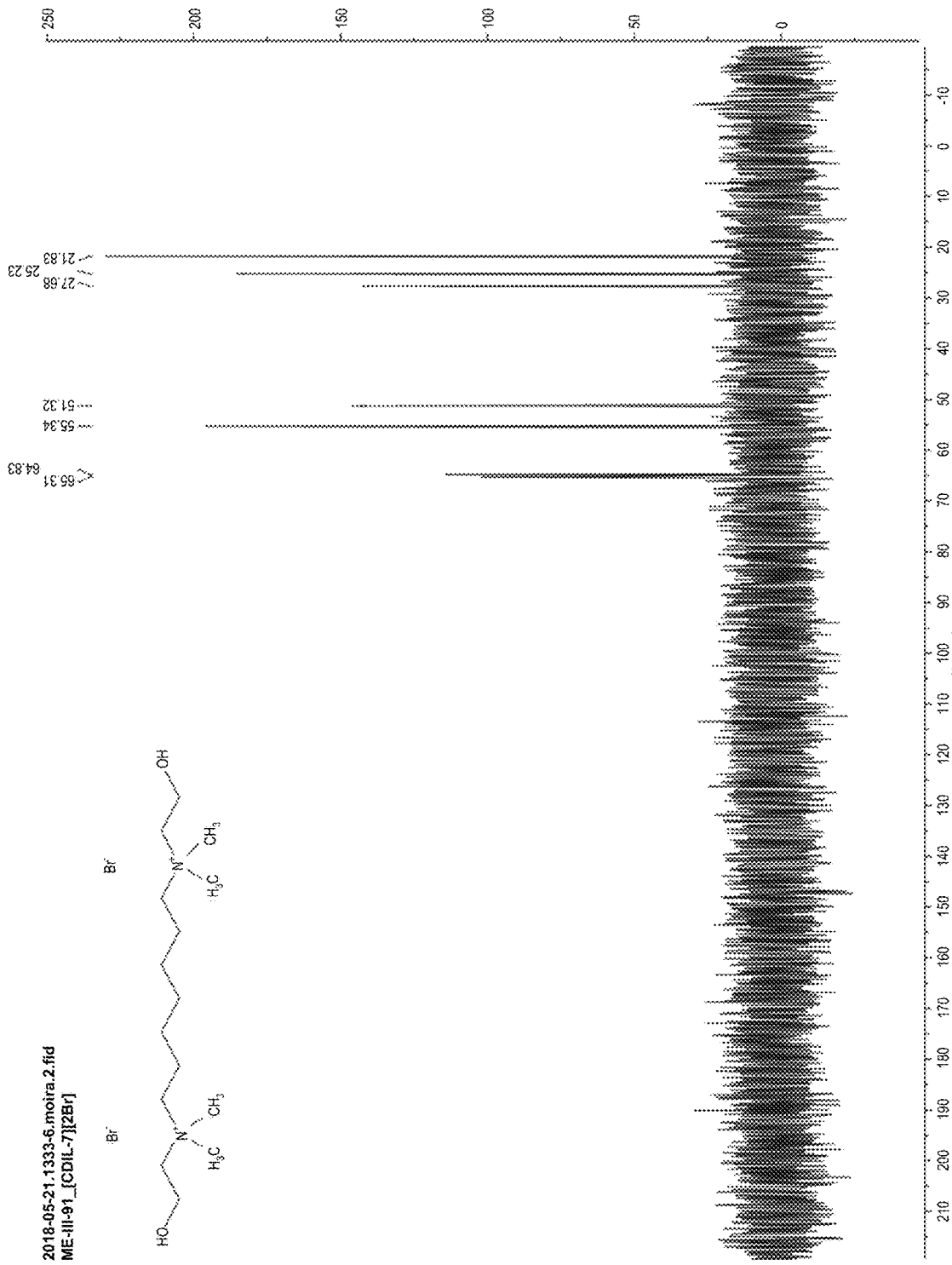
Figure 55:
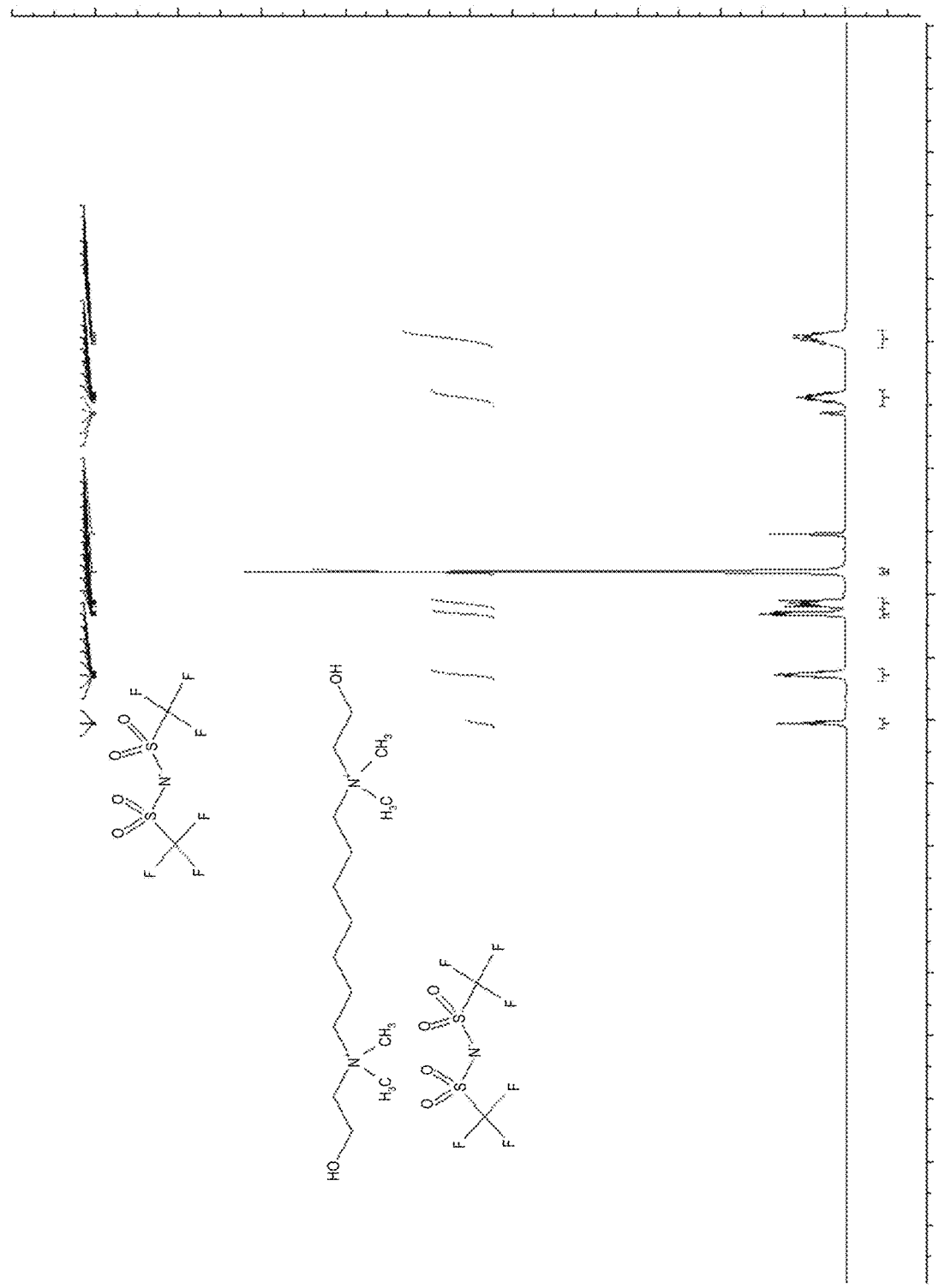
Figure 56:
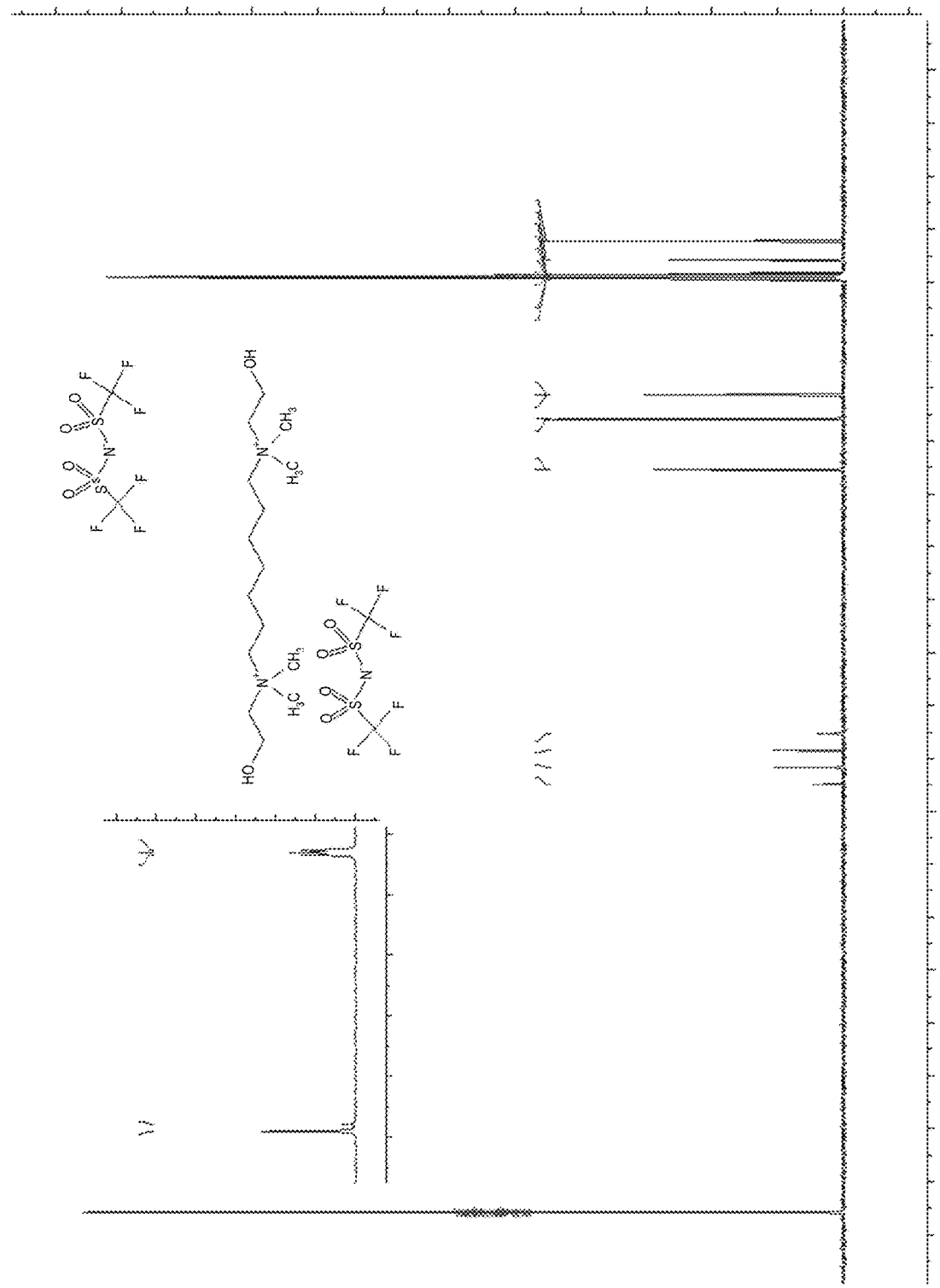
Figure 57:
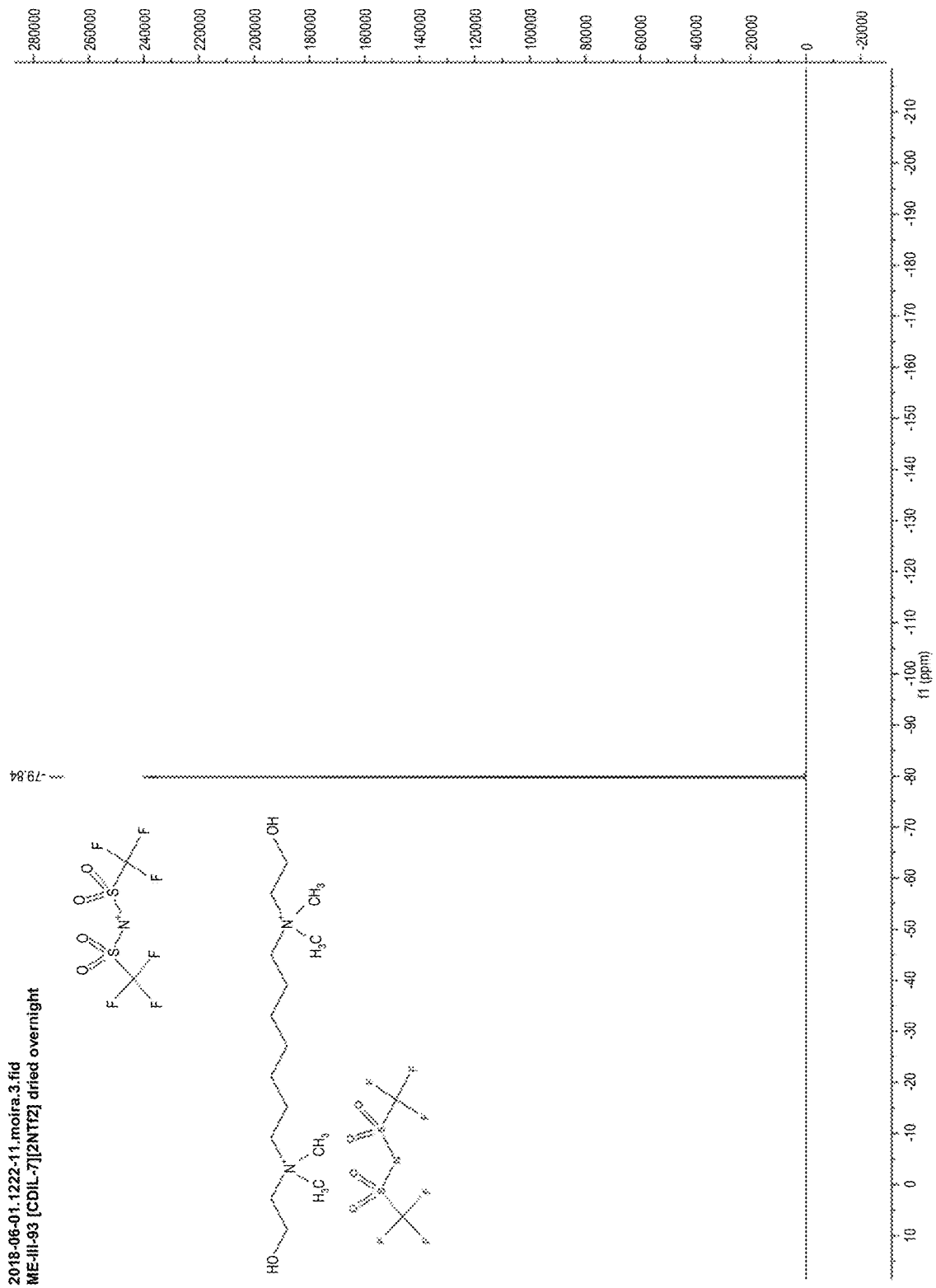

First, a water-soluble cholinium-based IL with hexanoate anion was synthesized using a simple neutralization reaction (FIG. 46B, 1)(FIGS. 52 and 53). The toxicity profile of cholinium-based ILs with carboxylate anions have been studied extensively in the literature.[54-57] Cholinium hexanoate ([Chol][Hex]) was identified as the most promising cholinium-based IL as it has the longest alkyl chain length in the anion that is still non-toxic. The length of the alkyl chain also mimics the length of the alkyl chain pendant off the sterol ring of both ergosterol and cholesterol (FIG. 46A).

Certain hydrophobic ILs have characteristically been categorized as toxic. The biocompatibility of ILs primarily depends on the cation with minor anionic effects. Alternatively, the composition of the anion primarily modulates the water-solubility with minor cationic effects. Hydrophobic ILs are typically formed from a combination of a hydrophobic anion and cation with long alkyl chains. These alkyl chains result in toxicity due to their interaction with the lipid bilayer of the cell membrane, resulting in cell death.[23,43,58,59] Without wishing to be bound to any particular theory, it was contemplated that a method for decreasing the toxicity of a hydrophobic IL would be to eliminate the ability of the alkyl chains to interact with the lipid bilayer via tethering the long alkyl chain between two cationic headgroups. Applicant synthesized a novel hydrophobic dicationic cholinium-based ionic liquid (DC), with a slightly modified procedure from previously reported syntheses of dicationic ammonium-based ILs (FIG. 46B, 3).[60] Alteration of the anion from a carboxylate anion to the bis(trifluoromethylsulfonyl)imide anion was expected to decrease the water solubility substantially.[12,40] Furthermore, the presence of hydrophobic and hydrophilic regions in the ILs was supposed to mimic the amphiphilic nature of AmB. Not only was this expected to increase the solubility of AmB in the ionic liquid, but also render the dicationic ILs more versatile, with the ability to solubilize a variety of pharmaceuticals.

While [DC-7][2NTf$_2$] is solid at room temperature, it exhibits supercooled behavior after melting close to room temperature (FIG. S1) allowing for easy preparation of solutions. A remarkably high concentration of AmB was able to be solubilized in both [Chol][Hex] and [DC-7][2NTf$_2$] (Table 1).

TABLE 10

Loading of AmB in synthesized ionic liquids

| Ionic Liquid | AmB (mg/mL) |
|---|---|
| [DC-7][2NTf$_2$] | 0.7 |
| [Chol][Hex] | 6 |

Figure 47A:
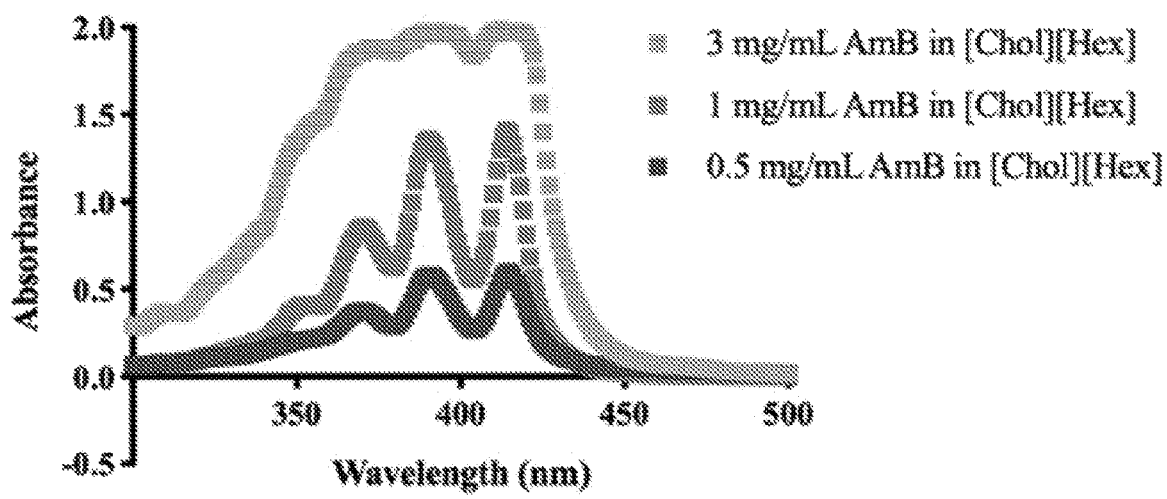
Figure 47B:
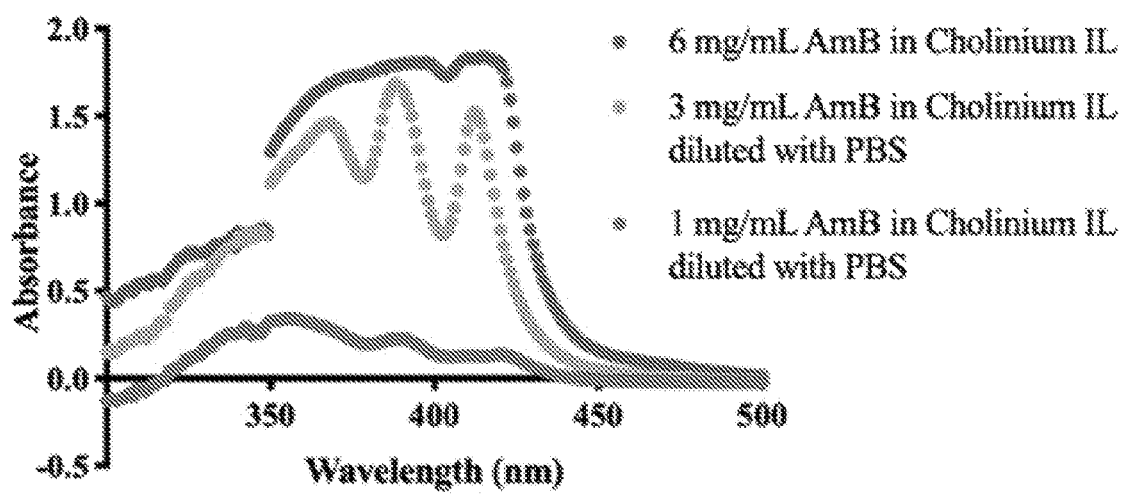
Figure 47C:
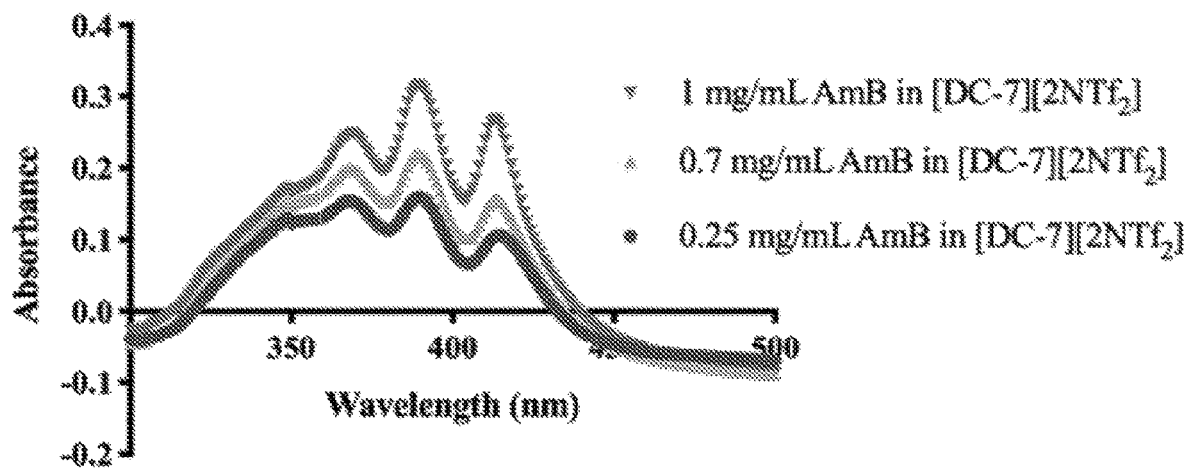
Figure 47D:
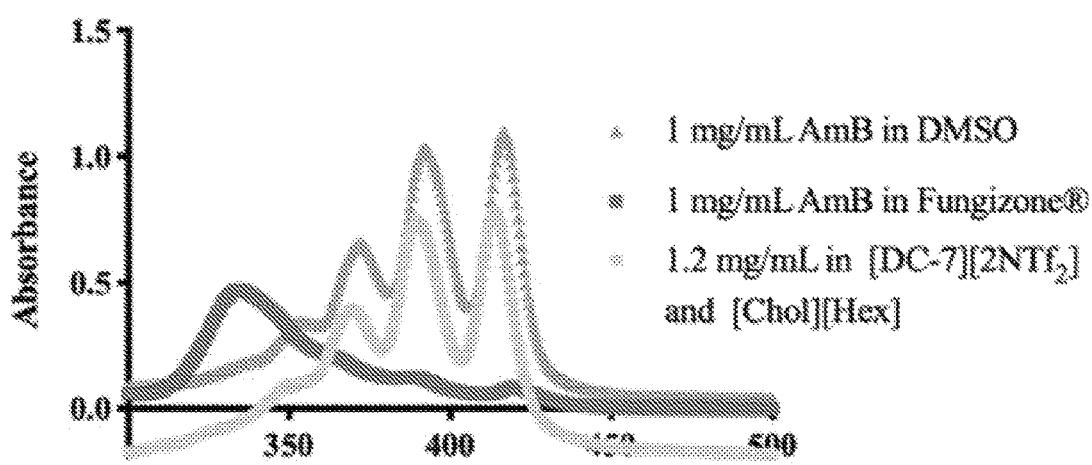

To further probe whether these ILs could be used for delivery of AmB, we examined the aggregation state of AmB in the ILs using UV/vis spectroscopy. AmB was solubilized in solely the monomeric form when in [Chol][Hex] (FIG. 47A). However, this IL displayed concentration-dependent aggregation, similar to that of FUNGIZONE™. Specifically, upon dilution with phosphate-buffered saline, the aggregation state of AmB shifted from monomeric to aggregated (FIG. 47B). This shift is clearly identified by a blue shift in the absorbance maximum from ~409 nm to ~328 nm. As such, it could not be used solely in any formulation without suffering from severe side-effects. Study of the aggregation state of AmB in [DC-7][2NTf$_2$] alone indicated a mixture of monomeric and aggregated AmB (FIGS. 47C and 66-69).

However, a mixture of both [Chol][Hex] and [DC-7][2NTf$_2$] result in a solely non-aggregated form (FIG. 2D). Mixtures of both hydrophobic and hydrophilic ILs are not a new concept and have been primarily used for extraction purposes. In these instances, a hydrophobic IL is used to recover a hydrophilic IL from an aqueous solution.[61] As such, it was thought that a mixture of hydrophobic and hydrophilic IL would result in the solubilization of AmB solely in the monomeric form and prevent any concentration-dependent aggregation.

Figure 45A:
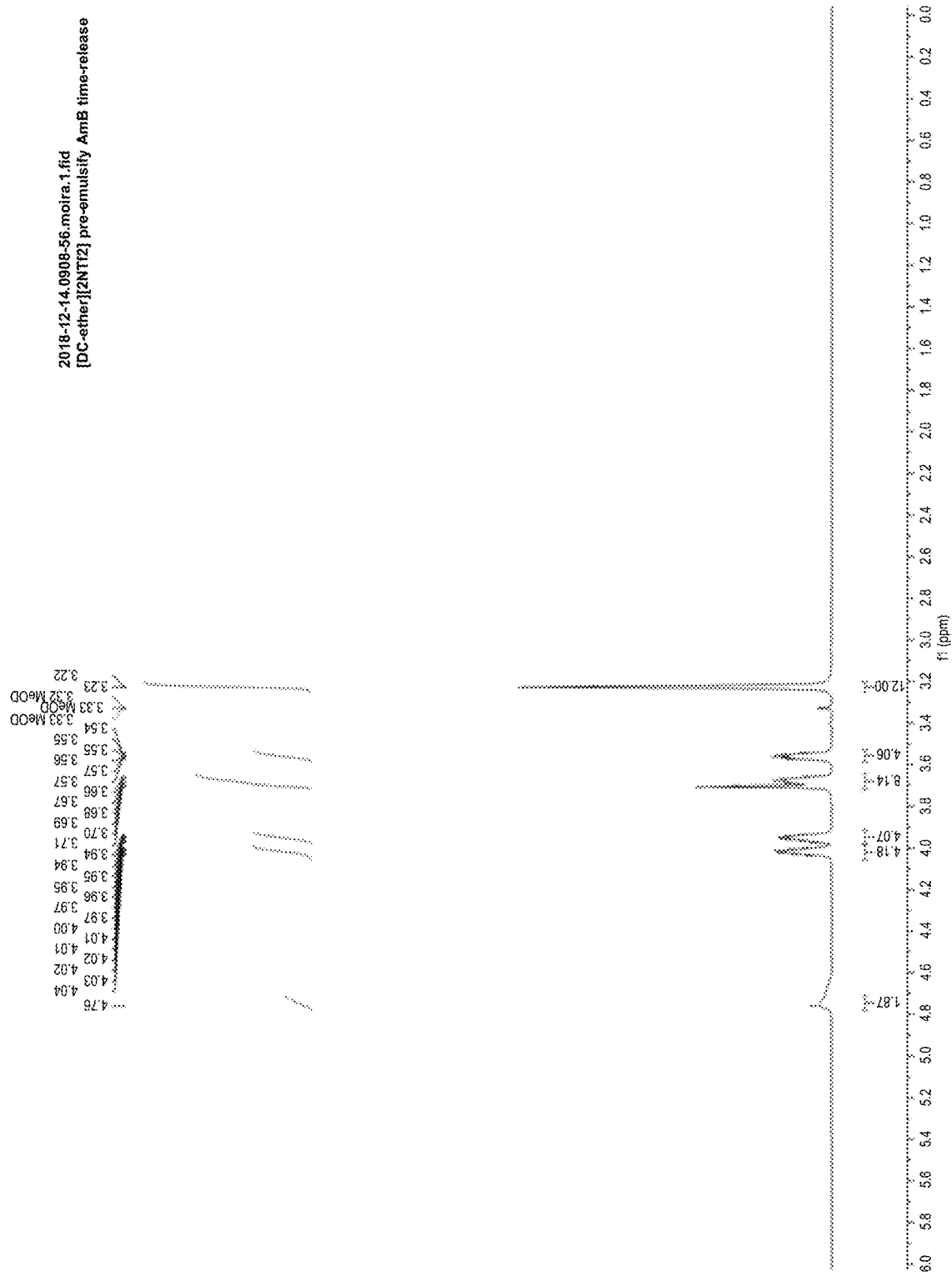
FIG. 45A. $^1$H NMR of [DC-ether][2NTf$_2$] hydrophobic ionic liquid in CD$_3$OD.
Figure 45B:
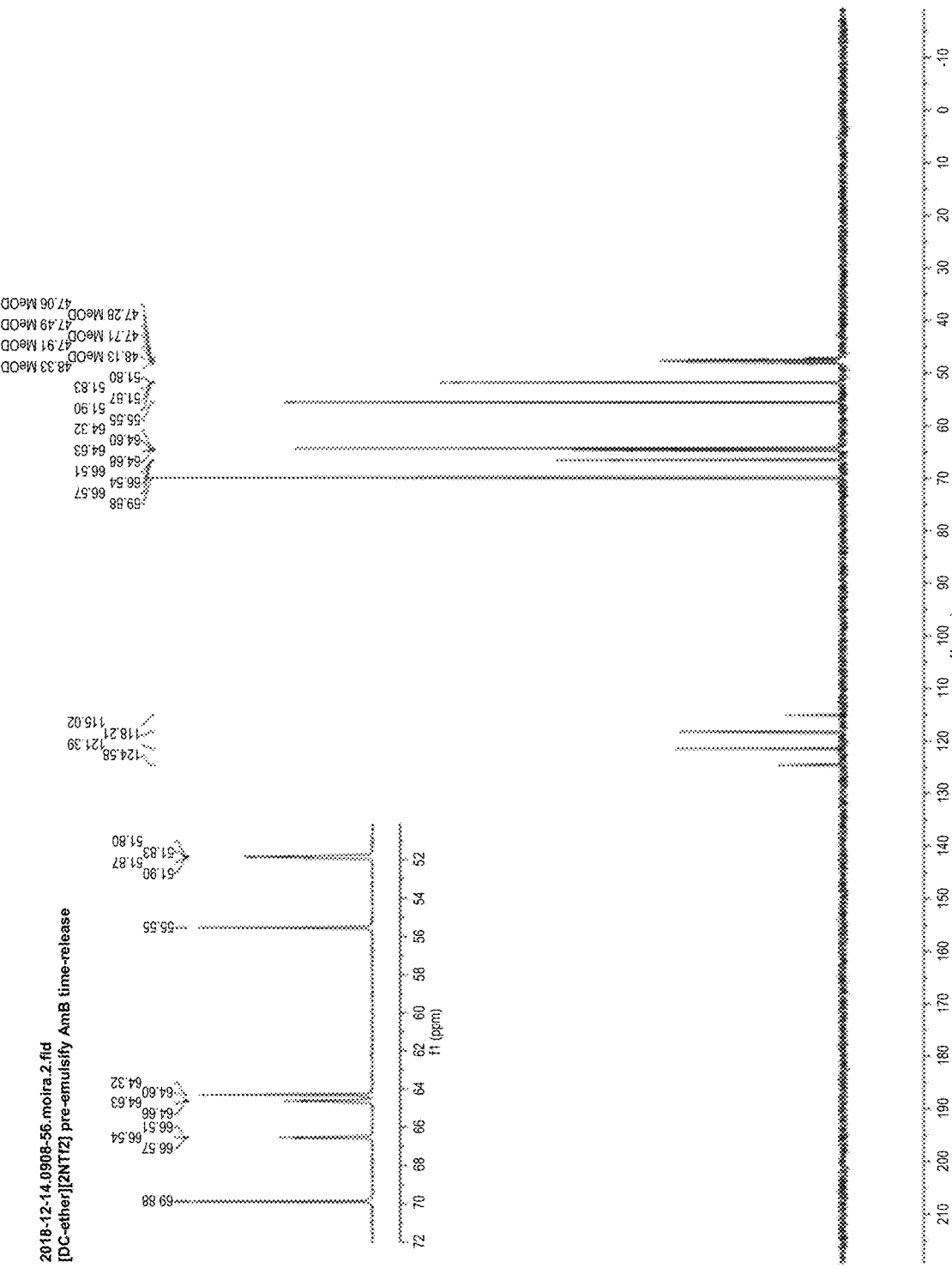
FIG. 45B. $^{13}$C NMR of [DC-ether][2NTf$_2$] hydrophobic ionic liquid in CD$_3$OD.
Figure 45C:
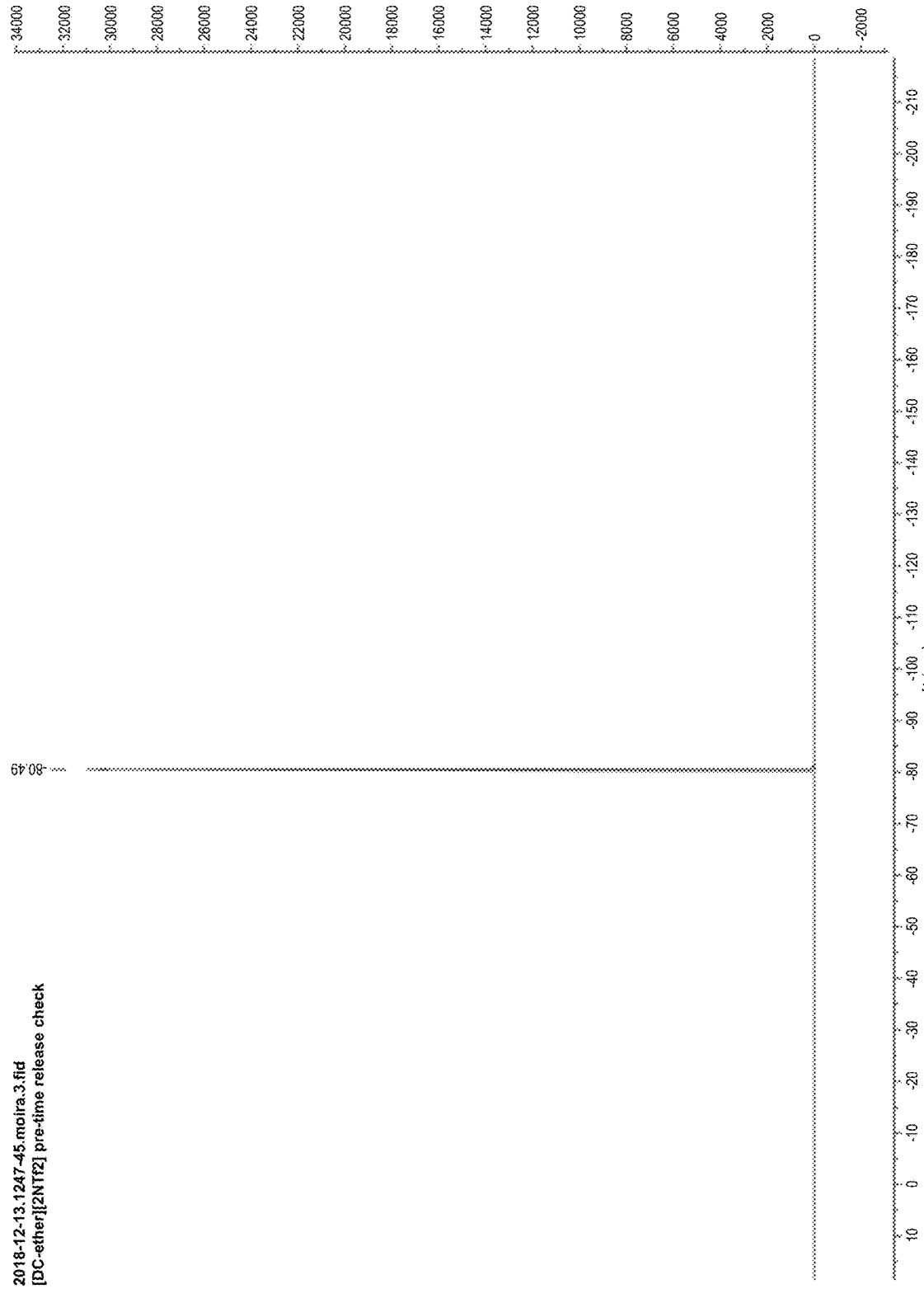
FIG. 45C. $^{19}$F NMR of [DC-ether][2NTf$_2$] hydrophobic ionic liquid in CD$_3$OD.
Figure 45D:
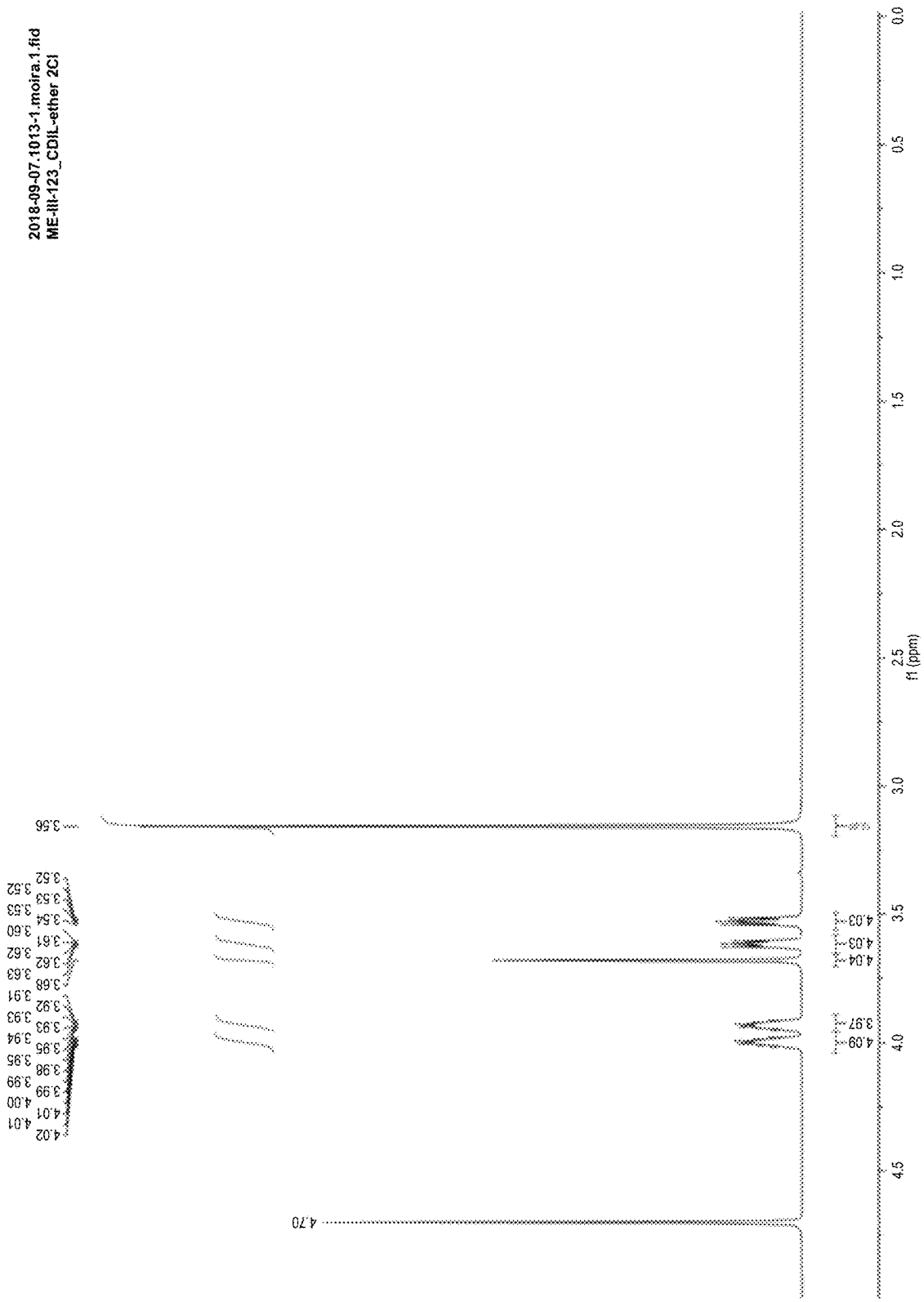
FIG. 45D. $^1$H NMR of [DC-ether][2Cl] hydrophilic ionic liquid precursor in D$_2$O.
Figure 45E:
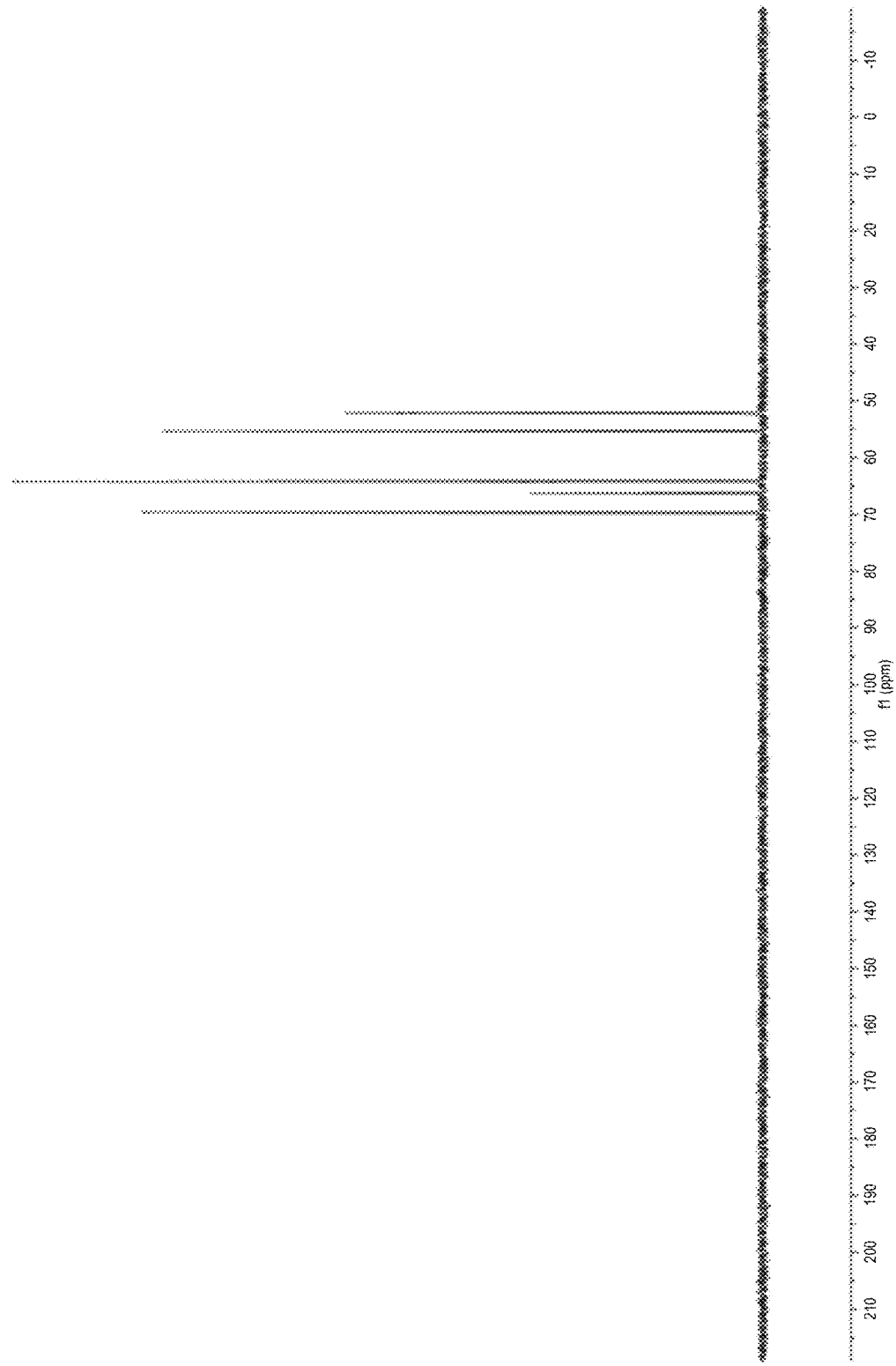
FIG. 45E. $^{13}$C NMR of [DC-ether][2Cl] hydrophilic ionic liquid precursor in D$_2$O.
Figure 45F:
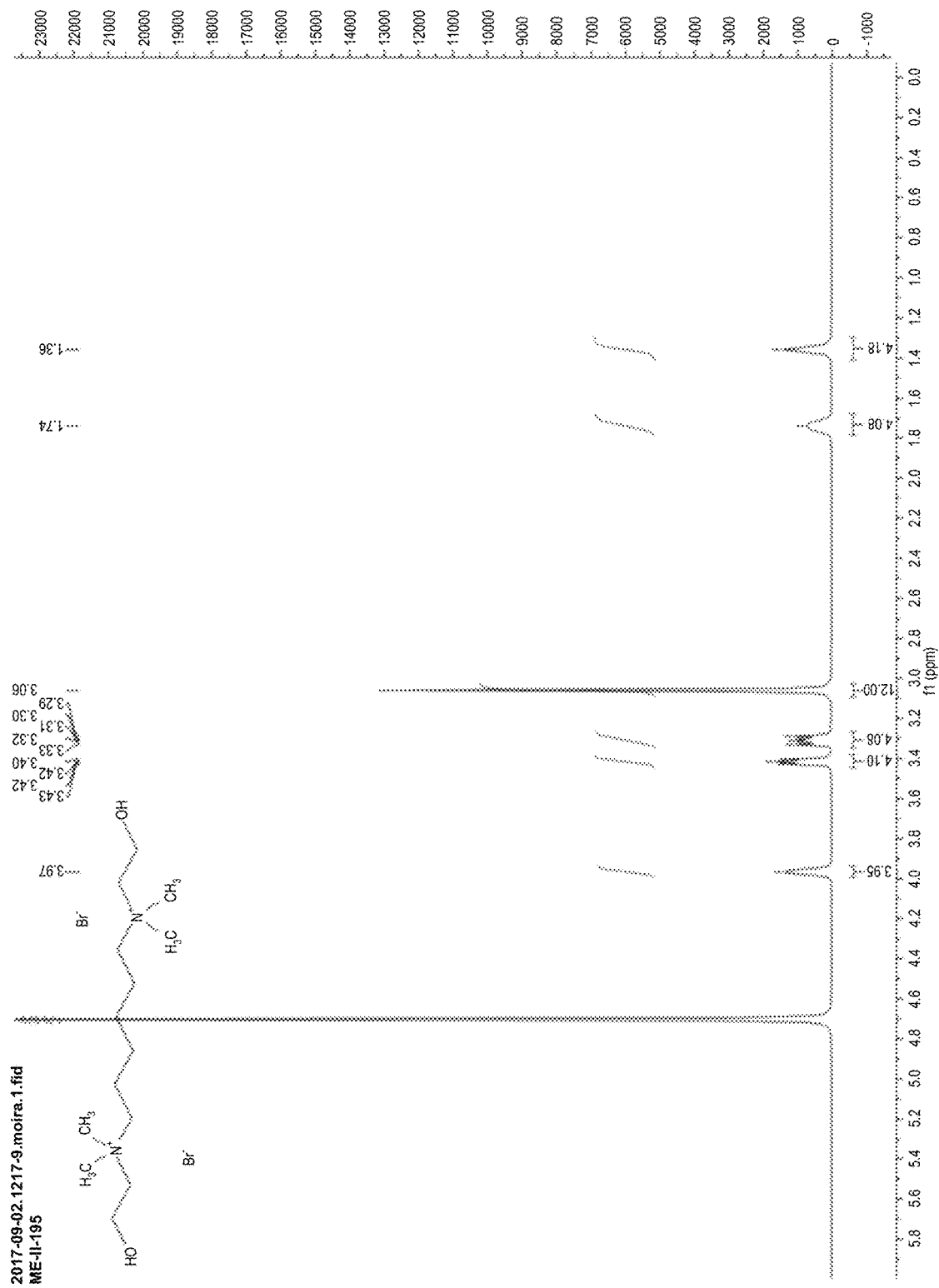
FIG. 45F. $^1$H NMR of [DC-6][2Br] hydrophilic ionic liquid precursor in D$_2$O.
Figure 45G:
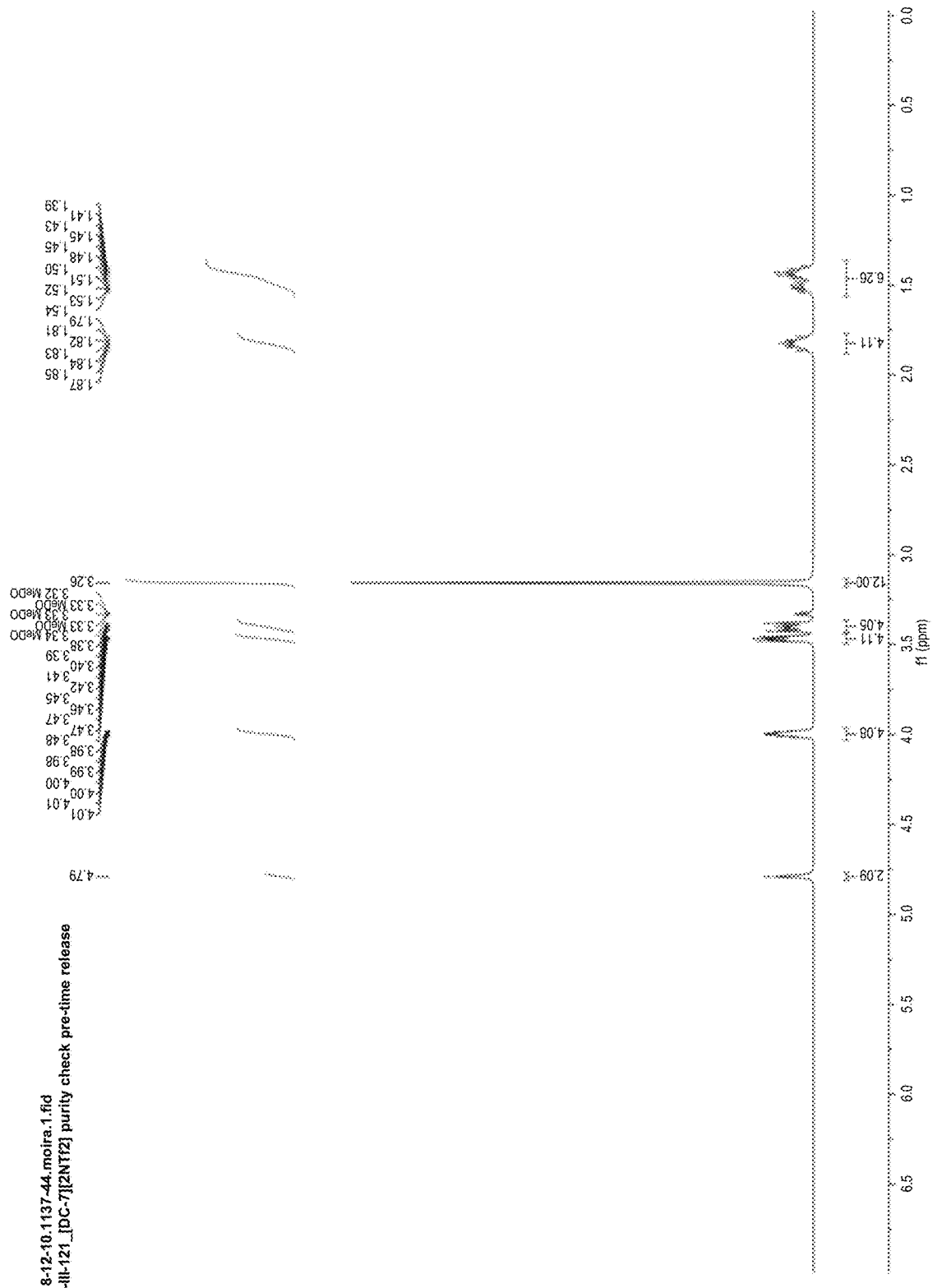
FIG. 45G. $^1$H NMR of [DC-7][2NTf$_2$] hydrophobic ionic liquid in CD$_3$OD.
Figure 45H:
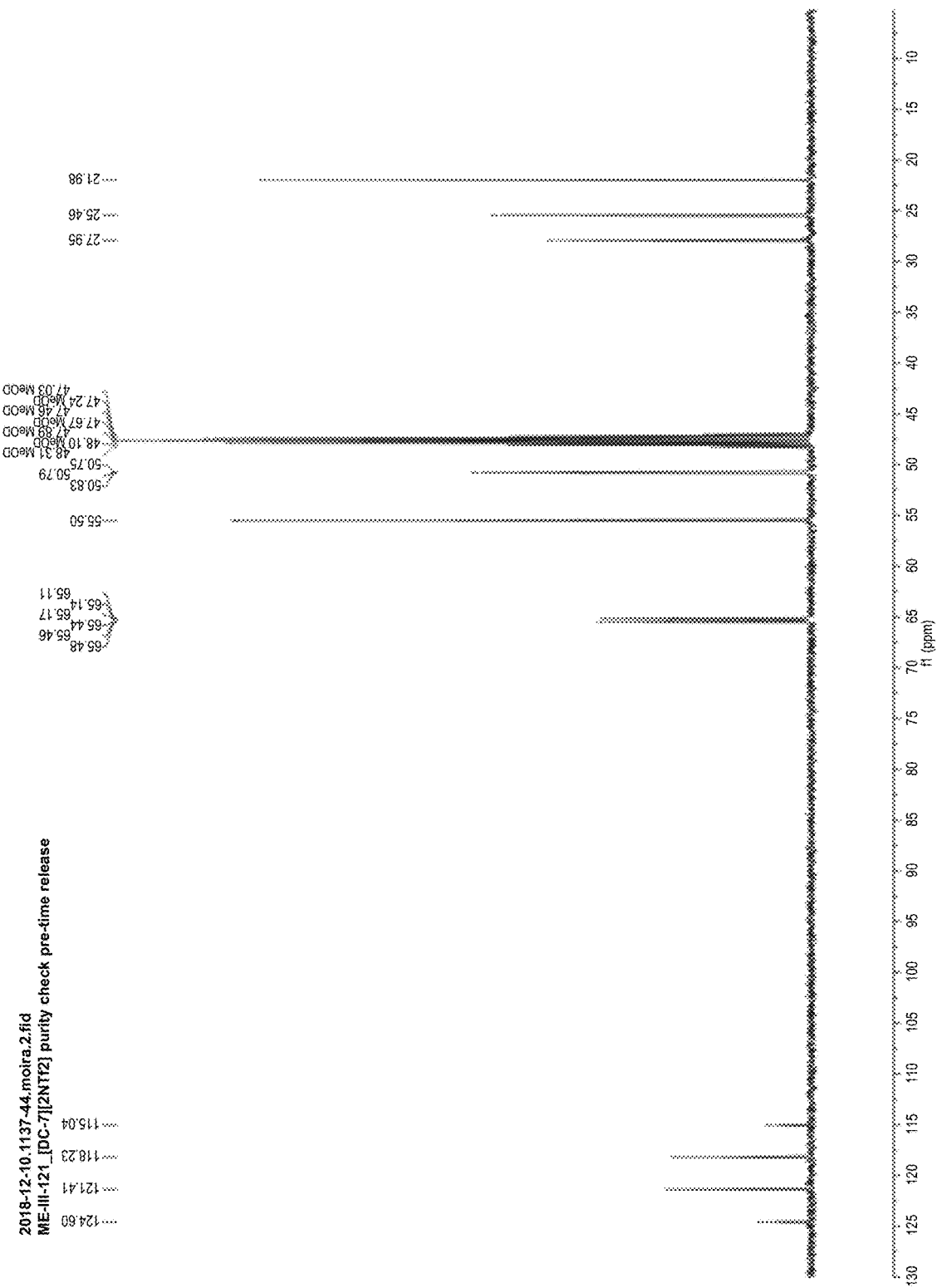
FIG. 45H. $^{13}$C NMR of [DC-7][2NTf$_2$] hydrophobic ionic liquid in CD$_3$OD.
Figure 45I:
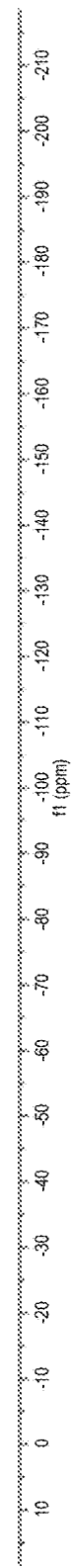
FIG. 45I. $^{19}$F NMR of [DC-7][2NTf$_2$] hydrophobic ionic liquid in CD$_3$OD.
Figure 45J:
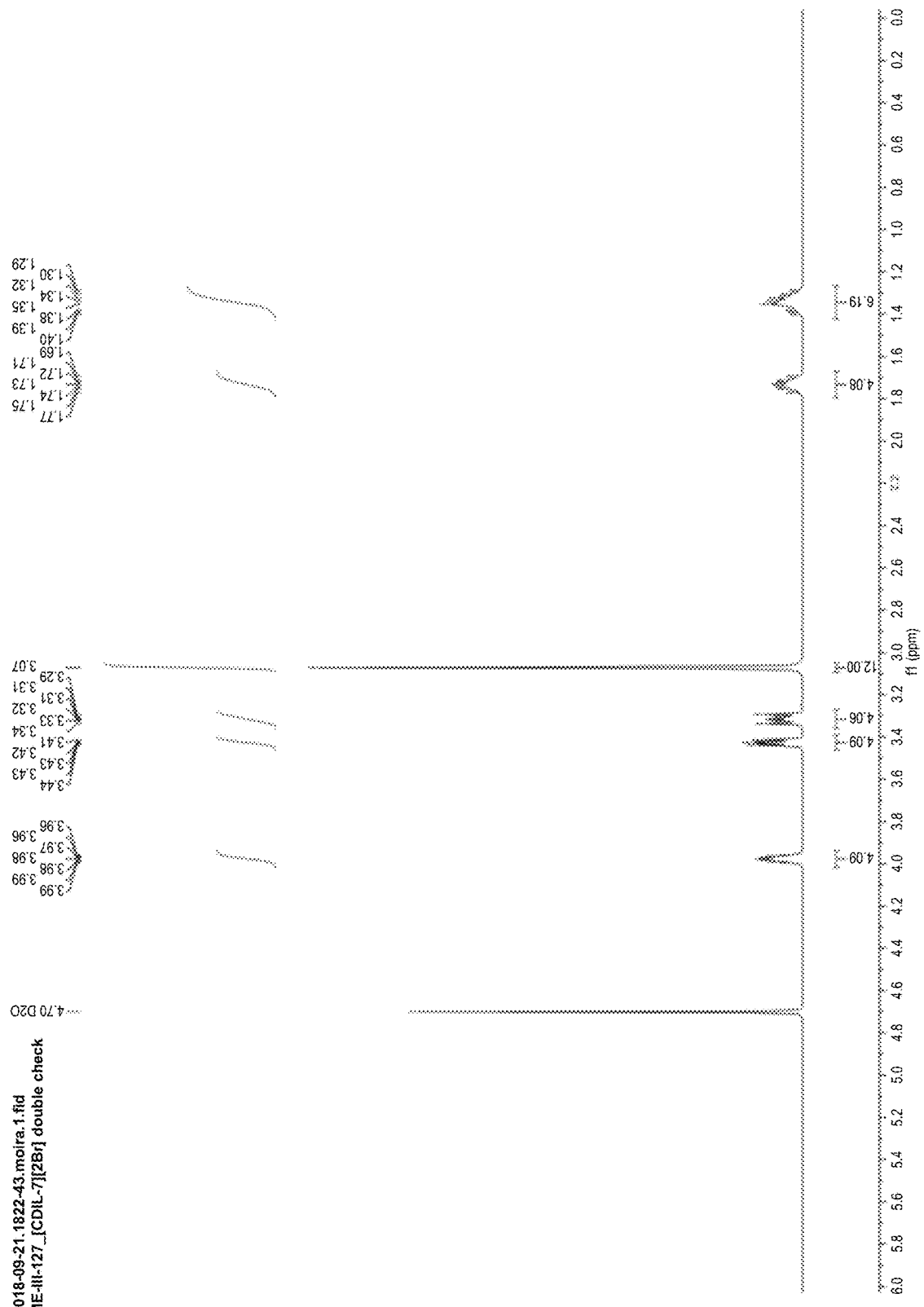
FIG. 45J. $^1$H NMR of [DC-7][2Cl] hydrophilic ionic liquid precursor in D$_2$O.
Figure 45K:
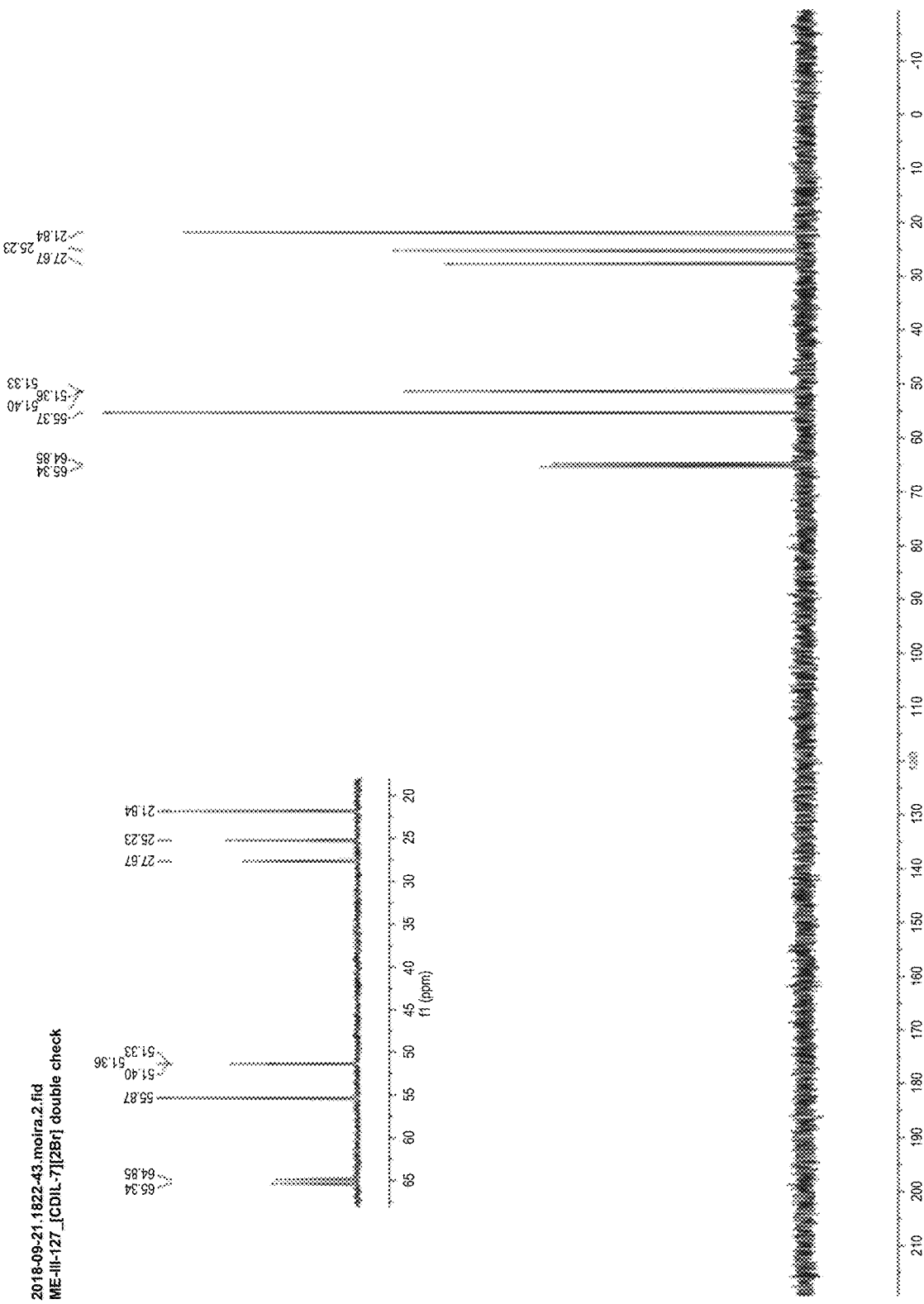
FIG. 45K. $^{13}$C NMR of [DC-7][2Cl] hydrophilic ionic liquid precursor in D$_2$O.
Figure 45L:
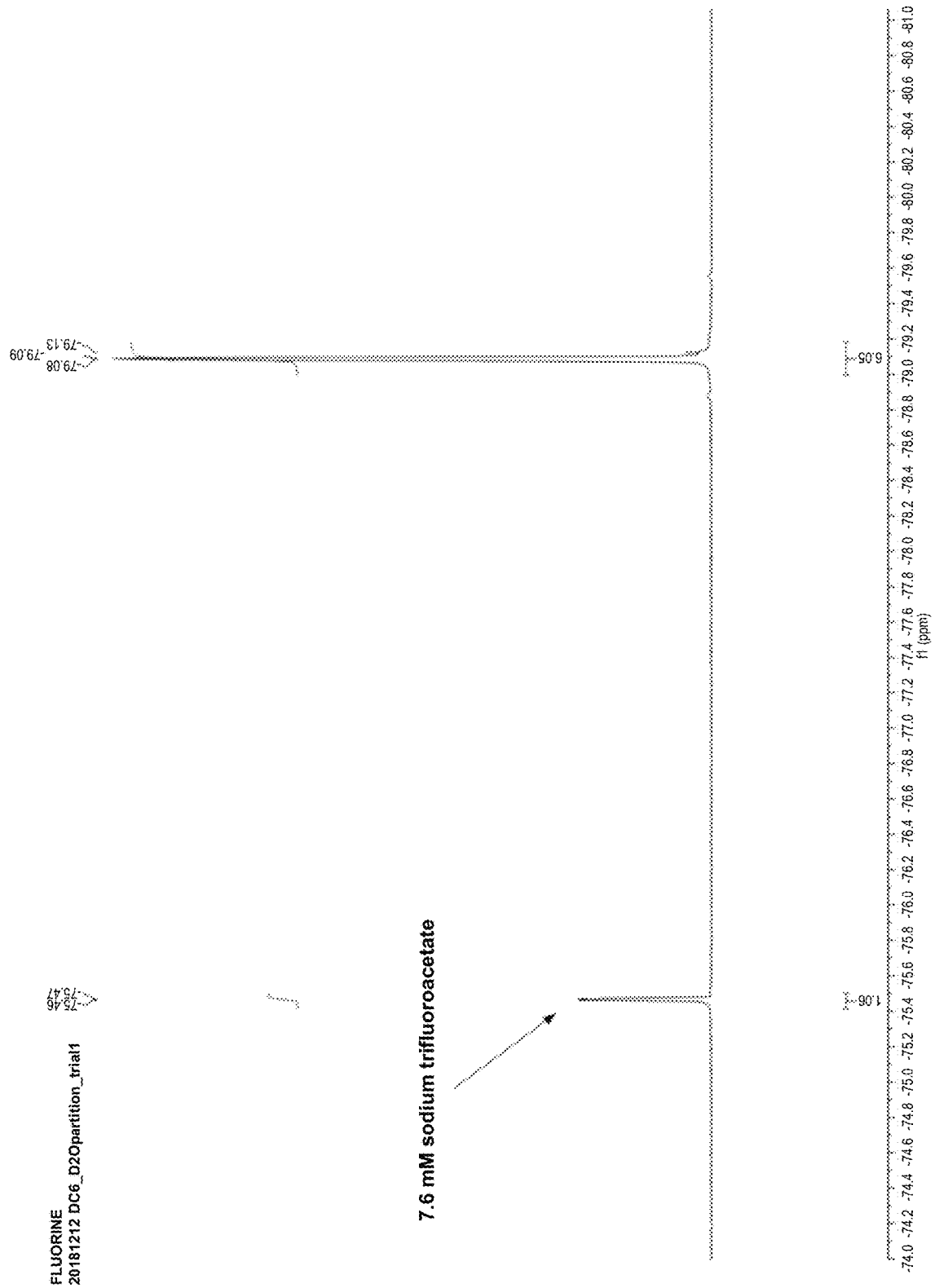
FIG. 45L. $^{19}$F NMR of [DC-6][2NTf$_2$] in D$_2$O.
Figure 45M:
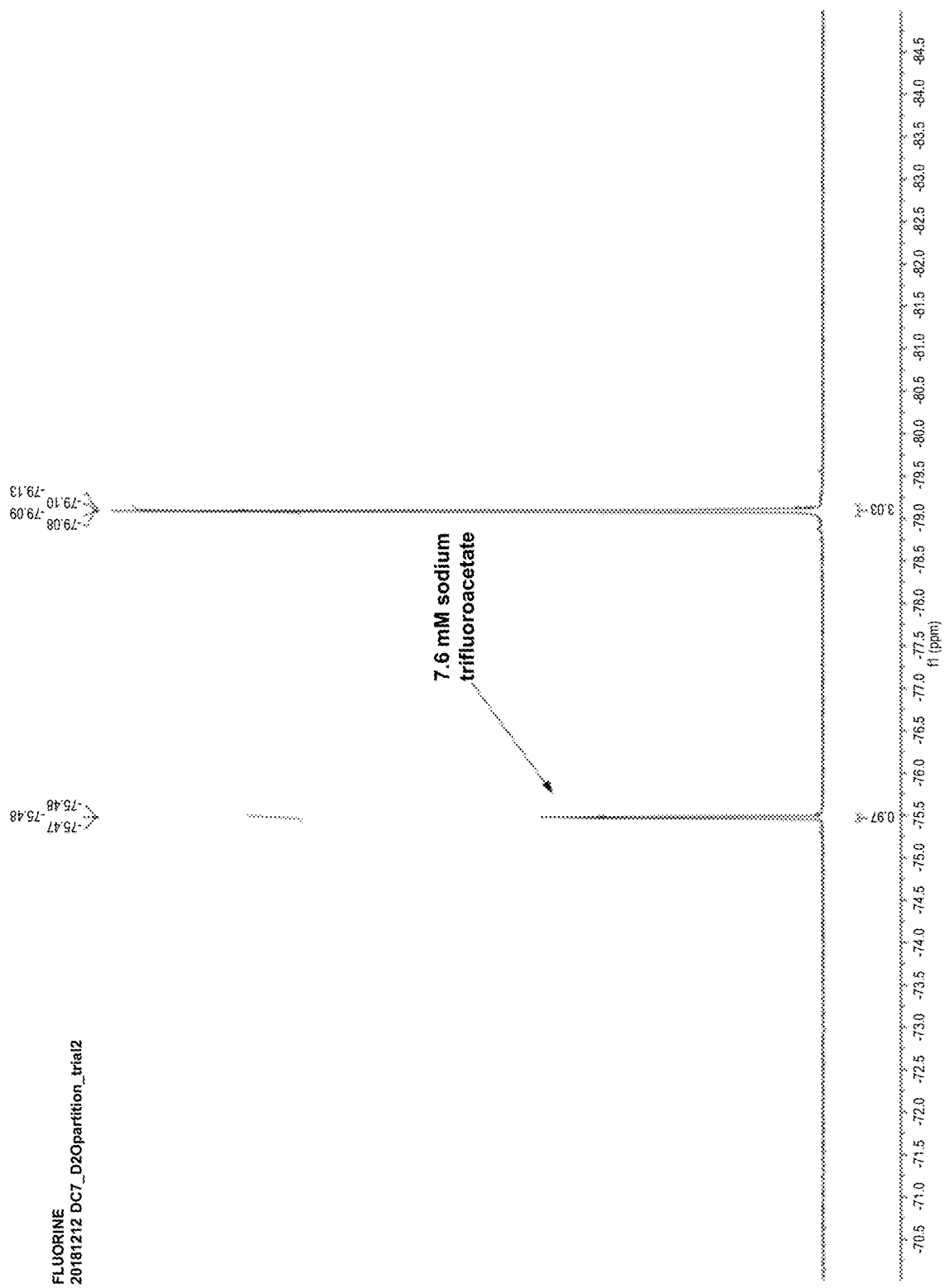
FIG. 45M. $^{19}$F NMR of [DC-7][2NTf$_2$] in D$_2$O.
Figure 45N:
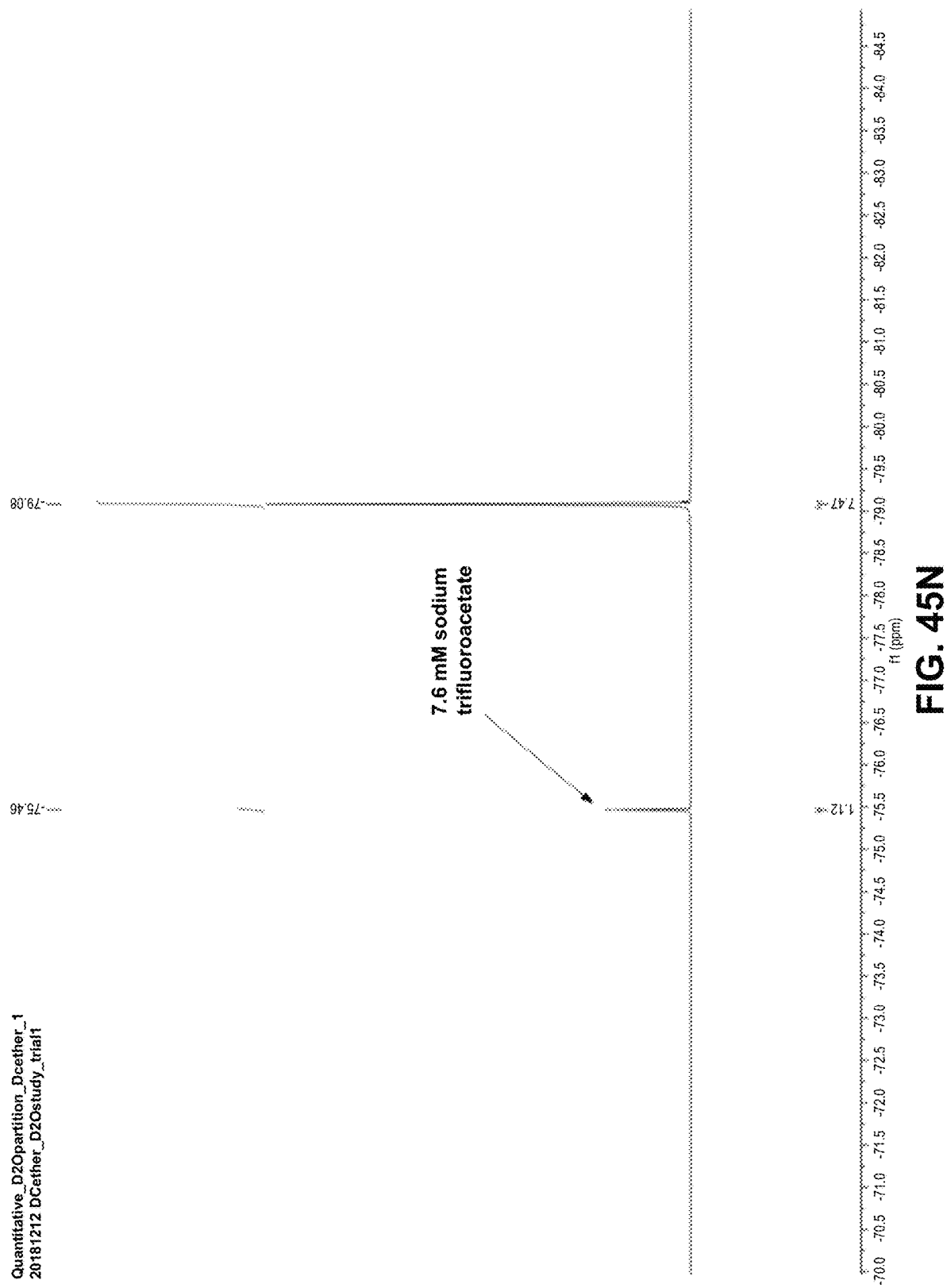
FIG. 45N. $^{19}$F NMR of [DC-ether][2NTf$_2$] in D$_2$O.
Figure 45O:
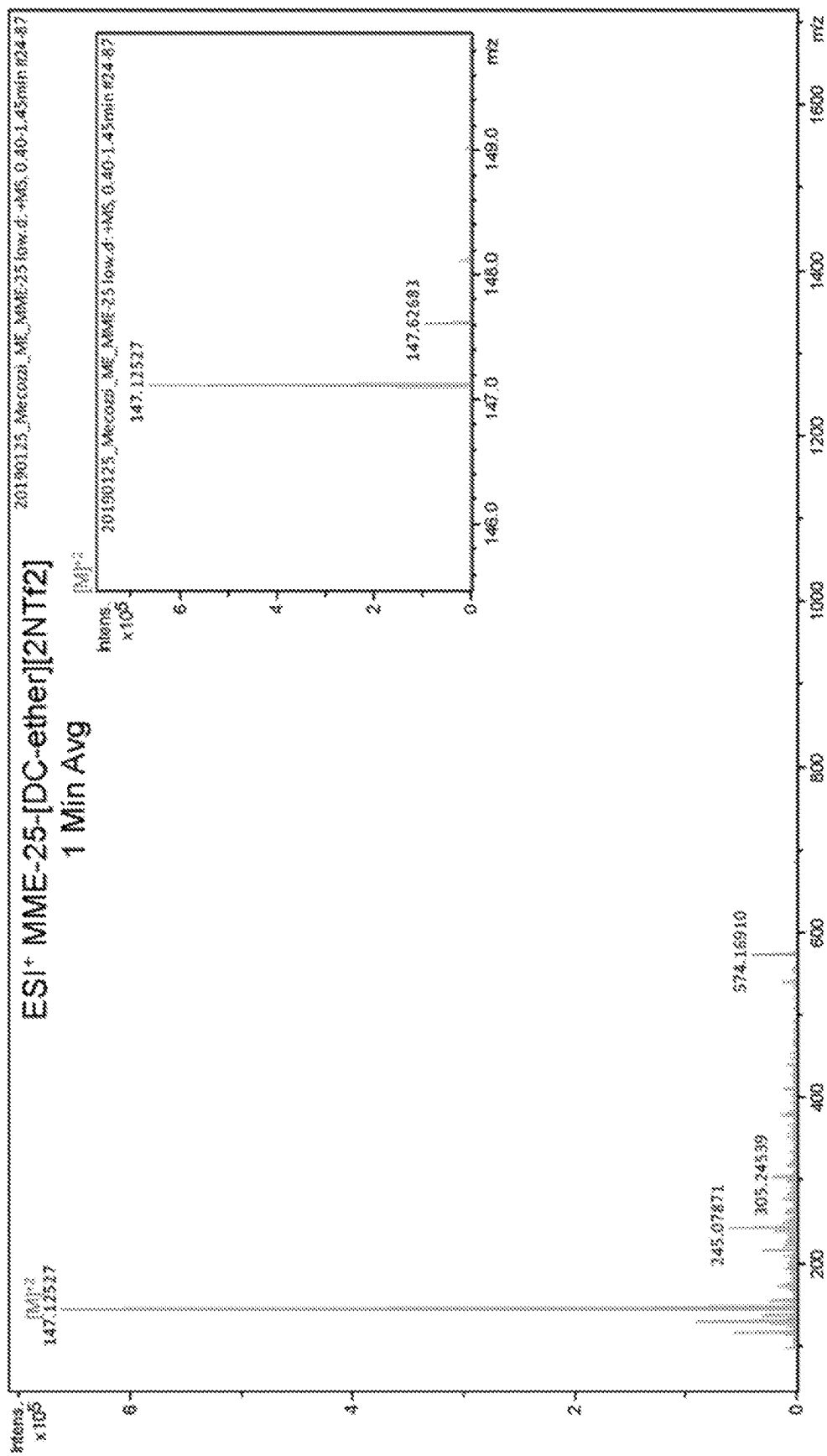
FIG. 45O. ESI-MS spectrum of [DC-ether][2NTf$_2$] hydrophobic ionic liquid in positive ion mode.
Figure 45P:
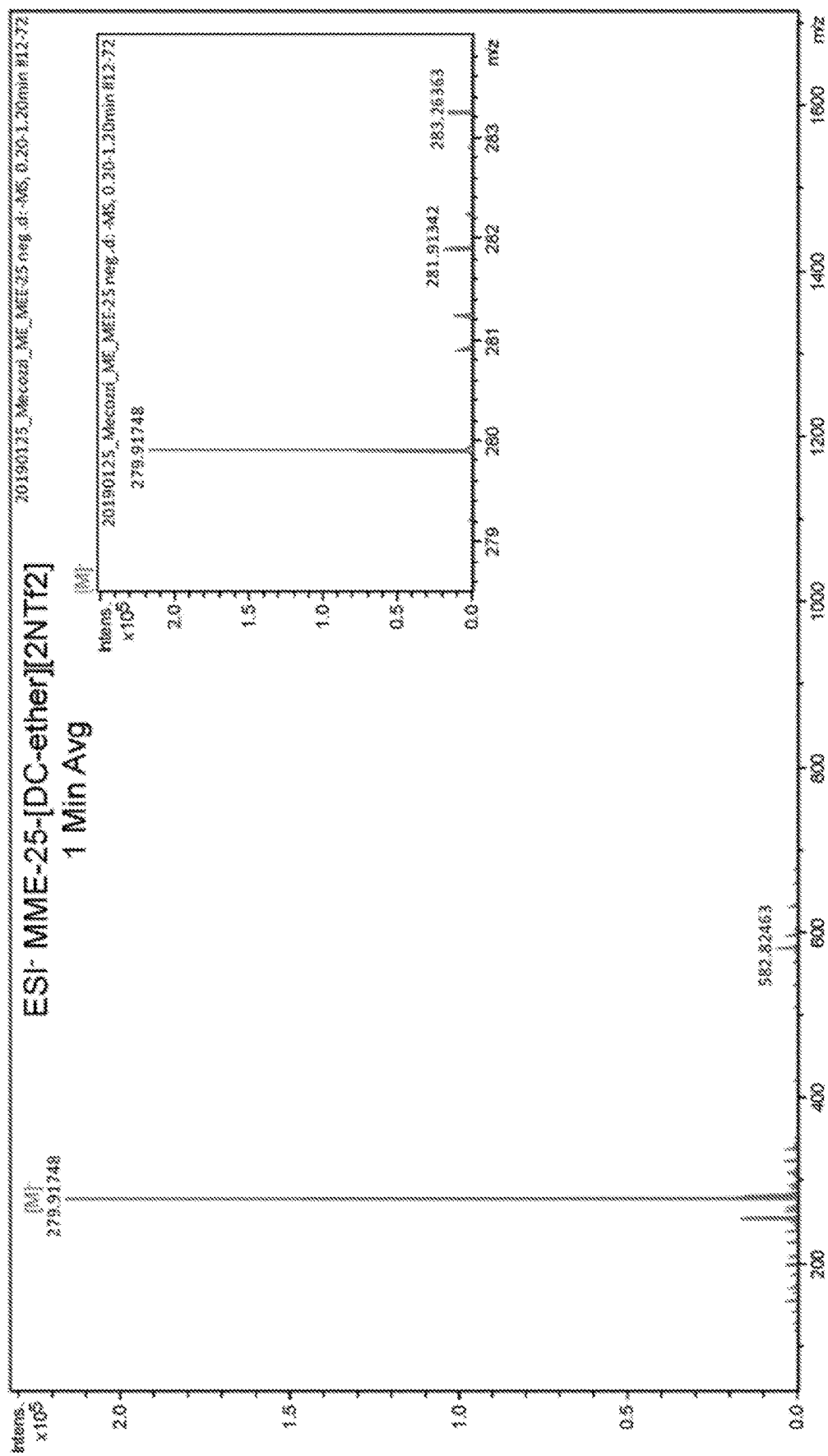
FIG. 45P. ESI-MS spectrum of [DC-ether][2NTf$_2$] hydrophobic ionic liquid in negative ion mode.
Figure 45Q:
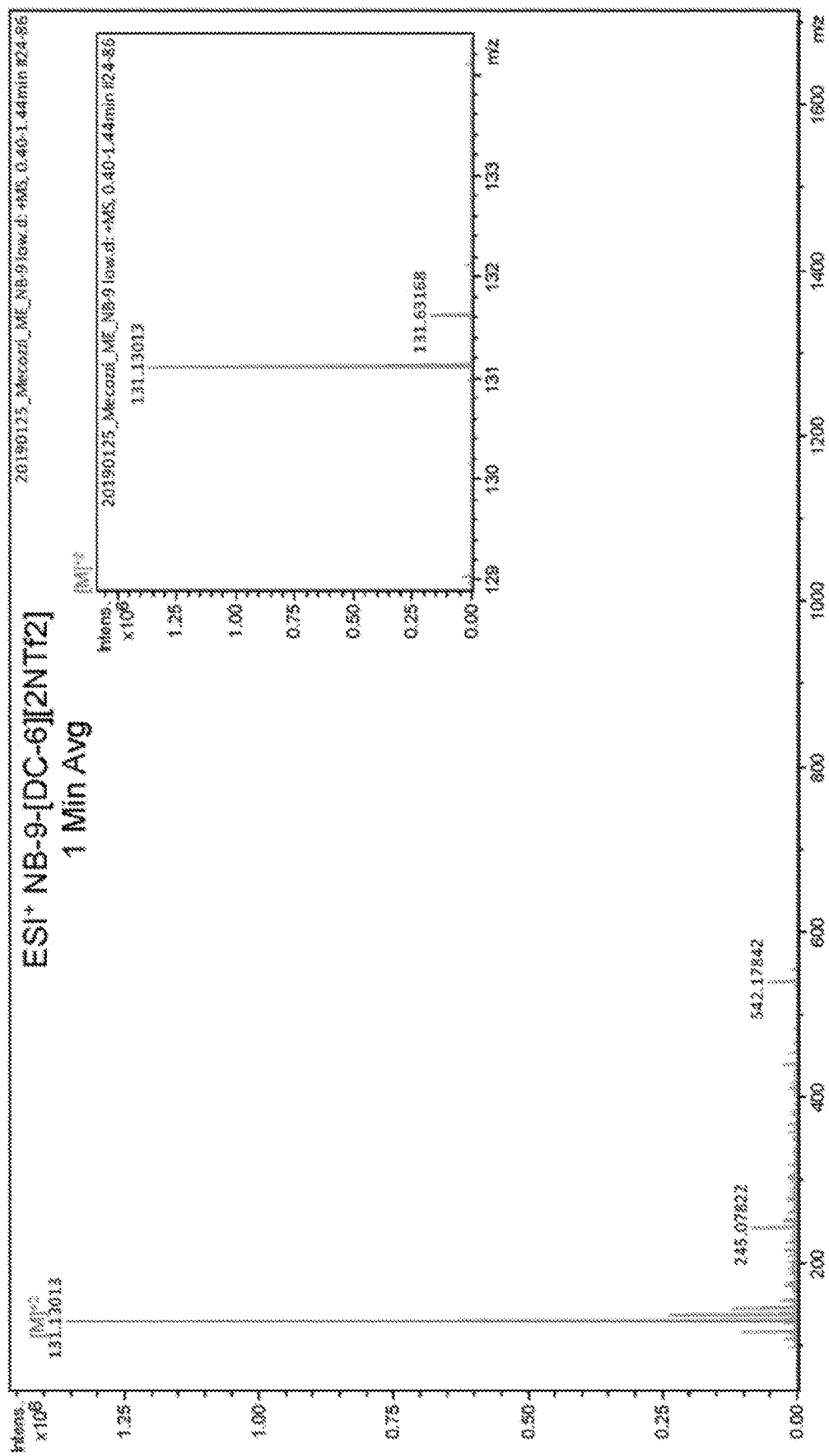
FIG. 45Q. ESI-MS spectrum of [DC-6][2NTf$_2$] hydrophobic ionic liquid in positive ion mode.
Figure 45R:
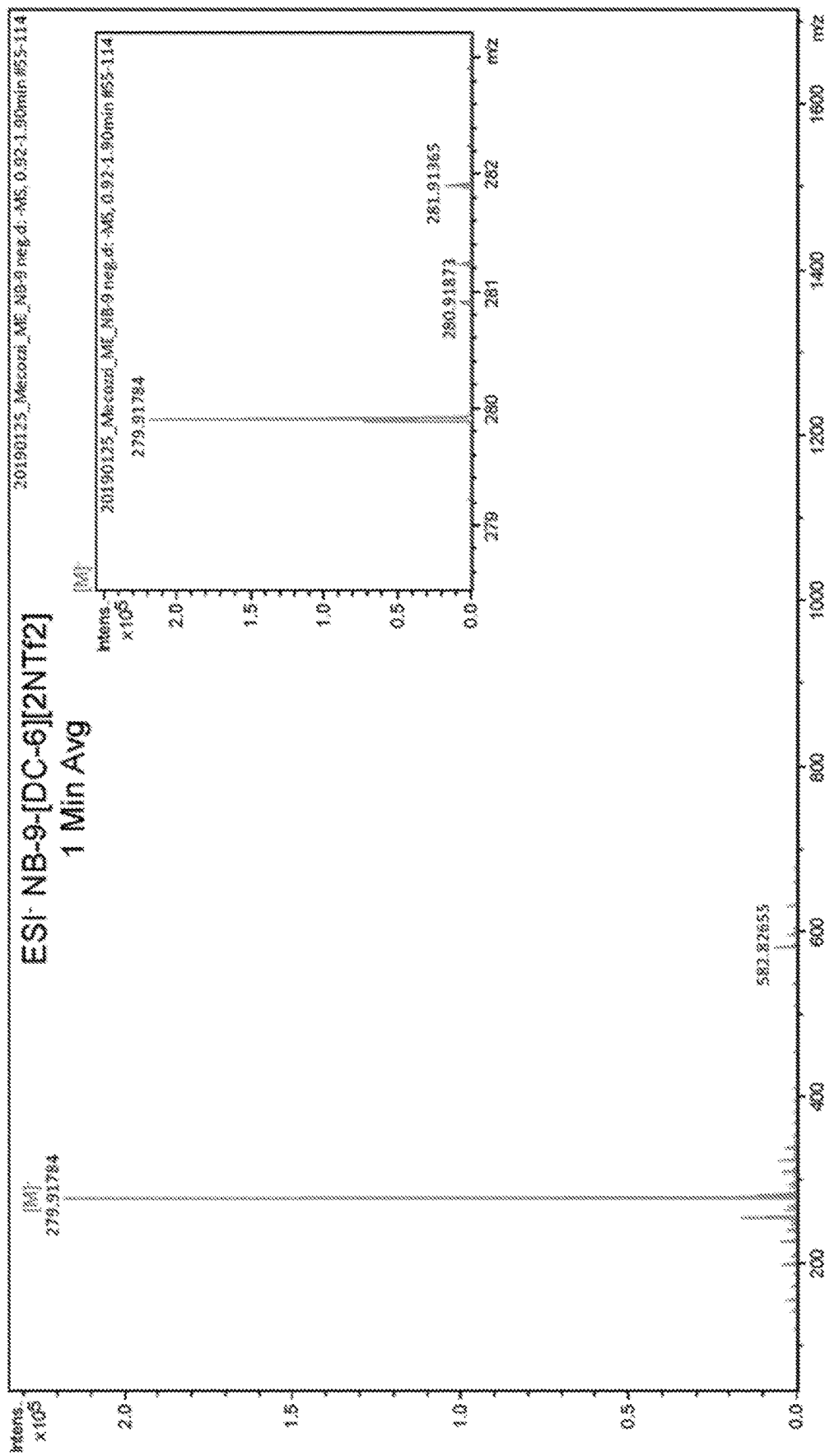
FIG. 45R. ESI-MS spectrum of [DC-6][2NTf$_2$] hydrophobic ionic liquid in negative ion mode.
Figure 45S:
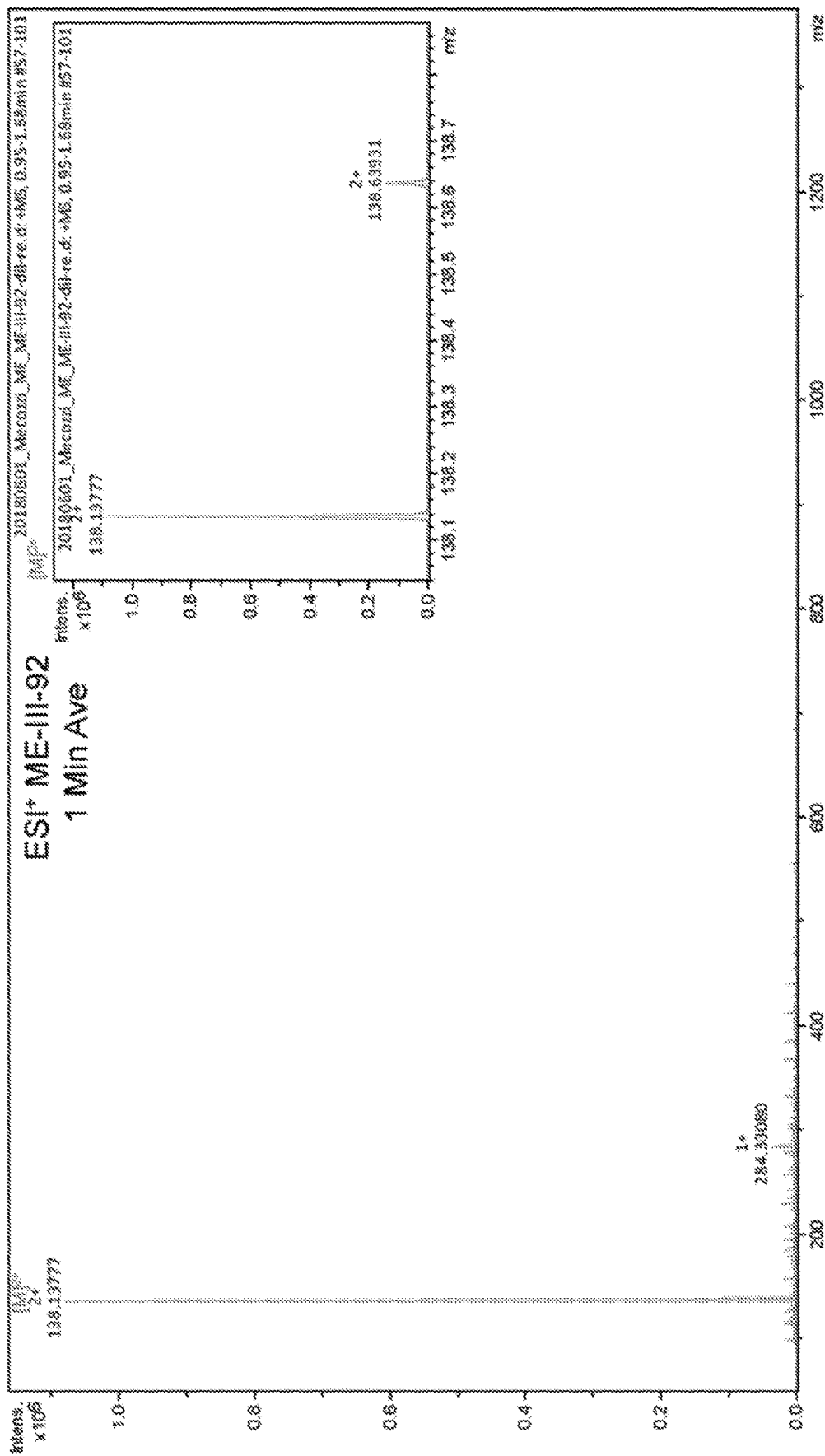
FIG. 45S. ESI-MS spectrum of [DC-7][2NTf$_2$] hydrophobic ionic liquid in positive ion mode.
Figure 45T:
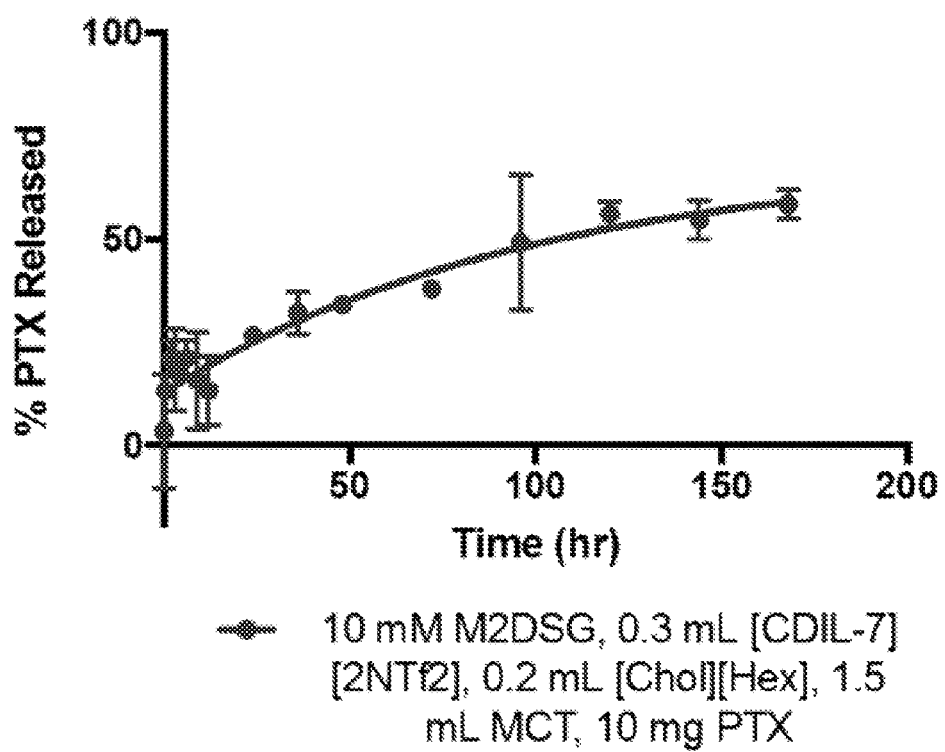
FIG. 45T shows a time course for release of PTX from a nanoemulsion in accordance with an embodiment of the present inv FIG. 63. Zebrafish survival 96 hours post-fertilization of water-soluble DC precursor ([DC-7][2Br], green), non-treated control (blue), and positive control perfluorooctanoic acid (PFOA, red).

While the toxicity profile of [Chol][Hex] has been studied in the literature, the in vivo toxicity profile of the novel [DC-7][2NTf$_2$] was unknown and, as such, was characterized. Due to the hydrophobic nature of [DC-7][2NTf$_2$] it could not be studied directly. As such, three essential in vivo developmental toxicity assays were completed using an embryo-larval zebrafish model to analyze the toxicity of the novel dicationic IL in the nanoemulsion, following previously established methods for analysis of the toxicity of components in nanoemulsion drug delivery systems[62,63]: (1) the water-soluble precursor of the novel cation ([DC-7][2Br], 2) was evaluated to analyze the toxicity of the novel cationic moiety and (2) the water-soluble precursor of the anion (sodium bis(trifluoromethylsulfonyl)imide) were analyzed to determine the toxicity profile of the cation and anion individually; (3) a water-solution saturated with [DC-7][2NTf$_2$] was evaluated to analyze the toxicity of the ionic liquid overall. The concentration of [DC-7][2NTf$_2$] in the saturated water-solution was determined using quantitative NMR (FIGS. 45L-45N), as described herein.

Figure 48A:
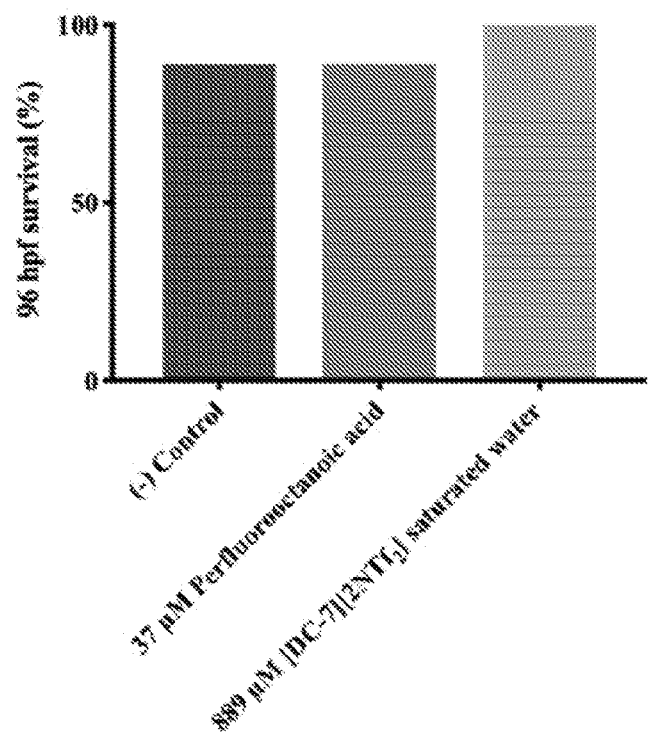
Figure 48B:
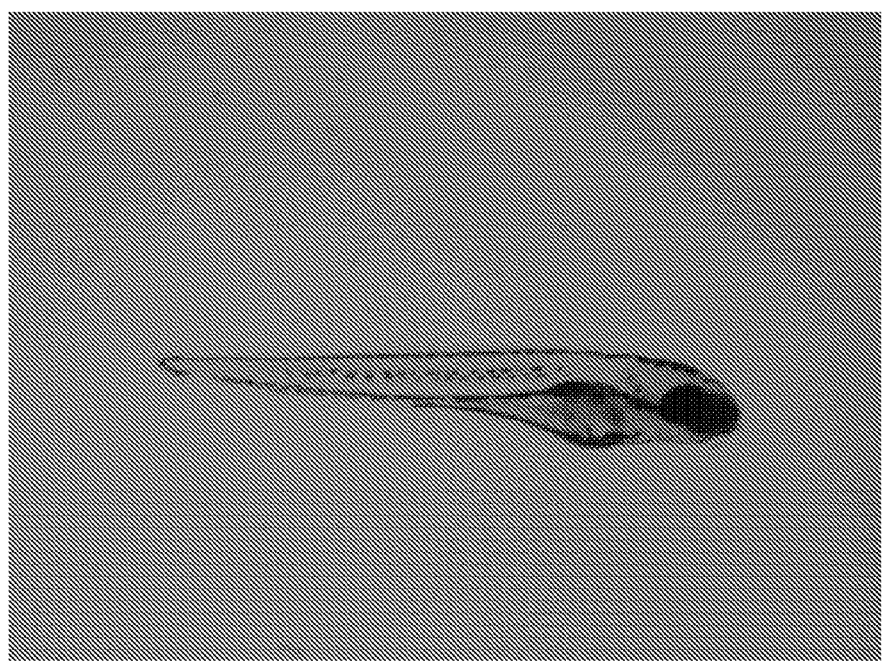
Figure 62:
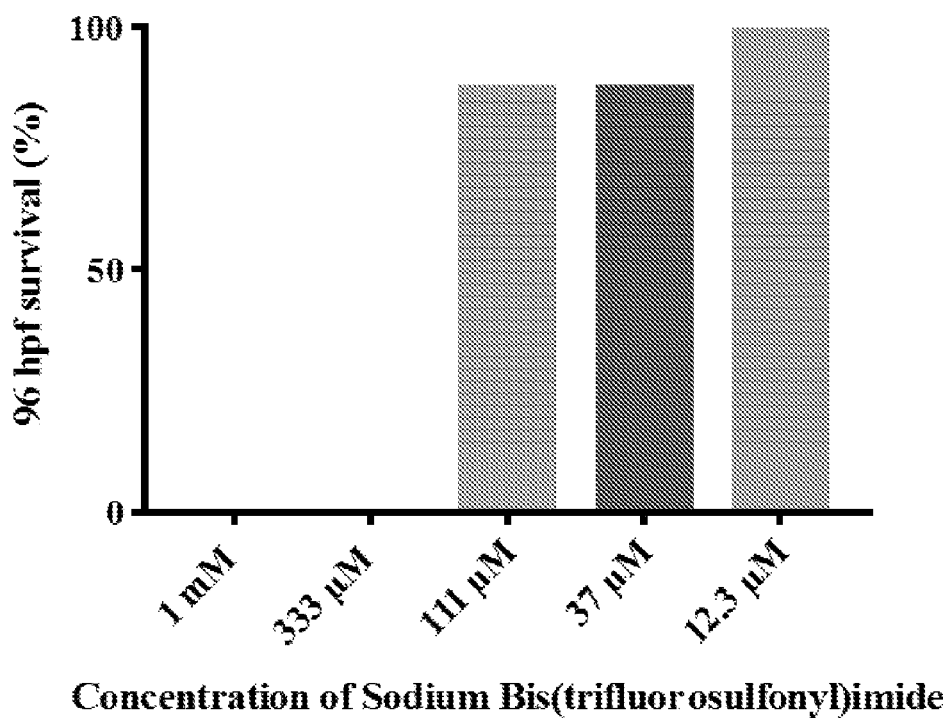
Figure 63:
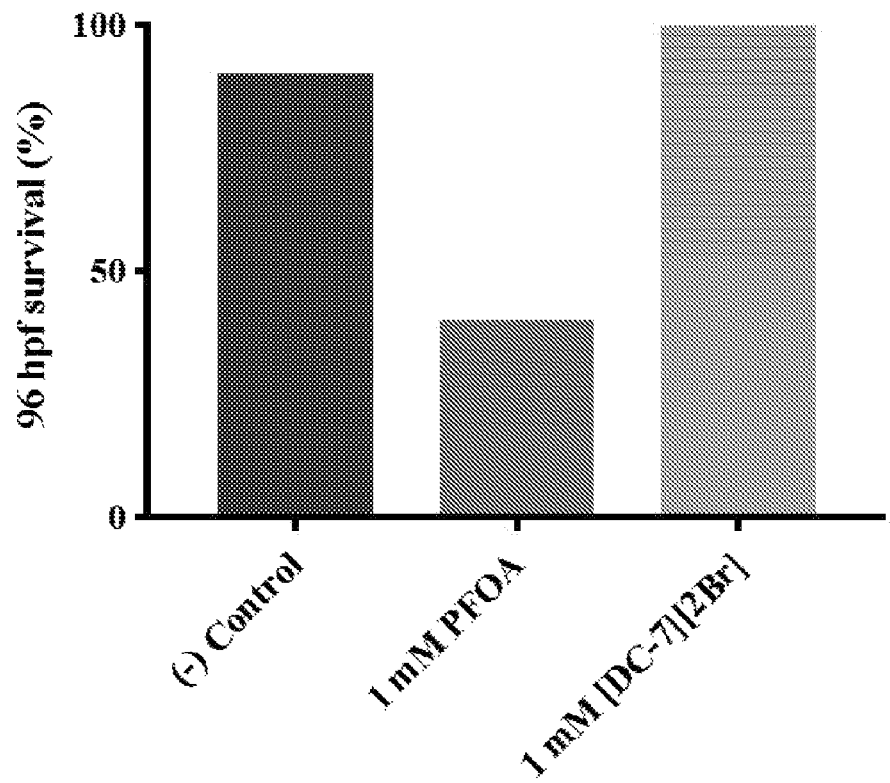
Figure 64:
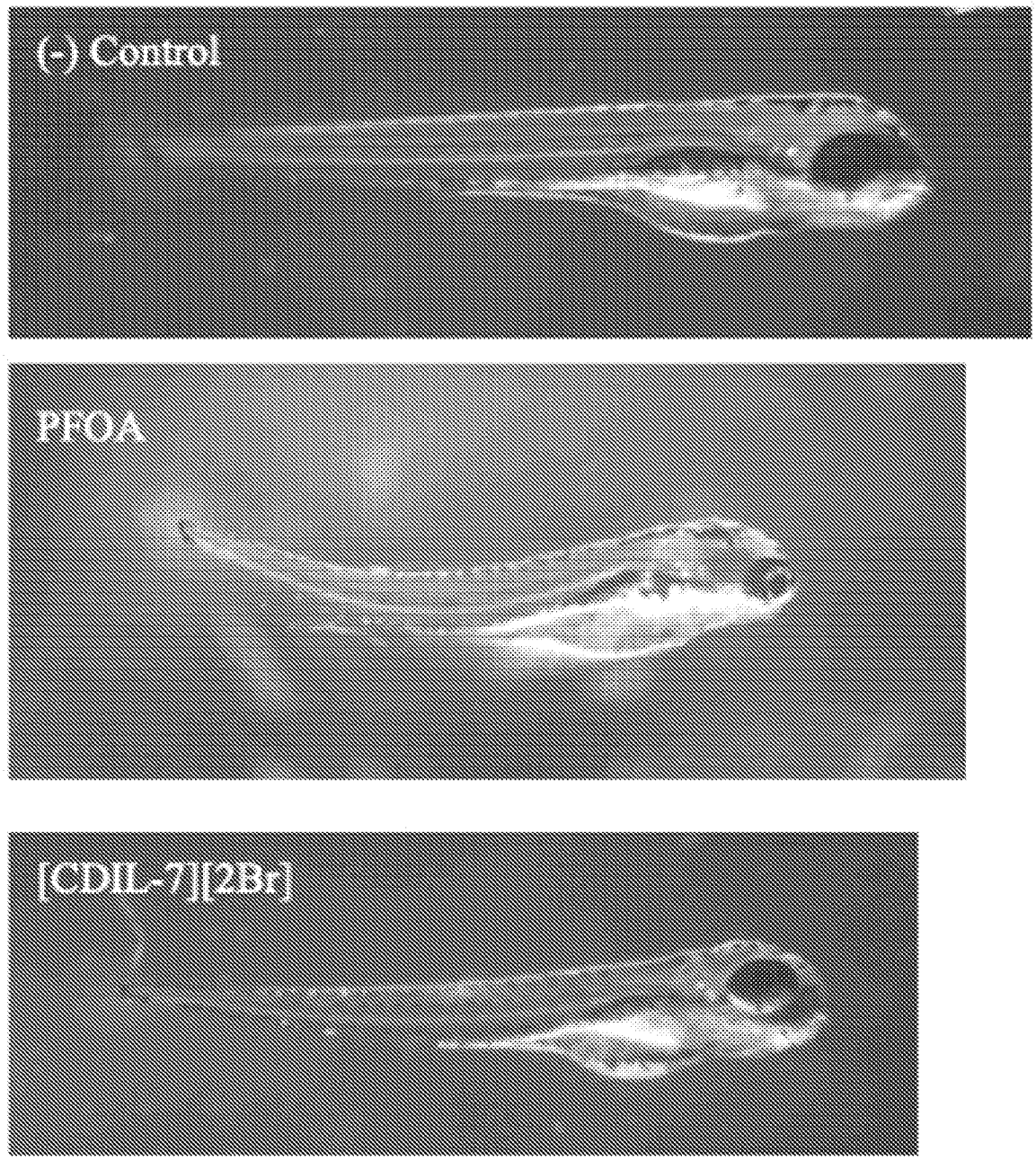
FIG. 64. Microscope images for malformation analysis of zebrafish 96 hours post-fertilization of water-soluble DC precursor ([DC-7][2Br], bottom labeled [CDIL-7][2Br]), non-treated control (top), and positive control perfluorooctanoic acid (PFOA, middle). Both the non-treated control and [DC-7][2Br] exhibit no malformations, in comparison to PFOA which exhibits spinal curvature.
Figure 65:
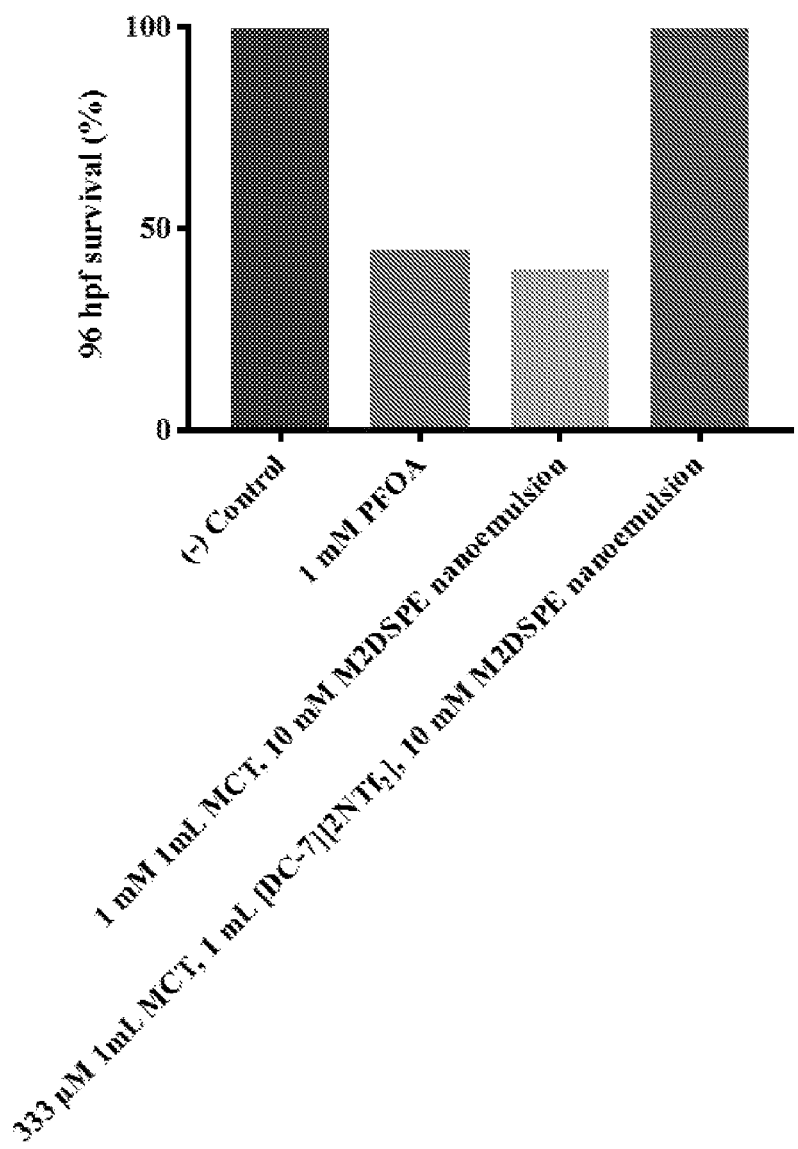
FIG. 65. Zebrafish survival 96 hours post-fertilization of nanoemulsion prepared with [DC-7][2NTf$_2$] (purple), non-treated control (blue), positive control perfluorooctanoic acid (PFOA, red), and an additional nanoemulsion to serve as control (green).
Figure 66:
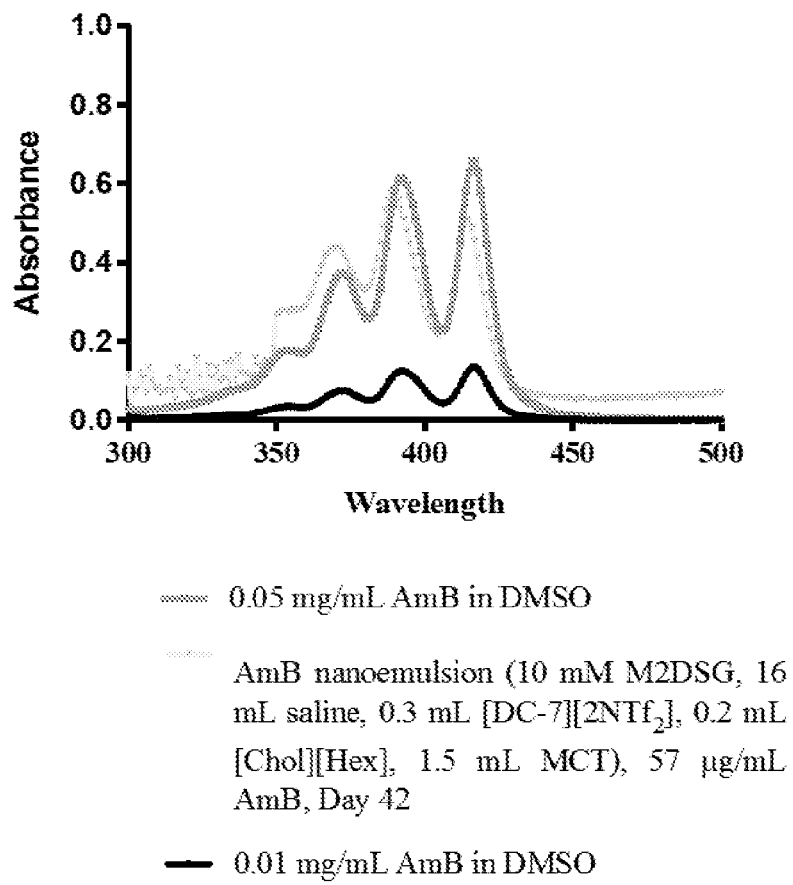
FIG. 66. UV/vis graph of AmB containing nanoemulsion (yellow) prepared 42 days prior to analysis with a concentration of 57 µg/mL AmB in comparison to monomeric AmB in DMSO at a concentration of 0.01 mg/mL (black) and 0.05 mg/mL (green). The prepared AmB nanoemulsion exhibits excellent monomerization and long-term stability.
Figure 67:
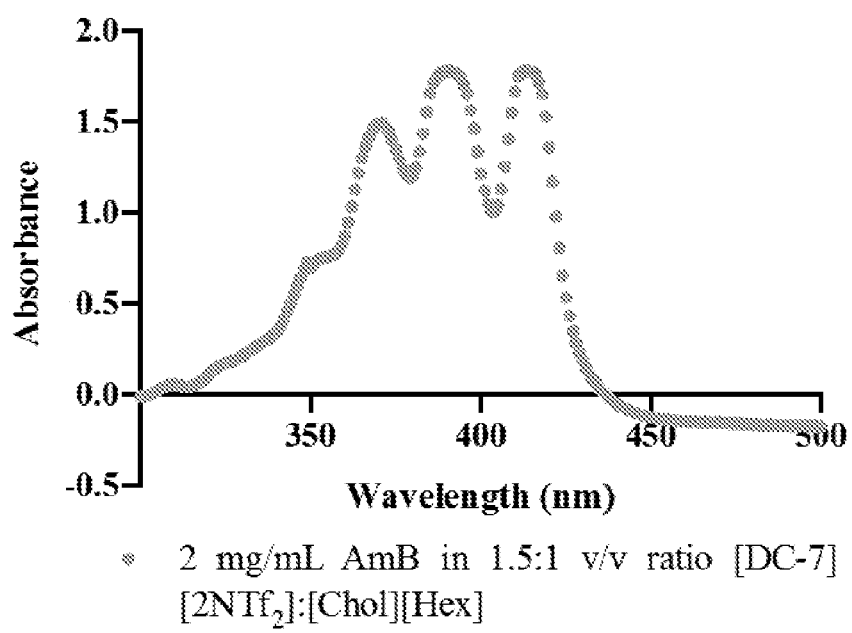
FIG. 67. UV/vis graph of AmB solubilized in a 1.5:1 v/v ratio [DC-7][2NTf$_2$]:[Chol][Hex] prior to emulsification. AmB present in the ionic liquid mixture exhibits excellent monomerization.
Figure 68:
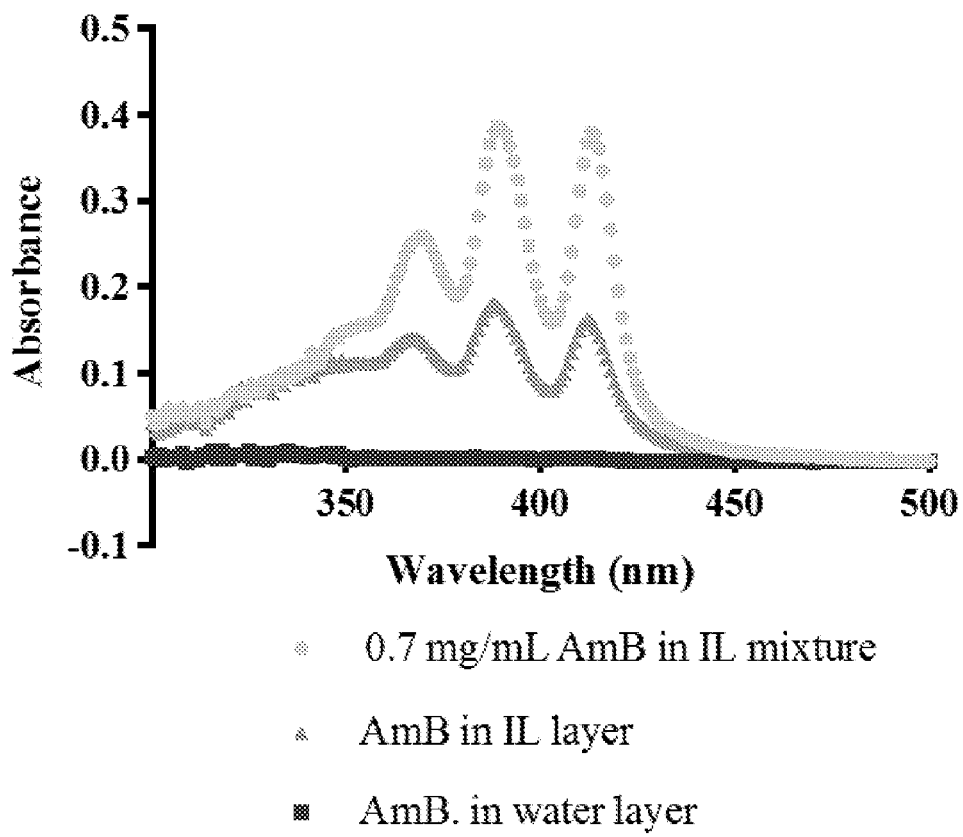
FIG. 68. UV/vis graph of AmB water partition analysis. AmB was solubilized in an ionic liquid mixture of 1.5:1 v/v [DC-7][2NTf$_2$]: [Chol][Hex] (yellow). AmB remaining in the IL mixture (green) was compared to AmB partitioned into water (blue). While a small amount of AmB may partition into the aqueous phase during the emulsification process, the AmB largely remains in the IL mixture.
Figure 69:
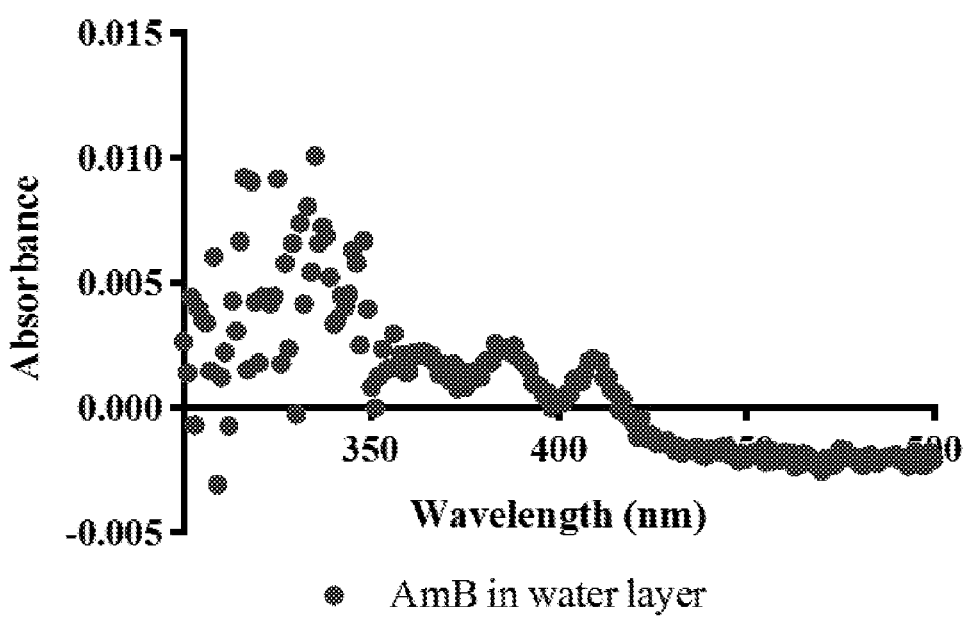
FIG. 69. UV/vis graph of AmB aqueous layer in water partition analysis. AmB partitions into the aqueous layer in both monomeric and aggregated form.

The water-soluble anion exhibited minimal toxicity, having an 87% survival rate at 111 μM concentration (FIG. 62). [DC-7][2Br] also exhibited negligible toxicity, having a 100% survival rate at 1 mM concentration with no malformations (FIGS. 53, 54, 63-65). Combination of cation and anion results in a biocompatible hydrophobic IL, demonstrated by the 100% survival rate at 889 μM concentration of the [DC-7][2NTf$_2$] saturated water solution (FIGS. 48A and 55, 56, and 57). At this concentration, the developed zebrafish exhibited no malformations (FIG. 48B) further indicating the biocompatibility of this novel IL.

Figure 49:
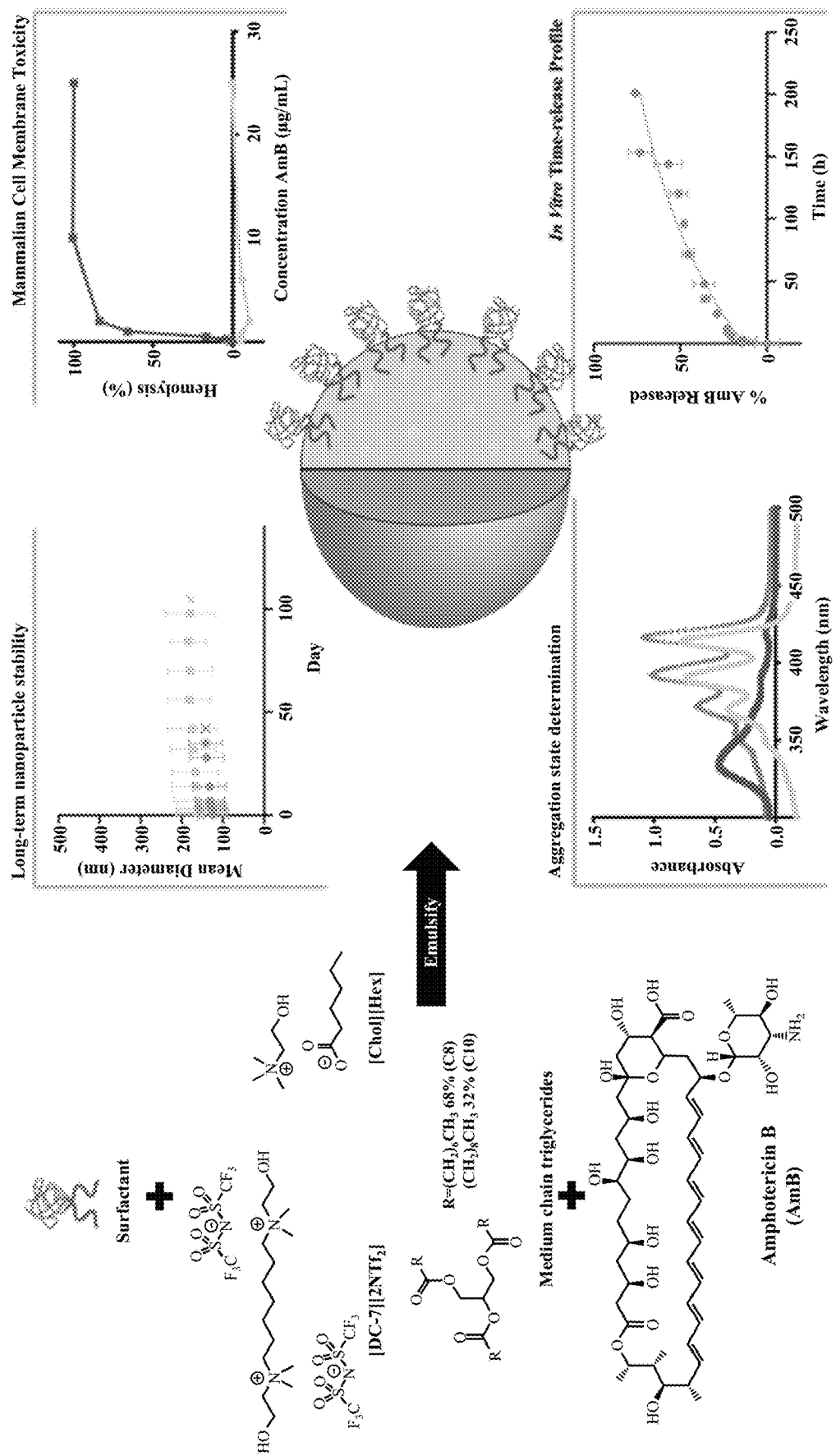

After evaluating the toxicity of each component of the proposed nanoemulsion, we prepared nanoemulsions using the commercially available surfactant 1,2-Distearoyl-rac-glycero-3-methylpolyoxyethylene (DSG-PEG, 2,000 g/mol average molecular weight of the PEG) and high-pressure microfluidization. Preparation of a nanoemulsion with a mixture of [Chol][Hex] and [DC-7][2NTf$_2$] as the hydrophobic media was unsuccessful, resulting in immediate phase separation. The emulsion instability can be attributed to the water solubility of the IL mixture. To impede this nanoemulsion destabilization, the two-component method was employed in which a hydrophobic additive was included in the hydrophobic media.[64] Commercially available medium chain triglycerides (MCT) derived from coconut oil were selected as the less-soluble additive due to its known biocompatibility.[63] Addition of MCT to the hydrophobic media resulted in successful emulsification of AmB (FIG. 49). Two nanoemulsions were prepared with differing volumes of hydrophobic media (FIG. 49). Both were stable for a minimum of 1 month. After emulsification and storage at 4° C. for 42 days, the aggregation state of AmB in the nanoemulsion was analyzed to evaluate the long-term stability of the prepared nanoemulsion. AmB remained in the non-aggregated form (FIG. 66) demonstrating that the prepared nanoemulsion exhibits long-term stability.

Figure 50A:
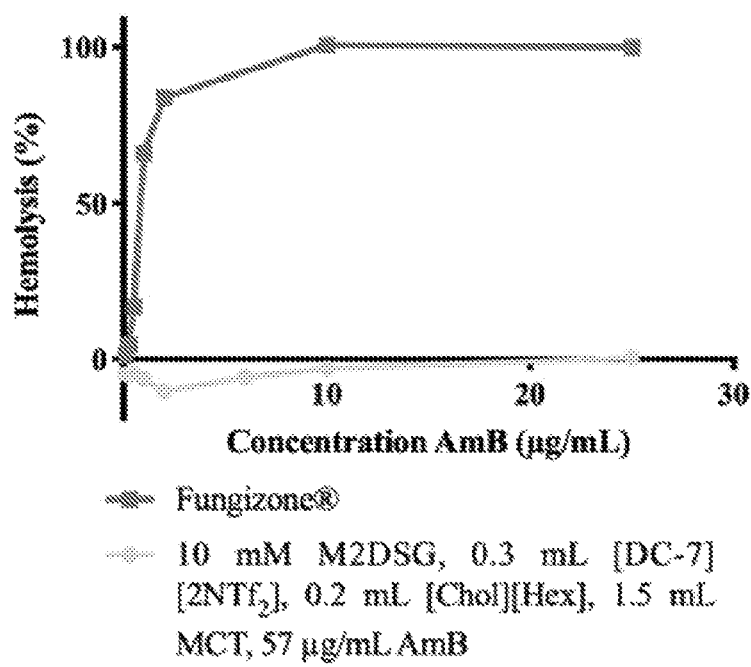

Hemolytic activity was used to assess the in vitro mammalian cell membrane toxicity of the AmB containing nanoemulsion in comparison to FUNGIZONE™. The AmB comprising nanoemulsion did not exceed 1% hemolysis at all analyzed concentrations (FIG. 50A). In contrast, FUNGIZONE™ was highly hemolytic even at low concentrations (2 μg/mL), which is consistent with previously analyzed hemolytic activity of FUNGIZONE™.[65] These results indicate that the prepared nanoemulsion formulation would be safe for intravenous delivery of AmB.

We next sought to test whether delivery of AmB in the nanoemulsion would affect the antifungal activity of AmB. In order to verify the fungicidal activity, we carried out a minimum inhibitory concentration assay using *Candida albicans*. The MIC of emulsified AmB against *C. albicans* ranged from 0.22-0.44 µg/mL (Table S4). This concentration range is comparable with that of FUNGIZONE™ (0.25-0.5 µg/mL).[66]

Figure 50B:
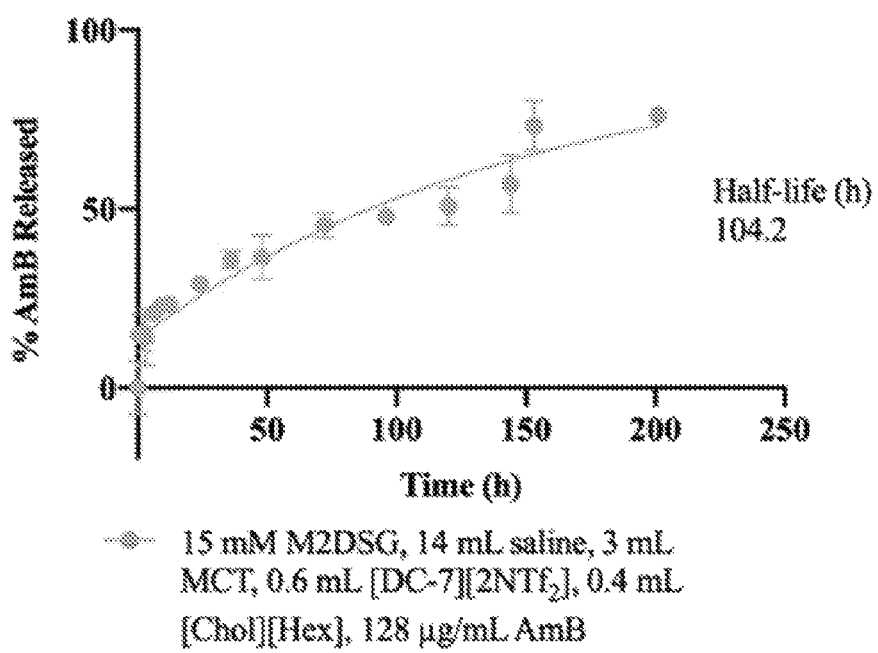
Figure 51:
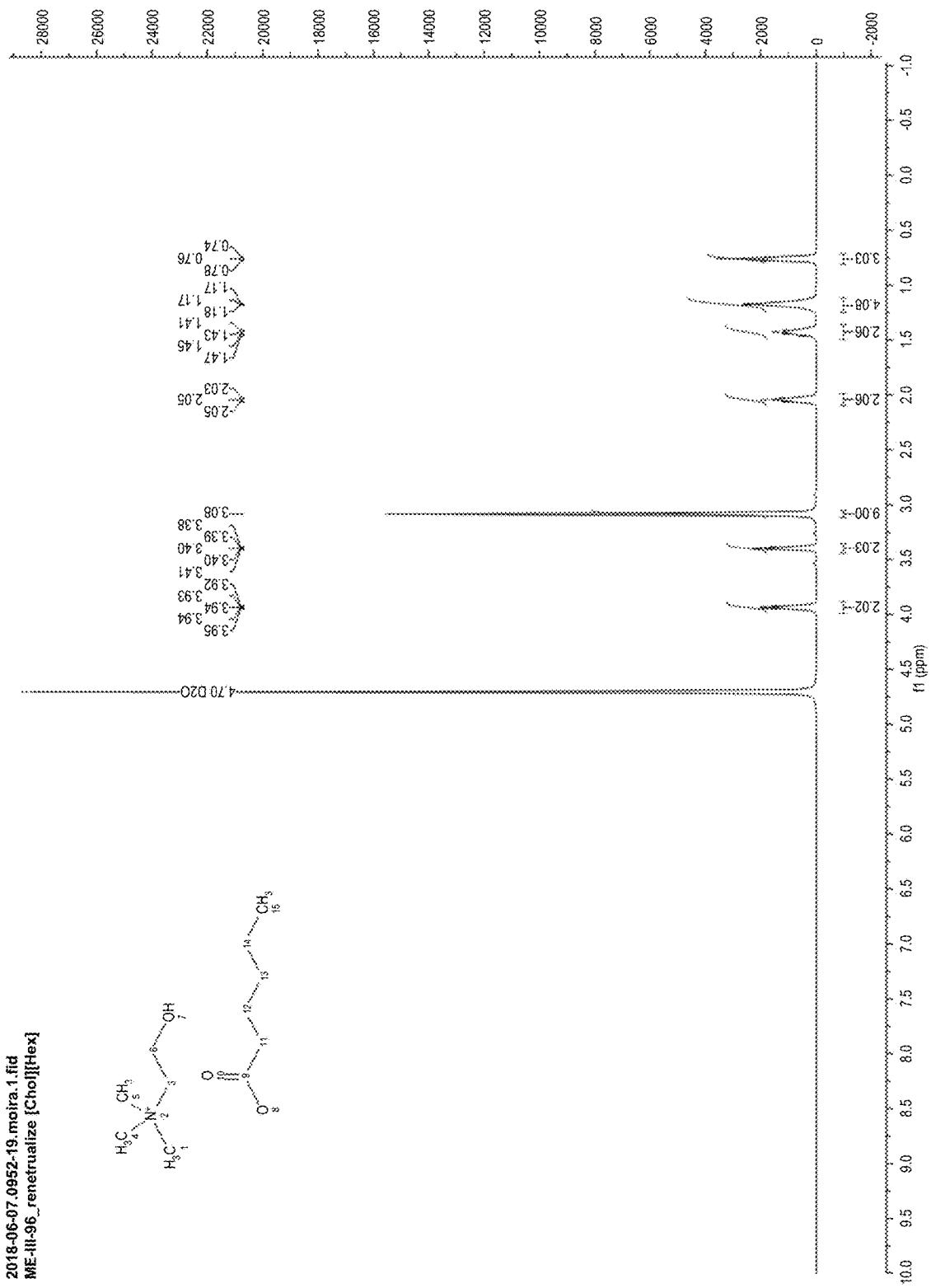

In vitro time-release study in which the nanoemulsion was dialyzed under sink conditions to simulate physiological conditions. A prolonged, sustained release of AmB in the monomeric form is desired as clinical studies have shown that a continuous infusion of AmB over 24 hours is better tolerated than a 2-4 hour infusion.[67-69] The dose-limiting toxicity of AmB precludes higher dosages of AmB or longer therapies, indicating that prolonged release is the best route to circumvent AmB's inherent toxicity. The IL-in-water nanoemulsion exhibits a sustained release (FIG. 50B). Despite the presence of a water-soluble ionic liquid, not all AmB is immediately released, validating the UV/vis analysis of the partition of AmB into water during emulsification. In the first 24 hours, less than 25% of AmB was released.

In conclusion, we have rationally designed a triphasic nanoemulsion drug delivery system for the hydrophobic antifungal agent Amphotericin B. Through the use of a relatively unstudied dicationic cholinium-based moiety coupled with a hydrophobic and non-toxic anion, we were successfully able to prepare a hydrophobic IL with negligible in vivo toxicity with a combination of hydrophobic and hydrophilic regions. This hydrophobic IL was rationally designed for the solubilization of a wide variety of pharmaceuticals. While the mammalian in vivo toxicity of the nanoemulsions remains to be evaluated, studies to address this question are underway. We have developed a novel nanoemulsion containing a hydrophobic IL with the potential to deliver pharmaceutical agents intravenously. The use of IL-in-water nanoemulsions could represent an effective strategy to reduce the toxicity of various pharmaceuticals.

REFERENCES (1) Centers for Disease Control and Prevention. Invasive Candidiasis Statistics https://www.cdc.gov/fungal/diseases/candidiasis/invasive/statistics.html.
(2) Bolard, J.; Legrand, P.; Heitz, F.; Cybulska, B. One-Sided Action of Amphotericin B on Cholesterol-Containing Membranes Is Determined by Its Self-Association in the Medium. Biochemistry 1991, 30 (23), 5707-5715.
(3) Legrand, P.; Romero, E. A.; Cohen, B. E.; Bolardl, J. Effects of Aggregation and Solvent on the Toxicity of Amphotericin B to Human Erythrocytes. Antimicrob. Agents Chemother. 1992, 36 (11), 2518-2522.
(4) Yamashita, K.; Janout, V.; Bernard, E. M.; Armstrong, D.; Regen, S. L. Micelle/Monomer Control over the Membrane-Disrupting Properties. J. Am. Chem. Soc. 1995, 117, 6249-6253.
(5) Torrado, J. J.; Espada, R.; Ballesteros, M. P.; Torrado-Santiago, S. Amphotericin B Formulations and Drug Targeting. J. Pharm. Sci. 2008, 97 (7), 2405-2425.
(6) Brajtburg, J.; Powderly, W. G.; Kobayashi, G. S.; Medoff, G. Amphotericin B: Delivery Systems. Antimicrob. Agents Chemother. 1990, 34 (3), 381-384.
(7) Noemı́, M.; Laniado-labon, R. Amphotericin B: Side Effects and Toxicity. Rev. Iberoam. Micol. 2009, 26 (4), 223-227.
(8) Starzyk, J.; Gruszecki, M.; Tutaj, K.; Luchowski, R.; Szlazak, R.; Wasko, P.; Grudzinski, W.; Czub, J.; Gruszecki, W. I. Self-Association of Amphotericin b: Spontaneous Formation of Molecular Structures Responsible for the Toxic Side Effects of the Antibiotic. J. Phys. Chem. B 2014, 118 (48), 13821-13832.
(9) Palacios, D. S.; Dailey, I.; Siebert, D. M.; Wilcock, B. C.; Burke, M. D. Synthesis-Enabled Functional Group Deletions Reveal Key Underpinnings of Amphotericin B Ion Channel and Antifungal Activities. PNAS 2011, 108 (17), 6733-6738.
(10) Takemoto, K.; Yamamoto, Y.; Ueda, Y.; Sumita, Y.; Yoshida, K.; Niki, Y. Comparative Studies on the Efficacy of AmBisome and FUNGIZONE™ in a Mouse Model of Disseminated Aspergillosis. J. Antimicrob. Chemother. 2004, 53 (2), 311-317.
(11) Lei, Z.; Chen, B.; Koo, Y. M.; Macfarlane, D. R. Introduction: Ionic Liquids. Chem. Rev. 2017, 117 (10), 6633-6635.
(12) Zhang, S.; Wang, J.; Lu, X.; Zhou, Q. Structures and Interactions of Ionic Liquids; Springer-Verlag: Berlin, Heidelberg, 2014.
(13) Welton, T. Room-Temperature Ionic Liquids. Solvents for Synthesis and Catalysis. Chem. Rev. 1999, 99 (8), 2071-2084.
(14) Peleteiro, S.; Rivas, S.; Alonso, J. L.; Santos, V.; Parajó, J. C. Furfural Production Using Ionic Liquids: A Review. Bioresour. Technol. 2016, 202, 181-191.
(15) Raut, D. G.; Sundman, O.; Su, W.; Virtanen, P.; Sugano, Y.; Kordas, K.; Mikkola, J. P. A Morpholinium Ionic Liquid for Cellulose Dissolution. Carbohydr. Polym. 2015, 130, 18-25.
(16) Markiewicz, B.; Poplawski, M.; Walkiewicz, F.; Łożyński, M.; Jankowski, S.; Kordala, R.; Fabiańska, A.; Pernak, J. Synthesis and Properties of Ammonium Ionic Liquids with Cyclohexyl Substituent and Dissolution of Cellulose. RSC Adv. 2012, 2 (22), 8429.
(17) Wasserscheid, P.; Steinrück, H.-P. Ionic Liquids in Catalysis. Catal. Lett. 2015, 145, 380-397.
(18) Wang, F.; He, S.; Zhu, C.; Rabausch, U.; Streit, W.; Wang, J. The Combined Use of a Continuous-Flow Microchannel Reactor and Ionic Liquid Cosolvent for Efficient Biocatalysis of Unpurified Recombinant Enzyme. J. Chem. Technol. Biotechnol. 2018, 93, 2671-2680.
(19) Mehnert, C. P.; Cook, R. A.; Dispenziere, N. C.; Afeworki, M. Supported Ionic Liquid Catalysis—A New Concept for Homogeneous Hydroformylation Catalysis. J. Am. Chem. Soc. 2002, 124, 12932-12933.
(20) Dai, C.; Zhang, J.; Huang, C.; Lei, Z. Ionic Liquids in Selective Oxidation: Catalysts and Solvents. Chem. Rev. 2017, 117, 6929-6983.
(21) Bharmoria, P.; Kumar, A. Unusually High Thermal Stability and Peroxidase Activity of Cytochrome c in Ionic Liquid Colloidal Formulation. Chem. Commun. 2016, 52 (3), 497-500.
(22) Kim, G. J.; Kim, J. H. Enhancement of Extraction Efficiency of Paclitaxel from Biomass Using Ionic Liquid-Methanol Co-Solvents under Acidic Conditions. Process Biochem. 2015, 50 (6), 989-996.
(23) Egorova, K. S.; Gordeev, E. G.; Ananikov, V. P. Biological Activity of Ionic Liquids and Their Application in Pharmaceutics and Medicine. Chem. Rev. 2017, 117 (10), 7132-7189.
(24) Ventura, P. M.; Silva, F. A.; Quental, M. V; Mondal, D.; Freire, M. G. Ionic-Liquid-Mediated Extraction and Separation Processes for Bioactive Compounds: Past, Present, and Future Trends So N. Chem. Rev. 2017, 117, 6984-7052.
(25) Kim, S. Y.; Hwang, J. Y.; Seo, J. W.; Shin, U. S. Production of CNT-Taxol-Embedded PCL Microspheres Using an Ammonium-Based Room Temperature Ionic Liquid: As a Sustained Drug Delivery System. J. Colloid Interface Sci. 2015, 442, 147-153.

(26) Oniruzzaman, M. M.; Oto, M. G. Ionic Liquids: Future Solvents and Reagents for Pharmaceuticals. 2011, 44 (6), 370-381.

(27) Kuchlyan, J.; Kundu, N.; sarkar, N. Ionic Liquids in Microemulsions: Formulation and Characterization. Curr. Opin. Colloid Interface Sci. 2016, 25, 27-38.

(28) Moniruzzaman, M.; Tamura, M.; Tahara, Y.; Kamiya, N.; Goto, M. Ionic Liquid-in-Oil Microemulsion as a Potential Carrier of Sparingly Soluble Drug: Characterization and Cytotoxicity Evaluation. Int. J. Pharm. 2010, 400 (1-2), 243-250.

(29) Goindi, S.; Arora, P.; Kumar, N.; Puri, A. Development of Novel Ionic Liquid-Based Microemulsion Formulation for Dermal Delivery of 5-Fluorouracil. AAPS PharmSciTech 2014, 15 (4), 810-821.

(30) Goto, M. Ionic Liquid-Mediated Transcutaneous Protein Delivery with Solid-in-Oil Nanodispersions. Med. Chem. Commun. 2015, 6 (12), 2124-2128.

(31) Hough, W. L.; Smiglak, M.; Rodriguez, H.; Swatloski, R. P.; Spear, S. K.; Daly, D. T.; Pernak, J.; Grisel, J. E.; Carliss, R. D.; Soutullo, M. D.; et al. The Third Evolution of Ionic Liquids: Active Pharmaceutical Ingredients. New J. Chem. 2007, 31 (8), 1429.

(32) Florindo, C.; Pereiro, A. B.; Vieira, N. S. M.; Matias, A. A.; Duarte, C. M. M.; Rebelo, P. N.; Marrucho, I. M. Cholinium-Based Ionic Liquids with Pharmaceutically Active Anions. RSC Adv. 2014, 4, 28126-28132.

(33) Sahbaz, Y.; Nguyen, T. H.; Ford, L.; McEvoy, C. L.; Williams, H. D.; Scammells, P. J.; Porter, C. J. H. Ionic Liquid Forms of Weakly Acidic Drugs in Oral Lipid Formulations: Preparation, Characterization, in Vitro Digestion, and in Vivo Absorption Studies. Mol. Pharm. 2017, 14 (11), 3669-3683.

(34) Banerjee, A.; Ibsen, K.; Iwao, Y.; Zakrewsky, M.; Mitragotri, S. Transdermal Protein Delivery Using Choline and Geranate (CAGE) Deep Eutectic Solvent. Adv. Healthc. Mater. 2017, 6, 1-11.

(35) Wakabayashi, R.; Tahara, Y.; Kamiya, N.; Moniruzzaman, M.; Goto, M. Ionic-Liquid-Based Paclitaxel Preparation: A New Potential Formulation for Cancer Treatment. Mol. Pharm. 2018, 15, 2484-2488.

(36) Mccrary, P. D.; Beasley, P. A.; Gurau, G.; Narita, A.; Barber, P. S.; Cojocaru, O. A.; Rogers, R. D. Drug Specific, Tuning of an Ionic Liquid's Hydrophilic-Lipophilic Balance of to Improve Water Solubility of Poorly Soluble Active Pharmaceutical Ingredients. New J. Chem. 2013, 37, 2196-2202.

(37) Smith, K. B.; Bridson, R. H.; Leeke, G. A. Solubilities of Pharmaceutical Compounds in Ionic Liquids. J. Chem. Eng. Data 2011, 56 (5), 2039-2043.

(38) Banerjee, A.; Ibsen, K.; Brown, T.; Chen, R.; Agatemor, C.; Mitragotri, S. Ionic Liquids for Oral Insulin Delivery. Proc. Natl. Acad. Sci. 2018, 115 (28), 7296-7301.

(39) Manic, M. S.; Najdanovic-Visak, V. Solubility of Erythromycin in Ionic Liquids. J. Chem. Thermodyn. 2012, 44 (1), 102-106.

(40) Freire, M. G.; Neves, C. M. S. S.; Carvalho, P. J.; Gardas, R. L.; Fernandes, A. M.; Marrucho, I. M.; Santos, L. M. N. B.; Coutinho, J. A. P. Mutual Solubilities of Water and Hydrophobic Ionic Liquids. J. Phys. Chem. B 2007, 111 (45), 13082-13089.

(41) Freire, M. G.; Neves, C. M. S. S.; Marrucho, I. M.; Coutinho, J. A. P.; Fernandes, A. M. Hydrolysis of Tetrafluoroborate and Hexafluorophosphate Counter Ions in Imidazolium-Based Ionic Liquids. J. Phys. Chem. A 2010, 114 (11), 3744-3749.

(42) Jameson, L. P.; Dzyuba, S. V. Effect of Imidazolium Room-Temperature Ionic Liquids on Aggregation of Amphotericin B: A Circular Dichroism Study. RSC Adv. 2015, 5 (98), 80325-80329.

(43) Jing, B.; Lan, N.; Qiu, J.; Zhu, Y. Interaction of Ionic Liquids with a Lipid Bilayer: A Biophysical Study of Ionic Liquid Cytotoxicity. J. Phys. Chem. B 2016, 120 (10), 2781-2789.

(44) Ruokonen, S.; Sanwald, C.; Sundvik, M.; Polnick, S.; Vyavaharkar, K.; Holding, A. J.; King, A. W. T.; Kilpela, I.; La, M.; Panula, P.; et al. Effect of Ionic Liquids on Zebrafish (Danio rerio) Viability, Behavior, and Histology; Correlation between Toxicity and Ionic Liquid Aggregation. Environ. Sci. Technol. 2016, 50, 7116-7125.

(45) Pretti, C.; Chiappe, C.; Baldetti, I.; Brunini, S.; Monni, G.; Intorre, L. Acute Toxicity of Ionic Liquids for Three Freshwater Organisms: *Pseudokirchneriella subcapitata*, *Daphnia magna* and *Danio rerio*. Ecotoxicol. Environ. Saf. 2009, 72, 1170-1176.

(46) Aramwit, P.; Yu, B. G.; Lavasanifar, A.; Samuel, J.; Kwon, G. S. The Effect of Serum Albumin on the Aggregation State and Toxicity of Amphotericin B. J. Pharm. Sci. 2000, 89 (12), 1589-1593.

(47) Santos, J. I.; Gonçalves, A. M. M.; Pereira, J. L.; Figueiredo, B. F. H. T.; Silva, F. A. e; Coutinho, J. A. P.; Ventura, S. P. M.; Gonçalves, F. Environmental Safety of Cholinium-Based Ionic Liquids: Assessing Structure— Ecotoxicity Relationships. Green Chem. 2015, 17 (9), 4657-4668.

(48) Juneidi, I.; Hayyan, M.; Hashim, M. A. Evaluation of Toxicity and Biodegradability for Cholinium-Based Deep Eutectic Solvents. RSC Adv. 2015, 5, 83636-83647.

(49) Schroeder, F.; Holland, J. F.; Bieber, L. L. Fluorometric Investigations of the Interaction of Polyene Antibiotics with Sterols. Biochemistry 1972, 11 (16), 3105-3111.

(50) Cybulska, B.; Herve, M.; Borowski, E.; Gary-Bobo, C. M. Effect of the Polar Head Structure of Polyene Macrolide Antifungal Antibiotics on the Mode of Permeabilization of Ergosterol- and Cholesterol-Containing Lipidic Vesicles Studied by 31P-NMR. Mol. Pharmacol. 1985, 29, 293-298.

(51) Langlet, J.; Bergès, J.; Caillet, J.; Demaret, J.-P. Theoretical Study of the Complexation of Amphotericin B with Sterols. Biochim. Biophys. Acta 1994, 1191, 79-93.

(52) De Kruijff, B.; Gerritsen, W. J.; Oerlemans, A.; Demel, R. A.; Van Deenen, L. L. Polyene Antibiotic-Sterol Interactions in Membranes of Acholeplasma-Laidlawii Cells and Lecithin Liposomes. 1. Specificity of Membrane-Permeability Changes Induced by Polyene Antibiotics. Biochim. Biophys. Acta 1974, 339, 30-43.

(53) Borisova, M. P.; Kasumov, K. M. Sterol Structure-Dependent Properties of Amphotericin B Channels. Stud. Biophys. 1978, 71, 197-202.

(54) Petkovic, M.; Ferguson, J. L.; Gunaratne, H. Q. N.; Ferreira, R.; Leitão, M. C.; Seddon, K. R.; Rebelo, L. P. N.; Pereira, C. S. Novel Biocompatible Cholinium-Based Ionic Liquids—Toxicity and Biodegradability. Green Chem. 2010, 12 (4), 643.

(55) Muhammad, N.; Hossain, M. I.; Man, Z.; El-Harbawi, M.; Bustam, M. A.; Noaman, Y. A.; Mohamed Alitheen, N. B.; Ng, M. K.; Hefter, G.; Yin, C. Y. Synthesis and Physical Properties of Choline Carboxylate Ionic Liquids. J. Chem. Eng. Data 2012, 57 (8), 2191-2196.

(56) Rengstl, D.; Kraus, B.; Van Vorst, M.; Elliott, G. D.; Kunz, W. Effect of Choline Carboxylate Ionic Liquids on Biological Membranes. Colloids Surfaces B Biointerfaces 2014, 123, 575-581.

(57) Rantamäki, A. H.; Ruokonen, S.-K.; Sklavounos, E.; Kyllönen, L.; King, A. W. T.; Wiedmer, S. K. Impact of Surface-Active Guanidinium-, Tetramethylguanidinium-, and Cholinium-Based Ionic Liquids on *Vibrio fischeri* Cells and Dipalmitoylphosphatidylcholine Liposomes. Sci. Rep. 2017, 7 (April), 46673.

(58) Yoo, B.; Shah, J. K.; Zhu, Y.; Maginn, E. J. Amphiphilic Interactions of Ionic Liquids with Lipid Biomembranes: A Molecular Simulation Study. Soft Matter 2014, 10 (43), 8641-8651.

(59) Bingham, R. J.; Ballone, P. Computational Study of Room-Temperature Ionic Liquids Interacting with a POPC Phospholipid Bilayer. J. Phys. Chem. B 2012, 116 (36), 11205-11216.

(60) Czerniak, K.; Walkiewicz, F. Synthesis and Antioxidant Properties of Dicationic Ionic Liquids. New J. Chem. 2017, 41 (2), 530-539.

(61) Jiang, Y.; Xia, H.; Guo, C.; Mahmood, I.; Liu, H. Phenomena and Mechanism for Separation and Recovery of Penicillin in Ionic Liquids Aqueous Solution. Ind. Eng. Chem. Res. 2007, 46, 6303-6312.

(62) Hill, A. J.; Teraoka, H.; Heideman, W.; Peterson, R. E. Zebrafish as a Model Vertebrate for Investigating Chemical Toxicity. Toxicol. Sci. 2005, 86 (1), 6-19.

(63) Barres, A. R.; Wimmer, M. R.; Mecozzi, S. Multicompartment Theranostic Nanoemulsions Stabilized by a Triphilic Semifluorinated Block Copolymer. Mol. Pharm. 2017, 14, 3916-3926.

(64) Kabal'nov, A. S.; Pertzov, A. V.; Shchukin, E. D. Ostwald Ripening in Two-Component Disperse Phase Systems: Application to Emulsion Stability. Colloids and Surfaces 1987, 24, 19-32.

(65) Yu, B. G.; Okano, T.; Kataoka, K.; Sardari, S.; Kwon, G. S. In Vitro Dissociation of Antifungal Efficacy and Toxicity for Amphotericin B-Loaded Poly(Ethylene Oxide)-Block-Poly(β-Benzyl-L-Aspartate) Micelles. J. Control. Release 1998, 56, 285-291.

(66) Alvarez, C.; Andes, D. R.; Kang, J. Y.; Krug, C.; Kwon, G. S. Antifungal Efficacy of an Intravenous Formulation Containing Monomeric Amphotericin B, 5-Fluorocytosine, and Saline for Sodium Supplementation. Pharm. Res. 2017, 34 (5), 1115-1124.

(67) Eriksson, U.; Seifert, B.; Schaffner, A. Comparison of Effects of Amphotericin B Deoxycholate Infused over 4 or 24 Hours: Randomised Controlled Trial. BMJ 2001, 322 (7286), 579-579.

(68) Peleg, A. Y.; Woods, M. L. Continuous and 4 h Infusion of Amphotericin B: A Comparative Study Involving High-Risk Haematology Patients. J. Antimicrob. Chemother. 2004, 54 (4), 803-808.

(69) Imhof, A.; Walter, R. B.; Schaffner, A. Continuous Infusion of Escalated Doses of Amphotericin B Deoxycholate: An Open-Label Observational Study. Clin. Infect. Dis. 2003, 36 (8), 943-951.

(70) Huang, W.; Zhang, Z.; Han, X.; Tang, J.; Wang, J.; Dong, S.; Wang, E. Ion Channel Behavior of Amphotericin B in Sterol-Free and Cholesterol- or Ergosterol-Containing Supported Phosphatidylcholine Bilayer Model Membranes Investigated by Electrochemistry and Spectroscopy. Biophys. J. 2002, 83 (6), 3245-3255.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention embodimented. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended embodiments. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the embodiments herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are embodimented, it should be understood that compounds known and available in the art prior to Applicant's invention, including compounds for which an enabling disclosure is provided in the references cited herein, are not intended to be included in the composition of matter embodiments herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the embodiment element. As used herein, "consisting essentially of" does not exclude materials or steps that do not materially affect the basic and novel characteristics of the embodiment. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention embodimented. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended embodiments.

The invention claimed is:

1. A nanoemulsion for delivery of a therapeutic agent, said emulsion comprising an oil in water emulsion comprising:
a hydrophobic liquid;
an aqueous solution;
said therapeutic agent;
an ionic liquid composition comprising an at least partially hydrophobic ionic liquid, wherein the at least partially hydrophobic ionic liquid comprises at least one dication comprising two monocationic groups linked by a bridging group, wherein the bridging group provides an at least partially hydrophobic character; wherein the dication is a compound of Formula 71

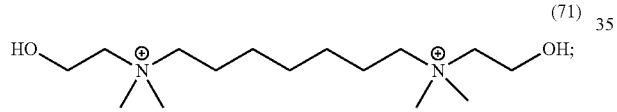
(71)

and
a polymer;
wherein said ionic liquid composition is capable of at least partially solubilizing the therapeutic agent.

2. The nanoemulsion of claim 1, wherein said ionic liquid composition further comprises at least one anion.

3. The nanoemulsion of claim 2, wherein the anion is characterized by a Formula II:

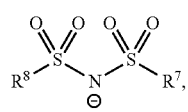
(II)

wherein each of $R^7$ and $R^8$ is independently a substituted or unsubstituted $C_1$-$C_{10}$ alkyl, substituted or unsubstituted $C_2$-$C_{10}$ hydroxyalkyl, or $C_1$-$C_{10}$haloalkyl.

4. The nanoemulsion of claim 2, wherein the anion is characterized by formula 36, 37, 38, 39, 40, 41, 42, 43 or 44:

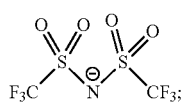
(36)

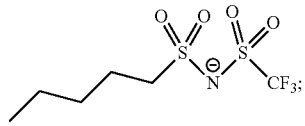
(37)

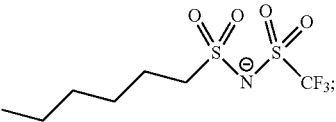
(38)

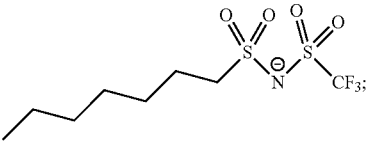
(39)

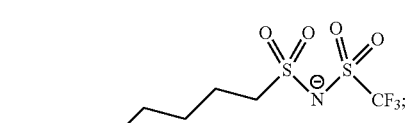
(40)

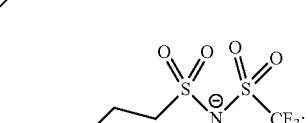
(41)

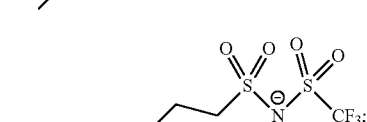
(42)

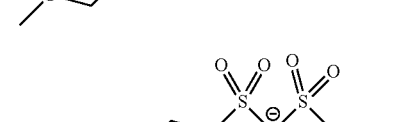
(43)

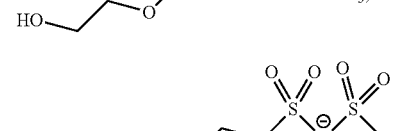
(44)

5. The nanoemulsion of claim 1, wherein the ionic liquid comprises dication and anions characterized by the formulas:

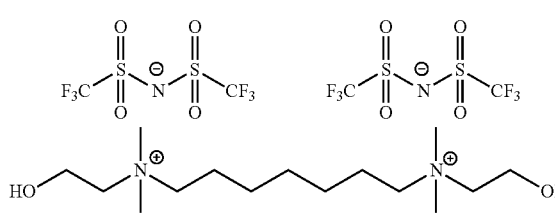

6. The nanoemulsion of claim 1, further comprising an at least partially hydrophilic ionic liquid, wherein the ratio of the hydrophilic ionic liquid to the at least partially hydrophobic ionic liquid is between 1:1 to 1:10 (v/v) and wherein the ratio of hydrophilic ionic liquid to the at least partially hydrophobic ionic liquid is 1:1.2 to 1:1.5 (v/v).

7. The nanoemulsion of claim 1, wherein said therapeutic agent is an anticancer agent or antifungal agent.

8. The nanoemulsion of claim 1, wherein said therapeutic agent is paclitaxel, doxorubicin, retinoic acid series, camptothecin, docetaxel, tamoxifen, anasterozole, itraconazole, topotecan, amphotericin B, belotecan, irinotecan, gleevec or vincristine, cisplatin or 5-fluorouracil (5-FU).

9. A nanoemulsion for delivery of a therapeutic agent, said emulsion comprising an oil in water emulsion comprising:
a hydrophobic liquid;
an aqueous solution;
said therapeutic agent;
an ionic liquid composition comprising a mixture of an at least partially hydrophilic ionic liquid and an at least partially hydrophobic ionic liquid;
wherein the at least partially hydrophobic ionic liquid comprises at least one dication comprising two monocationic groups linked by a bridging group, wherein the bridging group provides an at least partially hydrophobic character; wherein the dication is a compound of Formula 71

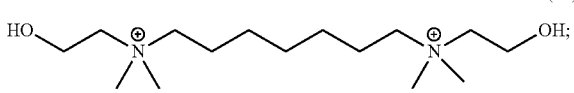
(71)

and
a polymer;
wherein said ionic liquid composition is capable of at least partially solubilizing the therapeutic agent.

10. The nanoemulsion of claim 1, wherein said hydrophobic liquid is one or more medium-chain triglycerides characterized by 5 to 10 carbons per carbon chain.

11. The nanoemulsion of claim 1, wherein the polymer comprises an amphiphilic polymer having a hydrophilic region and a hydrophobic region.

12. The nanoemulsion of claim 11, wherein the amphiphilic polymer is a PEG-PLA (polylactic acid) or PEG-PGLA.

13. The nanoemulsion of claim 11, wherein the amphiphilic polymer is a polyethylene glycol (PEG)-coupled lipid having a lipid moiety comprising a single chain or double chain C10-C24 alkyl and a polyethylene glycol moiety characterized by a molecular weight of 1,000 Da to 12,000 Da.

14. The nanoemulsion of claim 1, wherein the ratio of hydrophobic liquid to ionic liquid composition is between 1:0.1 to 1:0.8 (v/v), and wherein the polymer has a concentration of 0.01 mM to 100 mM or wherein the hydrophobic liquid:ionic liquid composition has a ratio of 1:0.2 to 1:0.6 (v/v), and wherein the polymer has a concentration of 2 mM to 30 mM.

15. The nanoemulsion of claim 1, wherein the therapeutic agent is a hydrophobic therapeutic agent.

16. A method of delivering a therapeutic agent to a mammalian subject in need thereof, said method comprising the steps of:
(a) providing a nanoemulsion according to claim 1; and
(b) administering an effective amount of said nanoemulsion to said subject.

* * * * *